US011827627B2

(12) United States Patent
Beck et al.

(10) Patent No.: US 11,827,627 B2
(45) Date of Patent: Nov. 28, 2023

(54) N-(HYDROXYALKYL (HETERO)ARYL) TETRAHYDROFURAN CARBOXAMIDES AS MODULATORS OF SODIUM CHANNELS

(71) Applicant: VERTEX PHARMACEUTICALS INCORPORATED, Boston, MA (US)

(72) Inventors: Elizabeth Mary Beck, Abingdon (GB); Steven John Durrant, Headington (GB); Sarah Skerratt, Cambridge (GB); Robert Pullin, Oxford (GB); Gorka Etxebarria Jardi, Badalona (ES); David Matthew Shaw, Oxford (GB); Nadia M. Ahmad, Hayes (GB); Christopher Wray, Berkshire (GB); Anisa Nizarali Virani, Thatcham (GB); Kiri North, Oxford (GB); James Dodd, Wallingford (GB); Michael Edward O'Donnell, Abingdon (GB); Bhairavi Galan, Abingdon (GB); Ronald Marcellus Knegtel, Abingdon (GB); Ewa Iwona Chudyk, Wantage (GB); Joanne Louise Pinder, Didcot (GB); Stephen Andrew Thomson, Durham, NC (US); Lidio Marx Carvalho Meireles, San Marcos, CA (US); Dean Stamos, Carlsbad, CA (US); Yvonne Schmidt, San Diego, CA (US); Joseph Pontillo, San Diego, CA (US); Sara S. Hadida Ruah, La Jolla, CA (US); Timothy Donald Neubert, San Diego, CA (US); Dennis James Hurley, San Marcos, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 17/831,842

(22) Filed: Jun. 3, 2022

(65) Prior Publication Data

US 2023/0009251 A1    Jan. 12, 2023

Related U.S. Application Data

(60) Provisional application No. 63/196,946, filed on Jun. 4, 2021.

(51) Int. Cl.
*C07D 405/12* (2006.01)

(52) U.S. Cl.
CPC ................... *C07D 405/12* (2013.01)

(58) Field of Classification Search
None
See application file for complete search history.

(56) References Cited

U.S. PATENT DOCUMENTS

| | | | |
|---|---|---|---|
| 4,844,732 | A | 7/1989 | Goto et al. |
| 5,304,121 | A | 4/1994 | Sahatjian |
| 5,356,897 | A | 10/1994 | Oku et al. |
| 5,387,709 | A | 2/1995 | Lardy et al. |
| 5,403,842 | A | 4/1995 | Leonardi et al. |
| 5,886,026 | A | 3/1999 | Hunter et al. |
| 5,942,508 | A | 8/1999 | Sawa |
| 5,968,965 | A | 10/1999 | Dinsmore et al. |
| 5,977,108 | A | 11/1999 | Kikuchi et al. |
| 6,099,562 | A | 8/2000 | Ding et al. |
| 6,179,882 | B1 | 1/2001 | Vidal et al. |
| 6,355,669 | B1 | 3/2002 | Yamauchi et al. |
| 8,389,734 | B2 | 3/2013 | Chen |
| 8,466,188 | B2 | 6/2013 | Chafeev et al. |
| 8,486,950 | B2 | 7/2013 | Goodacre et al. |
| 8,519,137 | B2 | 8/2013 | Joshi |
| 8,779,197 | B2 | 7/2014 | Chen |
| 8,841,483 | B2 | 9/2014 | Joshi |
| 8,865,771 | B2 | 10/2014 | Chen |
| 8,883,840 | B2 | 11/2014 | Chafeev et al. |
| 9,051,270 | B2 | 6/2015 | Hadida-Ruah |
| 9,108,903 | B2 | 8/2015 | Hadida-Ruah |
| 9,139,529 | B2 | 9/2015 | Hadida-Ruah |
| 9,163,042 | B2 | 10/2015 | Anderson |
| 9,393,235 | B2 | 7/2016 | Hadida-Ruah |
| 9,421,196 | B2 | 8/2016 | Hadida-Ruah |
| 9,464,102 | B2 | 10/2016 | Anderson |
| 9,758,483 | B2 | 9/2017 | Hadida-Ruah |
| 9,783,501 | B2 | 10/2017 | Hadida-Ruah |
| 9,828,397 | B2 | 11/2017 | Anderson |
| 10,087,143 | B2 | 10/2018 | Hadida Ruah |

(Continued)

FOREIGN PATENT DOCUMENTS

| | | |
|---|---|---|
| CA | 2742435 A1 | 5/2011 |
| CA | 2851462 A1 | 5/2014 |

(Continued)

OTHER PUBLICATIONS

Akopian, A.N., L. Sivilotti, and J.N. Wood, A tetrodotoxin-resistant voltage-gated sodium channel expressed by sensory neurons. *Nature*, 1996. 379(6562): p. 257-62.

Berge et al. describe pharmaceutically acceptable salts in detail in *J. Pharmaceutical Sciences*, 1977, 66, 1-19.

Black, J.A., et al., Multiple sodium channel isoforms and mitogen-activated protein kinases are present in painful human neuromas. *Ann. Neurol.*, 2008. 64(6): p. 644-53.

Blair, N.T. and B.P. Bean, Roles of tetrodotoxin (TTX)-sensitive Na+ current, TTX-resistant $Na^+$ current, and $Ca^{2+}$ current in the action potentials of nociceptive sensory neurons. *J. Neurosci.*, 2002. 22(23): p. 10277-90.

(Continued)

*Primary Examiner* — Samantha L Shterengarts
(74) *Attorney, Agent, or Firm* — Barnes & Thornburg LLP

(57) ABSTRACT

Compounds, and pharmaceutically acceptable salts thereof, useful as inhibitors of sodium channels are provided. Also provided are pharmaceutical compositions comprising the compounds or pharmaceutically acceptable salts and methods of using the compounds, pharmaceutically acceptable salts, and pharmaceutical compositions in the treatment of various disorders, including pain.

37 Claims, 6 Drawing Sheets

(56) References Cited

U.S. PATENT DOCUMENTS

| | | |
|---|---|---|
| 10,253,054 B2 | 4/2019 | Anderson |
| 10,647,661 B2 | 5/2020 | Ahmad |
| 10,738,009 B2 | 8/2020 | Hadida Ruah |
| 10,787,472 B2 | 9/2020 | Anderson |
| 11,203,571 B2 | 12/2021 | Hadida-Ruah et al. |
| 11,358,977 B2 | 6/2022 | Jiang et al. |
| 2002/0002183 A1 | 1/2002 | Zhu et al. |
| 2003/0195231 A1 | 10/2003 | Takemoto et al. |
| 2004/0180936 A1 | 9/2004 | Auvin et al. |
| 2004/0229839 A1 | 11/2004 | Babu et al. |
| 2005/0009894 A1 | 1/2005 | Babin et al. |
| 2007/0105943 A1 | 5/2007 | Nakamoto et al. |
| 2007/0238733 A1 | 10/2007 | Joshi |
| 2008/0312235 A1 | 12/2008 | Lane et al. |
| 2009/0048306 A1 | 2/2009 | Bagal et al. |
| 2009/0074884 A1 | 3/2009 | Chesney et al. |
| 2009/0099233 A1 | 4/2009 | Joshi |
| 2009/0118333 A1 | 5/2009 | Chen |
| 2009/0118338 A1 | 5/2009 | Chen |
| 2009/0163545 A1 | 6/2009 | Goldfarb |
| 2009/0326020 A1 | 12/2009 | Miller et al. |
| 2010/0069417 A1 | 3/2010 | Bouaboula et al. |
| 2010/0075948 A1 | 3/2010 | Ding et al. |
| 2010/0093668 A1 | 4/2010 | Babin et al. |
| 2010/0099694 A1 | 4/2010 | Babin et al. |
| 2010/0152190 A1 | 6/2010 | Bartkovitz et al. |
| 2010/0186626 A1 | 7/2010 | Shin et al. |
| 2010/0256113 A1 | 10/2010 | Onda et al. |
| 2011/0257196 A1 | 10/2011 | Lu et al. |
| 2011/0301181 A1 | 12/2011 | Maue et al. |
| 2011/0306607 A1 | 12/2011 | Hadida-Ruah et al. |
| 2012/0196869 A1 | 8/2012 | Hadida Ruah et al. |
| 2012/0220605 A1 | 8/2012 | Pajouhesh et al. |
| 2012/0245136 A1 | 9/2012 | Hadida-Ruah et al. |
| 2012/0264055 A1 | 10/2012 | Ichikawa et al. |
| 2012/0264749 A1 | 10/2012 | Hadida-Ruah et al. |
| 2013/0158031 A1 | 6/2013 | Cai et al. |
| 2013/0231370 A1 | 9/2013 | Chen |
| 2013/0274243 A1 | 10/2013 | Bagal et al. |
| 2013/0303535 A1 | 11/2013 | Tsuboi et al. |
| 2014/0005181 A1 | 1/2014 | Smith et al. |
| 2014/0011763 A1 | 1/2014 | Lakshman |
| 2014/0187533 A1 | 7/2014 | Pajouhesh et al. |
| 2014/0200215 A1 | 7/2014 | Buckman et al. |
| 2014/0213616 A1 | 7/2014 | Hadida-Ruah et al. |
| 2014/0221435 A1 | 8/2014 | Hadida-Ruah et al. |
| 2014/0228371 A1 | 8/2014 | Hadida-Ruah et al. |
| 2014/0296313 A1 | 10/2014 | Bagal et al. |
| 2015/0005304 A1 | 1/2015 | Hadida-Ruah et al. |
| 2015/0076062 A1 | 3/2015 | Barthelemy et al. |
| 2015/0166589 A1 | 6/2015 | Anderson et al. |
| 2015/0166890 A1 | 6/2015 | Archetti et al. |
| 2015/0210640 A1 | 7/2015 | Ikuma et al. |
| 2015/0246028 A1 | 9/2015 | Hadida-Ruah |
| 2015/0305999 A1 | 10/2015 | Daubresse |
| 2015/0322027 A1 | 11/2015 | Fujiwara et al. |
| 2015/0328196 A1 | 11/2015 | Hadida-Ruah |
| 2015/0336945 A1 | 11/2015 | Hadida-Ruah |
| 2015/0361038 A1 | 12/2015 | Smith et al. |
| 2015/0376174 A1 | 12/2015 | Kawana et al. |
| 2016/0009743 A1 | 1/2016 | Anderson |
| 2016/0046863 A1 | 2/2016 | Archetti et al. |
| 2016/0115151 A1 | 4/2016 | Kai |
| 2016/0145304 A1 | 5/2016 | Baumann et al. |
| 2016/0152561 A1 | 6/2016 | Hadida-Ruah et al. |
| 2016/0208171 A1 | 7/2016 | Kim et al. |
| 2016/0238930 A1 | 8/2016 | Hasegawa et al. |
| 2016/0333009 A1 | 11/2016 | Bartlett et al. |
| 2016/0376295 A1 | 12/2016 | Anderson |
| 2017/0037009 A1 | 2/2017 | Hadida-Ruah |
| 2017/0256727 A1 | 9/2017 | Lee et al. |
| 2018/0016235 A1 | 1/2018 | Hadida-Ruah |
| 2018/0044361 A1 | 2/2018 | Anderson et al. |
| 2018/0201600 A1 | 7/2018 | Jeschke et al. |
| 2018/0258076 A1 | 9/2018 | Sato et al. |
| 2019/0016671 A1 | 1/2019 | Ahmad et al. |
| 2019/0248745 A1 | 8/2019 | Hadida Ruah et al. |
| 2019/0276483 A1 | 9/2019 | Anderson et al. |
| 2019/0343817 A1 | 11/2019 | Agarwal et al. |
| 2020/0024270 A1 | 1/2020 | Li et al. |
| 2020/0030312 A1 | 1/2020 | Shao et al. |
| 2020/0079795 A1 | 3/2020 | Zhang et al. |
| 2020/0140411 A1 | 5/2020 | Arasappan et al. |
| 2020/0377535 A1 | 12/2020 | Anderson et al. |
| 2021/0047271 A1 | 2/2021 | Hadida Ruah et al. |
| 2021/0052610 A1 | 2/2021 | Agarwal et al. |
| 2021/0094906 A1 | 4/2021 | Ahmad et al. |
| 2021/0155643 A1 | 5/2021 | Jiang et al. |
| 2021/0198241 A1 | 7/2021 | Durrant |
| 2022/0110923 A1 | 4/2022 | Thomson |

FOREIGN PATENT DOCUMENTS

| | | |
|---|---|---|
| CN | 101855210 | 10/2010 |
| CN | 101883758 | 11/2010 |
| CN | 102264722 | 11/2011 |
| CN | 105906591 A | 8/2016 |
| CN | 105985330 A | 10/2016 |
| CN | 106518766 A | 3/2017 |
| CN | 106518767 A | 3/2017 |
| CN | 107033149 A | 8/2017 |
| CN | 108689942 A | 10/2018 |
| CN | 109320509 A | 2/2019 |
| CN | 109384712 A | 2/2019 |
| CN | 109553608 A | 4/2019 |
| CN | 111217776 | 6/2020 |
| CN | 111808019 | 11/2020 |
| CN | 112225695 | 1/2021 |
| CN | 112300051 | 2/2021 |
| CN | 112300069 | 2/2021 |
| CN | 112390745 | 2/2021 |
| CN | 112409331 A | 2/2021 |
| CN | 112441969 | 3/2021 |
| CN | 112457294 | 3/2021 |
| CN | 112479996 | 3/2021 |
| EP | 1336602 A1 | 8/2003 |
| EP | 1882475 A1 | 1/2008 |
| EP | 3023816 A1 | 5/2016 |
| FR | 3030242 A1 | 12/2014 |
| GB | 2300856 A | 11/1996 |
| IT | 1992RM0025 A1 | 7/1993 |
| JP | S62198663 A | 9/1987 |
| JP | S62198664 A | 9/1987 |
| JP | H 05107574 A | 4/1993 |
| JP | H 10213820 A | 8/1998 |
| JP | 2003/034671 A | 2/2003 |
| JP | 2005/145858 A | 6/2005 |
| JP | 2005/531501 | 10/2005 |
| JP | 2009/051827 A | 3/2009 |
| JP | 2009/051828 A | 3/2009 |
| JP | 2009/242540 A | 10/2009 |
| JP | 2010/059131 A | 3/2010 |
| JP | 2011/500599 | 1/2011 |
| JP | 2011/500600 | 1/2011 |
| JP | 2012/167027 A | 9/2012 |
| JP | 2013/195630 A | 9/2013 |
| JP | 2013/254084 A | 12/2013 |
| JP | 2014/232188 A | 12/2014 |
| JP | 2016/079098 A | 5/2016 |
| JP | WO 2017/090743 A1 | 6/2017 |
| KR | 201900076339 A | 7/2019 |
| KR | 10-2092838 B1 | 3/2020 |
| KR | 202000065978 A | 6/2020 |
| RU | 2010/118467 | 11/2011 |
| RU | 2010/118481 | 11/2011 |
| WO | WO 1991/000858 | 1/1991 |
| WO | WO 1992/001696 | 2/1992 |
| WO | WO 1993/000313 | 1/1993 |
| WO | WO 1993/017007 | 9/1993 |
| WO | WO 1994/008962 | 4/1994 |
| WO | WO 1997/014419 | 4/1997 |
| WO | WO 1997/027852 | 8/1997 |
| WO | WO 1998/016186 | 4/1998 |
| WO | WO 1998/018466 | 5/1998 |

(56) References Cited

FOREIGN PATENT DOCUMENTS

| | | |
|---|---|---|
| WO | WO 1999/026941 | 6/1999 |
| WO | WO 2000/018725 | 4/2000 |
| WO | WO 2000/025789 | 5/2000 |
| WO | WO 2000/064876 | 11/2000 |
| WO | WO 2001/012183 | 2/2001 |
| WO | WO 2001/019788 | 3/2001 |
| WO | WO 2001/019798 | 3/2001 |
| WO | WO 2001/030795 | 5/2001 |
| WO | WO 2001/064642 | 9/2001 |
| WO | WO 2001/064643 | 9/2001 |
| WO | WO 2001/066098 | 9/2001 |
| WO | WO 2002/008748 | 1/2002 |
| WO | WO 2002/020492 | 3/2002 |
| WO | WO 2002/036553 | 5/2002 |
| WO | WO 2002/051831 | 7/2002 |
| WO | WO 2002/055012 | 7/2002 |
| WO | WO 2002/060905 | 8/2002 |
| WO | WO 2002/070483 | 9/2002 |
| WO | WO 2002/083628 | 10/2002 |
| WO | WO 2003/000245 | 1/2003 |
| WO | WO 2003/026652 | 4/2003 |
| WO | WO 2003/037871 | 5/2003 |
| WO | WO 2003/045921 | 6/2003 |
| WO | WO 2003/048081 | 6/2003 |
| WO | WO 2003/048158 | 6/2003 |
| WO | WO 2003/062221 | 7/2003 |
| WO | WO 2003/068230 | 8/2003 |
| WO | WO 2003/070193 | 8/2003 |
| WO | WO 2003/070912 | 8/2003 |
| WO | WO 2003/072099 | 9/2003 |
| WO | WO 2003/072757 | 9/2003 |
| WO | WO 2004/041277 | 5/2004 |
| WO | WO 2004/062601 | 7/2004 |
| WO | WO 2004/063151 | 7/2004 |
| WO | WO 2004/083174 | 9/2004 |
| WO | WO 2004/090154 | 10/2004 |
| WO | WO 2004/091499 | 10/2004 |
| WO | WO 2005/000298 | 1/2005 |
| WO | WO 2005/000300 | 1/2005 |
| WO | WO 2005/000309 | 1/2005 |
| WO | WO 2005/013914 | 2/2005 |
| WO | WO 2005/019236 | 3/2005 |
| WO | WO 2005/019237 | 3/2005 |
| WO | WO 2005/021568 | 3/2005 |
| WO | WO 2005/044797 | 5/2005 |
| WO | WO 2005/049019 | 6/2005 |
| WO | WO 2005/051393 | 6/2005 |
| WO | WO 2006/011050 | 2/2006 |
| WO | WO 2006/017896 | 2/2006 |
| WO | WO 2006/028904 | 3/2006 |
| WO | WO 2006/094347 | 9/2006 |
| WO | WO 2006/113615 | 10/2006 |
| WO | WO 2006/122072 | 11/2006 |
| WO | WO 2006/123257 | 11/2006 |
| WO | WO 2006/124780 | 11/2006 |
| WO | WO 2006/127329 | 11/2006 |
| WO | WO 2006/130493 | 12/2006 |
| WO | WO 2007/024021 | 3/2007 |
| WO | WO 2007/052843 | 5/2007 |
| WO | WO 2007/081966 | 7/2007 |
| WO | WO 2007/088999 | 8/2007 |
| WO | WO 2007/095187 | 8/2007 |
| WO | WO 2007/097940 | 8/2007 |
| WO | WO 2007/106525 | 9/2007 |
| WO | WO 2007/109105 | 9/2007 |
| WO | WO 2007/120647 | 10/2007 |
| WO | WO 2007/146712 | 12/2007 |
| WO | WO 2008/001195 | 1/2008 |
| WO | WO 2008/005542 | 1/2008 |
| WO | WO 2008/014291 | 1/2008 |
| WO | WO 2008/018129 | 2/2008 |
| WO | WO 2008/019124 | 2/2008 |
| WO | WO 2008/033743 | 3/2008 |
| WO | WO 2008/033746 | 3/2008 |
| WO | WO 2008/065068 | 6/2008 |
| WO | WO 2008/073670 | 6/2008 |
| WO | WO 2008/094507 | 8/2008 |
| WO | WO 2008/115262 | 9/2008 |
| WO | WO 2008/115263 | 9/2008 |
| WO | WO 2008/133753 | 11/2008 |
| WO | WO 2008/135826 | 11/2008 |
| WO | WO 2008/156783 | 12/2008 |
| WO | WO 2009/000413 | 12/2008 |
| WO | WO 2009/012482 | 1/2009 |
| WO | WO 2009/036012 | 3/2009 |
| WO | WO 2009/036051 | 3/2009 |
| WO | WO 2009/036066 | 3/2009 |
| WO | WO 2009/041521 | 4/2009 |
| WO | WO 2009/047798 | 4/2009 |
| WO | WO 2009/049181 | 4/2009 |
| WO | WO 2009/049183 | 4/2009 |
| WO | WO 2009/056693 | 5/2009 |
| WO | WO 2009/069132 | 6/2009 |
| WO | WO 2009/076593 | 6/2009 |
| WO | WO 2009/091941 | 7/2009 |
| WO | WO 2009/114470 | 9/2009 |
| WO | WO 2009/126691 | 10/2009 |
| WO | WO 2010/003048 | 1/2010 |
| WO | WO 2010/027512 | 3/2010 |
| WO | WO 2010/031713 | 3/2010 |
| WO | WO 2010/037127 | 4/2010 |
| WO | WO 2010/037129 | 4/2010 |
| WO | WO 2010/048149 | 4/2010 |
| WO | WO 2010/051926 | 5/2010 |
| WO | WO 2010/060952 | 6/2010 |
| WO | WO 2010/063996 | 6/2010 |
| WO | WO 2010/066028 | 6/2010 |
| WO | WO 2010/072607 | 7/2010 |
| WO | WO 2010/075282 | 7/2010 |
| WO | WO 2010/107739 | 9/2010 |
| WO | WO 2010/115736 | 10/2010 |
| WO | WO 2010/129323 | 11/2010 |
| WO | WO 2010/129864 | 11/2010 |
| WO | WO 2010/137351 | 12/2010 |
| WO | WO 2010/138575 | 12/2010 |
| WO | WO 2010/138576 | 12/2010 |
| WO | WO 2011/005860 | 1/2011 |
| WO | WO 2011/026240 | 3/2011 |
| WO | WO 2011/032169 | 3/2011 |
| WO | WO 2011/037731 | 3/2011 |
| WO | WO 2011/047320 | 4/2011 |
| WO | WO 2011/098398 | 8/2011 |
| WO | WO 2011/103468 | 8/2011 |
| WO | WO 2011/109059 | 9/2011 |
| WO | WO 2011/140425 | 11/2011 |
| WO | WO 2011/141909 | 11/2011 |
| WO | WO 2011/151619 | 12/2011 |
| WO | WO 2012/007409 | 1/2012 |
| WO | WO 2012/016133 | 2/2012 |
| WO | WO 2012/017020 | 2/2012 |
| WO | WO 2012/020725 | 2/2012 |
| WO | WO 2012/106499 | 3/2012 |
| WO | WO 2012/048222 | 4/2012 |
| WO | WO 2012/049460 | 4/2012 |
| WO | WO 2012/052540 | 4/2012 |
| WO | WO 2012/056113 | 5/2012 |
| WO | WO 2012/069856 | 5/2012 |
| WO | WO 2012/073138 | 6/2012 |
| WO | WO 2012/080727 | 6/2012 |
| WO | WO 2012/080729 | 6/2012 |
| WO | WO 2012/094328 | 7/2012 |
| WO | WO 2012/097330 | 7/2012 |
| WO | WO 2012/106534 | 8/2012 |
| WO | WO 2012/112743 | 8/2012 |
| WO | WO 2012/116440 | 9/2012 |
| WO | WO 2012/125613 | 9/2012 |
| WO | WO 2012/125797 | 9/2012 |
| WO | WO 2012/129562 | 9/2012 |
| WO | WO 2012/155066 | 11/2012 |
| WO | WO 2012/166951 | 12/2012 |
| WO | WO 2012/170371 | 12/2012 |
| WO | WO 2012/178123 | 12/2012 |
| WO | WO 2013/004995 | 1/2013 |
| WO | WO 2013/005057 | 1/2013 |

(56) References Cited

FOREIGN PATENT DOCUMENTS

| | | |
|---|---|---|
| WO | WO 2013/022740 | 2/2013 |
| WO | WO 2013/040059 | 3/2013 |
| WO | WO 2013/049725 | 4/2013 |
| WO | WO 2013/061205 | 5/2013 |
| WO | WO 2013/086229 | 6/2013 |
| WO | WO 2013/109521 | 7/2013 |
| WO | WO 2013/114250 | 8/2013 |
| WO | WO 2013/117707 | 8/2013 |
| WO | WO 2013/124040 | 8/2013 |
| WO | WO 2013/131018 | 9/2013 |
| WO | WO 2013/132376 | 9/2013 |
| WO | WO 2013/132991 | 9/2013 |
| WO | WO 2013/134518 | 9/2013 |
| WO | WO 2013/151975 | 10/2013 |
| WO | WO 2013/178570 | 12/2013 |
| WO | WO 2013/188881 | 12/2013 |
| WO | WO 2014/003153 | 1/2014 |
| WO | WO 2014/005125 | 1/2014 |
| WO | WO 2014/014874 | 1/2014 |
| WO | WO 2014/015523 | 1/2014 |
| WO | WO 2014/015675 | 1/2014 |
| WO | WO 2014/018891 | 1/2014 |
| WO | WO 2014/020152 | 2/2014 |
| WO | WO 2014/039595 | 3/2014 |
| WO | WO 2014/045156 | 3/2014 |
| WO | WO 2014/047110 | 3/2014 |
| WO | WO 2014/075393 | 5/2014 |
| WO | WO 2014/078479 | 5/2014 |
| WO | WO 2014/088920 | 6/2014 |
| WO | WO 2014/108407 | 7/2014 |
| WO | WO 2014/118133 | 8/2014 |
| WO | WO 2014/120808 | 8/2014 |
| WO | WO 2014/120815 | 8/2014 |
| WO | WO 2014/120820 | 8/2014 |
| WO | WO 2014/130856 | 8/2014 |
| WO | WO 2014/134127 | 9/2014 |
| WO | WO 2014/151958 | 9/2014 |
| WO | WO 2014/179785 | 11/2014 |
| WO | WO 2014/200078 | 12/2014 |
| WO | WO 2014/201173 | 12/2014 |
| WO | WO 2014/201206 | 12/2014 |
| WO | WO 2014/202763 | 12/2014 |
| WO | WO 2015/003723 | 1/2015 |
| WO | WO 2015/003816 | 1/2015 |
| WO | WO 2015/003991 | 1/2015 |
| WO | WO 2015/010065 | 1/2015 |
| WO | WO 2015/011284 | 1/2015 |
| WO | WO 2015/035051 | 3/2015 |
| WO | WO 2015/038596 | 3/2015 |
| WO | WO 2015/049651 | 4/2015 |
| WO | WO 2015/051173 | 4/2015 |
| WO | WO 2015/054337 | 4/2015 |
| WO | WO 2015/084796 | 6/2015 |
| WO | WO 2015/085238 | 6/2015 |
| WO | WO 2015/089361 | 6/2015 |
| WO | WO 2015/089511 | 6/2015 |
| WO | WO 2015/103317 | 7/2015 |
| WO | WO 2015/157559 | 10/2015 |
| WO | WO 2015/162244 | 10/2015 |
| WO | WO 2015/196118 | 12/2015 |
| WO | WO 2015/196128 | 12/2015 |
| WO | WO 2015/196130 | 12/2015 |
| WO | WO 2016/003929 | 1/2016 |
| WO | WO 2016/007837 | 1/2016 |
| WO | WO 2016/011209 | 1/2016 |
| WO | WO 2016/012457 | 1/2016 |
| WO | WO 2016/029146 | 2/2016 |
| WO | WO 2016/040449 | 3/2016 |
| WO | WO 2016/040505 | 3/2016 |
| WO | WO 2016/073633 | 5/2016 |
| WO | WO 2016/094682 | 6/2016 |
| WO | WO 2016/100385 | 6/2016 |
| WO | WO 2016/141035 | 9/2016 |
| WO | WO 2016/145142 | 9/2016 |
| WO | WO 2016/170010 | 10/2016 |
| WO | WO 2016/172631 | 10/2016 |
| WO | WO 2016/196593 | 12/2016 |
| WO | WO 2016/198908 | 12/2016 |
| WO | WO 2017/001924 | 1/2017 |
| WO | WO 2017/011371 | 1/2017 |
| WO | WO 2017/051319 | 3/2017 |
| WO | WO 2017/059385 | 4/2017 |
| WO | WO 2017/059446 | 4/2017 |
| WO | WO 2017/062751 | 4/2017 |
| WO | WO 2017/066705 | 4/2017 |
| WO | WO 2017/066781 | 4/2017 |
| WO | WO 2017/066782 | 4/2017 |
| WO | WO 2017/066791 | 4/2017 |
| WO | WO 2017/090743 | 6/2017 |
| WO | WO 2017/103615 | 6/2017 |
| WO | WO 2017/158381 | 9/2017 |
| WO | WO 2017/161028 | 9/2017 |
| WO | WO 2017/173274 | 10/2017 |
| WO | WO 2017/223260 | 12/2017 |
| WO | WO 2018/014819 | 1/2018 |
| WO | WO 2018/045106 | 3/2018 |
| WO | WO 2018/055235 | 3/2018 |
| WO | WO 2018/060110 | 4/2018 |
| WO | WO 2018/064119 | 4/2018 |
| WO | WO 2018/067636 | 4/2018 |
| WO | WO 2018/138358 | 8/2018 |
| WO | WO 2018/161033 | 9/2018 |
| WO | WO 2018/177297 | 10/2018 |
| WO | WO 2018/183781 | 10/2018 |
| WO | WO 2018/183782 | 10/2018 |
| WO | WO 2018/183923 | 10/2018 |
| WO | WO 2018/186365 | 10/2018 |
| WO | WO 2018/191146 | 10/2018 |
| WO | WO 2018/195439 | 10/2018 |
| WO | WO 2018/195450 | 10/2018 |
| WO | WO 2018/213426 | 11/2018 |
| WO | WO 2018/237194 | 12/2018 |
| WO | WO 2019/014352 | 1/2019 |
| WO | WO 2019/036562 | 2/2019 |
| WO | WO 2019/036657 | 2/2019 |
| WO | WO 2019/079596 | 4/2019 |
| WO | WO 2019/079607 | 4/2019 |
| WO | WO 2019/084271 | 5/2019 |
| WO | WO 2019/086579 | 5/2019 |
| WO | WO 2019/094732 | 5/2019 |
| WO | WO 2019/097515 | 5/2019 |
| WO | WO 2019/122420 | 6/2019 |
| WO | WO 2019/137201 | 7/2019 |
| WO | WO 2019/154953 | 8/2019 |
| WO | WO 2019/154956 | 8/2019 |
| WO | WO 2019/195439 | 10/2019 |
| WO | WO 2019/206925 | 10/2019 |
| WO | WO 2019/207081 | 10/2019 |
| WO | WO 2019/222414 | 11/2019 |
| WO | WO 2019/246343 | 12/2019 |
| WO | WO 2020/014243 | 1/2020 |
| WO | WO 2020/014246 | 1/2020 |
| WO | WO 2020/025030 | 2/2020 |
| WO | WO 2020/033413 | 2/2020 |
| WO | WO 2020/034058 | 2/2020 |
| WO | WO 2020/034062 | 2/2020 |
| WO | WO 2020/051207 | 3/2020 |
| WO | WO 2020/069330 | 4/2020 |
| WO | WO 2020/072835 | 4/2020 |
| WO | WO 2020/073949 | 4/2020 |
| WO | WO 2020/081572 | 4/2020 |
| WO | WO 2020/092187 | 5/2020 |
| WO | WO 2020/092667 | 5/2020 |
| WO | WO 2020/117626 | 6/2020 |
| WO | WO 2020/118036 | 6/2020 |
| WO | WO 2020/123675 | 6/2020 |
| WO | WO 2020/140959 | 7/2020 |
| WO | WO 2020/146612 | 7/2020 |
| WO | WO 2020/146682 | 7/2020 |
| WO | WO 2020/147739 | 7/2020 |
| WO | WO 2020/151728 | 7/2020 |
| WO | WO 2020/152079 | 7/2020 |
| WO | WO 2020/159576 | 8/2020 |
| WO | WO 2020/160225 | 8/2020 |

(56) References Cited

FOREIGN PATENT DOCUMENTS

| | | |
|---|---|---|
| WO | WO 2020/191227 | 9/2020 |
| WO | WO 2020/191501 | 10/2020 |
| WO | WO 2020/221677 | 11/2020 |
| WO | WO 2020/228922 | 11/2020 |
| WO | WO 2020/230134 | 11/2020 |
| WO | WO 2020/230136 | 11/2020 |
| WO | WO 2020/251974 | 12/2020 |
| WO | WO 2020/254493 | 12/2020 |
| WO | WO 2020/261114 | 12/2020 |
| WO | WO 2021/001739 | 1/2021 |
| WO | WO 2021/032074 | 2/2021 |
| WO | WO 2021/047622 | 3/2021 |
| WO | WO 2021/074357 | 4/2021 |
| WO | WO 2021/113627 | 6/2021 |
| WO | WO 2021/229571 | 11/2021 |
| WO | WO 2021/239117 | 12/2021 |
| WO | WO 2021/252818 | 12/2021 |
| WO | WO 2021/252820 | 12/2021 |
| WO | WO 2021/252822 | 12/2021 |
| WO | WO 2021/257418 | 12/2021 |
| WO | WO 2021/257420 | 12/2021 |
| WO | WO 2021/257490 | 12/2021 |
| WO | WO 2022/023772 | 2/2022 |
| WO | WO 2022/036297 | 2/2022 |
| WO | WO 2022/037641 | 2/2022 |
| WO | WO 2022/037647 | 2/2022 |
| WO | WO 2022/063902 | 3/2022 |
| WO | WO 2022/070048 | 4/2022 |
| WO | WO 2022/086986 | 4/2022 |

OTHER PUBLICATIONS

CAS No. 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione.
CAS No. 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl] ester).
CAS Registry Compounds, database entry dates no later than Oct. 2017.
CAS Registry Compounds, database entry dates no later than Sep. 2018.
Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005).
Chahine, M., Chatelier, A., Babich, O., and Krupp, J. J., Voltage-gated sodium channels in neurological disorders. *CNS Neurol. Disord. Drug Targets* 7 (2), p. 144-58 (2008).
Choi, J.S. and S.G. Waxman, Physiological interactions between $Na_v1.7$ and $Na_v1.8$ sodium channels: a computer simulation study. *J. Neurophysiol.* 106(6): p. 3173-84.
Coward, K., et al., Immunolocalization of SNS/PN3 and NaN/SNS2 sodium channels in human pain states. *Pain*, 2000. 85(1-2): p. 41-50.
Dieleman, J.P., et al., Incidence rates and treatment of neuropathic pain conditions in the general population. *Pain*, 2008. 137(3): p. 681-8.
Ding, Qingjie et al., "Discovery of RG7388, a Potent and Selective p53-MDM2 Inhibitor in Clinical Development," J. Med. Chem., 56(14), pp. 5979-5983 (2013).
Dong, X.W., et al., Small interfering RNA-mediated selective knockdown of $Na_v1.8$ tetrodotoxin-resistant sodium channel reverses mechanical allodynia in neuropathic rats. *Neuroscience*, 2007. 146(2): p. 812-21.
England, S., Voltage-gated sodium channels: the search for subtype-selective analgesics. *Expert Opin. Investig. Drugs* 17 (12), p. 1849-64 (2008).
Fornwald et al., *Gene Expression in Mammalian Cells Using BacMam, a Modified Baculovirus System*, 1350 Methods in Molecular Biology 95-116 (2016).
Gonzalez, J.E. and Tsien, R.Y. "Improved indicators of cell membrane potential that use fluorescence resonance energy transfer," (1997) *Chem. Biol.* 4, 269-277.
Gonzalez, J.E. and Tsien, R.Y., "Voltage Sensing by Fluorescence Resonance Energy Transfer in Single Cells," (1995) *Biophys. J.* 69, 1272-1280.
Harbeson, S. L. and Tung, R. D., *Deuterium In Drug Discovery and Development*, Ann. Rep. Med. Chem. 2011, 46, 403-417.
Huang et al. *Characterization of voltage-gated sodium channel blockers by electrical stimulation and fluorescence detection of membrane potential*, 24 Nature Biotech. 439-46 (2006).
Huang, H.L., et al., Proteomic profiling of neuromas reveals alterations in protein composition and local protein synthesis in hyperexcitable nerves. *Mol. Pain*, 2008. 4: p. 33.
International Search Report and Written Opinion for PCT/US2020/063290, dated Feb. 2, 2021, 13 pgs.
International Search Report and Written Opinion for PCT/US2022/032116, dated Sep. 23, 2022, 13 pgs.
Jarvis, M.F., et al., A-803467, a potent and selective $Na_v1.8$ sodium channel blocker, attenuates neuropathic and inflammatory pain in the rat. *Proc. Natl. Acad. Sci.* USA, 2007. 104(20): p. 8520-5.
Joshi, S.K., et al., Involvement of the TTX-resistant sodium channel $Na_v1.8$ in inflammatory and neuropathic, but not post-operative, pain states. *Pain*, 2006. 123(1-2): pp. 75-82.
Kato, Tetsuzo et al., "Antitumor activity of compounds derived from diketene and their related compounds," Pharm. Inst., 97(6), pp. 676-684 (1977).
Krafte, D. S. and Bannon, A. W., Sodium channels and nociception: recent concepts and therapeutic opportunities. *Curr. Opin. Pharmacol.* 8 (1), p. 50-56 (2008).
Lai, J., et al., Inhibition of neuropathic pain by decreased expression of the tetrodotoxin-resistant sodium channel, $Na_v1.8$. *Pain*, 2002. 95(1-2): p. 143-52.
Liu, Jianzhong et al.,"Pd(II)—Catalyzed Pyridine N-Oxides Directed Arylation of Unactivated Csp3-H Bonds," Am. Chem. Society, 80(9), pp. 4618-4626 (2015).
National Center for Biotechnology Information (2022); Pub Chem Compound Summary for CID 136583999, Created Jan. 24, 2019; Retrieved Apr. 1, 2022 from https://pubchem.ncbi.nim.nih.gov/compound/136583999 (Year: 2019).
Qiu, F., et al., Increased expression of tetrodotoxin-resistant sodium channels $Na_v1.8$ and $Na_v1.9$ within dorsal root ganglia in a rat model of bone cancer pain. *Neurosci. Lett.*, 512(2): p. 61-6.
Renganathan, M., T.R. Cummins, and S.G. Waxman, Contribution of $Na_{(v)}1.8$ sodium channels to action potential electrogenesis in DRG neurons. *J. Neurophysiol.*, 2001. 86(2): p. 629-40.
Roza, C., et al., The tetrodotoxin-resistant $Na^+$ channel $Na_v1.8$ is essential for the expression of spontaneous activity in damaged sensory axons of mice. *J. Physiol.*, 2003. 550(Pt 3): p. 921-6.
Ruangsri, S., et al., Relationship of axonal voltage-gated sodium channel 1.8 ($Na_v1.8$) mRNA accumulation to sciatic nerve injury-induced painful neuropathy in rats. *J. Biol. Chem.* 286(46): p. 39836-47).
Rush, A.M. and T.R. Cummins, *Painful Research: Identification of a Small-Molecule Inhibitor that Selectively Targets $Na_v1.8$ Sodium Channels*. Mol. Interv., 2007. 7(4): p. 192-5).
Rush, A.M., et al., A single sodium channel mutation produces hyper- or hypoexcitability in different types of neurons. *Proc. Natl. Acad. Sci. USA*, 2006. 103(21): p. 8245-50).
Soderpalm, B., Anticonvulsants: aspects of their mechanisms of action. *Eur. J. Pain* 6 Suppl. A, p. 3-9 (2002).
Strickland, I.T., et al., Changes in the expression of $Na_v1.7$, $Na_v1.8$ and $Na_v1.9$ in a distinct population of dorsal root ganglia innervating the rat knee joint in a model of chronic inflammatory joint pain. *Eur. J. Pain*, 2008. 12(5): p. 564-72.
Sun, W., et al., Reduced conduction failure of the main axon of polymodal nociceptive C-fibers contributes to painful diabetic neuropathy in rats. *Brain*, 135(Pt 2): p. 359-75.
Wang et al., "NHC-Catalyzed Asymmetric Synthesis of Functionalized Succinimides from Enals and α-Ketoamides," Chem. A EP Jour. 21(22), (2015), pp. 8033-8037.

(56) References Cited

OTHER PUBLICATIONS

Wang, G. K., Mitchell, J., and Wang, S. Y., Block of persistent late Na$^+$ currents by antidepressant sertraline and paroxetine. *J. Membr. Biol.* 222 (2), p. 79-90 (2008).

Yiangou, Y., et al., SNS/PN3 and SNS2/NaN sodium channel-like immunoreactivity in human adult and neonate injured sensory nerves. *FEBS Lett.*, 2000. 467(2-3): p. 249-52.

N-(HYDROXYALKYL (HETERO)ARYL) TETRAHYDROFURAN CARBOXAMIDES AS MODULATORS OF SODIUM CHANNELS

CROSS-REFERENCE TO RELATED APPLICATIONS

This application claims the benefit of U.S. Provisional Application No. 63/196,946, filed Jun. 4, 2021, which is incorporated by reference herein in its entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post-herpetic neuropathy, diabetic neuropathy, and drug-induced neuropathy. Discrete nerve injury indications include post-amputation pain, post-surgical nerve injury pain, and nerve entrapment injuries like neuropathic back pain.

Voltage-gated sodium channels ($Na_Vs$) are involved in pain signaling. $Na_Vs$ are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_Vs$ in pain sensation (Rush, A. M. and T. R. Cummins, *Painful Research: Identification of a Small-Molecule Inhibitor that Selectively Targets $Na_V1.8$ Sodium Channels*. Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_Vs$ mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, Mass., 2001)). Because of the role $Na_Vs$ play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_Vs$ form a subfamily of the voltage-gated ion channel super-family and comprises 9 isoforms, designated $Na_V1.1$-$Na_V1.9$. The tissue localizations of the nine isoforms vary. $Na_V1.4$ is the primary sodium channel of skeletal muscle, and $Na_V1.5$ is primary sodium channel of cardiac myocytes. $Na_Vs$ 1.7, 1.8 and 1.9 are primarily localized to the peripheral nervous system, while $Na_Vs$ 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379 (6562): p. 257-62). Since then, $Na_V1.8$ has been shown to be a carrier of the sodium current that maintains action potential firing in small dorsal root ganglia (DRG) neurons (Blair, N. T. and B. P. Bean, Roles of tetrodotoxin (TTX)-sensitive $Na+$ current, TTX-resistant $Na+$ current, and $Ca^{2+}$ current in the action potentials of nociceptive sensory neurons. *J. Neurosci.*, 2002. 22(23): p. 10277-90). $Na_V1.8$ is involved in spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc. Natl. Acad. Sci. USA*, 2007. 104(20): p. 8520-5; Joshi, S. K., et al., Involvement of the TTX-resistant sodium channel $Na_V1.8$ in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na_V1.8$ tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol. Pain*, 2008. 4: p. 33; Black, J. A., et al., Multiple sodium channel isoforms and mitogen-activated protein kinases are present in painful human neuromas. *Ann. Neurol.*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett.*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.* 286(46): p. 39836-47). The small DRG neurons where $Na_V1.8$ is expressed include the nociceptors involved in pain signaling. $Na_V1.8$ mediates large amplitude action potentials in small neurons of the dorsal root ganglia (Blair, N. T. and B. P. Bean, Roles of tetrodotoxin (TTX)-sensitive Na+ current, TTX-resistant Na+ current, and Ca$^{2+}$ current in the action potentials of nociceptive sensory neurons. *J. Neurosci.*, 2002. 22(23): p. 10277-90). Na$_V$1.8 is necessary for rapid repetitive action potentials in nociceptors, and for spontaneous activity of damaged neurons. (Choi, J. S. and S. G. Waxman, Physiological interactions between Na$_V$1.7 and Na$_V$1.8 sodium channels: a computer simulation study. *J. Neurophysiol.* 106(6): p. 3173-84; Renganathan, M., T. R. Cummins, and S. G. Waxman, Contribution of Na$_{(V)}$1.8 sodium channels to action potential electrogenesis in DRG neurons. *J. Neurophysiol.*, 2001. 86(2): p. 629-40; Roza, C., et al., The tetrodotoxin-resistant Na+ channel Na$_V$1.8 is essential for the expression of spontaneous activity in damaged sensory axons of mice. *J. Physiol.*, 2003. 550(Pt 3): p. 921-6). In depolarized or damaged DRG neurons, Na$_V$1.8 appears to be a driver of hyper-excitablility (Rush, A. M., et al., A single sodium channel mutation produces hyper- or hypoexcitability in different types of neurons. *Proc. Natl. Acad. Sci. USA,* 2006. 103(21): p. 8245-50). In some animal pain models, Na$_V$1.8 mRNA expression levels have been shown to increase in the DRG (Sun, W., et al., Reduced conduction failure of the main axon of polymodal nociceptive C-fibers contributes to painful diabetic neuropathy in rats. *Brain,* 135(Pt 2): p. 359-75; Strickland, I. T., et al., Changes in the expression of Na$_V$1.7, Na$_V$1.8 and Na$_V$1.9 in a distinct population of dorsal root ganglia innervating the rat knee joint in a model of chronic inflammatory joint pain. *Eur. J Pain,* 2008. 12(5): p. 564-72; Qiu, F., et al., Increased expression of tetrodotoxin-resistant sodium channels Na$_V$1.8 and Na$_V$1.9 within dorsal root ganglia in a rat model of bone cancer pain. *Neurosci. Lett.,* 512(2): p. 61-6).

The inventors have discovered that some voltage-gated sodium channel inhibitors have limitations as therapeutic agents due to, for example, a poor therapeutic window (e.g., due to a lack of Na$_V$ isoform selectivity, low potency, and/or other reasons). Accordingly, there remains a need to develop selective voltage-gated sodium channel inhibitors, such as selective Na$_V$1.8 inhibitors.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

Figure 1:
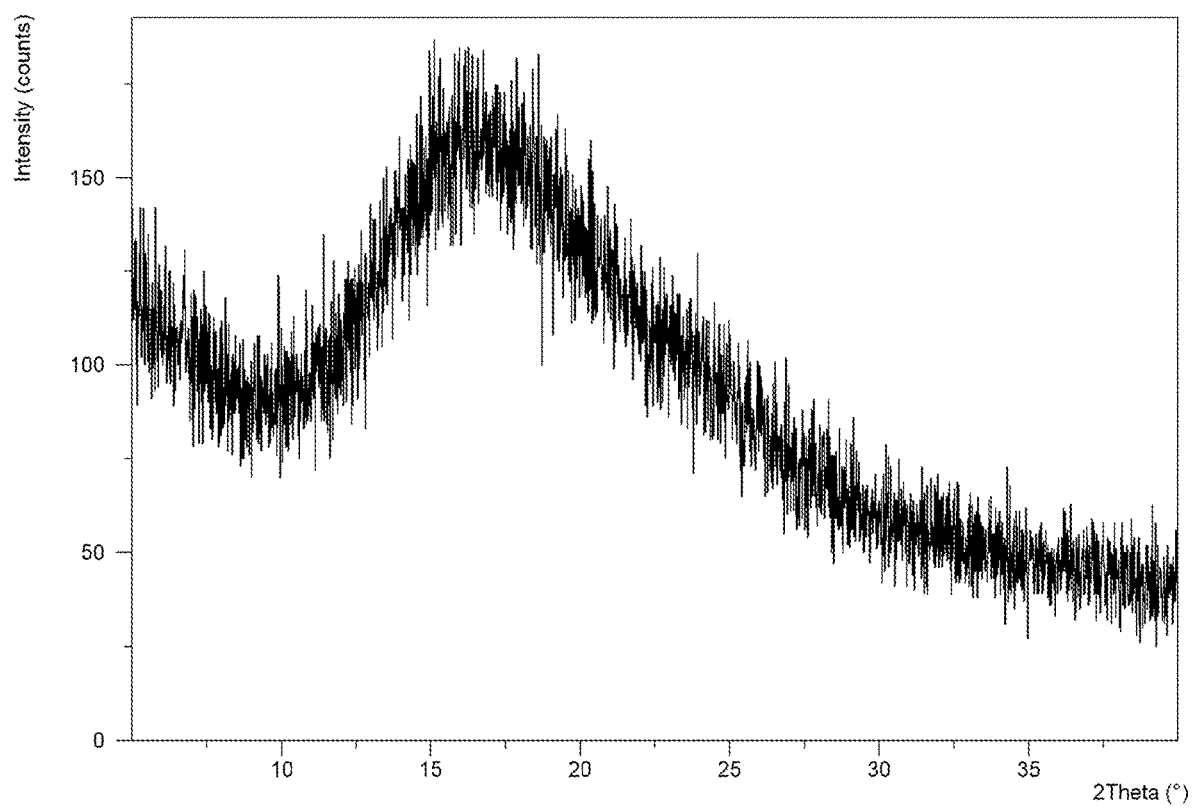
FIG. 1 depicts an XRPD pattern characteristic of amorphous Compound 1.

In one aspect, the invention relates to a compound of formula (I)

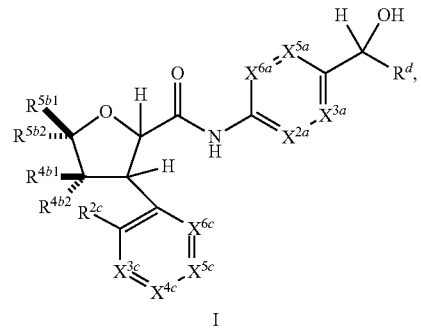

or a pharmaceutically acceptable salt thereof, wherein:

$X^{2a}$ is N, N$^+$—O$^-$, or C—R$^{2a}$;

$X^{3a}$ is N or N$^+$—O$^-$;

$X^{5a}$ is N, N$^+$—O$^-$, or C—R$^{5a}$;

$X^{6a}$ is N, N$^+$—O$^-$, or C—R$^{6a}$;

$R^d$ is $(CH_2)_m(CHR^e)_n(CH_2)_pH$;

m, n, and p are each independently 0 or 1;

$R^e$ is H, OH, halo, $C_1$-$C_6$ alkoxy, or $C_1$-$C_6$ haloalkoxy;

$R^{2a}$ and $R^{6a}$ are each independently H, halo, $C_1$-$C_6$ alkyl, or $C_1$-$C_6$ haloalkyl;

$R^{5a}$ is H, halo, $CH_2OH$, $C_1$-$C_6$ alkyl, or $C_1$-$C_6$ haloalkyl;

$R^{4b1}$ and $R^{4b2}$ are each independently H, $C_1$-$C_6$ alkyl, $C_3$-$C_6$ cycloalkyl, or $C_1$-$C_6$ haloalkyl;

$R^{5b1}$ and $R^{5b2}$ are each independently H, $C_1$-$C_6$ alkyl, $C_3$-$C_6$ cycloalkyl, or $C_1$-$C_6$ haloalkyl;

$X^{3c}$ is N or C—R$^{3c}$;

$X^{4c}$ is N or C—R$^{4c}$;

$X^{5c}$ is N or C—R$^{5c}$;

$X^{6c}$ is N or C—R$^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -L$^1$-L$^2$-($C_3$-$C_6$ cycloalkyl), wherein said cycloalkyl is optionally substituted with 1-2 halo;

$L^1$ is a bond or O;

$L^2$ is a bond or $C_1$-$C_6$ alkylene;

$R^{3c}$ is H, halo, $C_1$-$C_6$ alkyl, or $C_1$-$C_6$ haloalkyl; or $X^{3c}$ is C—R$^{3c}$, and R$^{2c}$ and R$^{3c}$, together with the carbon atoms to which they are attached, form a ring of formula:

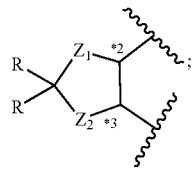

$Z_1$ and $Z_2$ are each independently O or $CH_2$;
each R is independently H or halo;
$R^{4c}$ is H, halo, $C_1$-$C_6$ alkyl, $C_1$-$C_6$ haloalkyl, $C_1$-$C_6$ alkoxy, or $C_1$-$C_6$ haloalkoxy;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl;
provided that no more than two of $X^{2a}$, $X^{3a}$, $X^{5a}$, and $X^{6a}$ are N or $N^+$—$O^-$; and
provided that no more than one of $X^{3c}$, $X^{4c}$, $X^{5c}$, and $X^{6c}$ is N.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formula (I), and all of the embodiments thereof (e.g., formulas (I-A), etc.), as described herein, and to the compounds identified in Table A.

As described herein, the compounds of the invention comprise multiple variable groups (e.g., $R^1$, $X^{3a}$, $R^{5b}$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The chemical structures depicted herein are intended to be understood as they would be understood by one of ordinary skill in the art. For example, with respect to formulas (I), (I-A), (I-B), and (I-C), $X^{2a}$ and $X^{3a}$ are connected by a single bond, $X^{5a}$ and $X^{6a}$ are connected by a double bond, and $X^{4c}$ and $X^{5c}$ are connected by a single bond, even though the bonds between these groups may be obscured by the atom labels in the chemical structures. Using a different ChemDraw style, formula (I) could be drawn as follows to show the bonds in question:

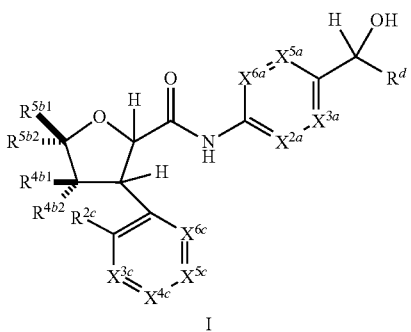

I

Moreover, a substituent depicted as "$CF_3$" or "$F_3C$" in a chemical structure refers to a trifluoromethyl substituent, regardless of which depiction appears in the chemical structure.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "alkenyl" refers to a straight or branched hydrocarbon chain radical group consisting solely of carbon and hydrogen atoms, containing one or more carbon-carbon double bonds, and having the specified number of carbon atoms, which is attached to the rest of the molecule by a single bond. For example, a "$C_2$-$C_6$ alkenyl" group is an alkenyl group having between two and six carbon atoms.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond. For example, a "$C_3$-$C_8$ cycloalkyl" group is a cycloalkyl group having between three and eight carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —$OR_a$ where $R_a$ is an alkyl group having the specified number of carbon atoms. For example, a "$C_1$-$C_6$ alkoxy" group is a radical of the formula —$OR_a$ where $R_a$ is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "alkylene" refers to a divalent, straight or branched hydrocarbon chain radical group consisting solely of carbon and hydrogen atoms, containing no unsaturation, and having the specified number of carbon atoms, which is attached to the rest of the molecule by two single bonds. For example, a "$C_1$-$C_6$ alkylene" group is an alkylene group having between one and six carbon atoms.

As used herein, the term "optionally substituted" refers to a group that is either unsubstituted or substituted with the subsequently identified substituents. For example, a group that is "optionally substituted with 1-2 halo" is either unsubstituted, substituted with 1 halo group, or substituted with 2 halo groups.

As used herein, "*2" and "*3" in the following structure designate the carbon atoms to which the $R^2$ and $R^{3c}$ groups, respectively, are attached.

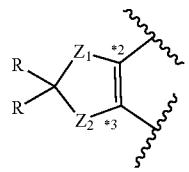

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers of the compounds identified by the chemical names and chemical structures provided herein. In addition, single stereoisomers, double bond isomers, conformational isomers, and tautomers as well as mixtures of stereoisomers, double bond isomers, conformational isomers, and tautomers are within the scope of the invention.

As used herein, in any chemical structure or formula, a non-bold, straight bond attached to a stereocenter of a compound, such as in

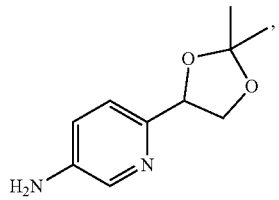

denotes that the configuration of the stereocenter is unspecified. The compound may have any configuration, or a mixture of configurations, at the stereocenter.

As used herein, in any chemical structure or formula, a bold or hashed straight bond attached to a stereocenter of a compound, such as in

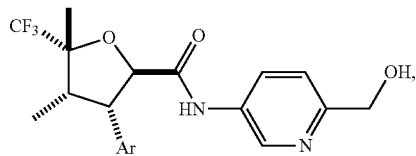

denotes the relative stereochemistry of the stereocenter, relative to other stereocenter(s) to which bold or hashed straight bonds are attached.

As used herein, in any chemical structure or formula, a bold or hashed wedge bond attached to a stereocenter of a compound, such as in

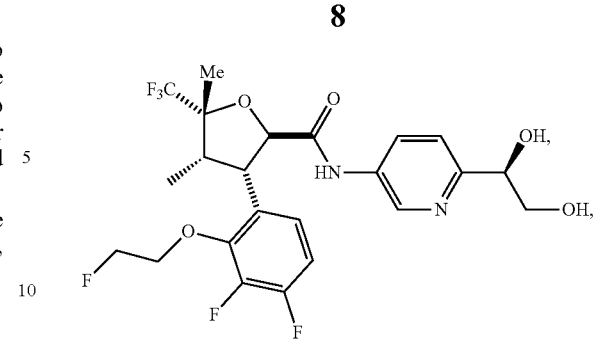

denotes the absolute stereochemistry of the stereocenter, as well as the relative stereochemistry of the stereocenter, relative to other stereocenter(s) to which bold or hashed wedge bonds are attached.

As used herein, the prefix "rac-," when used in connection with a chiral compound, refers to a racemic mixture of the compound. In a compound bearing the "rac-" prefix, the (R)- and (S)-designators in the chemical name reflect the relative stereochemistry of the compound.

As used herein, the prefix "rel-," when used in connection with a chiral compound, refers to a single enantiomer of unknown absolute configuration. In a compound bearing the "rel-" prefix, the (R)- and (S)-designators in the chemical name reflect the relative stereochemistry of the compound, but do not necessarily reflect the absolute stereochemistry of the compound. Where the relative stereochemistry of a given stereocenter is unknown, no stereochemical designator is provided. In some instances, the absolute configuration of some stereocenters is known, while only the relative configuration of the other stereocenters is known. In these instances, the stereochemical designators associated with the stereocenters of known absolute configuration are marked with an asterisk (*), e.g., (R*)- and (S*)-, while the stereochemical designators associated with stereocenters of unknown absolute configuration are not so marked. The unmarked stereochemical designators associated with the stereocenters of unknown absolute configuration reflect the relative stereochemistry of those stereocenters with respect to other stereocenters of unknown absolute configuration, but do not necessarily reflect the relative stereochemistry with respect to the stereocenters of known absolute configuration.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, colloid, or pharmaceutical composition, or dosage form) with one or more other substances, or in the form of a hydrate, solvate, or co-crystal.

As used herein, the term "amorphous" refers to a solid material having no long-range order in the position of its molecules. Amorphous solids are generally glasses or supercooled liquids in which the molecules are arranged in a random manner so that there is no well-defined arrangement, e.g., molecular packing, and no long-range order. Amorphous solids are generally rather isotropic, i.e., exhibit similar properties in all directions and do not have definite melting points. Instead, they typically exhibit a glass transition temperature which marks a transition from glassy amorphous state to supercooled liquid amorphous state upon heating. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e., the material is not crystalline, but is amorphous, as determined by XRPD). Instead, one or several broad peaks (e.g., halos) may appear in the XRPD pattern of the material. See US 2004/0006237 for a representative comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, solid state NMR may also be used to characterize crystalline or amorphous forms.

As used herein, the term "crystalline" refers to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, and solid state nuclear magnetic resonance (e.g., $^{13}$C, $^{19}$F, $^{15}$N, and $^{31}$P SSNMR).

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^{1}$H and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "$^{1}$H" refers to protium. Where an atom in a compound of the invention, or a pharmaceutically acceptable salt thereof, is designated as protium, protium is present at the specified position at at least the natural abundance concentration of protium.

As used herein, "D," "d," and "$^{2}$H" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labeled" compounds and salts). Examples of stable isotopes which are commercially available and suitable for the invention include without limitation isotopes of hydrogen, carbon, nitrogen, oxygen, and phosphorus, for example $^{2}$H, $^{13}$C, $^{15}$N, $^{18}$O, $^{17}$O, and $^{31}$P, respectively.

The isotope-labeled compounds and salts can be used in a number of beneficial ways, including as medicaments. In some embodiments, the isotope-labeled compounds and salts are deuterium ($^{2}$H)-labeled. Deuterium ($^{2}$H)-labeled compounds and salts are therapeutically useful with potential therapeutic advantages over the non-$^{2}$H-labeled compounds. In general, deuterium ($^{2}$H)-labeled compounds and salts can have higher metabolic stability as compared to those that are not isotope-labeled owing to the kinetic isotope effect described below. Higher metabolic stability translates directly into an increased in vivo half-life or lower dosages, which under most circumstances would represent a preferred embodiment of the present invention. The isotope-labeled compounds and salts can usually be prepared by carrying out the procedures disclosed in the synthesis schemes, the examples and the related description, replacing a non-isotope-labeled reactant by a readily available isotope-labeled reactant.

The deuterium ($^{2}$H)-labeled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For example, if deuterium is bonded to a carbon atom at a non-exchangeable position, rate differences of $k_H/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labeled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (~45% deuterium incorporation). In some embodiments, the isotopic enrichment factor is at least 3500 (~52.5% deuterium incorporation), at least 4000 (~60% deuterium incorporation), at least 4500 (~67.5% deuterium incorporation), at least 5000 (~75% deuterium incorporation), at least 5500 (~82.5% deuterium incorporation), at least 6000 (~90% deuterium incorporation), at least 6333.3 (~95% deuterium incorporation), at least 6466.7 (~97% deuterium incorporation), at least 6600 (~99% deuterium incorporation), or at least 6633.3 (~99.5% deuterium incorporation).

In some embodiments, the invention relates to a compound of formula (I-A)

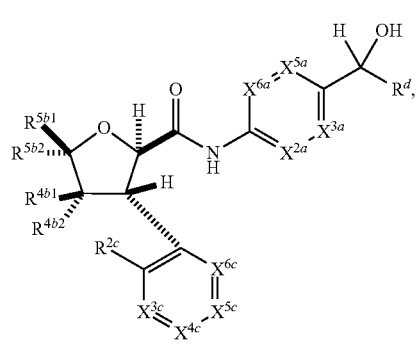

or a pharmaceutically acceptable salt thereof, wherein $X^{2a}$, $X^{3a}$, $X^{5a}$, $X^{6a}$, $R^d$, $R^{4b1}$, $R^{4b2}$, $R^{5b1}$, $R^{5b2}$, $X^{3c}$, $X^{4c}$, $X^{5c}$, $X^{6c}$, and $R^{2c}$ are defined as set forth above in connection with formula (I).

In some embodiments, the invention relates to a compound of formula (I-A-1)

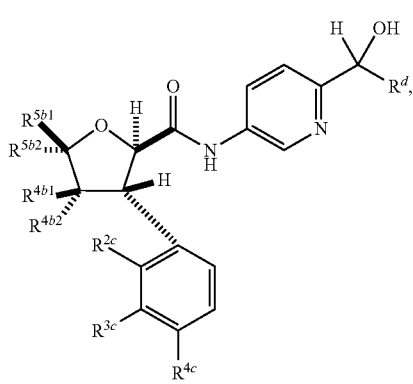

or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-A-2)

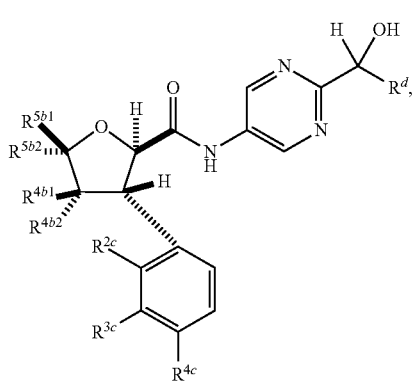

or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-A-3)

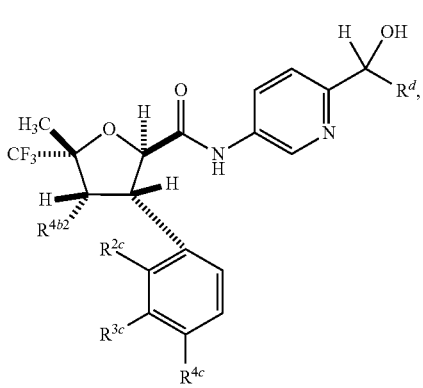

or a pharmaceutically acceptable salt thereof, wherein $R^d$, $R^{4b2}$, $R^{2c}$, $R^{3c}$, and $R^{4c}$ are defined as set forth above in connection with formula (I).

In some embodiments, the invention relates to a compound of formula (I-B)

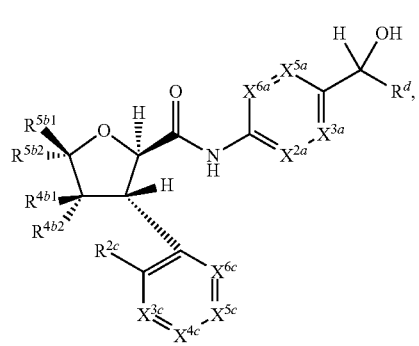

or a pharmaceutically acceptable salt thereof, wherein $X^{2a}$, $X^{3a}$, $X^{5a}$, $X^{6a}$, $R^d$, $R^{4b1}$, $R^{4b2}$, $R^{5b1}$, $R^{5b2}$, $X^{3c}$, $X^{4c}$, $X^{5c}$, $X^{6c}$, and $R^{2c}$ are defined as set forth above in connection with formula (I).

In some embodiments, the invention relates to a compound of formula (I-B-1)

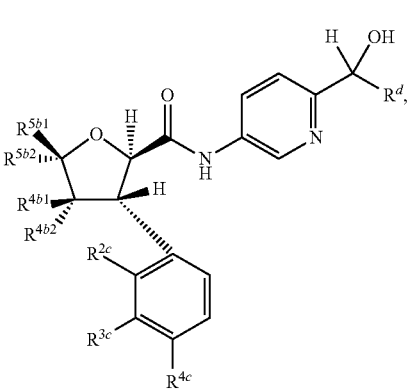

or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-B-2)

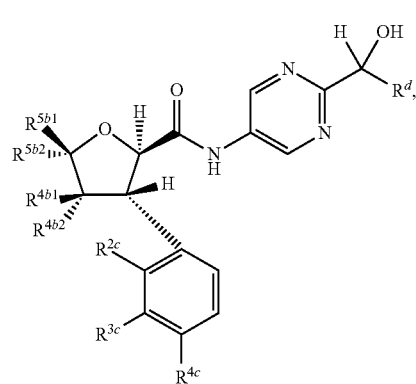

I-B-2 or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-B-3)

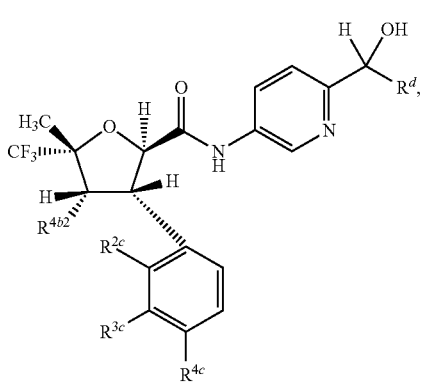

I-B-3 or a pharmaceutically acceptable salt thereof, wherein $R^d$, $R^{4b2}$, $R^{2c}$, $R^{3c}$, and $R^{4c}$ are defined as set forth above in connection with formula (I).

In some embodiments, the invention relates to a compound of formula (I-C)

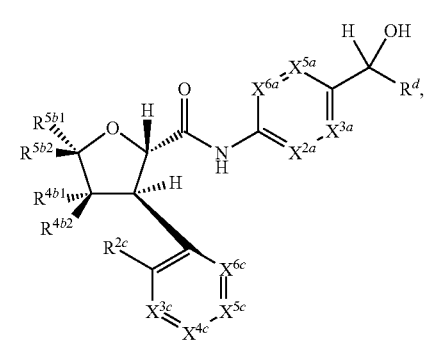

I-C or a pharmaceutically acceptable salt thereof, wherein $X^{2a}$, $X^{3a}$, $X^{5a}$, $X^{6a}$, $R^d$, $R^{4b1}$, $R^{4b2}$, $R^{5b1}$, $R^{5b2}$, $X^{3c}$, $X^{4c}$, $X^{5c}$, $X^{6c}$, and $R^{2c}$ are defined as set forth above in connection with formula (I).

In some embodiments, the invention relates to a compound of formula (I-C-1)

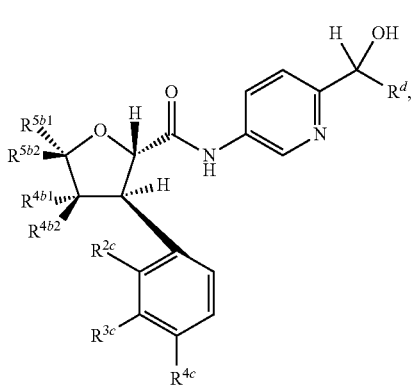

I-C-1 or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-C-2)

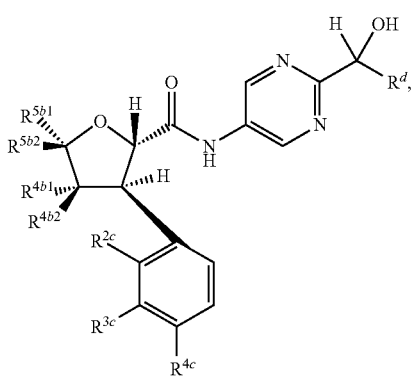

I-C-2 or a pharmaceutically acceptable salt thereof, wherein $R^d$, $R^{4b1}$, $R^{4b2}$, $R^{5b1}$, $R^{5b2}$, $R^{2c}$, $R^{3c}$, and $R^{4c}$ are defined as set forth above in connection with formula (I).

In some embodiments, the invention relates to a compound of formula (I-C-3)

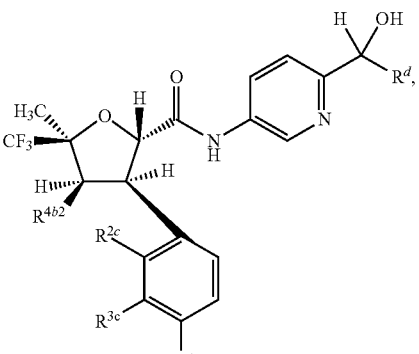

I-C-3 or a pharmaceutically acceptable salt thereof, wherein $R^d$, $R^{4b2}$, $R^{2c}$, $R^{3c}$, and $R^{4c}$ are defined as set forth above in connection with formula (I).

In some embodiments, the invention relates to a compound of any one of formulas (I), (I-A), (I-B), and (I-C), or a pharmaceutically acceptable salt thereof, wherein $X^{2a}$ is C—$R^{2a}$. In other embodiments, $X^{2a}$ is C—$R^{2a}$; and $R^{2a}$ is H.

In some embodiments, the invention relates to a compound of any one of formulas (I), (I-A), (I-B), and (I-C), or a pharmaceutically acceptable salt thereof, wherein $X^{3a}$ is N. In other embodiments, $X^{3a}$ is $N^+$—$O^-$.

In some embodiments, the invention relates to a compound of any one of formulas (I), (I-A), (I-B), and (I-C), or a pharmaceutically acceptable salt thereof, wherein $X^{5a}$ is N or C—$R^{5a}$; and $R^{5a}$ is H, halo, or $CH_2OH$. In other embodiments, $X^{5a}$ is N. In other embodiments, $X^{5a}$ is C—$R^{5a}$. In other embodiments, $X^{5a}$ is C—$R^{5a}$; and $R^{5a}$ is H, halo, or $CH_2OH$. In other embodiments, $X^{5a}$ is C—$R^{5a}$; and $R^{5a}$ is H, F, or $CH_2OH$. In other embodiments, $X^{5a}$ is C—$R^{5a}$; and $R^{5a}$ is H. In other embodiments, $X^{5a}$ is C—$R^{5a}$; and $R^{5a}$ is halo. In other embodiments, $X^{5a}$ is C—$R^{5a}$; and $R^{5a}$ is F. In other embodiments, $X^{5a}$ is C—$R^{5a}$; and $R^{5a}$ is $CH_2OH$.

In some embodiments, the invention relates to a compound of any one of formulas (I), (I-A), (I-B), and (I-C), or a pharmaceutically acceptable salt thereof, wherein $X^{6a}$ is N or C—$R^{6a}$; and $R^{6a}$ is H. In other embodiments, $X^{6a}$ is N. In other embodiments, $X^{6a}$ is C—$R^{6a}$. In other embodiments, $X^{6a}$ is C—$R^{6a}$; and $R^{6a}$ is H.

In some embodiments, the invention relates to a compound of any one of formulas (I), (I-A), (I-A-1), (I-A-2), (I-B), (I-B-1), (I-B-2), (I-C), (I-C-1), and (I-C-2), or a pharmaceutically acceptable salt thereof, wherein $R^{4b1}$ is H or $C_1$-$C_6$ alkyl. In other embodiments, $R^{4b1}$ is H. In other embodiments, $R^{4b1}$ is $C_1$-$C_6$ alkyl. In other embodiments, $R^{4b1}$ is H or $CH_3$. In other embodiments, $R^{4b1}$ is $CH_3$.

In some embodiments, the invention relates to a compound of any one of formulas (I), (I-A), (I-A-1), (I-A-2), (I-A-3), (I-B), (I-B-1), (I-B-2), (I-B-3), (I-C), (I-C-1), (I-C-2), and (I-C-3), or a pharmaceutically acceptable salt thereof, wherein $R^{4b2}$ is H or $C_1$-$C_6$ alkyl. In other embodiments, $R^{4b2}$ is H. In other embodiments, $R^{4b2}$ is $C_1$-$C_6$ alkyl. In other embodiments, $R^{4b2}$ is H or $CH_3$. In other embodiments, $R^{4b2}$ is $CH_3$.

In some embodiments, the invention relates to a compound of any one of formulas (I), (I-A), (I-A-1), (I-A-2), (I-B), (I-B-1), (I-B-2), (I-C), (I-C-1), and (I-C-2), or a pharmaceutically acceptable salt thereof, wherein $R^{5b1}$ is $C_1$-$C_6$ alkyl or $C_1$-$C_6$ haloalkyl. In other embodiments, $R^{5b1}$ is $C_1$-$C_6$ alkyl. In other embodiments, $R^{5b1}$ is $C_1$-$C_6$ haloalkyl. In other embodiments, $R^{5b1}$ is $CH_3$ or $CF_3$. In other embodiments, $R^{5b1}$ is $CH_3$. In other embodiments, $R^{5b1}$ is $CF_3$.

In some embodiments, the invention relates to a compound of any one of formulas (I), (I-A), (I-A-1), (I-A-2), (I-B), (I-B-1), (I-B-2), (I-C), (I-C-1), and (I-C-2), or a pharmaceutically acceptable salt thereof, wherein $R^{5b2}$ is $C_1$-$C_6$ alkyl or $C_1$-$C_6$ haloalkyl. In other embodiments, $R^{5b2}$ is $C_1$-$C_6$ alkyl. In other embodiments, $R^{5b2}$ is $C_1$-$C_6$ haloalkyl. In other embodiments, $R^{5b2}$ is $CH_3$ or $CF_3$. In other embodiments, $R^{5b2}$ is $CH_3$. In other embodiments, $R^{5b2}$ is $CF_3$.

In some embodiments, the invention relates to a compound of any one of formulas (I), (I-A), (I-A-1), (I-A-2), (I-A-3), (I-B), (I-B-1), (I-B-2), (I-B-3), (I-C), (I-C-1), (I-C-2), and (I-C-3), or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy. In other embodiments, $R^{2c}$ is OH. In other embodiments, $R^{2c}$ is halo. In other embodiments, $R^{2c}$ is $C_1$-$C_6$ alkyl. In other embodiments, $R^{2c}$ is $C_1$-$C_6$ alkoxy. In other embodiments, $R^{2c}$ is $C_1$-$C_6$ haloalkoxy. In other embodiments, $R^{2c}$ is OH, Cl, $CH_3$, $OCH_3$, $OCD_3$, $OCH_2CH_3$, $OCH(CH_3)_2$, $OCH_2CH_2F$, or $OCH_2CHF_2$. In other embodiments, $R^{2c}$ is Cl. In other embodiments, $R^{2c}$ is $CH_3$. In other embodiments, $R^{2c}$ is $OCH_3$. In other embodiments, $R^{2c}$ is $OCD_3$. In other embodiments, $R^{2c}$ is $OCH_2CH_3$. In other embodiments, $R^{2c}$ is $OCH(CH_3)_2$. In other embodiments, $R^{2c}$ is $OCH_2CH_2F$. In other embodiments, $R^{2c}$ is $OCH_2CHF_2$.

In some embodiments, the invention relates to a compound of any one of formulas (I), (I-A), (I-B), and (I-C), or a pharmaceutically acceptable salt thereof, wherein $X^{3c}$ is N or C—$R^{3c}$; and $R^{3c}$ is H, halo, $C_1$-$C_6$ alkyl, or $C_1$-$C_6$ haloalkyl. In other embodiments, $X^{3c}$ is N. In other embodiments, $X^{3c}$ is C—$R^{3c}$. In other embodiments, $X^{3c}$ is C—$R^{3c}$; and $R^{3c}$ is H. In other embodiments, $X^{3c}$ is C—$R^{3c}$; and $R^{3c}$ is halo. In other embodiments, $X^{3c}$ is C—$R^{3c}$; and $R^{3c}$ is $C_1$-$C_6$ alkyl. In other embodiments, $X^{3c}$ is C—$R^{3c}$; and $R^{3c}$ is $C_1$-$C_6$ haloalkyl. In other embodiments, $X^{3c}$ is C—$R^{3c}$; and $R^{3c}$ is H, F, $CH_3$, $CHF_2$, or $CF_3$. In other embodiments, $X^{3c}$ is C—$R^{3c}$; and $R^{3c}$ is F. In other embodiments, $X^{3c}$ is C—$R^{3c}$; and $R^{3c}$ is $CH_3$. In other embodiments, $X^{3c}$ is C—$R^{3c}$; and $R^{3c}$ is $CHF_2$. In other embodiments, $X^{3c}$ is C—$R^{3c}$; and $R^{3c}$ is $CF_3$.

In some embodiments, the invention relates to a compound of any one of formulas (I-A-1), (I-A-2), (I-A-3), (I-B-1), (I-B-2), (I-B-3), (I-C-1), (I-C-2), and (I-C-3), or a pharmaceutically acceptable salt thereof, wherein $R^{3c}$ is H, halo, $C_1$-$C_6$ alkyl, or $C_1$-$C_6$ haloalkyl. In other embodiments, $R^{3c}$ is H. In other embodiments, $R^{3c}$ is halo. In other embodiments, $R^{3c}$ is $C_1$-$C_6$ alkyl. In other embodiments, $R^{3c}$ is $C_1$-$C_6$ haloalkyl. In other embodiments, $R^{3c}$ is H, F, $CH_3$, $CHF_2$, or $CF_3$. In other embodiments, $R^{3c}$ is F. In other embodiments, $R^{3c}$ is $CH_3$. In other embodiments, $R^{3c}$ is $CHF_2$. In other embodiments, $R^{3c}$ is $CF_3$.

In some embodiments, the invention relates to a compound of any one of formulas (I), (I-A), (I-B), and (I-C), or a pharmaceutically acceptable salt thereof, wherein $X^{3c}$ is C—$R^{3c}$; and $R^{2c}$ and $R^{3c}$, together with the carbon atoms to which they are attached, form a ring of formula:

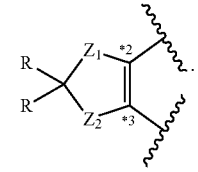

In other embodiments, the ring is of formula:

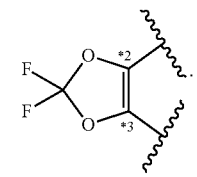 [SMILES: *C1=C(*)OC(F)(F)O1]

In some embodiments, the invention relates to a compound of any one of formulas (I-A-1), (I-A-2), (I-A-3), (I-B-1), (I-B-2), (I-B-3), (I-C-1), (I-C-2), and (I-C-3), or a pharmaceutically acceptable salt thereof, wherein $R^{2c}$ and $R^{3c}$, together with the carbon atoms to which they are attached, form a ring of formula:

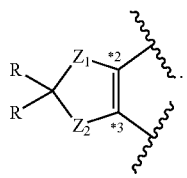

In other embodiments, the ring is of formula:

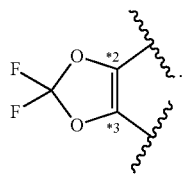

In some embodiments, the invention relates to a compound of any one of formulas (I), (I-A), (I-B), and (I-C), or a pharmaceutically acceptable salt thereof, wherein $X^{4c}$ is C—$R^{4c}$; and $R^4$ is H, halo, $C_1$-$C_6$ haloalkyl, $C_1$-$C_6$ alkoxy, or $C_1$-$C_6$ haloalkoxy. In other embodiments, $X^{4c}$ is C—$R^{4c}$. In other embodiments, $X^{4c}$ is C—$R^{4c}$; and $R^{4c}$ is H. In other embodiments, $X^{4c}$ is C—$R^{4c}$; and $R^{4c}$ is halo. In other embodiments, $X^{4c}$ is C—$R^{4c}$; and $R^{4c}$ is $C_1$-$C_6$ haloalkyl. In other embodiments, $X^{4c}$ is C—$R^{4c}$; and $R^{4c}$ is $C_1$-$C_6$ alkoxy. In other embodiments, $X^{4c}$ is C—$R^{4c}$; and $R^{4c}$ is $C_1$-$C_6$ haloalkoxy. In other embodiments, $X^{4c}$ is C—$R^{4c}$; and $R^{4c}$ is H, F, $CHF_2$, $OCH_2CH_3$, $OCHF_2$, $OCF_3$. In other embodiments, $X^{4c}$ is C—$R^{4c}$; and $R^{4c}$ is F. In other embodiments, $X^{4c}$ is C—$R^{4c}$; and $R^{4c}$ is $CHF_2$. In other embodiments, $X^{4c}$ is C—$R^{4c}$; and $R^{4c}$ is $OCH_2CH_3$. In other embodiments, $X^{4c}$ is C—$R^{4c}$; and $R^{4c}$ is $OCHF_2$. In other embodiments, $X^{4c}$ is C—$R^{4c}$; and $R^{4c}$ is $OCF_3$.

In some embodiments, the invention relates to a compound of any one of formulas (I-A-1), (I-A-2), (I-A-3), (I-B-1), (I-B-2), (I-B-3), (I-C-1), (I-C-2), and (I-C-3), or a pharmaceutically acceptable salt thereof, wherein $R^{4c}$ is H, halo, $C_1$-$C_6$ haloalkyl, $C_1$-$C_6$ alkoxy, or $C_1$-$C_6$ haloalkoxy. In other embodiments, $R^{4c}$ is H. In other embodiments, $R^{4c}$ is halo. In other embodiments, $R^{4c}$ is $C_1$-$C_6$ haloalkyl. In other embodiments, $R^{4c}$ is $C_1$-$C_6$ alkoxy. In other embodiments, $R^{4c}$ is $C_1$-$C_6$ haloalkoxy. In other embodiments, $R^{4c}$ is H, F, $CHF_2$, $OCH_2CH_3$, $OCHF_2$, $OCF_3$. In other embodiments, $R^{4c}$ is F. In other embodiments, $R^{4c}$ is $CHF_2$. In other embodiments, $R^{4c}$ is $OCH_2CH_3$. In other embodiments, $R^{4c}$ is $OCHF_2$. In other embodiments, $R^{4c}$ is $OCF_3$.

In some embodiments, the invention relates to a compound of any one of formulas (I), (I-A), (I-B), and (I-C), or a pharmaceutically acceptable salt thereof, wherein $X^{5c}$ is C—$R^{5c}$; and $R^{5c}$ is H.

In some embodiments, the invention relates to a compound of any one of formulas (I), (I-A), (I-B), and (I-C), or a pharmaceutically acceptable salt thereof, wherein $X^{6c}$ is C—$R^{6c}$; and $R^{6c}$ is H.

In some embodiments, the invention relates to a compound of any one of formulas (I), (I-A), (I-A-1), (I-A-2), (I-A-3), (I-B), (I-B-1), (I-B-2), (I-B-3), (I-C), (I-C-1), (I-C-2), and (I-C-3), or a pharmaceutically acceptable salt thereof, wherein $R^d$ is $(CH_2)_p$H. In other embodiments, $R^d$ is H or $CH_3$. In other embodiments, $R^d$ is $(CHR^e)_n(CH_2)_p$H. In other embodiments, $R^d$ is $CH_2F$, $CH_2OH$, or $CH(OH)CH_3$.

In other embodiments, $R^d$ is $(CH_2)_m(CHR^e)_n$H. In other embodiments, $R^d$ is $CH_2OCH_3$ or $CH_2CH_2OCH_3$.

In some embodiments, the invention relates to a compound of any one of formulas (I), (I-A), (I-A-1), (I-A-2), (I-A-3), (I-B), (I-B-1), (I-B-2), (I-B-3), (I-C), (I-C-1), (I-C-2), and (I-C-3), or any embodiment thereof, i.e., the compound in non-salt form.

In some embodiments, the invention relates to a compound selected from Table A, or a pharmaceutically acceptable salt thereof. In other embodiments, the invention relates to a compound selected from Table A, i.e., the compound in non-salt form.

TABLE A

Compound Structures and Names.

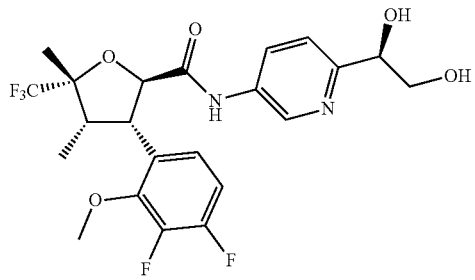 [SMILES: COc1c([C@H]2[C@H](C(=O)Nc3ccc([C@@H](O)CO)nc3)O[C@@](C)(C(F)(F)F)[C@H]2C)ccc(F)c1F]

(2R,3S,4S,5R)-3-(3,4-difluoro-2-methoxyphenyl)-N-(6-((R)-1,2-dihydroxyethyl)pyridin-3-yl)-4,5-dimethyl-5-(trifluoromethyl)tetrahydrofuran-2-carboxamide

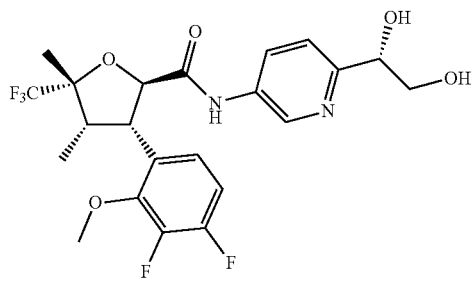 [SMILES: COc1c([C@H]2[C@H](C(=O)Nc3ccc([C@H](O)CO)nc3)O[C@@](C)(C(F)(F)F)[C@H]2C)ccc(F)c1F]

(2R,3S,4S,5R)-3-(3,4-difluoro-2-methoxyphenyl)-N-(6-((S)-1,2-dihydroxyethyl)pyridin-3-yl)-4,5-dimethyl-5-(trifluoromethyl)tetrahydrofuran-2-carboxamide

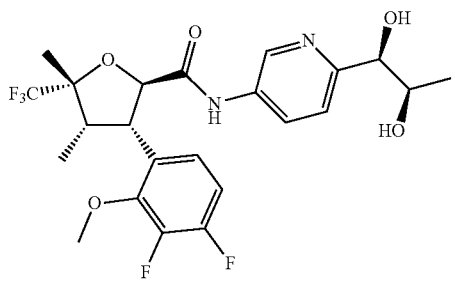 [SMILES: COc1c([C@H]2[C@H](C(=O)Nc3ccc([C@@H](O)[C@@H](C)O)nc3)O[C@@](C)(C(F)(F)F)[C@H]2C)ccc(F)c1F]

(2R,3S,4S,5R)-3-(3,4-difluoro-2-methoxyphenyl)-N-(6-((1R,2R)-1,2-dihydroxypropyl)pyridin-3-yl)-4,5-dimethyl-5-(trifluoromethyl)tetrahydrofuran-2-carboxamide TABLE A-continued Compound Structures and Names.

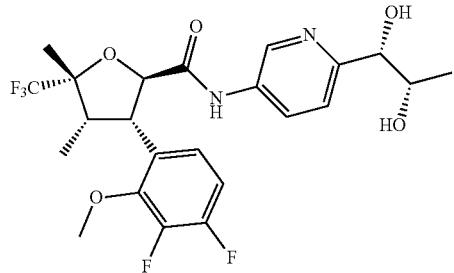 [SMILES: COc1c([C@H]2[C@H](C(=O)Nc3ccc([C@H](O)[C@H](C)O)nc3)O[C@@](C)(C(F)(F)F)[C@H]2C)ccc(F)c1F]

(2R,3S,4S,5R)-3-(3,4-difluoro-2-
methoxyphenyl)-N-(6-((1S,2S)-1,2-
dihydroxypropyl)pyridin-3-yl)-4,5-dimethyl-5-
(trifluoromethyl)tetrahydrofuran-2-carboxamide

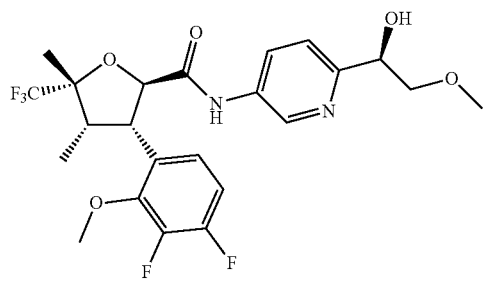 [SMILES: COC[C@H](O)c1ccc(NC(=O)[C@@H]2O[C@@](C)(C(F)(F)F)[C@@H](C)[C@H]2c2ccc(F)c(F)c2OC)cn1]

(2R,3S,4S,5R)-3-(3,4-difluoro-2-
methoxyphenyl)-N-(6-((R)-1-hydroxy-2-
methoxyethyl)pyridin-3-yl)-4,5-dimethyl-5-
(trifluoromethyl)tetrahydrofuran-2-carboxamide

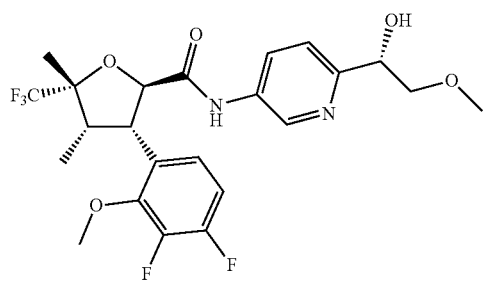 [SMILES: COC[C@@H](O)c1ccc(NC(=O)[C@@H]2O[C@@](C)(C(F)(F)F)[C@@H](C)[C@H]2c2ccc(F)c(F)c2OC)cn1]

(2R,3S,4S,5R)-3-(3,4-difluoro-2-
methoxyphenyl)-N-(6-((S)-1-hydroxy-2-
methoxyethyl)pyridin-3-yl)-4,5-dimethyl-5-
(trifluoromethyl)tetrahydrofuran-2-carboxamide

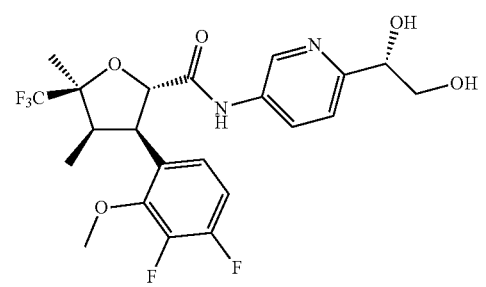 [SMILES: COc1c([C@@H]2[C@@H](C(=O)Nc3ccc([C@H](O)CO)nc3)O[C@](C)(C(F)(F)F)[C@@H]2C)ccc(F)c1F]

(2S,3R,4R,5S)-3-(3,4-difluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide TABLE A-continued Compound Structures and Names.

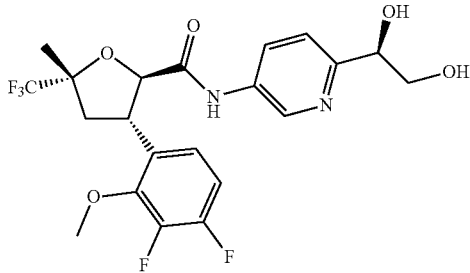 [SMILES: COc1c([C@@H]2C[C@](C)(C(F)(F)F)O[C@H]2C(=O)Nc2ccc([C@@H](O)CO)nc2)ccc(F)c1F]

(2R,3S,5R)-3-(3,4-difluoro-2-methoxyphenyl)-
N-(6-((R)-1,2-dihydroxyethyl)pyridin-3-yl)-5-
methyl-5-(trifluoromethyl)tetrahydrofuran-2-
carboxamide

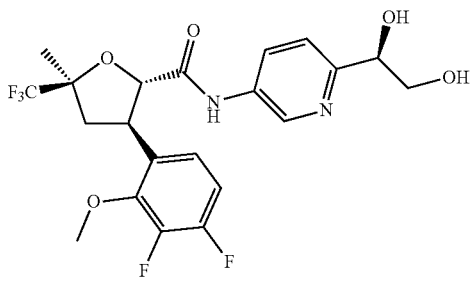 [SMILES: COc1c([C@H]2C[C@@](C)(C(F)(F)F)O[C@@H]2C(=O)Nc2ccc([C@@H](O)CO)nc2)ccc(F)c1F]

(2S,3R,5S)-3-(3,4-difluoro-2-methoxyphenyl)-
N-(6-((R)-1,2-dihydroxyethyl)pyridin-3-yl)-5-
methyl-5-(trifluoromethyl)tetrahydrofuran-2-
carboxamide

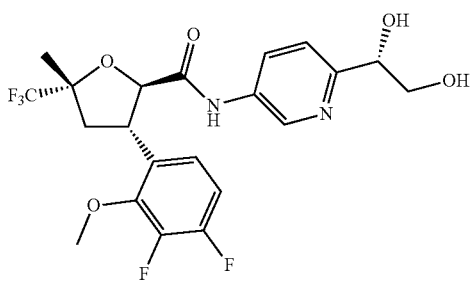 [SMILES: COc1c([C@@H]2C[C@](C)(C(F)(F)F)O[C@H]2C(=O)Nc2ccc([C@H](O)CO)nc2)ccc(F)c1F]

(2R,3S,5R)-3-(3,4-difluoro-2-methoxyphenyl)-
N-(6-((S)-1,2-dihydroxyethyl)pyridin-3-yl)-5-
methyl-5-(trifluoromethyl)tetrahydrofuran-2-
carboxamide

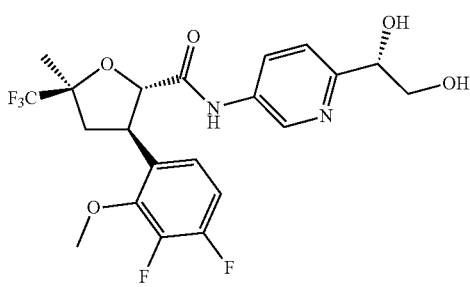 [SMILES: COc1c([C@H]2C[C@@](C)(C(F)(F)F)O[C@@H]2C(=O)Nc2ccc([C@H](O)CO)nc2)ccc(F)c1F]

(2S,3R,5S)-3-(3,4-difluoro-2-methoxyphenyl)-
N-(6-((S)-1,2-dihydroxyethyl)pyridin-3-yl)-5-
methyl-5-(trifluoromethyl)tetrahydrofuran-2-
carboxamide TABLE A-continued Compound Structures and Names.

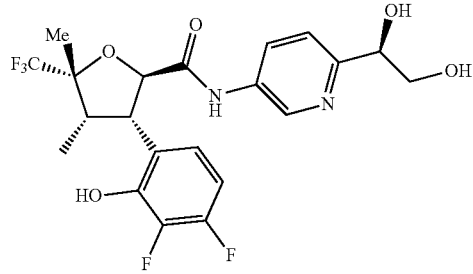 [SMILES: C[C@H]1[C@@H](c2ccc(F)c(F)c2O)[C@H](C(=O)Nc2ccc([C@@H](O)CO)nc2)O[C@@]1(C)C(F)(F)F]

(2R,3S,4S,5R)-3-(3,4-difluoro-2-
hydroxyphenyl)-N-(6-((R)-1,2-
dihydroxyethyl)pyridin-3-yl)-4,5-dimethyl-5-
(trifluoromethyl)tetrahydrofuran-2-carboxamide

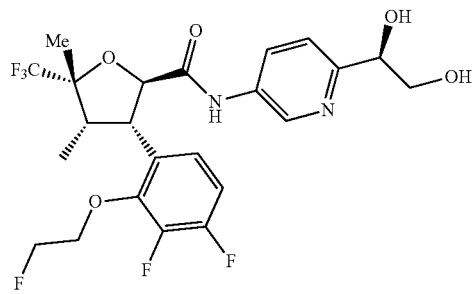 [SMILES: C[C@H]1[C@@H](c2ccc(F)c(F)c2OCCF)[C@H](C(=O)Nc2ccc([C@@H](O)CO)nc2)O[C@@]1(C)C(F)(F)F]

(2R,3S,4S,5R)-3-(3,4-difluoro-2-(2-
fluoroethoxy)phenyl)-N-(6-((R)-1,2-
dihydroxyethyl)pyridin-3-yl)-4,5-dimethyl-5-
(trifluoromethyl)tetrahydrofuran-2-carboxamide

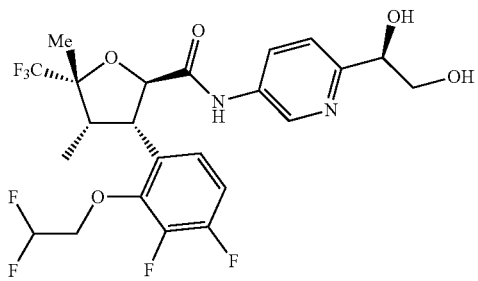 [SMILES: C[C@H]1[C@@H](c2ccc(F)c(F)c2OCC(F)F)[C@H](C(=O)Nc2ccc([C@@H](O)CO)nc2)O[C@@]1(C)C(F)(F)F]

(2R,3S,4S,5R)-3-(2-(2,2-difluoroethoxy)-3,4-
difluorophenyl)-N-(6-((R)-1,2-
dihydroxyethyl)pyridin-3-yl)-4,5-dimethyl-5-
(trifluoromethyl)tetrahydrofuran-2-carboxamide

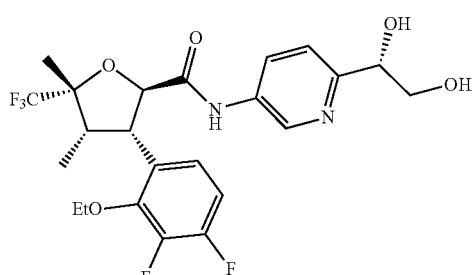

(2R,3S,4S,5R)-N-(6-((S)-1,2-
dihydroxyethyl)pyridin-3-yl)-3-(2-ethoxy-3,4-
difluorophenyl)-4,5-dimethyl-5-
(trifluoromethyl)tetrahydrofuran-2-carboxamide TABLE A-continued Compound Structures and Names.

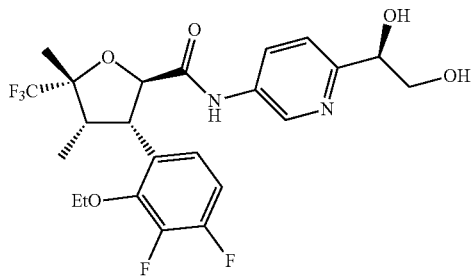 [SMILES: CCOc1c([C@H]2[C@H](C(=O)Nc3ccc([C@@H](O)CO)nc3)O[C@@](C)(C(F)(F)F)[C@H]2C)ccc(F)c1F]

(2R,3S,4S,5R)-N-(6-((R)-1,2-
dihydroxyethyl)pyridin-3-yl)-3-(2-ethoxy-3,4-
difluorophenyl)-4,5-dimethyl-5-
(trifluoromethyl)tetrahydrofuran-2-carboxamide

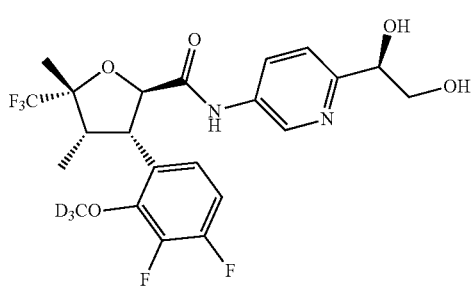

(2R,3S,4S,5R)-3-(3,4-difluoro-2-(methoxy-
$d_3$)phenyl)-N-(6-((R)-1,2-dihydroxyethyl)pyridin-
3-yl)-4,5-dimethyl-5-
(trifluoromethyl)tetrahydrofuran-2-carboxamide

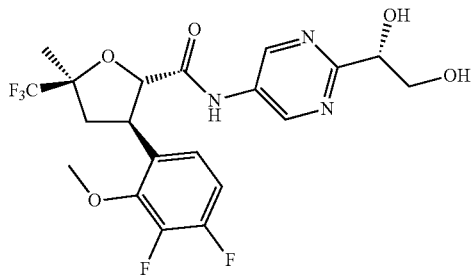

(2S,3R,5S)-3-(3,4-difluoro-2-methoxyphenyl)-
N-(2-((S)-1,2-dihydroxyethyl)pyrimidin-5-yl)-5-
methyl-5-(trifluoromethyl)tetrahydrofuran-2-
carboxamide

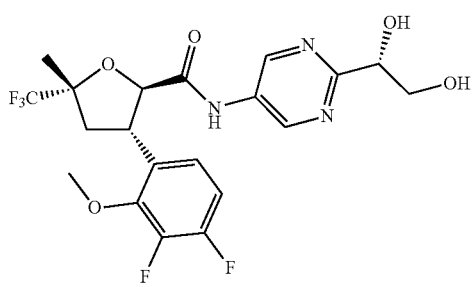 [SMILES: COc1c([C@@H]2C[C@](C)(C(F)(F)F)O[C@H]2C(=O)Nc2cnc([C@H](O)CO)nc2)ccc(F)c1F]

(2R,3S,5R)-3-(3,4-difluoro-2-methoxyphenyl)-
N-(2-((S)-1,2-dihydroxyethyl)pyrimidin-5-yl)-5-
methyl-5-(trifluoromethyl)tetrahydrofuran-2-
carboxamide TABLE A-continued Compound Structures and Names.

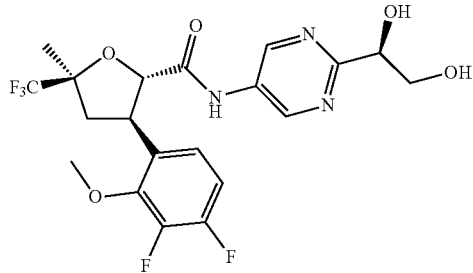 [SMILES: COc1c([C@H]2C[C@@](C)(C(F)(F)F)O[C@@H]2C(=O)Nc2cnc([C@@H](O)CO)nc2)ccc(F)c1F]

(2S,3R,5S)-3-(3,4-difluoro-2-methoxyphenyl)-
N-(2-((R)-1,2-dihydroxyethyl)pyrimidin-5-yl)-5-
methyl-5-(trifluoromethyl)tetrahydrofuran-2-
carboxamide

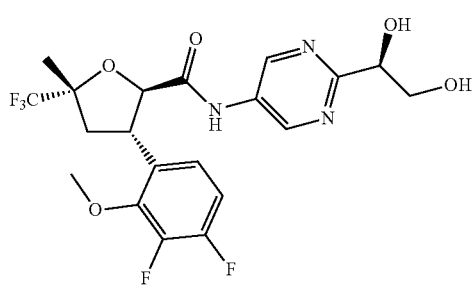 [SMILES: COc1c([C@@H]2C[C@](C)(C(F)(F)F)O[C@H]2C(=O)Nc2cnc([C@@H](O)CO)nc2)ccc(F)c1F]

(2R,3S,5R)-3-(3,4-difluoro-2-methoxyphenyl)-
N-(2-((R)-1,2-dihydroxyethyl)pyrimidin-5-yl)-5-
methyl-5-(trifluoromethyl)tetrahydrofuran-2-
carboxamide

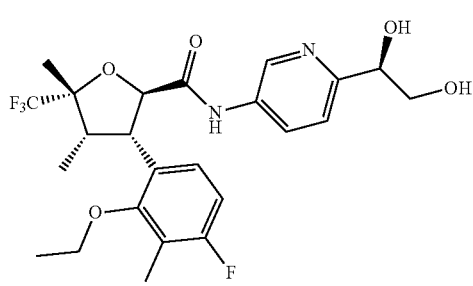 [SMILES: CCOc1c([C@H]2[C@H](C(=O)Nc3ccc([C@@H](O)CO)nc3)O[C@@](C)(C(F)(F)F)[C@H]2C)ccc(F)c1C]

(2R,3S,4S,5R)-N-(6-((R)-1,2-
dihydroxyethyl)pyridin-3-yl)-3-(2-ethoxy-4-
fluoro-3-methylphenyl)-4,5-dimethyl-5-
(trifluoromethyl)tetrahydrofuran-2-carboxamide

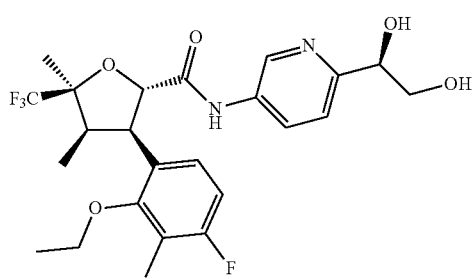 [SMILES: CCOc1c([C@@H]2[C@@H](C(=O)Nc3ccc([C@@H](O)CO)nc3)O[C@](C)(C(F)(F)F)[C@@H]2C)ccc(F)c1C]

(2S,3R,4R,5S)-N-(6-((R)-1,2-
dihydroxyethyl)pyridin-3-yl)-3-(2-ethoxy-4-
fluoro-3-methylphenyl)-4,5-dimethyl-5-
(trifluoromethyl)tetrahydrofuran-2-carboxamide TABLE A-continued Compound Structures and Names.

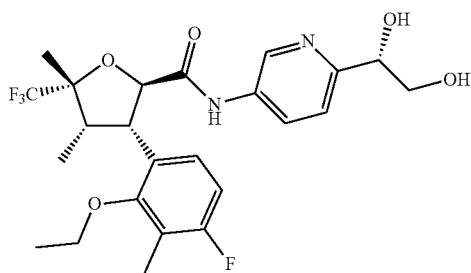 [SMILES: CCOc1c([C@H]2[C@H](C(=O)Nc3ccc([C@H](O)CO)nc3)O[C@@](C)(C(F)(F)F)[C@H]2C)ccc(F)c1C]

(2R,3S,4S,5R)-N-(6-((S)-1,2-
dihydroxyethyl)pyridin-3-yl)-3-(2-ethoxy-4-
fluoro-3-methylphenyl)-4,5-dimethyl-5-
(trifluoromethyl)tetrahydrofuran-2-carboxamide

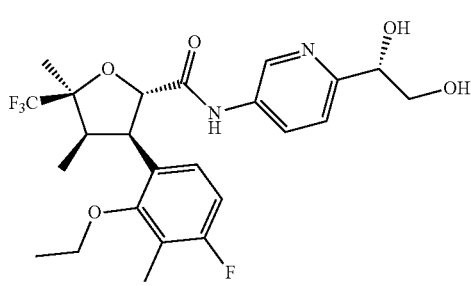 [SMILES: CCOc1c([C@@H]2[C@@H](C(=O)Nc3ccc([C@H](O)CO)nc3)O[C@](C)(C(F)(F)F)[C@@H]2C)ccc(F)c1C]

(2S,3R,4R,5S)-N-(6-((S)-1,2-
dihydroxyethyl)pyridin-3-yl)-3-(2-ethoxy-4-
fluoro-3-methylphenyl)-4,5-dimethyl-5-
(trifluoromethyl)tetrahydrofuran-2-carboxamide

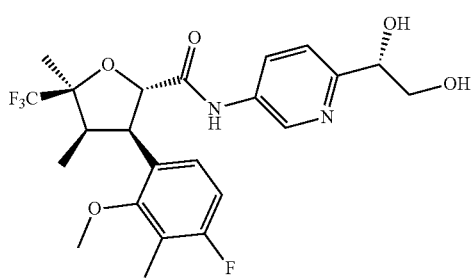 [SMILES: COc1c([C@@H]2[C@@H](C(=O)Nc3ccc([C@H](O)CO)nc3)O[C@](C)(C(F)(F)F)[C@@H]2C)ccc(F)c1C]

(2S,3R,4R,5S)-N-(6-((S)-1,2-
dihydroxyethyl)pyridin-3-yl)-3-(4-fluoro-2-
methoxy-3-methylphenyl)-4,5-dimethyl-5-
(trifluoromethyl)tetrahydrofuran-2-carboxamide

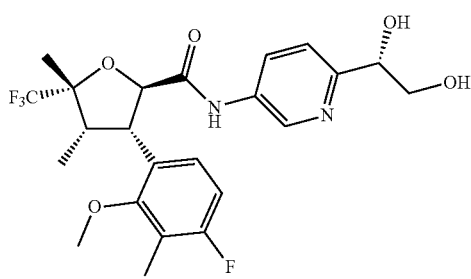 [SMILES: COc1c([C@H]2[C@H](C(=O)Nc3ccc([C@H](O)CO)nc3)O[C@@](C)(C(F)(F)F)[C@H]2C)ccc(F)c1C]

(2R,3S,4S,5R)-N-(6-((S)-1,2-
dihydroxyethyl)pyridin-3-yl)-3-(4-fluoro-2-
methoxy-3-methylphenyl)-4,5-dimethyl-5-
(trifluoromethyl)tetrahydrofuran-2-carboxamide TABLE A-continued Compound Structures and Names.

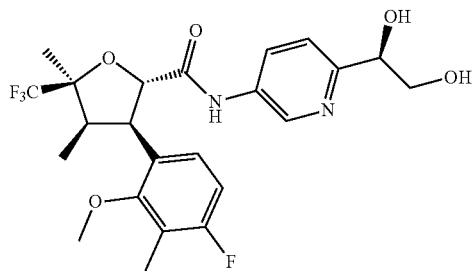 [SMILES: COc1c([C@@H]2[C@@H](C(=O)Nc3ccc([C@@H](O)CO)nc3)O[C@](C)(C(F)(F)F)[C@@H]2C)ccc(F)c1C]

(2S,3R,4R,5S)-N-(6-((R)-1,2-
dihydroxyethyl)pyridin-3-yl)-3-(4-fluoro-2-
methoxy-3-methylphenyl)-4,5-dimethyl-5-
(trifluoromethyl)tetrahydrofuran-2-carboxamide

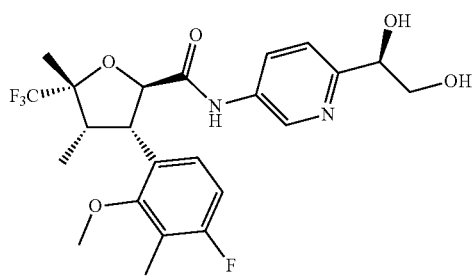 [SMILES: COc1c([C@H]2[C@H](C(=O)Nc3ccc([C@@H](O)CO)nc3)O[C@@](C)(C(F)(F)F)[C@H]2C)ccc(F)c1C]

(2R,3S,4S,5R)-N-(6-((R)-1,2-
dihydroxyethyl)pyridin-3-yl)-3-(4-fluoro-2-
methoxy-3-methylphenyl)-4,5-dimethyl-5-
(trifluoromethyl)tetrahydrofuran-2-carboxamide

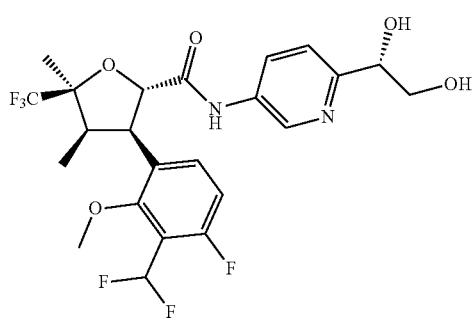 [SMILES: COc1c([C@@H]2[C@@H](C(=O)Nc3ccc([C@H](O)CO)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide

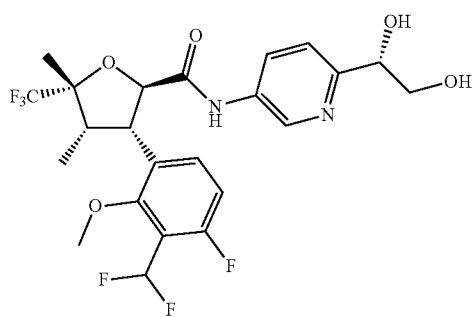 [SMILES: COc1c([C@H]2[C@H](C(=O)Nc3ccc([C@H](O)CO)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide TABLE A-continued Compound Structures and Names.

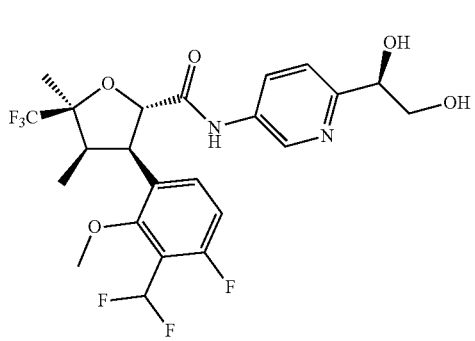 [SMILES: COc1c([C@@H]2[C@@H](C(=O)Nc3ccc([C@@H](O)CO)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(6-((R)-1,2-
dihydroxyethyl)pyridin-3-yl)-4,5-dimethyl-5-
(trifluoromethyl)tetrahydrofuran-2-carboxamide

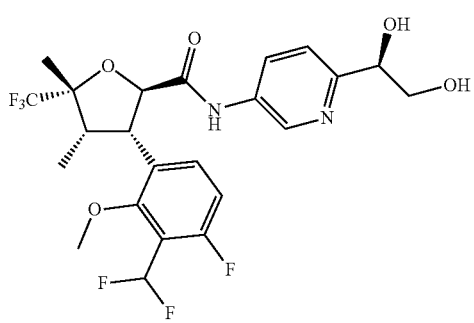 [SMILES: COc1c([C@H]2[C@H](C(=O)Nc3ccc([C@@H](O)CO)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-((R)-1,2-
dihydroxyethyl)pyridin-3-yl)-4,5-dimethyl-5-
(trifluoromethyl)tetrahydrofuran-2-carboxamide

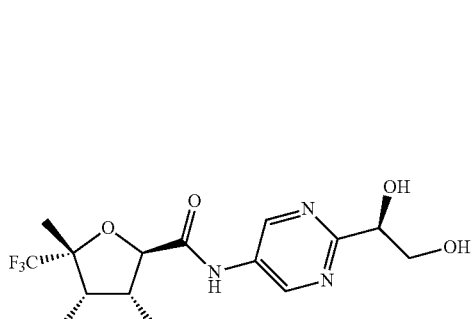

(2R,3S,4S,5R)-3-(3,4-difluoro-2-
isopropoxyphenyl)-N-(2-((R)-1,2-
dihydroxyethyl)pyrimidin-5-yl)-4,5-dimethyl-5-
(trifluoromethyl)tetrahydrofuran-2-carboxamide TABLE A-continued Compound Structures and Names.

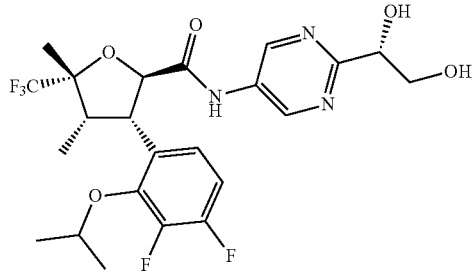 [SMILES: CC(C)Oc1c([C@H]2[C@H](C(=O)Nc3cnc([C@H](O)CO)nc3)O[C@@](C)(C(F)(F)F)[C@H]2C)ccc(F)c1F]

(2R,3S,4S,5R)-3-(3,4-difluoro-2-
isopropoxyphenyl)-N-(2-((S)-1,2-
dihydroxyethyl)pyrimidin-5-yl)-4,5-dimethyl-5-
(trifluoromethyl)tetrahydrofuran-2-carboxamide

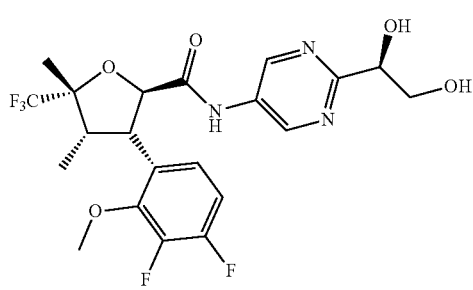

(2R,3S,4S,5R)-3-(3,4-difluoro-2-
methoxyphenyl)-N-(2-((R)-1,2-
dihydroxyethyl)pyrimidin-5-yl)-4,5-dimethyl-5-
(trifluoromethyl)tetrahydrofuran-2-carboxamide

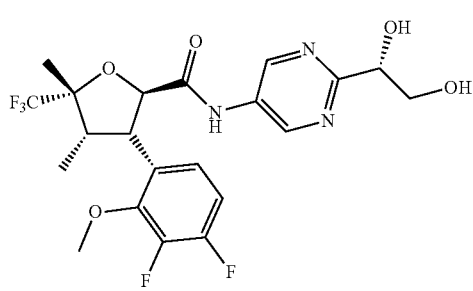

(2R,3S,4S,5R)-3-(3,4-difluoro-2-
methoxyphenyl)-N-(2-((S)-1,2-
dihydroxyethyl)pyrimidin-5-yl)-4,5-dimethyl-5-
(trifluoromethyl)tetrahydrofuran-2-carboxamide

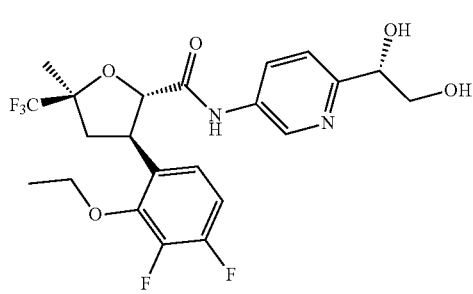 [SMILES: CCOc1c([C@H]2C[C@@](C)(C(F)(F)F)O[C@@H]2C(=O)Nc2ccc([C@H](O)CO)nc2)ccc(F)c1F]

(2S,3R,5S)-N-(6-((S)-1,2-dihydroxyethyl)pyridin-
3-yl)-3-(2-ethoxy-3,4-difluorophenyl)-5-methyl-5-
(trifluoromethyl)tetrahydrofuran-2-carboxamide TABLE A-continued Compound Structures and Names.

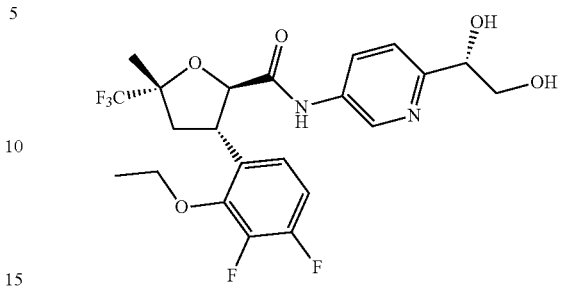

(2R,3S,5R)-N-(6-((S)-1,2-
dihydroxyethyl)pyridin-3-yl)-3-(2-ethoxy-3,4-
difluorophenyl)-5-methyl-5-
(trifluoromethyl)tetrahydrofuran-2-carboxamide

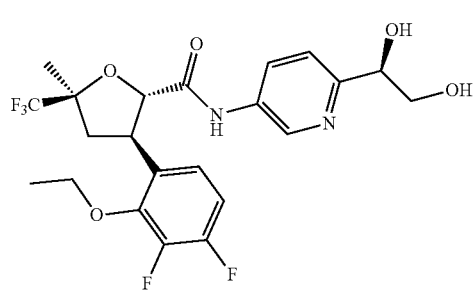 [SMILES: CCOc1c([C@H]2C[C@@](C)(C(F)(F)F)O[C@@H]2C(=O)Nc2ccc([C@@H](O)CO)nc2)ccc(F)c1F]

(2S,3R,5S)-N-(6-((R)-1,2-dihydroxyethyl)pyridin-
3-yl)-3-(2-ethoxy-3,4-difluorophenyl)-5-methyl-5-
(trifluoromethyl)tetrahydrofuran-2-carboxamide

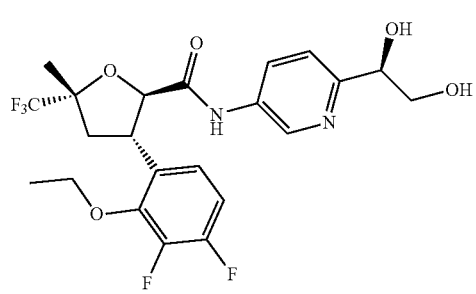 [SMILES: CCOc1c([C@@H]2C[C@](C)(C(F)(F)F)O[C@H]2C(=O)Nc2ccc([C@@H](O)CO)nc2)ccc(F)c1F]

(2R,3S,5R)-N-(6-((R)-1,2-
dihydroxyethyl)pyridin-3-yl)-3-(2-ethoxy-3,4-
difluorophenyl)-5-methyl-5-
(trifluoromethyl)tetrahydrofuran-2-carboxamide

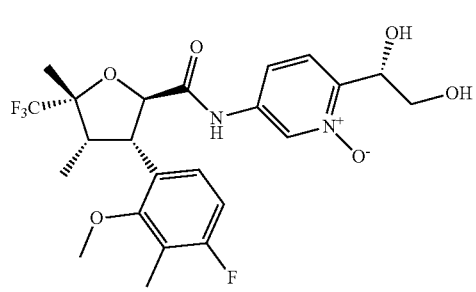 [SMILES: COc1c([C@H]2[C@H](C(=O)Nc3ccc([C@H](O)CO)[n+]([O-])c3)O[C@@](C)(C(F)(F)F)[C@H]2C)ccc(F)c1C]

2-((S)-1,2-dihydroxyethyl)-5-((2R,3S,4S,5R)-3-
(4-fluoro-2-methoxy-3-methylphenyl)-4,5-
dimethyl-5-(trifluoromethyl)tetrahydrofuran-2-
carboxamido)pyridine 1-oxide TABLE A-continued Compound Structures and Names.

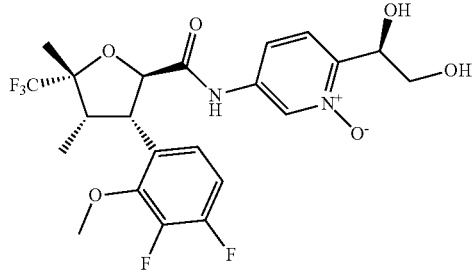 [SMILES: COc1c([C@H]2[C@H](C(=O)Nc3ccc([C@@H](O)CO)[n+]([O-])c3)O[C@@](C)(C(F)(F)F)[C@H]2C)ccc(F)c1F]

5-((2R,3S,4S,5R)-3-(3,4-difluoro-2-
methoxyphenyl)-4,5-dimethyl-5-
(trifluoromethyl)tetrahydrofuran-2-carboxamido)-2-
((R)-1,2-dihydroxyethyl)pyridine 1-oxide

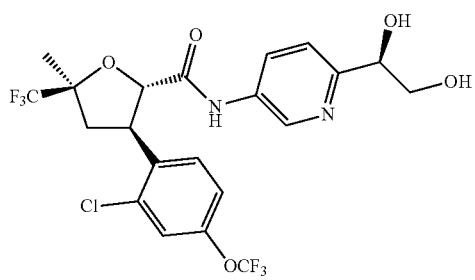 [SMILES: C[C@@]1(C(F)(F)F)C[C@H](c2ccc(OC(F)(F)F)cc2Cl)[C@@H](C(=O)Nc2ccc([C@@H](O)CO)nc2)O1]

(2S,3R,5S)-3-(2-chloro-4-
(trifluoromethoxy)phenyl)-N-(6-((R)-1,2-
dihydroxyethyl)pyridin-3-yl)-5-methyl-5-
(trifluoromethyl)tetrahydrofuran-2-carboxamide

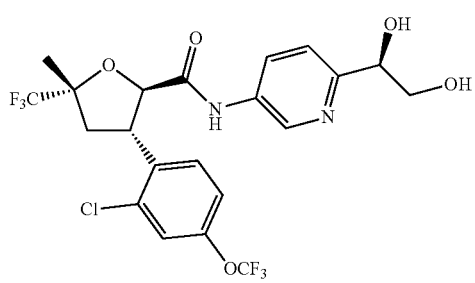 [SMILES: C[C@]1(C(F)(F)F)C[C@@H](c2ccc(OC(F)(F)F)cc2Cl)[C@H](C(=O)Nc2ccc([C@@H](O)CO)nc2)O1]

(2R,3S,5R)-3-(2-chloro-4-
(trifluoromethoxy)phenyl)-N-(6-((R)-1,2-
dihydroxyethyl)pyridin-3-yl)-5-methyl-5-
(trifluoromethyl)tetrahydrofuran-2-carboxamide

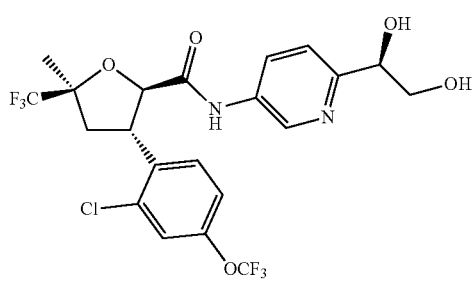 [SMILES: C[C@@]1(C(F)(F)F)C[C@@H](c2ccc(OC(F)(F)F)cc2Cl)[C@H](C(=O)Nc2ccc([C@@H](O)CO)nc2)O1]

(2R,3S,5S)-3-(2-chloro-4-
(trifluoromethoxy)phenyl)-N-(6-((R)-1,2-
dihydroxyethyl)pyridin-3-yl)-5-methyl-5-
(trifluoromethyl)tetrahydrofuran-2-carboxamide TABLE A-continued Compound Structures and Names.

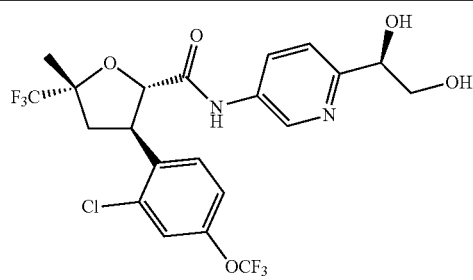

(2S,3R,5R)-3-(2-chloro-4-
(trifluoromethoxy)phenyl)-N-(6-((R)-1,2-
dihydroxyethyl)pyridin-3-yl)-5-methyl-5-
(trifluoromethyl)tetrahydrofuran-2-carboxamide

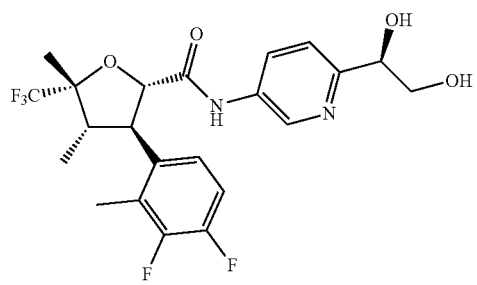 [SMILES: Cc1c([C@@H]2[C@@H](C(=O)Nc3ccc([C@@H](O)CO)nc3)O[C@@](C)(C(F)(F)F)[C@H]2C)ccc(F)c1F]

(2S,3R,4S,5R)-3-(3,4-difluoro-2-
methylphenyl)-N-(6-((R)-1,2-
dihydroxyethyl)pyridin-3-yl)-4,5-dimethyl-5-
(trifluoromethyl)tetrahydrofuran-2-
carboxamide

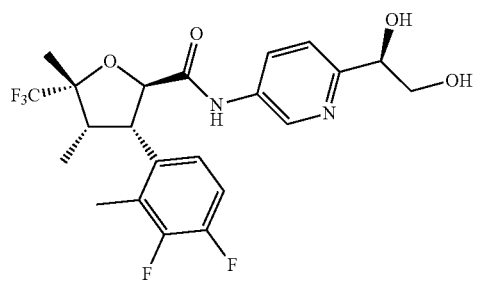 [SMILES: Cc1c([C@H]2[C@H](C(=O)Nc3ccc([C@@H](O)CO)nc3)O[C@@](C)(C(F)(F)F)[C@H]2C)ccc(F)c1F]

(2R,3S,4S,5R)-3-(3,4-difluoro-2-methylphenyl)-
N-(6-((R)-1,2-dihydroxyethyl)pyridin-3-yl)-4,5-
dimethyl-5-(trifluoromethyl)tetrahydrofuran-2-
carboxamide

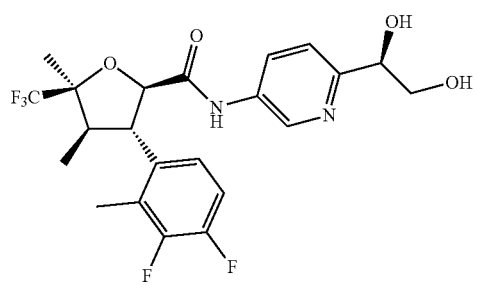 [SMILES: Cc1c([C@@H]2[C@@H](C)[C@@](C)(C(F)(F)F)O[C@H]2C(=O)Nc2ccc([C@@H](O)CO)nc2)ccc(F)c1F]

(2R,3S,4R,5S)-3-(3,4-difluoro-2-methylphenyl)-
N-(6-((R)-1,2-dihydroxyethyl)pyridin-3-yl)-4,5-
dimethyl-5-(trifluoromethyl)tetrahydrofuran-2-
carboxamide TABLE A-continued Compound Structures and Names.

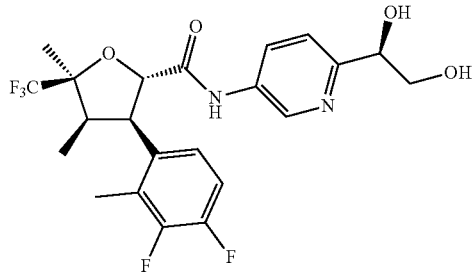 [SMILES: Cc1c([C@@H]2[C@@H](C(=O)Nc3ccc([C@@H](O)CO)nc3)O[C@](C)(C(F)(F)F)[C@@H]2C)ccc(F)c1F]

(2S,3R,4R,5S)-3-(3,4-difluoro-2-methylphenyl)-
N-(6-((R)-1,2-dihydroxyethyl)pyridin-3-yl)-4,5-
dimethyl-5-(trifluoromethyl)tetrahydrofuran-2-
carboxamide

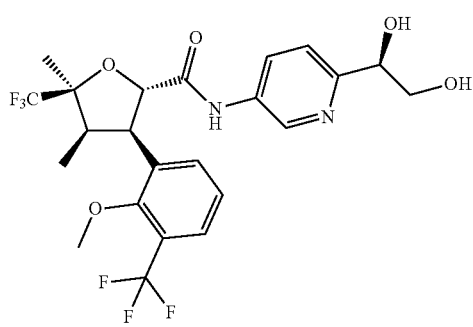 [SMILES: COc1c([C@@H]2[C@@H](C(=O)Nc3ccc([C@@H](O)CO)nc3)O[C@](C)(C(F)(F)F)[C@@H]2C)cccc1C(F)(F)F]

(2S,3R,4R,5S)-N-(6-((R)-1,2-
dihydroxyethyl)pyridin-3-yl)-3-(2-methoxy-3-
(trifluoromethyl)phenyl)-4,5-dimethyl-5-
(trifluoromethyl)tetrahydrofuran-2-carboxamide

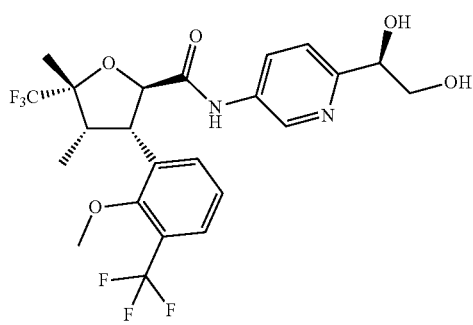 [SMILES: COc1c([C@H]2[C@H](C(=O)Nc3ccc([C@@H](O)CO)nc3)O[C@@](C)(C(F)(F)F)[C@H]2C)cccc1C(F)(F)F]

(2R,3S,4S,5R)-N-(6-((R)-1,2-
dihydroxyethyl)pyridin-3-yl)-3-(2-methoxy-3-
(trifluoromethyl)phenyl)-4,5-dimethyl-5-
(trifluoromethyl)tetrahydrofuran-2-carboxamide TABLE A-continued Compound Structures and Names.

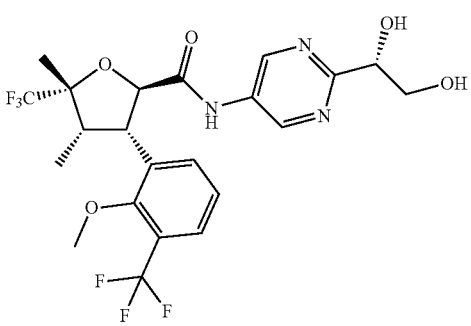 [SMILES: COc1c([C@H]2[C@H](C(=O)Nc3cnc([C@H](O)CO)nc3)O[C@@](C)(C(F)(F)F)[C@H]2C)cccc1C(F)(F)F]

(2R,3S,4S,5R)-N-(2-((S)-1,2-
dihydroxyethyl)pyrimidin-5-yl)-3-(2-methoxy-3-
(trifluoromethyl)phenyl)-4,5-dimethyl-5-
(trifluoromethyl)tetrahydrofuran-2-carboxamide

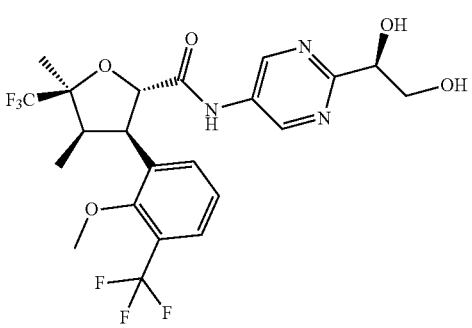 [SMILES: COc1c([C@@H]2[C@@H](C(=O)Nc3cnc([C@@H](O)CO)nc3)O[C@](C)(C(F)(F)F)[C@@H]2C)cccc1C(F)(F)F]

(2S,3R,4R,5S)-N-(2-((R)-1,2-
dihydroxyethyl)pyrimidin-5-yl)-3-(2-methoxy-3-
(trifluoromethyl)phenyl)-4,5-dimethyl-5-
(trifluoromethyl)tetrahydrofuran-2-carboxamide

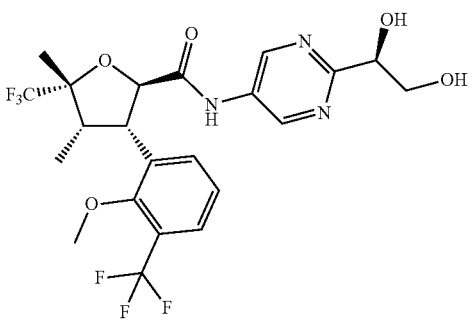 [SMILES: COc1c([C@H]2[C@H](C(=O)Nc3cnc([C@@H](O)CO)nc3)O[C@@](C)(C(F)(F)F)[C@H]2C)cccc1C(F)(F)F]

(2R,3S,4S,5R)-N-(2-((R)-1,2-
dihydroxyethyl)pyrimidin-5-yl)-3-(2-methoxy-3-
(trifluoromethyl)phenyl)-4,5-dimethyl-5-
(trifluoromethyl)tetrahydrofuran-2-carboxamide TABLE A-continued Compound Structures and Names.

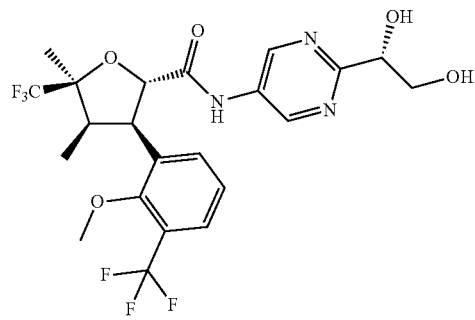 [SMILES: COc1c([C@@H]2[C@@H](C(=O)Nc3cnc([C@H](O)CO)nc3)O[C@](C)(C(F)(F)F)[C@@H]2C)cccc1C(F)(F)F]

(2S,3R,4R,5S)-N-(2-((S)-1,2-
dihydroxyethyl)pyrimidin-5-yl)-3-(2-methoxy-3-
(trifluoromethyl)phenyl)-4,5-dimethyl-5-
(trifluoromethyl)tetrahydrofuran-2-carboxamide

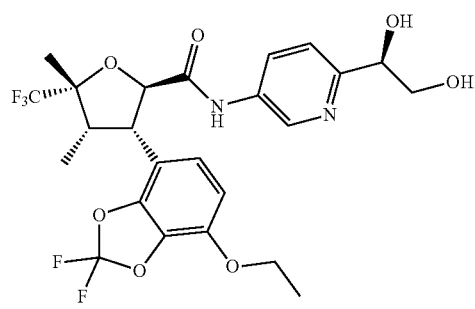 [SMILES: CCOc1ccc([C@H]2[C@H](C(=O)Nc3ccc([C@@H](O)CO)nc3)O[C@@](C)(C(F)(F)F)[C@H]2C)c2c1OC(F)(F)O2]

(2R,3S,4S,5R)-N-(6-((R)-1,2-
dihydroxyethyl)pyridin-3-yl)-3-(7-ethoxy-2,2-
difluorobenzo[d][1,3]dioxol-4-yl)-4,5-dimethyl-5-
(trifluoromethyl)tetrahydrofuran-2-carboxamide

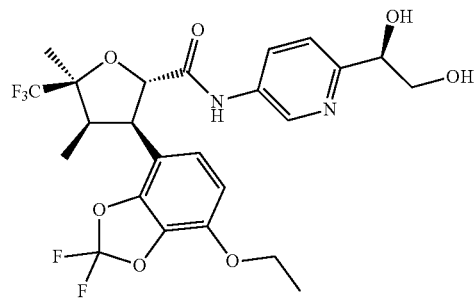 [SMILES: CCOc1ccc([C@@H]2[C@@H](C(=O)Nc3ccc([C@@H](O)CO)nc3)O[C@](C)(C(F)(F)F)[C@@H]2C)c2c1OC(F)(F)O2]

(2S,3R,4R,5S)-N-(6-((R)-1,2-dihydroxyethyl)pyridin-
3-yl)-3-(7-ethoxy-2,2-difluorobenzo[d][1,3]dioxol-4-
yl)-4,5-dimethyl-5-(trifluoromethyl)tetrahydrofuran-2-
carboxamide

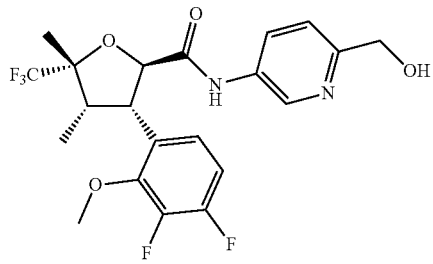 [SMILES: COc1c([C@H]2[C@H](C(=O)Nc3ccc(CO)nc3)O[C@@](C)(C(F)(F)F)[C@H]2C)ccc(F)c1F]

(2R,3S,4S,5R)-3-(3,4-difluoro-2-
methoxyphenyl)-N-(6-(hydroxymethyl)pyridin-
3-yl)-4,5-dimethyl-5-
(trifluoromethyl)tetrahydrofuran-2-carboxamide TABLE A-continued Compound Structures and Names.

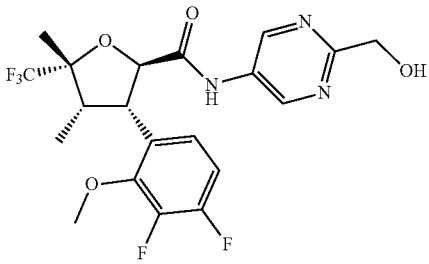 [SMILES: COc1c([C@H]2[C@H](C(=O)Nc3cnc(CO)nc3)O[C@@](C)(C(F)(F)F)[C@H]2C)ccc(F)c1F]

(2R,3S,4S,5R)-3-(3,4-difluoro-2-
methoxyphenyl)-N-(2-(hydroxymethyl)pyrimidin-
5-yl)-4,5-dimethyl-5-
(trifluoromethyl)tetrahydrofuran-2-carboxamide

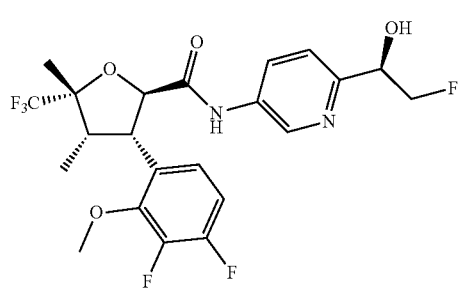 [SMILES: COc1c([C@H]2[C@H](C(=O)Nc3ccc([C@@H](O)CF)nc3)O[C@@](C)(C(F)(F)F)[C@H]2C)ccc(F)c1F]

(2R,3S,4S,5R)-3-(3,4-difluoro-2-
methoxyphenyl)-N-(6-((R)-2-fluoro-1-
hydroxyethyl)pyridin-3-yl)-4,5-dimethyl-5-
(trifluoromethyl)tetrahydrofuran-2-carboxamide

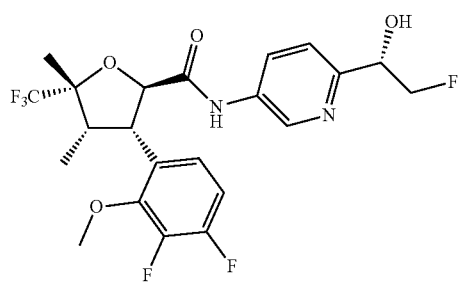 [SMILES: COc1c([C@H]2[C@H](C(=O)Nc3ccc([C@H](O)CF)nc3)O[C@@](C)(C(F)(F)F)[C@H]2C)ccc(F)c1F]

(2R,3S,4S,5R)-3-(3,4-difluoro-2-
methoxyphenyl)-N-(6-((S)-2-fluoro-1-
hydroxyethyl)pyridin-3-yl)-4,5-dimethyl-5-
(trifluoromethyl)tetrahydrofuran-2-carboxamide

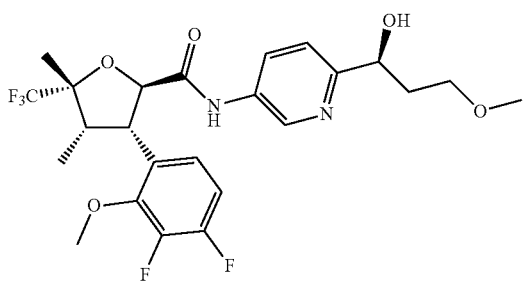 [SMILES: COCC[C@H](O)c1ccc(NC(=O)[C@@H]2O[C@@](C)(C(F)(F)F)[C@@H](C)[C@H]2c2ccc(F)c(F)c2OC)cn1]

(2R,3S,4S,5R)-3-(3,4-difluoro-2-
methoxyphenyl)-N-(6-((S)-1-hydroxy-3-
methoxypropyl)pyridin-3-yl)-4,5-dimethyl-5-
(trifluoromethyl)tetrahydrofuran-2-carboxamide TABLE A-continued Compound Structures and Names.

(2R,3S,4S,5R)-3-(3,4-difluoro-2-methoxyphenyl)-N-(6-((R)-1-hydroxy-3-methoxypropyl)pyridin-3-yl)-4,5-dimethyl-5-(trifluoromethyl)tetrahydrofuran-2-carboxamide (2R,3S,4S,5R)-3-(3,4-difluoro-2-hydroxyphenyl)-N-(2-(hydroxymethyl)pyrimidin-5-yl)-4,5-dimethyl-5-(trifluoromethyl)tetrahydrofuran-2-carboxamide (2R,3S,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (2S,3R,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (2S,3R,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (2R,3S,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (2S,3R,4R,5S)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide (2R,3S,4S,5R)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide TABLE A-continued Compound Structures and Names.

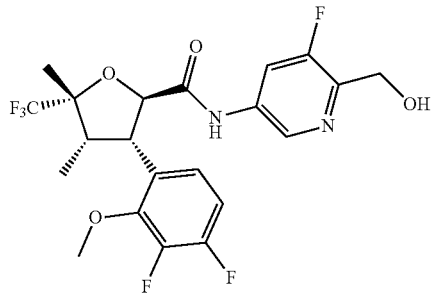 [SMILES: COc1c([C@H]2[C@H](C(=O)Nc3cnc(CO)c(F)c3)O[C@@](C)(C(F)(F)F)[C@H]2C)ccc(F)c1F]

(2R,3S,4S,5R)-3-(3,4-difluoro-2-
methoxyphenyl)-N-(5-fluoro-6-
(hydroxymethyl)pyridin-3-yl)-4,5-dimethyl-5-
(trifluoromethyl)tetrahydrofuran-2-carboxamide

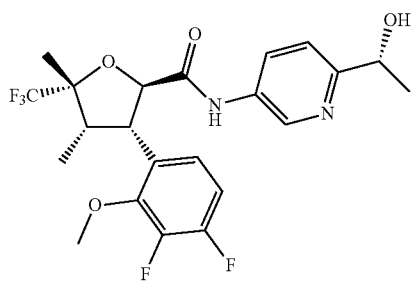 [SMILES: COc1c([C@H]2[C@H](C(=O)Nc3ccc([C@@H](C)O)nc3)O[C@@](C)(C(F)(F)F)[C@H]2C)ccc(F)c1F]

(2R,3S,4S,5R)-3-(3,4-difluoro-2-
methoxyphenyl)-N-(6-((R)-1-
hydroxyethyl)pyridin-3-yl)-4,5-dimethyl-5-
(trifluoromethyl)tetrahydrofuran-2-carboxamide

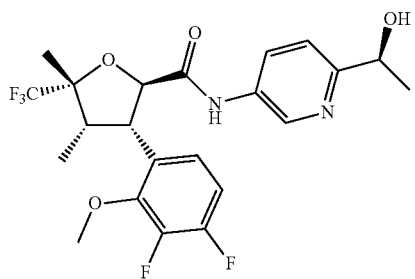 [SMILES: COc1c([C@H]2[C@H](C(=O)Nc3ccc([C@H](C)O)nc3)O[C@@](C)(C(F)(F)F)[C@H]2C)ccc(F)c1F]

(2R,3S,4S,5R)-3-(3,4-difluoro-2-
methoxyphenyl)-N-(6-((S)-1-
hydroxyethyl)pyridin-3-yl)-4,5-dimethyl-5-
(trifluoromethyl)tetrahydrofuran-2-carboxamide

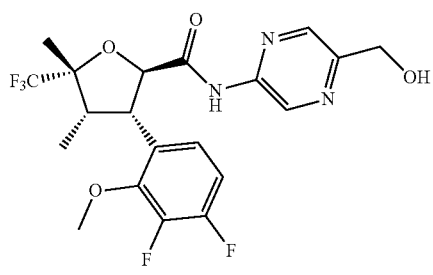 [SMILES: COc1c([C@H]2[C@H](C(=O)Nc3cnc(CO)cn3)O[C@@](C)(C(F)(F)F)[C@H]2C)ccc(F)c1F]

(2R,3S,4S,5R)-3-(3,4-difluoro-2-
methoxyphenyl)-N-(5-(hydroxymethyl)pyrazin-
2-yl)-4,5-dimethyl-5-
(trifluoromethyl)tetrahydrofuran-2-carboxamide TABLE A-continued Compound Structures and Names.

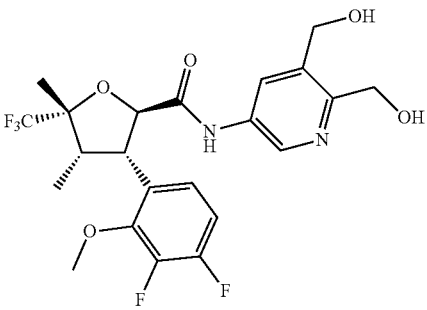 [SMILES: COc1c([C@H]2[C@H](C(=O)Nc3cnc(CO)c(CO)c3)O[C@@](C)(C(F)(F)F)[C@H]2C)ccc(F)c1F]

(2R,3S,4S,5R)-N-(5,6-
bis(hydroxymethyl)pyridin-3-yl)-3-(3,4-difluoro-
2-methoxyphenyl)-4,5-dimethyl-5-
(trifluoromethyl)tetrahydrofuran-2-carboxamide

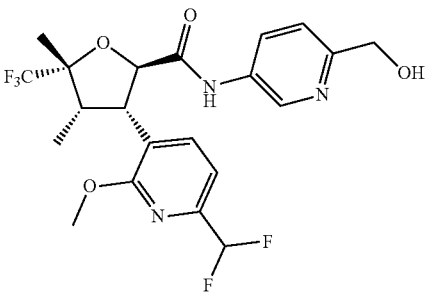 [SMILES: COc1nc(C(F)F)ccc1[C@H]1[C@H](C(=O)Nc2ccc(CO)nc2)O[C@@](C)(C(F)(F)F)[C@H]1C]

(2R,3S,4S,5R)-3-(6-(difluoromethyl)-2-
methoxypyridin-3-yl)-N-(6-(hydroxymethyl)pyridin-
3-yl)-4,5-dimethyl-5-
(trifluoromethyl)tetrahydrofuran-2-carboxamide

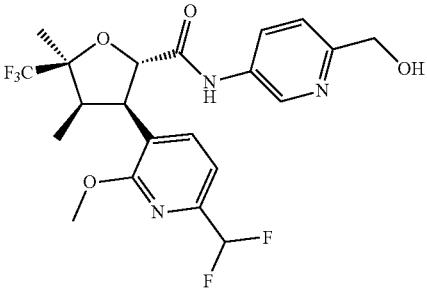 [SMILES: COc1nc(C(F)F)ccc1[C@@H]1[C@@H](C(=O)Nc2ccc(CO)nc2)O[C@](C)(C(F)(F)F)[C@@H]1C]

(2S,3R,4R,5S)-3-(6-(difluoromethyl)-2-
methoxypyridin-3-yl)-N-(6-(hydroxymethyl)pyridin-
3-yl)-4,5-dimethyl-5-
(trifluoromethyl)tetrahydrofuran-2-carboxamide

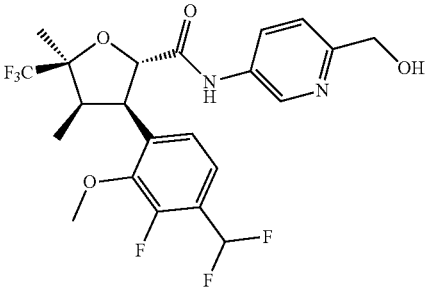 [SMILES: COc1c([C@@H]2[C@@H](C(=O)Nc3ccc(CO)nc3)O[C@](C)(C(F)(F)F)[C@@H]2C)ccc(C(F)F)c1F]

(2S,3R,4R,5S)-3-(4-(difluoromethyl)-3-fluoro-2-
methoxyphenyl)-N-(6-(hydroxymethyl)pyridin-
3-yl)-4,5-dimethyl-5-
(trifluoromethyl)tetrahydrofuran-2-carboxamide TABLE A-continued Compound Structures and Names.

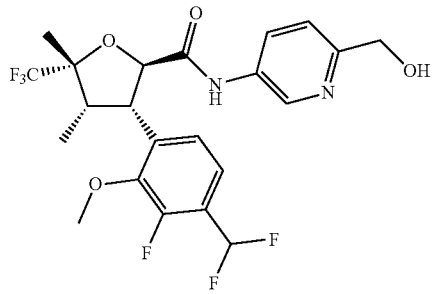 [SMILES: COc1c([C@H]2[C@H](C(=O)Nc3ccc(CO)nc3)O[C@@](C)(C(F)(F)F)[C@H]2C)ccc(C(F)F)c1F]

(2R,3S,4S,5R)-3-(4-(difluoromethyl)-3-fluoro-2-
methoxyphenyl)-N-(6-(hydroxymethyl)pyridin-
3-yl)-4,5-dimethyl-5-
(trifluoromethyl)tetrahydrofuran-2-carboxamide

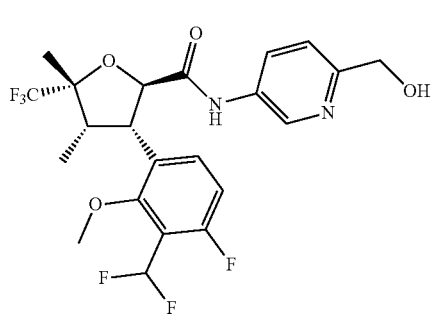 [SMILES: COc1c([C@H]2[C@H](C(=O)Nc3ccc(CO)nc3)O[C@@](C)(C(F)(F)F)[C@H]2C)ccc(F)c1C(F)F]

(2S,3R,4R,5S)-3-(3-(difluoromethyl)-4-fluoro-2-
methoxyphenyl)-N-(6-(hydroxymethyl)pyridin-
3-yl)-4,5-dimethyl-5-
(trifluoromethyl)tetrahydrofuran-2-carboxamide (2R,3S,4S,5R)-3-(3-(difluoromethyl)-4-fluoro-2-
methoxyphenyl)-N-(6-(hydroxymethyl)pyridin-3-
yl)-4,5-dimethyl-5-
(trifluoromethyl)tetrahydrofuran-2-carboxamide TABLE A-continued Compound Structures and Names.

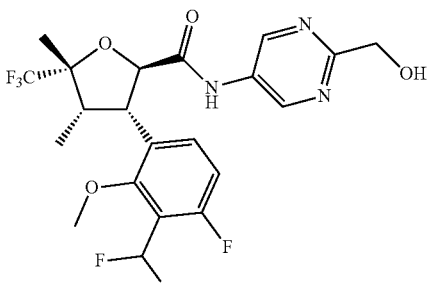

(2R,3S,4S,5R)-3-(3-(difluoromethyl)-4-fluoro-2-
methoxyphenyl)-N-(2-(hydroxymethyl)pyrimidin-
5-yl)-4,5-dimethyl-5-
(trifluoromethyl)tetrahydrofuran-2-carboxamide

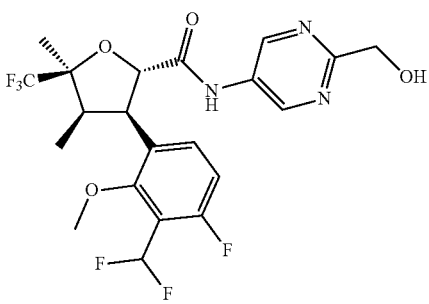 [SMILES: COc1c([C@@H]2[C@@H](C(=O)Nc3cnc(CO)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(2-
(hydroxymethyl)pyrimidin-5-yl)-4,5-dimethyl-5-
(trifluoromethyl)tetrahydrofuran-2-carboxamide

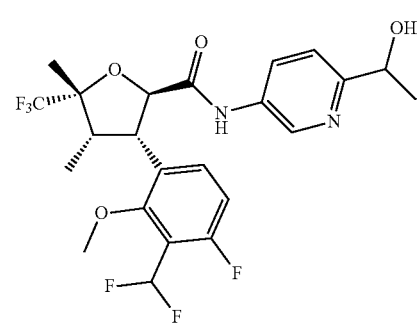 [SMILES: COc1c([C@H]2[C@H](C(=O)Nc3ccc(C(C)O)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-(1-hydroxyethyl)pyridin-3-
yl)-4,5-dimethyl-5-
(trifluoromethyl)tetrahydrofuran-2-carboxamide

TABLE A-continued

Compound Structures and Names.

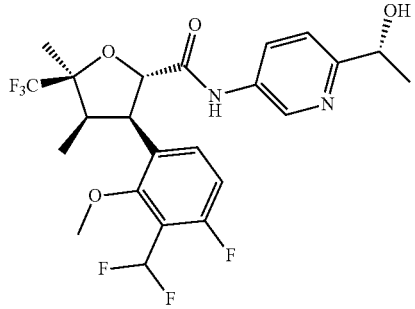 [SMILES: COc1c([C@@H]2[C@@H](C(=O)Nc3ccc([C@@H](C)O)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(6-((R)-1-
hydroxyethyl)pyridin-3-yl)-4,5-dimethyl-5-
(trifluoromethyl)tetrahydrofuran-2-carboxamide

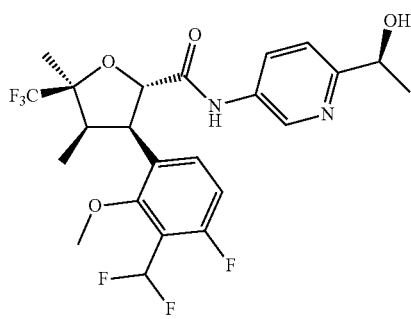 [SMILES: COc1c([C@@H]2[C@@H](C(=O)Nc3ccc([C@H](C)O)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(6-((S)-1-
hydroxyethyl)pyridin-3-yl)-4,5-dimethyl-5-
(trifluoromethyl)tetrahydrofuran-2-carboxamide

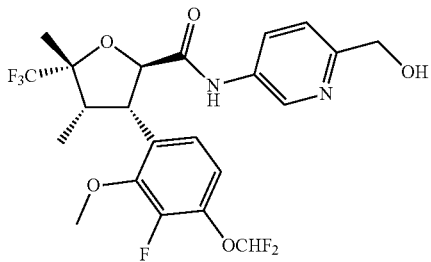 [SMILES: COc1c([C@H]2[C@H](C(=O)Nc3ccc(CO)nc3)O[C@@](C)(C(F)(F)F)[C@H]2C)ccc(OC(F)F)c1F]

(2R,3S,4S,5R)-3-(4-(difluoromethoxy)-3-fluoro-
2-methoxyphenyl)-N-(6-
(hydroxymethyl)pyridin-3-yl)-4,5-dimethyl-5-
(trifluoromethyl)tetrahydrofuran-2-carboxamide

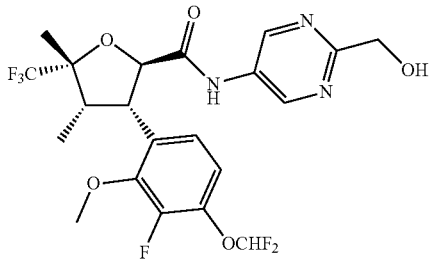 [SMILES: COc1c([C@H]2[C@H](C(=O)Nc3cnc(CO)nc3)O[C@@](C)(C(F)(F)F)[C@H]2C)ccc(OC(F)F)c1F]

(2R,3S,4S,5R)-3-(4-(difluoromethoxy)-3-fluoro-
2-methoxyphenyl)-N-(2-
(hydroxymethyl)pyrimidin-5-yl)-4,5-dimethyl-5-
(trifluoromethyl)tetrahydrofuran-2-carboxamide

TABLE A-continued

Compound Structures and Names.

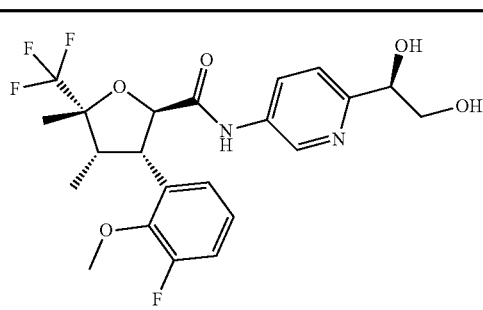

(2R,3S,4S,5R)-N-(6-((R)-1,2-
dihydroxyethyl)pyridin-3-yl)-3-(3-fluoro-2-
methoxyphenyl)-4,5-dimethyl-5-
(trifluoromethyl)tetrahydrofuran-2-carboxamide

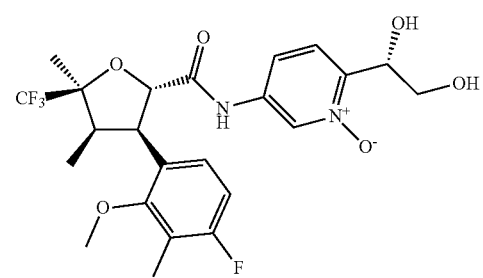

2-((S)-1,2-dihydroxyethyl)-5-((2S,3R,4R,5S)-3-
(4-fluoro-2-methoxy-3-methylphenyl)-4,5-
dimethyl-5-(trifluoromethyl)tetrahydrofuran-2-
carboxamido)pyridine 1-oxide

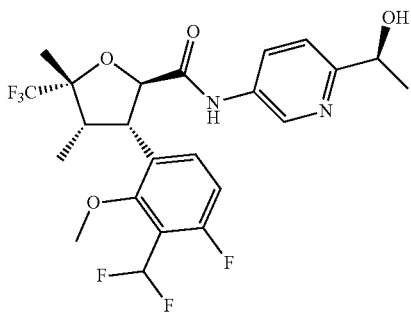 [SMILES: COc1c([C@H]2[C@H](C(=O)Nc3ccc([C@H](C)O)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-((S)-1-
hydroxyethyl)pyridin-3-yl)-4,5-dimethyl-5-
(trifluoromethyl)tetrahydrofuran-2-carboxamide TABLE A-continued Compound Structures and Names.

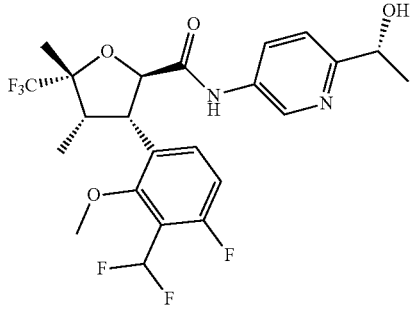 [SMILES: COc1c([C@H]2[C@H](C(=O)Nc3ccc([C@@H](C)O)nc3)O[C@@](C)(C(F)(F)F)[C@H]2C)ccc(F)c1C(F)F]

(2R,3S,4S,5R)-3-(3-(difluoromethyl)-4-fluoro-2-methoxyphenyl)-N-(6-((R)-1-hydroxyethyl)pyridin-3-yl)-4,5-dimethyl-5-(trifluoromethyl)tetrahydrofuran-2-carboxamide In some embodiments, the invention relates to a compound of formula

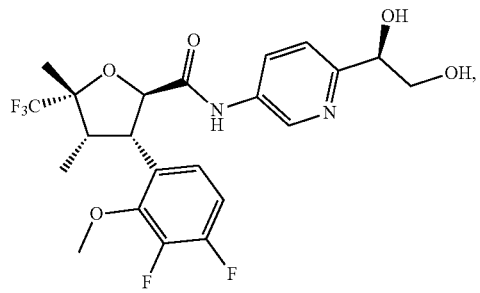 [SMILES: COc1c([C@H]2[C@H](C(=O)Nc3ccc([C@@H](O)CO)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

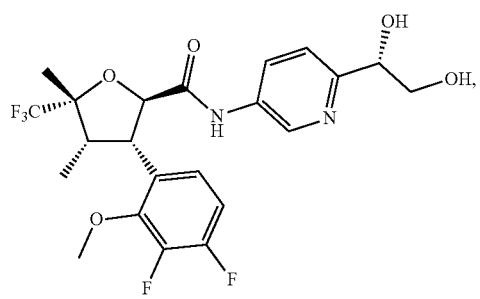 [SMILES: COc1c([C@H]2[C@H](C(=O)Nc3ccc([C@H](O)CO)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

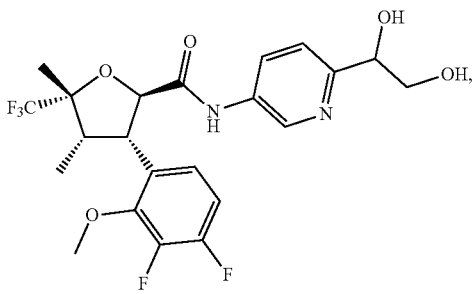 [SMILES: COc1c([C@H]2[C@H](C(=O)Nc3ccc(C(O)CO)nc3)O[C@@](C)(C(F)(F)F)[C@H]2C)ccc(F)c1F]

or a pharmaceutically acceptable salt thereof, wherein the compound has the absolute and relative stereochemistry corresponding to the first eluting isomer when the two diastereoisomers of (2R,3S,4S,5R)-3-(3,4-difluoro-2-methoxyphenyl)-N-(6-(2,2-dimethyl-1,3-dioxolan-4-yl)pyridin-3-yl)-4,5-dimethyl-5-(trifluoromethyl)tetrahydrofuran-2-carboxamide are separated by SFC as described in Example 1, Step 15. In other embodiments, the invention relates to the foregoing compound in non-salt form. Such compound is considered to be a "compound of the invention," as that term is used herein.

In some embodiments, the invention relates to a compound of formula

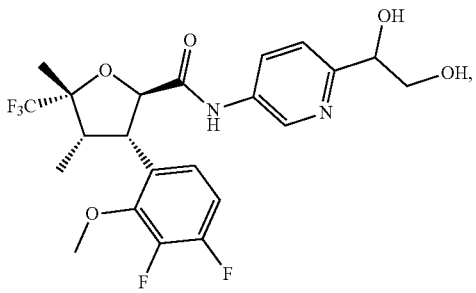

or a pharmaceutically acceptable salt thereof, wherein the compound has the absolute and relative stereochemistry corresponding to the second eluting isomer when the two diastereoisomers of (2R,3S,4S,5R)-3-(3,4-difluoro-2-methoxyphenyl)-N-(6-(2,2-dimethyl-1,3-dioxolan-4-yl)pyridin-3-yl)-4,5-dimethyl-5-(trifluoromethyl)tetrahydrofuran-2-carboxamide are separated by SFC as described in Example 1, Step 15. In other embodiments, the invention relates to the foregoing compound in non-salt form. Such compound is considered to be a "compound of the invention," as that term is used herein.

In some embodiments, the invention relates to a compound of formula

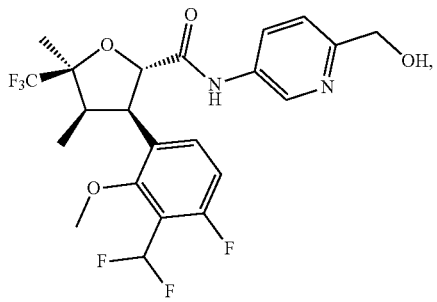 [SMILES: COc1c([C@@H]2[C@@H](C(=O)Nc3ccc(CO)nc3)O[C@](C)(C(F)(F)F)[C@@H]2C)ccc(F)c1C(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

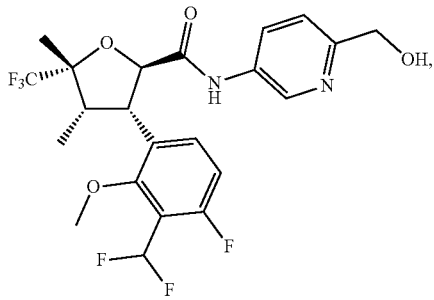 [SMILES: COc1c([C@H]2[C@H](C(=O)Nc3ccc(CO)nc3)O[C@@](C)(C(F)(F)F)[C@H]2C)ccc(F)c1C(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

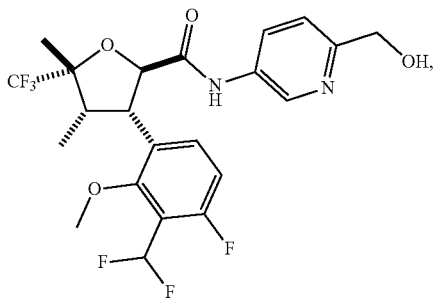 [SMILES: COc1c([C@H]2[C@H](C(=O)Nc3ccc(CO)nc3)O[C@@](C)(C(F)(F)F)[C@H]2C)ccc(F)c1C(F)F]

or a pharmaceutically acceptable salt thereof, wherein the compound has the absolute and relative stereochemistry of the first eluting isomer when rac-(2R,3S,4S,5R)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide is separated by SFC as described in Example 6. In other embodiments, the invention relates to the foregoing compound in non-salt form. Such compound is considered to be a "compound of the invention," as that term is used herein.

In some embodiments, the invention relates to a compound of formula

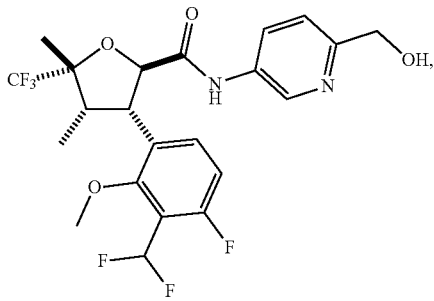 [SMILES: COc1c([C@H]2[C@H](C(=O)Nc3ccc(CO)nc3)O[C@@](C)(C(F)(F)F)[C@H]2C)ccc(F)c1C(F)F]

or a pharmaceutically acceptable salt thereof, wherein the compound has the absolute and relative stereochemistry of the second eluting isomer when rac-(2R,3S,4S,5R)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide is separated by SFC as described in Example 6. In other embodiments, the invention relates to the foregoing compound in non-salt form. Such compound is considered to be a "compound of the invention," as that term is used herein.

In some embodiments, the invention relates to a compound of formula

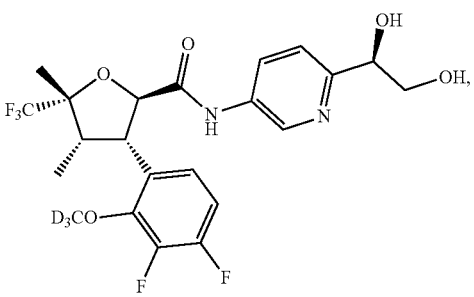

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

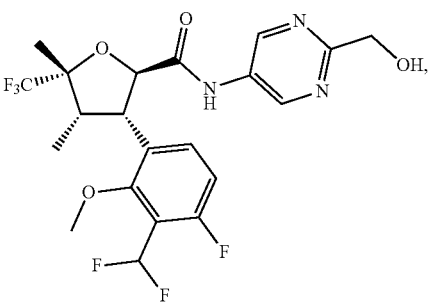 [SMILES: COc1c([C@H]2[C@H](C(=O)Nc3cnc(CO)nc3)O[C@@](C)(C(F)(F)F)[C@H]2C)ccc(F)c1C(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

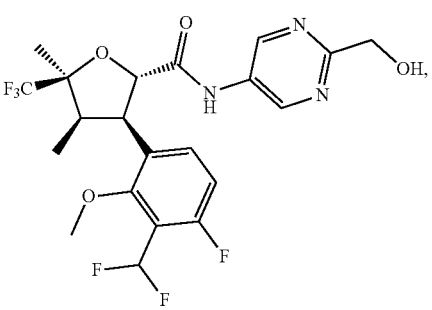 [SMILES: COc1c([C@@H]2[C@@H](C(=O)Nc3cnc(CO)nc3)O[C@](C)(C(F)(F)F)[C@@H]2C)ccc(F)c1C(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

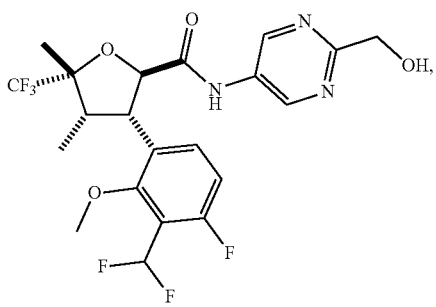 [SMILES: COc1c([C@H]2[C@H](C(=O)Nc3cnc(CO)nc3)O[C@@](C)(C(F)(F)F)[C@H]2C)ccc(F)c1C(F)F]

or a pharmaceutically acceptable salt thereof, wherein the compound has the absolute and relative stereochemistry corresponding to the first eluting isomer when the two enantiomers of rac-(5-((2R,3S,4S,5R)-3-(3-(difluoromethyl)-4-fluoro-2-methoxyphenyl)-4,5-dimethyl-5-(trifluoromethyl)tetrahydrofuran-2-carboxamido)pyrimidin-2-yl) methyl benzoate are separated by SFC as described in Example 6. In other embodiments, the invention relates to the foregoing compound in non-salt form. Such compound is considered to be a "compound of the invention," as that term is used herein.

In some embodiments, the invention relates to a compound of formula

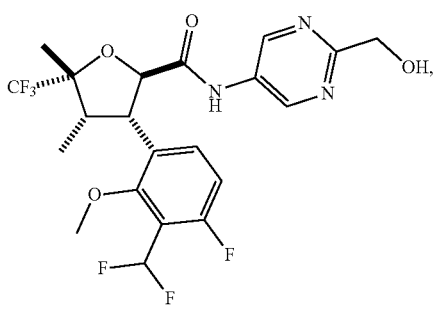 [SMILES: COc1c([C@H]2[C@H](C(=O)Nc3cnc(CO)nc3)O[C@@](C)(C(F)(F)F)[C@H]2C)ccc(F)c1C(F)F]

or a pharmaceutically acceptable salt thereof, wherein the compound has the absolute and relative stereochemistry corresponding to the second eluting isomer when the two enantiomers of rac-(5-((2R,3S,4S,5R)-3-(3-(difluoromethyl)-4-fluoro-2-methoxyphenyl)-4,5-dimethyl-5-(trifluoromethyl)tetrahydrofuran-2-carboxamido)pyrimidin-2-yl) methyl benzoate are separated by SFC as described in Example 6. In other embodiments, the invention relates to the foregoing compound in non-salt form. Such compound is considered to be a "compound of the invention," as that term is used herein.

In some embodiments, the invention relates to a compound of formula

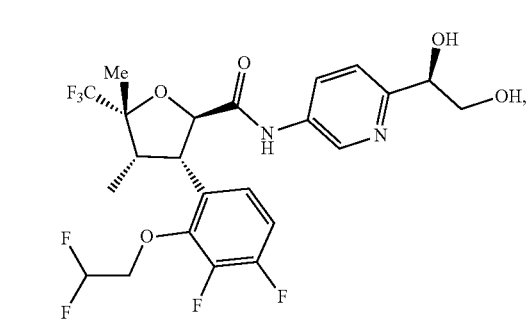 [SMILES: C[C@H]1[C@@H](c2ccc(F)c(F)c2OCC(F)F)[C@H](C(=O)Nc2ccc([C@@H](O)CO)nc2)O[C@@]1(C)C(F)(F)F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

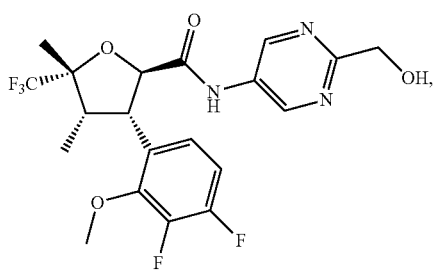 [SMILES: COc1c([C@H]2[C@H](C(=O)Nc3cnc(CO)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

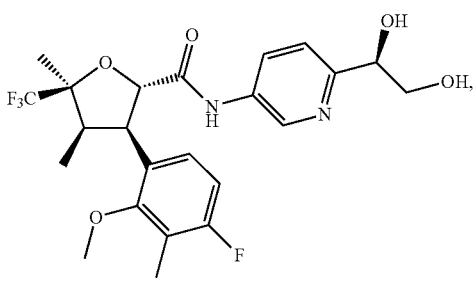 [SMILES: COc1c([C@@H]2[C@@H](C(=O)Nc3ccc([C@@H](O)CO)nc3)O[C@](C)(C(F)(F)F)[C@@H]2C)ccc(F)c1C]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

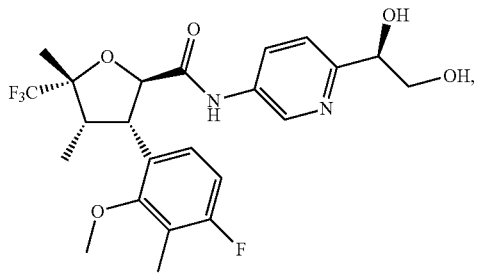 [SMILES: COc1c([C@H]2[C@H](C(=O)Nc3ccc([C@@H](O)CO)nc3)O[C@@](C)(C(F)(F)F)[C@H]2C)ccc(F)c1C]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound rel-(2S,3R,4R,5S)—N-(6-((R*)-1,2-dihydroxyethyl) pyridin-3-yl)-3-(4-fluoro-2-methoxy-3-methylphenyl)-4,5-dimethyl-5-(trifluoromethyl)tetrahydrofuran-2-carboxamide, or a pharmaceutically acceptable salt thereof, wherein the compound has the absolute and relative stereochemistry corresponding to the first eluting isomer when the two diastereoisomers rel-(2S,3R,4R,5S)—N-(6-((R*)-2,2-dimethyl-1,3-dioxolan-4-yl)pyridin-3-yl)-3-(4-fluoro-2-methoxy-3-methylphenyl)-4,5-dimethyl-5-(trifluoromethyl)tetrahydrofuran-2-carboxamide and rel-(2R,3S,4S,5R)—N-(6-((R*)-2,2-dimethyl-1,3-dioxolan-4-yl)pyridin-3-yl)-3-(4-fluoro-2-methoxy-3-methylphenyl)-4,5-dimethyl-5-(trifluoromethyl)tetrahydrofuran-2-carboxamide are separated by SFC as described in Example 5. In other embodiments, the invention relates to the foregoing compound in non-salt form. Such compound is considered to be a "compound of the invention," as that term is used herein.

In some embodiments, the invention relates to a compound rel-(2R,3S,4S,5R)—N-(6-((R*)-1,2-dihydroxyethyl) pyridin-3-yl)-3-(4-fluoro-2-methoxy-3-methylphenyl)-4,5-dimethyl-5-(trifluoromethyl)tetrahydrofuran-2-carboxamide, or a pharmaceutically acceptable salt thereof, wherein the compound has the absolute and relative stereochemistry of the second eluting isomer when the two diastereoisomers rel-(2S,3R,4R,5S)—N-(6-((R*)-2,2-dimethyl-1,3-dioxolan-4-yl)pyridin-3-yl)-3-(4-fluoro-2-methoxy-3-methylphenyl)-4,5-dimethyl-5-(trifluoromethyl)tetrahydrofuran-2-carboxamide and rel-(2R,3S,4S,5R)—N-(6-((R*)-2,2-dimethyl-1, 3-dioxolan-4-yl)pyridin-3-yl)-3-(4-fluoro-2-methoxy-3-methylphenyl)-4,5-dimethyl-5-(trifluoromethyl)tetrahydrofuran-2-carboxamide are separated by SFC as described in Example 5. In other embodiments, the invention relates to the foregoing compound in non-salt form. Such compound is considered to be a "compound of the invention," as that term is used herein.

In some embodiments, the invention relates to a compound of formula

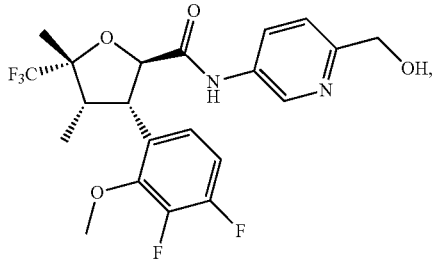 [SMILES: COc1c([C@H]2[C@H](C(=O)Nc3ccc(CO)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

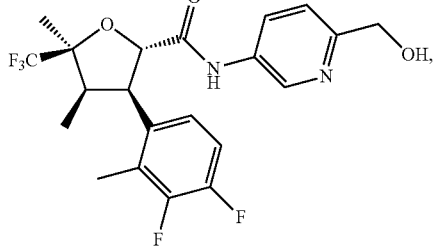

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

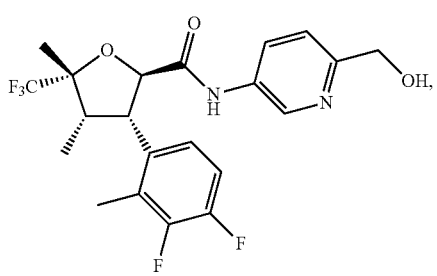 [SMILES: Cc1c([C@H]2[C@H](C(=O)Nc3ccc(CO)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

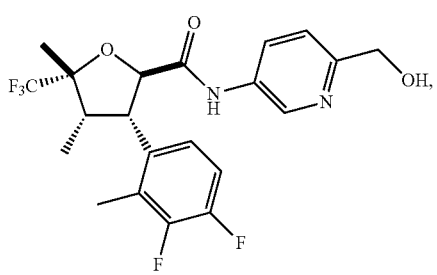 [SMILES: Cc1c([C@H]2[C@H](C(=O)Nc3ccc(CO)nc3)O[C@@](C)(C(F)(F)F)[C@H]2C)ccc(F)c1F]

or a pharmaceutically acceptable salt thereof, wherein the compound has the absolute and relative stereochemistry corresponding to the first eluting isomer when the two enantiomers of rac-(2R,3S,4S,5R)—N-(6-(((tert-butyldimethylsilyl)oxy)methyl)pyridin-3-yl)-3-(3,4-difluoro-2-methylphenyl)-4,5-dimethyl-5-(trifluoromethyl)tetrahydrofuran-2-carboxamide are separated by SFC as described in Example 9. In other embodiments, the invention relates to the foregoing compound in non-salt form. Such compound is considered to be a "compound of the invention," as that term is used herein.

In some embodiments, the invention relates to a compound of formula

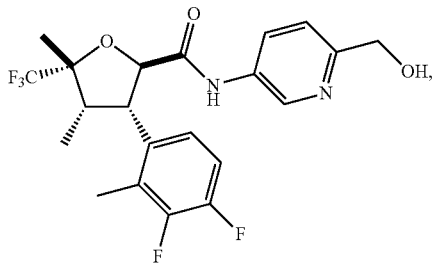 [SMILES: Cc1c([C@H]2[C@H](C(=O)Nc3ccc(CO)nc3)O[C@@](C)(C(F)(F)F)[C@H]2C)ccc(F)c1F]

or a pharmaceutically acceptable salt thereof, wherein the compound has the absolute and relative stereochemistry corresponding to the second eluting isomer when the two enantiomers of rac-(2R,3S,4S,5R)—N-(6-(((tert-butyldimethylsilyl)oxy)methyl)pyridin-3-yl)-3-(3,4-difluoro-2-methylphenyl)-4,5-dimethyl-5-(trifluoromethyl)tetrahydrofuran-2-carboxamide are separated by SFC as described in Example 9. In other embodiments, the invention relates to the foregoing compound in non-salt form. Such compound is considered to be a "compound of the invention," as that term is used herein.

In some embodiments, the invention relates to a compound of formula

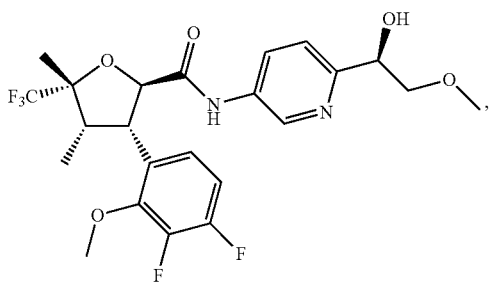 [SMILES: COC[C@H](O)c1ccc(NC(=O)[C@@H]2O[C@@](C)(C(F)(F)F)[C@@H](C)[C@H]2c2ccc(F)c(F)c2OC)cn1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

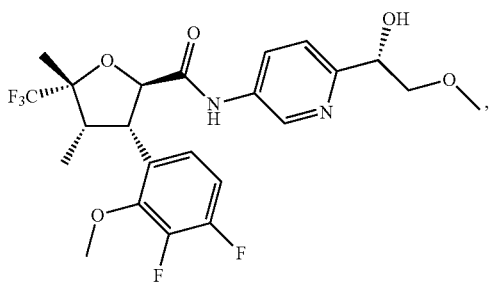 [SMILES: COC[C@@H](O)c1ccc(NC(=O)[C@@H]2O[C@@](C)(C(F)(F)F)[C@@H](C)[C@H]2c2ccc(F)c(F)c2OC)cn1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

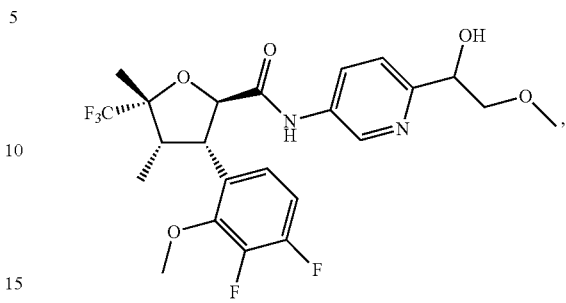

or a pharmaceutically acceptable salt thereof, wherein the compound has the absolute and relative stereochemistry corresponding to the first eluting isomer when the two diastereoisomers of (2R,3S,4S,5R)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide are separated by SFC as described in Example 2, Step 2. In other embodiments, the invention relates to the foregoing compound in non-salt form. Such compound is considered to be a "compound of the invention," as that term is used herein.

In some embodiments, the invention relates to a compound of formula

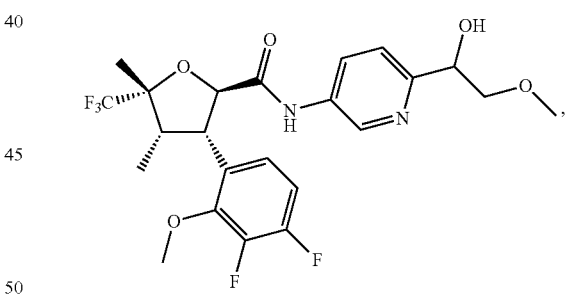

or a pharmaceutically acceptable salt thereof, wherein the compound had the absolute and relative stereochemistry corresponding to the second eluting isomer when the two diastereoisomers of (2R,3S,4S,5R)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide are separated by SFC as described in Example 2, Step 2. In other embodiments, the invention relates to the foregoing compound in non-salt form. Such compound is considered to be a "compound of the invention," as that term is used herein.

In some embodiments, the invention relates to a compound of formula

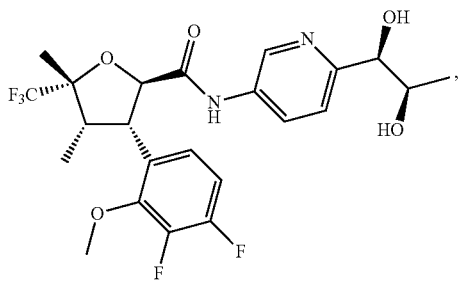 [SMILES: COc1c([C@H]2[C@H](C(=O)Nc3ccc([C@@H](O)[C@@H](C)O)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

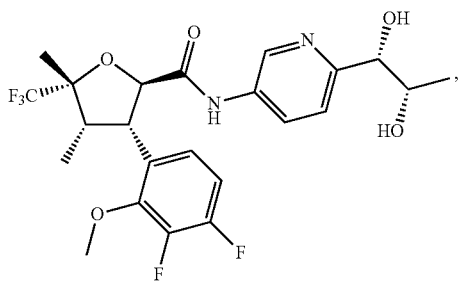 [SMILES: COc1c([C@H]2[C@H](C(=O)Nc3ccc([C@H](O)[C@H](C)O)nc3)O[C@@](C)(C(F)(F)F)[C@H]2C)ccc(F)c1F]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound rel-(2R*,3S*,4S*,5R*)-3-(3,4-difluoro-2-methoxyphenyl)-N-(6-((1R,2R)-1,2-dihydroxypropyl)pyridin-3-yl)-4,5-dimethyl-5-(trifluoromethyl)tetrahydrofuran-2-carboxamide, or a pharmaceutically acceptable salt thereof, wherein the compound has the absolute and relative stereochemistry corresponding to the first eluting isomer when the two diastereoisomers rel-(2R*,3S*,4S*,5R*)-3-(3,4-difluoro-2-methoxyphenyl)-4,5-dimethyl-5-(trifluoromethyl)-N-(6-((4R,5R)-2,2,5-trimethyl-1,3-dioxolan-4-yl)pyridin-3-yl)tetrahydrofuran-2-carboxamide and rel-(2R*,3S*,4S*,5R*)-3-(3,4-difluoro-2-methoxyphenyl)-4,5-dimethyl-5-(trifluoromethyl)-N-(6-((4S,5S)-2,2,5-trimethyl-1,3-dioxolan-4-yl)pyridin-3-yl)tetrahydrofuran-2-carboxamide are separated by SFC as described in Example 1. In other embodiments, the invention relates to the foregoing compound in non-salt form. Such compound is considered to be a "compound of the invention," as that term is used herein.

In some embodiments, the invention relates to a compound rel-(2R*,3S*,4S*,5R*)-3-(3,4-difluoro-2-methoxyphenyl)-N-(6-((1S,2S)-1,2-dihydroxypropyl)pyridin-3-yl)-4,5-dimethyl-5-(trifluoromethyl)tetrahydrofuran-2-carboxamide, or a pharmaceutically acceptable salt thereof, wherein the compound has the absolute and relative stereochemistry corresponding to the second eluting isomer when the two diastereoisomers rel-(2R*,3S*,4S*,5R*)-3-(3,4-difluoro-2-methoxyphenyl)-4,5-dimethyl-5-(trifluoromethyl)-N-(6-((4R,5R)-2,2,5-trimethyl-1,3-dioxolan-4-yl)pyridin-3-yl)tetrahydrofuran-2-carboxamide and rel-(2R*,3S*,4S*, 5R*)-3-(3,4-difluoro-2-methoxyphenyl)-4,5-dimethyl-5-(trifluoromethyl)-N-(6-((4S,5S)-2,2,5-trimethyl-1,3-dioxolan-4-yl)pyridin-3-yl)tetrahydrofuran-2-carboxamide are separated by SFC as described in Example 1. In other embodiments, the invention relates to the foregoing compound in non-salt form. Such compound is considered to be a "compound of the invention," as that term is used herein.

In some embodiments, the invention relates to a compound of formula

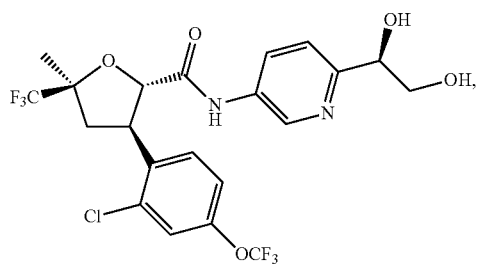 [SMILES: C[C@@]1(C(F)(F)F)C[C@H](c2ccc(OC(F)(F)F)cc2Cl)[C@@H](C(=O)Nc2ccc([C@@H](O)CO)nc2)O1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound of formula

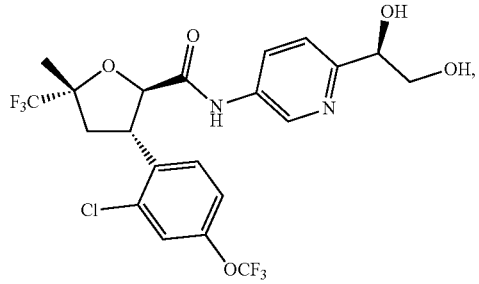 [SMILES: C[C@]1(C(F)(F)F)C[C@@H](c2ccc(OC(F)(F)F)cc2Cl)[C@H](C(=O)Nc2ccc([C@@H](O)CO)nc2)O1]

or a pharmaceutically acceptable salt thereof. In other embodiments, the invention relates to the foregoing compound in non-salt form. Such compound is considered to be a "compound of the invention," as that term is used herein.

In some embodiments, the invention relates to a compound rel-(2S,3R,5S)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide, or a pharmaceutically acceptable salt thereof, wherein the compound has the absolute and relative stereochemistry corresponding to the first eluting isomer when the two diastereomers rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide and rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide are separated by SFC as described in Example 8. In other embodiments, the invention relates to the foregoing compound in non-salt form. Such compound is considered to be a "compound of the invention," as that term is used herein.

In some embodiments, the invention relates to a compound rel-(2R,3S,5R)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide, or a pharmaceutically acceptable salt thereof, wherein the compound has the absolute and relative stereochemistry corresponding to the second eluting isomer when the two diastereomers rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide and rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide are separated by SFC as described in Example 8. In other embodiments, the invention relates to the foregoing compound in non-salt form. Such compound is considered to be a "compound of the invention," as that term is used herein.

Salts, Compositions, Uses, Formulation, Administration and Additional Agents

Pharmaceutically Acceptable Salts and Compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain, heriorrhaphy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is $Na_V1.8$.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain, herniorrhaphy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., joint replacement pain, soft tissue surgery pain, herniorrhaphy pain, bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of herniorrhaphy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method of treating or lessening the severity in a subject of a neurodegenerative disease comprising administering an effective amount of a compound of the invention, a pharmaceutically acceptable salt thereof or a pharmaceutical composition thereof. In some aspects, the neurodegenerative disease comprises multiple sclerosis. In some aspects, the neurodegenerative disease comprises Pitt Hopkins Syndrome (PTHS).

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a method of treating or lessening the severity in a subject of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, post-surgical pain (e.g., joint replacement pain, soft tissue surgery pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia rheumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodiscitis, transverse myelitis, Ehlers-Danlos syndrome, Fabry's disease, mastocytosis, neurofibromatosis, ocular neuropathic pain, sarcoidosis, spondylolysis, spondylolisthesis, chemotherapy induced oral mucositis, Charcot neuropathic osteoarthropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy). As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, small fiber neuropathy, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute postoperative pain.

In another aspect, the invention features a compound of the invention, or a pharmaceutically acceptable salt or pharmaceutical composition thereof, for use in a method of treating or lessening the severity in a subject of postsurgical pain (e.g., joint replacement pain, soft tissue surgery pain, heriorrhaphy pain, bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of heriorrhaphy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method of treating or lessening the severity in a subject of a neurodegenerative disease. In some aspects, the neurodegenerative disease comprises multiple sclerosis. In some aspects, the neurodegenerative disease comprises Pitt Hopkins Syndrome (PTHS).

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is $Na_V1.8$.

In another aspect, the invention features a compound of the invention, or a pharmaceutically acceptable salt or pharmaceutical composition thereof, for use in a method of treating or lessening the severity in a subject of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, post-surgical pain (e.g., joint replacement pain, soft tissue surgery pain, heriorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia rheumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodiscitis, transverse myelitis, Ehlers-Danlos syndrome, Fabry's disease, mastocytosis, neurofibromatosis, ocular neuropathic pain, sarcoidosis, spondylolysis, spondylolisthesis, chemotherapy induced oral mucositis, Charcot neuropathic osteoarthropathy, temporo-mandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

In another aspect, the invention features a compound of the invention, or a pharmaceutically acceptable salt or pharmaceutical composition thereof, for use in a method of treating or lessening the severity in a subject of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or post-amputation pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is $Na_V1.8$.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., herniorrhaphy pain, bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, herniorrhaphy pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia, small fiber neuropathy, diabetic neuropathy, or idiopathic small-fiber neuropathy. In some aspects, the neuropathic pain comprises diabetic neuropathy (e.g., diabetic peripheral neuropathy).

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, antiretroviral therapy induced neuralgia; post spinal cord injury pain, small fiber neuropathy, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., joint replacement pain, soft tissue surgery pain, herniorrhaphy pain, bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of herniorrhaphy pain.

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for the manufacture of a medicament for use in treating or lessening the severity in a subject of a neurodegenerative disease. In some aspects, the neurodegenerative disease comprises multiple sclerosis.

In some aspects, the neurodegenerative disease comprises Pitt Hopkins Syndrome (PTHS).

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, sub-acute and chronic pain, nociceptive pain, neuropathic pain, inflammatory pain, nociplastic pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, central neuropathic pain of multiple sclerosis and irritable bowel syndrome, incontinence, pathological cough, visceral pain, osteoarthritis pain, postherpetic neuralgia, diabetic neuropathy, radicular pain, sciatica, back pain, unspecific chronic back pain, head pain, neck pain, moderate pain, severe pain, intractable pain, nociceptive pain, breakthrough pain, postsurgical pain (e.g., joint replacement pain, soft tissue surgery pain, herniorrhaphy pain, bunionectomy pain or abdominoplasty pain), cancer pain including chronic cancer pain and breakthrough cancer pain, stroke (e.g., post stroke central neuropathic pain), whiplash associated disorders, fragility fractures, spinal fractures, ankylosing spondylitis, pemphigus, Raynaud's Disease, scleroderma, systemic lupus erythematosus, Epidermolysis bullosa, gout, juvenile idiopathic arthritis, melorheostosis, polymyalgia rheumatica, pyoderma gangrenosum, chronic widespread pain, diffuse idiopathic skeletal hyperostosis, disc degeneration/herniation pain, radiculopathy, facet joint syndrome, failed back surgery syndrome, burns, carpal tunnel syndrome, Paget's disease pain, spinal canal stenosis, spondylodiscitis, transverse myelitis, Ehlers-Danlos syndrome, Fabry's disease, mastocytosis, neurofibromatosis, ocular neuropathic pain, sarcoidosis, spondylolysis, spondylolisthesis, chemotherapy induced oral mucositis, Charcot neuropathic osteoarthropathy, temporomandibular joint disorder, painful joint arthroplasties, non-cardiac chest pain, pudendal, renal colic, biliary tract diseases, vascular leg ulcers, pain in Parkinson's disease, pain in Alzheimer's disease, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; persistent/chronic post-surgical pain (e.g., post amputation, post-thoracotomy, post-cardiac surgery), post-mastectomy pain; central pain; spinal cord injury pain; post-stroke pain; thalamic pain; phantom pain (e.g., following removal of lower extremity, upper extremity, breast); intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

In another aspect, the invention provides the use of a compound of the invention, a pharmaceutically acceptable salt thereof, or a pharmaceutical composition thereof for the manufacture of a medicament for use in treating or lessening the severity of trigeminal neuralgia, migraines treated with botox, cervical radiculopathy, occipital neuralgia, axillary neuropathy, radial neuropathy, ulnar neuropathy, brachial plexopathy, thoracic radiculopathy, intercostal neuralgia, lumbrosacral radiculopathy, iliolingual neuralgia, pudendal neuralgia, femoral neuropathy, meralgia paresthetica, saphenous neuropathy, sciatic neuropathy, peroneal neuropathy, tibial neuropathy, lumbosacral plexopathy, traumatic neuroma stump pain or postamputation pain.

Administration of Compounds, Pharmaceutically Acceptable Salts, and Compositions In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 1000 mg/kg, one or more times a day, effective to obtain the desired therapeutic effect.

Liquid dosage forms for oral administration include, but are not limited to, pharmaceutically acceptable emulsions, microemulsions, solutions, suspensions, syrups, and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: non-opioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, IV meloxicam (e.g., Anjeso®), nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1,2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anesthetic such as mexiletine;

(20) a corticosteroid such as dexamethasone;

(21) a 5-HT receptor agonist or antagonist, particularly a 5-HT$_{1B/1D}$ agonist such as eletriptan, sumatriptan, naratriptan, zolmitriptan or rizatriptan;

(22) a 5-HT$_2$A receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), IV Tramadol, Tapentadol ER (Nucynta®);

(25) a PDE5 inhibitor, such as 5-[ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4] triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl) pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L- cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(15)-1-({[5-chloro-2-(3-fluorophenoxy)pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) a $Na_v1.7$ blocker, such as XEN-402, XEN403, TV-45070, PF-05089771, CNV1014802, GDC-0276, RG7893 BIIB-074 (Vixotrigine), BIIB-095, ASP-1807, DSP-3905, OLP-1002, RQ-00432979, FX-301, DWP-1706, DWP-17061, IMB-110, IMB-111, IMB-112 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, WO2013/109521 (US2015005304), WO2020/117626, and CN111217776, the entire contents of each application hereby incorporated by reference;

(38a) a $Na_v1.7$ blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone, 1-(4-benzhydrylp- iperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) a $Na_v1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), WO2015/089361 (US20150166589), WO2019/014352 (US20190016671), WO2018/213426, WO2020/146682, WO2020/146612, WO2020/014243, WO2020/014246, WO2020/092187, WO2020/092667 (US2020140411), WO2020/261114, WO2020/140959, WO2020/151728, WO2021/032074, CN112390745, CN111808019, CN112225695, CN112457294, CN112300051, CN112300069, CN112441969, and CN112479996 (WO2021/047622), the entire contents of each application hereby incorporated by reference;

(39a) a $Na_v1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)

benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, 2-(4-fluoro-2-methyl-phenoxy)-N-(2-oxo-1H-pyridin-4-yl)-4-(trifluoromethyl)benzamide, [4-[[2-(4-fluoro-2-methyl-phenoxy)-4-(trifluoromethyl)benzoyl]amino]-2-oxo-1-pyridyl]methyl dihydrogen phosphate, 2-(4-fluoro-2-(methyl-$d_3$)phenoxy)-N-(2-oxo-1,2-dihydropyridin-4-yl)-4-(trifluoromethyl)benzamide, (4-(2-(4-fluoro-2-(methyl-$d_3$)phenoxy)-4-(trifluoromethyl)benzamido)-2-oxopyridin-1(2H)-yl) methyl dihydrogen phosphate, 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido)benzoic acid, 5-(4,5-dichloro-2-(2,4-difluorophenoxy)benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide, N-(3-sulfamoylphenyl)-2-(4-(trifluoromethoxy)phenoxy)-4-(trifluoromethyl)benzamide, N-(3-carbamoyl-4-fluoro-phenyl)-2-fluoro-6-[2-(trideuteriomethoxy)-4-(trifluoromethoxy)phen-oxy]-3-(trifluoromethyl)benzamide, N-(3-carbamoyl-4-fluoro-phenyl)-2-fluoro-6-[2-methoxy-4-(trifluoromethoxy)phenoxy]-3-(trifluoromethyl)benzamide, N-(3-carbamoyl-4-fluoro-phenyl)-2-fluoro-6-[2-(trideuteriomethoxy)-4-(trifluoromethoxy)phenoxy]-3-(trifluoromethoxy)benzamide, 4-[[2-fluoro-6-[2-methoxy-4-(trifluoromethoxy)phenoxy]-3-(trifluoromethyl)benzoyl]amino]pyridine-2-carboxamide, 4-[[3-chloro-2-fluoro-6-[2-methoxy-4-(trifluoromethoxy)phenoxy]benzoyl]amino]pyridine-2-carboxamide, 4-[[2-fluoro-6-[2-(trideuteriomethoxy)-4-(trifluoromethoxy)phenoxy]-3-(trifluoromethyl)benzoyl]amino]pyridine-2-carboxamide, N-(3-carbamoyl-4-fluoro-phenyl)-3-(difluoromethyl)-2-fluoro-6-[2-methoxy-4-(trifluoromethoxy)phenoxy]benzamide, 4-[[2-fluoro-6-[2-(trideute- riomethoxy)-4-(trifluoromethoxy)phenoxy]-3-(trifluoromethoxy)benzoyl]amino]pyridine-2-carboxamide, N-(3-carbamoyl-4-fluoro-phenyl)-6-[2-chloro-4-(trifluoromethoxy)phenoxy]-2-fluoro-3-(trifluorom- ethyl)benzamide, N-(3-carbamoyl-4-fluoro-phenyl)-2-fluoro-6-[2-methyl-4-(trifluoromethoxy)phenoxy]-3-(trifluoromethyl)benzamide, N-(3-carbamoyl-4-fluoro-phenyl)-2,3,4-trifluoro-6-[2-methoxy-4-(trifluorom- ethoxy)phenoxy]benzamide, N-(2-carbamoyl-4-pyr- idyl)-3-fluoro-5-[2-methoxy-4-(trifluoromethoxy)phenoxy]-2-(trifluoromethyl)pyridine-4-carboxamide, 4-[[6-[2-(difluoromethoxy)-4-(trifluoromethoxy)phenoxy]-2-fluoro-3-(trifluoromethyl)benzoyl]amino]pyridine-2-carboxamide, N-(3-carbamoyl-4-fluoro-phenyl)-6-[3-chloro-4-(trifluoromethoxy)phenoxy]-2-fluoro-3-(trifluoromethyl)benzamide, N-(3-carbamoyl-4-fluoro-phenyl)-2-fluoro-6-[4-(trifluoromethoxy)phenoxy]-3-(trifluoromethyl)benzamide, N-(4-carbamoyl-3-fluoro-phenyl)-2-fluoro-6-[2-methoxy-4-(trifluoromethoxy)phenoxy]-3-(trifluoromethyl)benzamide, 4-[[2-fluoro-6-[2-(trideuteriomethoxy)-4-(trifluoromethoxy)phenoxy]-4-(trifluoromethyl)benzoyl]amino]pyridine-2-carboxamide, N-(3-carbamoyl-4-fluoro-phenyl)-2-fluoro-6-[3-fluoro-4-(trifluorom- ethoxy)phenoxy]-3-(trifluoromethyl)benzamide, N-(3-carbamoyl-4-fluoro-phenyl)-2-[2-methoxy-4-(trifluoromethoxy)phenoxy]-5-(1,1,2,2,2-pentafluoroethyl)benzamide, 4-[[4-(difluoromethoxy)-2-fluoro-6-[2-methoxy-4-(trifluoromethoxy)phenoxy]benzoyl]amino]pyridine-2-carboxamide, N-(3-carbamoyl-4-flu- oro-phenyl)-2-fluoro-6-[2-fluoro-4-(trifluoromethoxy)phenoxy]-3-(trifluoromethyl)benzamide, 4-[[4-cyclopropyl-2-fluoro-6-[2-methoxy-4-(trifluoromethoxy)phenoxy]benzoyl]amino]pyridine-2-carboxamide, N-(3-carbamoyl-4-fluoro-phenyl)-5-fluoro-2-[2-methoxy-4-(trifluoromethoxy)phenoxy]-4-(trifluoromethyl)benzamide, 5-[[2-fluoro-6-[2-(trideuteriomet- hoxy)-4-(trifluoromethoxy)phenoxy]-3-(trifluoromethyl)benzoyl]amino]pyridine-2-carboxamide, N-(3-carbamoyl-4-fluoro-phenyl)-2-fluoro-6-(4-fluorophenoxy)-3-(trifluoromethyl)benzamide, 4-(2-fluoro-6-(2-methoxy-4-(trifluoromethoxy)phenoxy)-3-(trifluor- omethyl)benzamido)picolinamide, or 4-[[2-fluoro-6-[3-fluoro-2-methoxy-4-(trifluoromethyl)phenoxy]-3-(trifluoromethyl)benzoyl]amino]pyridine-2-carboxamide;

(40) a combined $Na_V1.7$ and $Na_V1.8$ blocker, such as DSP-2230, Lohocla201 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®) bupivacaine ER (Posimir), bupivacaine collagen (Xaracoll) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is selected from a GlyT2/5HT2 inhibitor, such as Operanserin (VVZ149), a TRPV modulator such as CA008, CMX-020, NE06860, FTABS, CNTX4975, MCP101, MDR16523, or MDR652, a EGRI inhibitor such as Brivoglide (AYX1), an NGF inhibitor such as Tanezumab, Fasinumab, ASP6294, MEDI7352, a Mu opioid agonist such as Cebranopadol, NKTR181 (oxycodegol), a CB-1 agonist such as NEO1940 (AZN1940), an imidazoline I2 agonist such as CR4056 or a p75NTR-Fc modulator such as LEVI-04.

In another embodiment, the additional therapeutic agent is oliceridine or ropivacaine (TLC590).

In another embodiment, the additional therapeutic agent is a $Na_V1.7$ blocker such as ST-2427 or ST-2578 and those disclosed in WO2010129864, WO2015157559, WO2017059385, WO2018183781, WO2018183782, WO2020072835, and WO2022036297 the entire contents of each application hereby incorporated by reference. In some embodiments, the additional therapeutic agent is a $Na_V1.7$ blocker disclosed in WO2020072835. In some embodiments, the additional therapeutic agent is a $Na_V1.7$ blocker disclosed in WO2022036297.

In another embodiment, the additional therapeutic agent is ASP18071, CC-8464, ANP-230, ANP-231, NOC-100, NTX-1175, ASN008, NW3509, AM-6120, AM-8145, AM-0422, BL-017881, NTM-006, Opiranserin (Unafra™), brivoligide, SR419, NRD.E1, LX9211, LY3016859, ISC-17536, NFX-88, LAT-8881, AP-235, NYX 2925, CNTX-6016, S-600918, S-637880, RQ-00434739, KLS-2031, MEDI 7352, or XT-150.

In another embodiment, the additional therapeutic agent is Olinvyk, Zynrelef, Seglentis, Neumentum, Nevakar, HTX-034, CPL-01, ACP-044, HRS-4800, Tarlige, BAY2395840, LY3526318, Eliapixant, TRV045, RTA901, NRD1355-E1, MT-8554, LY3556050, AP-325, tetrodotoxin, Otenaproxesul, CFTX-1554, Funapide, iN1011-N17, JMKX000623, ETX-801, or ACD440.

In another embodiment, the additional therapeutic agent is a compound disclosed in WO2021257490, WO2021257420, WO2021257418, WO2020014246, WO2020092187, WO2020092667, WO2020261114, CN112457294, CN112225695, CN111808019, WO2021032074, WO2020151728, WO2020140959, WO2022037641, WO2022037647, CN112300051, CN112300069, WO2014120808, WO2015089361, WO2019014352, WO2021113627, WO2013086229, WO2013134518, WO2014211173, WO2014201206, WO2016141035, WO2021252818, WO2021252822, and WO2021252820.

In some embodiments, the additional therapeutic agent is a compound disclosed in WO2013086229. In some embodiments, the additional therapeutic agent is a compound disclosed in WO2013134518. In some embodiments, the additional therapeutic agent is a compound disclosed in WO2014211173. In some embodiments, the additional therapeutic agent is a compound disclosed in WO2014201206. In some embodiments, the additional therapeutic agent is a compound disclosed in WO2016141035. In some embodiments, the additional therapeutic agent is a compound disclosed in WO2021252818. In some embodiments, the additional therapeutic agent is a compound disclosed in WO2021252822. In some embodiments, the additional therapeutic agent is a compound disclosed in WO2021252820. In some embodiments, the additional therapeutic agent is a compound disclosed in WO2020072835. In some embodiments, the additional therapeutic agent is a compound disclosed in WO2022036297.

In another embodiment, the additional therapeutic agent is a sodium channel inhibitor (also known as a sodium channel blocker), such as the $Na_V1.7$ and $Na_V1.8$ blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

Synthesis of the Compounds of the Invention

The compounds of the invention can be prepared from known materials by the methods described in the Examples, other similar methods, and other methods known to one skilled in the art. As one skilled in the art would appreciate, the functional groups of the intermediate compounds in the methods described below may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, as described herein, including all embodiments thereof, except that one or more atoms has been replaced with a radioisotope of the atom present in the compounds of the invention.

As used herein, the term "radioisotope" refers to an isotope of an element that is known to undergo spontaneous radioactive decay. Examples of radioisotopes include $^3H$, $^{14}C$, $^{32}P$, $^{35}S$, $^{18}F$, $^{36}Cl$, and the like, as well as the isotopes for which a decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium ($^3H$)- and/or carbon-14 ($^{14}C$)-labeled compounds may be useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

ENUMERATED EMBODIMENTS

Further embodiments of the disclosure are set out in the following numbered clauses:

1. A compound of formula (I)

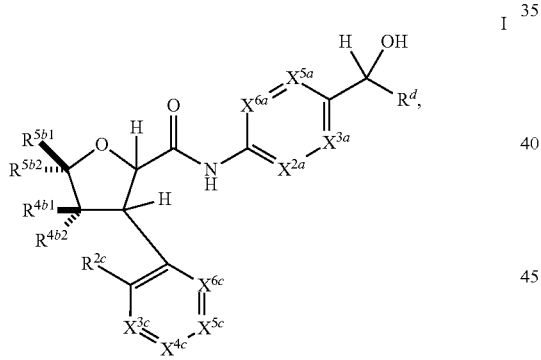

or a pharmaceutically acceptable salt thereof, wherein:
$X^{2a}$ is N, $N^+$—$O^-$, or C—$R^{2a}$;
$X^{3a}$ is N or $N^+$—$O^-$;
$X^{5a}$ is N, $N^+$—$O^-$, or C—$R^{5a}$;
$X^{6a}$ is N, $N^+$—$O^-$, or C—$R^{6a}$;
$R^d$ is $(CH_2)_m(CHR^e)_n(CH_2)_pH$;
m, n, and p are each independently 0 or 1;
$R^e$ is H, OH, halo, $C_1$-$C_6$ alkoxy, or $C_1$-$C_6$ haloalkoxy;
$R^{2a}$ and $R^{6a}$ are each independently H, halo, $C_1$-$C_6$ alkyl, or $C_1$-$C_6$ haloalkyl;
$R^{5a}$ is H, halo, $CH_2OH$, $C_1$-$C_6$ alkyl, or $C_1$-$C_6$ haloalkyl;
$R^{4b1}$ and $R^{4b2}$ are each independently H, $C_1$-$C_6$ alkyl, $C_3$-$C_6$ cycloalkyl, or $C_1$-$C_6$ haloalkyl;
$R^{5b1}$ and $R^{5b2}$ are each independently H, $C_1$-$C_6$ alkyl, $C_3$-$C_6$ cycloalkyl, or $C_1$-$C_6$ haloalkyl;
$X^{3c}$ is N or C—$R^{3c}$;
$X^{4c}$ is N or C—$R^{4c}$;
$X^{5c}$ is N or C—$R^{5c}$;
$X^{6c}$ is N or C—$R^{6c}$;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;
$L^1$ is a bond or O;
$L^2$ is a bond or C1-$C_6$ alkylene;
$R^{3c}$ is H, halo, $C_1$-$C_6$ alkyl, or $C_1$-$C_6$ haloalkyl; or $X^{3c}$ is C—$R^{3c}$, and $R^{2c}$ and $R^{3c}$, together with the carbon atoms to which they are attached, form a ring of formula:

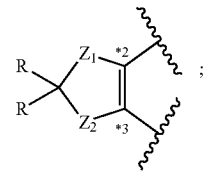

$Z_1$ and $Z_2$ are each independently O or $CH_2$;
each R is independently H or halo;
$R^{4c}$ is H, halo, $C_1$-$C_6$ alkyl, $C_1$-$C_6$ haloalkyl, $C_1$-$C_6$ alkoxy, or $C_1$-$C_6$ haloalkoxy;
$R^{5c}$ is H, halo, $C_1$-$C_6$ alkyl, or $C_1$-$C_6$ haloalkyl; and
$R^{6c}$ is H, halo, $C_1$-$C_6$ alkyl, or $C_1$-$C_6$ haloalkyl; provided that no more than two of $X^{2a}$, $X^{3a}$, $X^{5a}$, and $X^{6a}$ are N or $N^+$—$O^-$; and provided that no more than one of $X^{3c}$, $X^{4c}$, $X^{5c}$, and $X^{6c}$ is N.

2. The compound of clause 1, wherein the compound has formula (I-A)

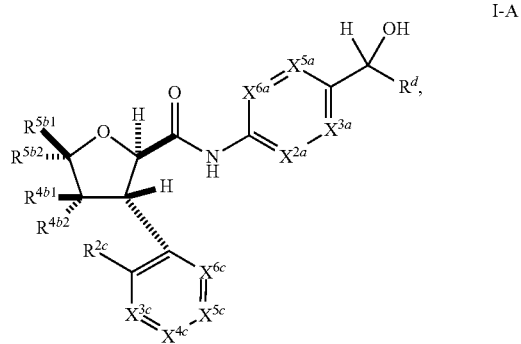

or a pharmaceutically acceptable salt thereof.

3. The compound of clause 1, wherein the compound has formula (I-A-1)

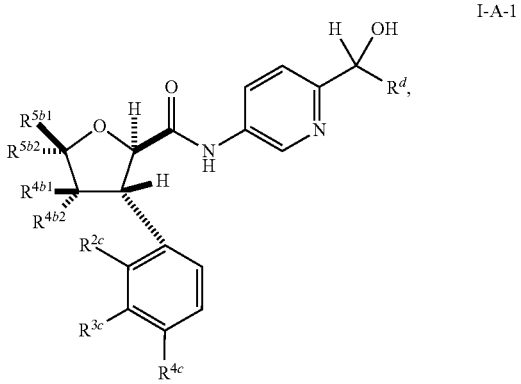

or a pharmaceutically acceptable salt thereof.

4. The compound of clause 1, wherein the compound has formula (I-B)

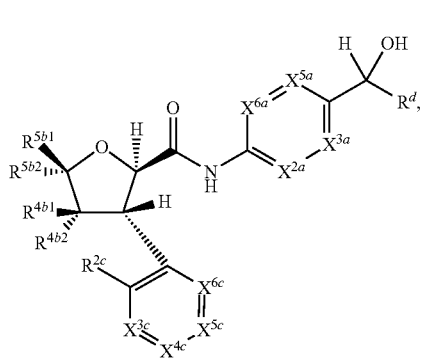

I-B or a pharmaceutically acceptable salt thereof.

5. The compound of clause 1, wherein the compound has formula (I-B-1)

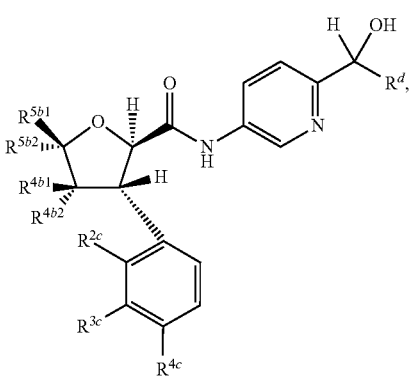

I-B-1 or a pharmaceutically acceptable salt thereof.

6. The compound of any one of clauses 1, 2, and 4, or a pharmaceutically acceptable salt thereof, wherein $X^{2a}$ is C—$R^{2a}$; and $R^{2a}$ is H.

7. The compound of any one of clauses 1, 2, 4, and 6, or a pharmaceutically acceptable salt thereof, wherein $X^{3a}$ is N.

8. The compound of any one of clauses 1, 2, 4, and 6, or a pharmaceutically acceptable salt thereof, wherein $X^{3a}$ is $N^+$—$O^-$.

9. The compound of any one of clauses 1, 2, 4, and 6-8, or a pharmaceutically acceptable salt thereof, wherein $X^{5a}$ is N or C—$R^{5a}$; and $R^{5a}$ is H, halo, or $CH_2OH$.

10. The compound of clause 9, or a pharmaceutically acceptable salt thereof, wherein $X^{5a}$ is N.

11. The compound of clause 9, or a pharmaceutically acceptable salt thereof, wherein $X^{5a}$ is C—$R^{5a}$; and $R^{5a}$ is H, F, or $CH_2OH$.

12. The compound of any one of clauses 1, 2, 4, and 6-11, or a pharmaceutically acceptable salt thereof, wherein $X^{6a}$ is N or C—$R^{6a}$; and $R^{6a}$ is H.

13. The compound of clause 12, or a pharmaceutically acceptable salt thereof, wherein $X^{6a}$ is C—$R^{6a}$; and $R^{6a}$ is H.

14. The compound of any one of clauses 1-13, or a pharmaceutically acceptable salt thereof, wherein $R^{4b1}$ is H or $C_1$-$C_6$ alkyl.

15. The compound of clause 14, or a pharmaceutically acceptable salt thereof, wherein $R^{4b1}$ is H or $CH_3$.

16. The compound of any one of clauses 1-15, or a pharmaceutically acceptable salt thereof, wherein $R^{4b2}$ is H or $C_1$-$C_6$ alkyl.

17. The compound of clause 16, or a pharmaceutically acceptable salt thereof, wherein $R^{4b2}$ is H or $CH_3$.

18. The compound of any one of clauses 1-17, or a pharmaceutically acceptable salt thereof, wherein $R^{5b1}$ is $C_1$-$C_6$ alkyl or $C_1$-$C_6$ haloalkyl.

19. The compound of clause 18, or a pharmaceutically acceptable salt thereof, wherein $R^{5b1}$ is $CH_3$ or $CF_3$.

20. The compound of any one of clauses 1-19, or a pharmaceutically acceptable salt thereof, wherein $R^{5b2}$ is $C_1$-$C_6$ alkyl or $C_1$-$C_6$ haloalkyl.

21. The compound of clause 20, or a pharmaceutically acceptable salt thereof, wherein $R^{5b2}$ is $CH_3$ or $CF_3$.

22. The compound of any one of clauses 1-21, or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy.

23. The compound of clause 22, or a pharmaceutically acceptable salt thereof, wherein $R^{2c}$ is OH, Cl, $CH_3$, $OCH_3$, $OCD_3$, $OCH_2CH_3$, $OCH(CH_3)_2$, $OCH_2CH_2F$, or $OCH_2CHF_2$.

24. The compound of any one of clauses 1-23, or a pharmaceutically acceptable salt thereof, wherein $X^{3c}$ is N or C—$R^{3c}$; and $R^{3c}$ is H, halo, $C_1$-$C_6$ alkyl, or $C_1$-$C_6$ haloalkyl.

25. The compound of clause 24, or a pharmaceutically acceptable salt thereof, wherein $X^{3c}$ is N.

26. The compound of clause 24, or a pharmaceutically acceptable salt thereof, wherein $X^{3c}$ is C—$R^{3c}$; and $R^{3c}$ is H, F, $CH_3$, $CHF_2$, or $CF_3$.

27. The compound of any one of clauses 1-23, or a pharmaceutically acceptable salt thereof, wherein $X^{3c}$ is C—$R^{3c}$; and $R^{2c}$ and $R^{3c}$, together with the carbon atoms to which they are attached, form a ring of formula:

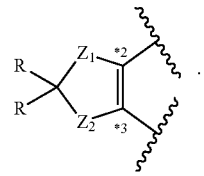

28. The compound of clause 27, or a pharmaceutically acceptable salt thereof, wherein the ring is of formula:

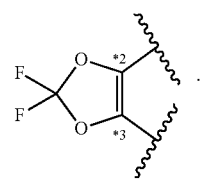

29. The compound of any one of clauses 1-28, or a pharmaceutically acceptable salt thereof, wherein $X^{4c}$ is C—$R^{4c}$; and $R^{4c}$ is H, halo, $C_1$-$C_6$ haloalkyl, $C_1$-$C_6$ alkoxy, or $C_1$-$C_6$ haloalkoxy.

30. The compound of clause 29, or a pharmaceutically acceptable salt thereof, wherein $X^{4c}$ is C—$R^{4c}$; and $R^{4c}$ is H, F, $CHF_2$, $OCH_2CH_3$, $OCHF_2$, $OCF_3$.
31. The compound of any one of clauses 1-30, or a pharmaceutically acceptable salt thereof, wherein $X^{5c}$ is C—$R^{5c}$; and $R^{5c}$ is H.
32. The compound of any one of clauses 1-31, or a pharmaceutically acceptable salt thereof, wherein $X^{6c}$ is C—$R^{6c}$; and $R^{6c}$ is H.
33. The compound of any one of clauses 1-32, or a pharmaceutically acceptable salt thereof, wherein $R^d$ is $(CH_2)_pH$.
34. The compound of clause 33, or a pharmaceutically acceptable salt thereof, wherein $R^d$ is H or $CH_3$.
35. The compound of any one of clauses 1-32, or a pharmaceutically acceptable salt thereof, wherein $R^d$ is $(CHR^e)_n(CH_2)_pH$.
36. The compound of clause 35, or a pharmaceutically acceptable salt thereof, wherein $R^d$ is $CH_2F$, $CH_2OH$, or $CH(OH)CH_3$.
37. The compound of any one of clauses 1-32, or a pharmaceutically acceptable salt thereof, wherein $R^d$ is $(CH_2)_m(CHR^e)_nH$.
38. The compound of clause 37, or a pharmaceutically acceptable salt thereof, wherein $R^d$ is $CH_2OCH_3$ or $CH_2CH_2OCH_3$.
39. A compound selected from Table A, or a pharmaceutically acceptable salt thereof.
40. The compound of any one of clauses 1-39 in non-salt form.
41. A pharmaceutical composition comprising a therapeutically effective amount of the compound of any one of clauses 1-39, or a pharmaceutically acceptable salt thereof, or the compound of clause 40 and one or more pharmaceutically acceptable carriers or vehicles.
42. A pharmaceutical composition comprising the compound of any one of clauses 1-39, or a pharmaceutically acceptable salt thereof, or the compound of clause 40 and one or more pharmaceutically acceptable carriers or vehicles.
43. A method of inhibiting a voltage-gated sodium channel in a subject comprising administering to the subject the compound of any one of clauses 1-39, or a pharmaceutically acceptable salt thereof, the compound of clause 40, or the pharmaceutical composition of clause 41 or 42.
44. The method of clause 43, wherein the voltage-gated sodium channel is $Na_V1.8$.
45. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of any one of clauses 1-39, or a pharmaceutically acceptable salt thereof, the compound of clause 40, or the pharmaceutical composition of clause 41 or 42.
46. The method of clause 45, where the method comprises treating or lessening the severity in the subject of neuropathic pain.
47. The method of clause 46, wherein the neuropathic pain comprises post-herpetic neuralgia.
48. The method of clause 46, wherein the neuropathic pain comprises small-fiber neuropathy.
49. The method of clause 46, wherein the neuropathic pain comprises idiopathic small-fiber neuropathy.
50. The method of clause 46, wherein the neuropathic pain comprises diabetic neuropathy.
51. The method of clause 50, wherein the diabetic neuropathy comprises diabetic peripheral neuropathy.
52. The method of clause 45, wherein the method comprises treating or lessening the severity in the subject of musculoskeletal pain.
53. The method of clause 52, wherein the musculoskeletal pain comprises osteoarthritis pain.
54. The method of clause 45, wherein the method comprises treating or lessening the severity in the subject of acute pain.
55. The method of clause 54, wherein the acute pain comprises acute post-operative pain.
56. The method of clause 45, wherein the method comprises treating or lessening the severity in the subject of postsurgical pain.
57. The method of clause 56, wherein the postsurgical pain comprises bunionectomy pain.
58. The method of clause 56, wherein the postsurgical pain comprises abdominoplasty pain.
59. The method of clause 56, wherein the postsurgical pain comprises herniorrhaphy pain.
60. The method of clause 45, wherein the method comprises treating or lessening the severity in the subject of visceral pain.
61. The method of any one of clauses 43-60, wherein said subject is treated with one or more additional therapeutic agents administered concurrently with, prior to, or subsequent to treatment with the compound, pharmaceutically acceptable salt, or pharmaceutical composition.
62. Use of the compound of any one of clauses 1-39, or a pharmaceutically acceptable salt thereof, the compound of clause 40, or the pharmaceutical composition of clause 41 or 42, as a medicament.

EXAMPLES

General methods. $^1H$ NMR spectra were obtained as solutions in an appropriate deuterated solvent such as dimethyl sulfoxide-$d_6$ (DMSO-d6).

Compound purity, retention time, and electrospray mass spectrometry (ESI-MS) data were determined by LC/MS analysis.

LC/MS Method: LC/MS analysis was conducted using an Acquity UPLC BEH $C_8$ column (50×2.1 mm, 1.7 m particle) made by Waters (pn: 186002877) with a (2.1×5 mm, 1.7 μm particle) guard column (pn: 186003978), and a dual gradient run from 2-98% mobile phase B over 4.45 minutes. Mobile phase A=$H_2O$ (10 mM ammonium formate with 0.05% ammonium hydroxide). Mobile phase B=acetonitrile. Flow rate=0.6 mL/min, injection volume=2 μL, and column temperature=45° C.

X-ray powder diffraction analysis Method A: X-ray powder diffraction (XRPD) analysis was performed at room temperature in transmission mode using a PANalytical Empyrean system equipped with a sealed tube source and a PIXcel 1D Medipix-2 detector (Malvern PANalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 5° to about 40° 2θ with a step size of 0.0131303° and 8.67 s×5 (wobbled omega=0, ±1, ±2) per step.

X-ray powder diffraction analysis Method B: X-ray powder diffraction (XRPD) analysis was performed at room temperature in transmission mode using a PANalytical Empyrean system equipped with a sealed tube source and a PIXcel 3D Medipix-3 detector (Malvern PANalytical Inc, Westborough, Mass.). The X-Ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40° 2θ with a step size of 0.01313030 and 49 s per step.

ABBREVIATIONS

Unless otherwise noted, or where the context dictates otherwise, the following abbreviations shall be understood to have the following meanings:

| Abbreviation | Meaning |
|---|---|
| NMR | Nuclear magnetic resonance |
| ESI-MS | Electrospray mass spectrometry |
| LC/MS | Liquid chromatography-mass spectrometry |
| UPLC | Ultra performance liquid chromatography |
| HPLC/MS/MS | High performance liquid chromatography/tandem mass spectrometry |
| IS | Internal standard |
| HPLC | High performance liquid chromatography |
| SFC | Supercritical fluid chromatography |
| ESI | Electrospray ionization |
| g | Grams |
| mg | Milligrams |
| kg | Kilograms |
| L | Liter(s) |
| mL | Milliliters |
| μL | Microliters |
| nL | Nanoliters |
| mol | Moles |
| mmol | Millimoles |
| hr, h | Hours |
| min | Minutes |
| ms | Millisecond |
| mm | Millimeters |
| μm | Micrometers |
| nm | Nanometer |
| MHz | Megahertz |
| Hz | Hertz |
| N | Normal (concentration) |
| M | Molar (concentration) |
| mM | Millimolar (concentration) |
| μM | Micromolar (concentration) |
| ppm | Parts per million |
| % w/v | Weight-volume concentration |
| % w/w | Weight-weight concentration |
| t-BuOH | Tert-butyl alcohol |
| CDI | 1,1′-Carbonyl diimidazole |
| DAST | Diethylaminosulfur trifluoride |
| DCM | Dichloromethane |
| DCE | Dichloroethane |
| DIEA, DIPEA | N,N-Diisopropyl ethyl amine |
| DMA | N,N-Dimethylacetamide |
| DMAP | N,N-Dimethylaminopyridine |
| DMF | N,N-Dimethylformamide |
| DMSO | Dimethyl sulfoxide |
| DRG | Dorsal root ganglia |
| EDC•HCl | Ethyl carbodiimide hydrochloride |
| EtOH | Ethanol |
| EtOAc | Ethyl acetate |
| HATU | 1-[Bis(dimethylamino)methylene]-1H-1,2,3-triazolo[4,5-b]pyridinium 3-Oxide hexafluorophosphate |
| HOBt | Hydroxybenzotriazole |
| EDCl | 1-Ethyl-3-(3-dimethylaminopropyl)carbodiimide |
| T3P | Propylphosphonic anhydride, i.e., 2,4,6-tripropyl-1,3,5,2,4,6-trioxatriphosphinane 2,4,6-trioxide |
| KOAc | Potassium acetate |
| m-CPBA | Meta-chloroperoxybenzoic acid |
| MeOH | Methanol |
| MTBE | Methyl tert-butyl ether |
| NaOH | Sodium hydroxide |
| NBS | N-Bromosuccinimide |
| NMP | N-Methylpyrrolidone |
| NMO | N-Methylmorpholine N-oxide |
| PPTS | Pyridinium para-toluene sulfonate |
| TBAB | Tetra-n-butylammonium bromide |
| TBAF | Tetra-n-butylammonium fluoride |
| TBSCl | Tert-butyldimethylsilyl chloride |
| TBSOTf | Tert-butyldimethylsilyl trifluoromethanesulfonate |
| THF | Tetrahydrofuran |
| TEA | Triethylamine |
| TFA | Trifluoroacetic acid |
| RB | Round bottom (flask) |
| RT | Room temperature |
| ca. | Circa (approximately) |
| E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-Hydroxyethyl)piperazin-1-yl]ethanesulfonic acid |
| DiSBAC$_6$(3) | Bis-(1,3-dihexyl-thiobarbituric acid) trimethine oxonol |
| CC2-DMPE | Chlorocoumarin-2-dimyristoyl phosphatidylethanolamine |
| VABSC-1 | Voltage Assay Background Suppression Compound |
| HS | Human serum |
| BSA | Bovine Serum Albumin |

Example 1

(2R,3S,4S,5R)-3-(3,4-difluoro-2-methoxyphenyl)-N-(6-((R)-1,2-dihydroxyethyl)pyridin-3-yl)-4,5-dimethyl-5-(trifluoromethyl)tetrahydrofuran-2-carboxamide (1)

(2R,3S,4S,5R)-3-(3,4-difluoro-2-methoxyphenyl)-N-(6-((S)-1,2-dihydroxyethyl)pyridin-3-yl)-4,5-dimethyl-5-(trifluoromethyl)tetrahydrofuran-2-carboxamide (2)

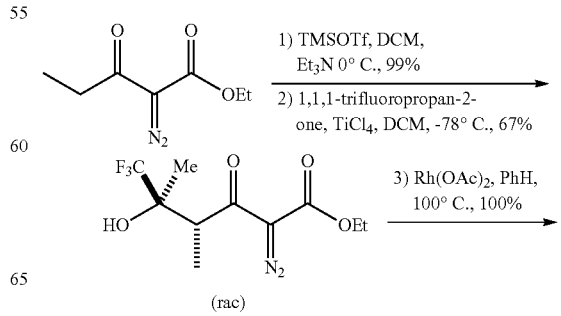

-continued
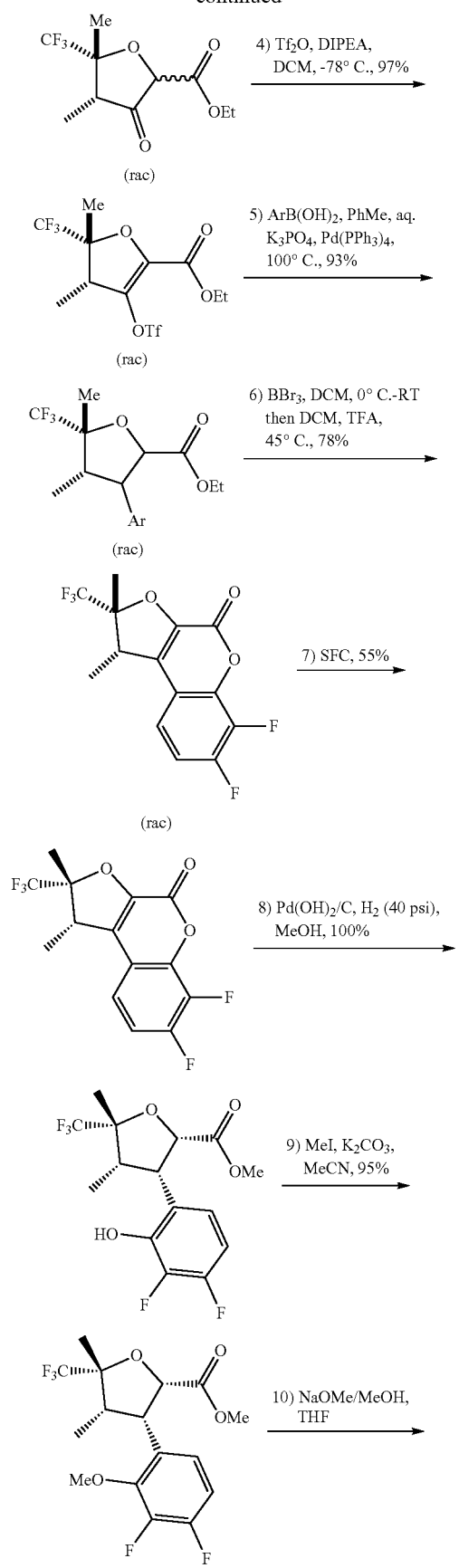
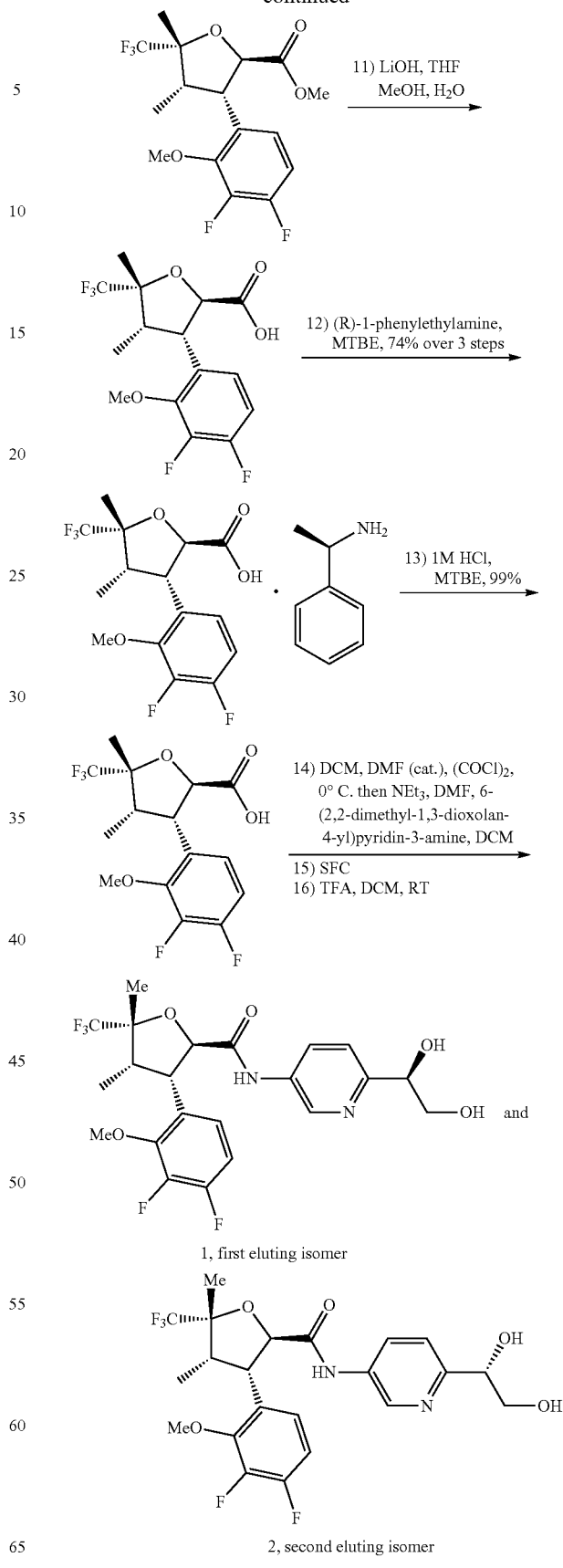
1, first eluting isomer
and
2, second eluting isomer Step 1:

NEt$_3$ (7.7 mL, 55.2 mmol) was added to a solution of ethyl 2-diazo-3-oxo-pentanoate (6.69 g, 39.3 mmol) in DCM (80 mL) with stirring at 0° C. under nitrogen. Trimethylsilyl trifluoromethanesulfonate (8.5 mL, 47.0 mmol) was added dropwise over 5 min and the mixture was stirred for a further 30 min at 0° C. The reaction mixture was diluted with pentane (100 mL), the layers separated and the organic phase washed with dilute aqueous sodium bicarbonate (100 mL) and brine (100 mL). The organic layer was dried (MgSO$_4$), and concentrated in vacuo to give ethyl (Z)-2-diazo-3-trimethylsilyloxy-pent-3-enoate (9.4 g, 99%) as a red oil. $^1$H NMR (500 MHz, Chloroform-d) δ 5.33 (q, J=7.0 Hz, 1H), 4.25 (q, J=7.1 Hz, 2H), 1.67 (d, J=7.0 Hz, 3H), 1.29 (t, J=7.1 Hz, 3H), 0.22 (s, 9H) ppm.

Step 2:

To a stirred solution of 1,1,1-trifluoropropan-2-one (8 mL, 89.4 mmol) in DCM (80 mL) at −78° C. was added TiCl$_4$ (70 mL of 1 M in DCM, 70.00 mmol) via cannula. To the resulting solution, a solution of ethyl (Z)-2-diazo-3-trimethylsilyloxy-pent-3-enoate (36.1 g of 31.3% w/w, 46.6 mmol) in DCM (40 mL) was added dropwise over 15 min. After stirring for 100 min, the reaction was carefully quenched with water, allowing the temperature to rise slowly, and then extracted with DCM. The combined organic layers were dried (MgSO$_4$), filtered, and concentrated in vacuo. Purification by silica gel chromatography (330 g SiO$_2$, 0 to 20% EtOAc in heptane) gave ethyl rac-(4R,5R)-2-diazo-6,6,6-trifluoro-5-hydroxy-4,5-dimethyl-3-oxohexanoate (8.82 g, 67%) as the main diastereoisomer, which was stored as a solution in toluene. $^1$H NMR (500 MHz, Chloroform-d) δ 4.33 (q, J=7.1 Hz, 2H), 4.14 (q, J=7.0 Hz, 1H), 3.98 (s, 1H), 1.43 (q, J=1.2 Hz, 3H), 1.35 (t, J=7.1 Hz, 3H), 1.31 (dq, J=7.0, 1.4 Hz, 3H) ppm. ESI-MS m/z calc. 282.08273, found 283.1 (M+1)$^+$; 281.0 (M−1)$^-$.

Step 3:

A solution of rhodium tetraacetate (245 mg, 0.55 mmol) in benzene (32 mL) was heated at reflux for 10 min before a solution of ethyl rac-(4R,5R)-2-diazo-6,6,6-trifluoro-5-hydroxy-4,5-dimethyl-3-oxohexanoate (10 g, 35.4 mmol) in benzene (13 mL) was added slowly via addition funnel while refluxing for 60 min. The mixture was concentrated in vacuo to give ethyl rac-(4R,5R)-4,5-dimethyl-3-oxo-5-(trifluoromethyl)tetrahydrofuran-2-carboxylate (9.0 g, 100%) as a green coloured residue containing residual catalyst, and as a mixture of epimers at the position next to the ester. This material was used without further purification in the next step. $^1$H NMR (500 MHz, Chloroform-d) δ 4.83-4.57 (m, 1H), 4.38-4.16 (m, 2H), 2.60 (dddd, J=9.3, 8.2, 5.6, 1.4 Hz, 1H), 1.73-1.63 (m, 3H), 1.30 (t, J=7.1 Hz, 3H), 1.24 (ddq, J=6.4, 4.1, 1.9 Hz, 3H) ppm.

Step 4:

To a stirred solution of ethyl rac-(4R,5R)-4,5-dimethyl-3-oxo-5-(trifluoromethyl)tetrahydrofuran-2-carboxylate (48 g, 188.83 mmol) in DCM (400 mL) at −78° C. was added DIPEA (29.680 g, 40 mL, 229.64 mmol). A solution of trifluoromethylsulfonyl trifluoromethanesulfonate (53.440 g, 32 mL, 189.41 mmol) in DCM (200 mL) was added to the reaction mixture at the same temperature over 1 h. The reaction mixture was stirred for 30 min at 0° C. before being quenched with 100 mL saturated aqueous NaHCO$_3$ solution. The organic layer was separated and aqueous layer extracted with DCM (160 mL). The combined organic layers were dried (MgSO$_4$) and concentrated in vacuo to give ethyl rac-(4R,5R)-2,3-dimethyl-2-(trifluoromethyl)-4-(trifluoromethylsulfonyloxy)-3H-furan-5-carboxylate (71 g, 97%). $^1$H NMR (400 MHz, Chloroform-d) δ 4.38-4.32 (m, 2H), 3.29-3.23 (m, 1H), 1.64 (s, 3H), 1.37-1.33 (m, 6H) ppm.

Step 5:

To stirred a solution of ethyl rac-(4R,5R)-2,3-dimethyl-2-(trifluoromethyl)-4-(trifluoromethylsulfonyloxy)-3H-furan-5-carboxylate (26 g, 67.311 mmol) in toluene (130.00 mL) was added (3,4-difluoro-2-methoxy-phenyl)boronic acid (14 g, 74.5 mmol) followed by K$_3$PO$_4$ (100 mL of 2 M, 200.00 mmol) under an argon atmosphere. The reaction was degassed before tetrakis(triphenylphosphine)palladium (0) (4 g, 3.46 mmol) was added. After further degassing, the reaction was heated at 100° C. for 2 h. The reaction was diluted in water and the aqueous layer extracted with EtOAc (2×100 mL). The combined organic layers were concentrated in vacuo. Purification by silica gel chromatography (SiO$_2$, 0 to 10% EtOAc in heptane) gave ethyl 4-(3,4-difluoro-2-methoxy-phenyl)-2,3-dimethyl-2-(trifluoromethyl)-3H-furan-5-carboxylate (24.4 g, 93%) as a 6:1 diastereomeric mixture, with the major isomer believed to be ethyl rac-(4S,5R)-4-(3,4-difluoro-2-methoxyphenyl)-2,3-dimethyl-2-(trifluoromethyl)-3H-furan-5-carboxylate. Major isomer: $^1$H NMR (400 MHz, Chloroform-d) δ 6.88-6.79 (m, 2H), 4.17-4.09 (m, 2H), 3.90 (s, 3H), 3.46 (q, J=7.4 Hz, 1H), 1.67 (s, 3H), 1.12 (t, J=7.4 Hz, 3H), 1.06 (dd, J=5.4, 2.7 Hz, 3H) ppm. Minor isomer: $^1$H NMR (400 MHz, Chloroform-d) δ 6.88-6.79 (m, 2H), 4.17-4.09 (m, 2H), 3.88 (s, 3H), 3.76-3.71 (m, 1H), 1.51 (s, 3H), 1.12 (t, J=7.4 Hz, 3H), 0.99 (dd, J=5.4, 2.7 Hz, 3H) ppm. ESI-MS m/z calc. 380.1047, found 381.02 (M+1)$^+$.

Step 6:

To an ice-cooled solution of ethyl rac-(4S,5R)-4-(3,4-difluoro-2-methoxyphenyl)-2,3-dimethyl-2-(trifluoromethyl)-3H-furan-5-carboxylate (110 g, 243.0 mmol) in DCM (360 mL) was added BBr$_3$ (370 mL of 1 M, 370.0 mmol) dropwise. Upon addition completion, the mixture was quenched by addition of water and aqueous sodium bicarbonate solution. The aqueous layer was extracted with DCM and the combined organic layers were dried (MgSO$_4$), filtered and concentrated in vacuo. The residue was dissolved in DCM (430 mL) at ambient temperature and TFA (40 mL, 519.2 mmol) was added. The reaction was heated to 45° C. Upon reaction completion, the mixture was quenched by addition of aqueous sodium bicarbonate solution and the aqueous layer extracted with DCM, dried (MgSO$_4$), filtered and concentrated in vacuo to give the desired product in a 5:1 mixture of diastereomers. Recrystallization was carried out by solubilizing the crude material in the smallest possible amount of DCM and adding a layer of heptane on top of this solution (liquid-liquid diffusion). After approximately 1 h, 56.5 g (d.r. 97:3 syn:anti) from the first and second crystallization was obtained, and a further 4.6 g (d.r. 96:4 syn:anti) from the third crystallization was obtained. The first to third batches were combined to give 6,7-difluoro-1,2-dimethyl-2-(trifluoromethyl)-1H-furo[2,3-c]chromen-4-one (61 g, 78%), with the major isomer believed to be rac-(1S,2R)-6,7-difluoro-1,2-dimethyl-2-(trifluoromethyl)-1,2-dihydro-4H-furo[2,3-c]chromen-4-one. ESI-MS m/z calc. 320.04718, found 321.5 (M+1)$^+$; 319.6 (M−1)$^-$.

Step 7:

rac-(1S,2R)-6,7-difluoro-1,2-dimethyl-2-(trifluoromethyl)-1,2-dihydro-4H-furo[2,3-c]chromen-4-one (1348 g, 4.366 mol) was separated by chiral SFC using a (R,R)-Whelk-01 column, 5 m particle size, 15 cm×3 cm from Regis Technologies on a MultiGram III SFC instrument from Berger Instruments using a mobile phase made up of MeOH (containing 5 mM ammonia) and CO$_2$ to give:

First Eluting Isomers (rt=1.85 min): (1R,2S)-6,7-difluoro-1,2-dimethyl-2-(trifluoromethyl)-1,2-dihydro-4H-furo[2,3-c]chromen-4-one (only an analytical sample was collected).

¹H NMR (400 MHz, DMSO-d₆) δ 7.57 (ddd, J=9.0, 5.5, 2.0 Hz, 1H), 7.51 (ddd, J=10.3, 9.0, 7.0 Hz, 1H), 4.03 (q, J=7.2 Hz, 1H), 1.65 (s, 3H), 1.45 (dt, J=6.9, 2.2 Hz, 3H) ppm. ESI-MS m/z calc. 320.04718, found 321.3 (M+1); 319.4 (M−1)⁻.

Second Eluting Isomer (rt=2.38 min): (1S,2R)-6,7-Difluoro-1,2-dimethyl-2-(trifluoromethyl)-1,2-dihydro-4H-furo[2,3-c]chromen-4-one (366.99 g, 26%). ¹H NMR (400 MHz, DMSO-d₆) δ 7.57 (ddd, J=9.0, 5.5, 2.0 Hz, 1H), 7.50 (ddd, J=10.3, 9.0, 7.0 Hz, 1H), 4.03 (q, J=7.2 Hz, 1H), 1.65 (s, 3H), 1.45 (dt, J=6.9, 2.2 Hz, 3H) ppm. ESI-MS m/z calc. 320.04518, found 321.4 (M+1)⁺; 319.4 (M−1)⁻.

Step 8:

A solution of (1S,2R)-6,7-Difluoro-1,2-dimethyl-2-(trifluoromethyl)-1,2-dihydro-4H-furo[2,3-c]chromen-4-one (0.89 kg, 2.78 mol) and 20% palladium hydroxide on carbon (50% wet, 0.39 kg, 0.278 mol) in MeOH (12 L) was stirred under a 40 psi pressure of hydrogen overnight. An increase in the reaction temperature to 37° C. was observed after reacting overnight and the mixture was cooled to 24° C. The hydrogenation was continued for a total of 48 h. The mixture was filtered through celite, washing with MeOH (20 L) and the filtrates were concentrated in vacuo. The residue was dissolved in toluene (4 L) and concentrated in vacuo, and this process repeated. The residue was dried under vacuum at 40° C. overnight to give methyl (2S,3S,4S,5R)-3-(3,4-difluoro-2-hydroxyphenyl)-4,5-dimethyl-5-(trifluoromethyl)tetrahydrofuran-2-carboxylate (1.0 kg at 91% purity, 100%) as a beige solid. ¹H NMR (400 MHz, DMSO-d₆) 10.20 (br s, 1H), 6.94 (br t, J=7.4 Hz, 1H), 6.79-6.69 (m, 1H), 5.10 (d, J=6.0 Hz, 1H), 4.20 (dd, J=6.1, 8.2 Hz, 1H), 3.43 (s, 3H), 2.94 (quin, J=7.7 Hz, 1H), 1.46 (s, 3H), 0.77 (br d, J=6.8 Hz, 3H) ppm.

Step 9:

Potassium carbonate (2.0 kg, 14.4 mol) and iodomethane (800 mL, 12.8 mol) were sequentially added to a solution of methyl (2S,3S,4S,5R)-3-(3,4-difluoro-2-hydroxyphenyl)-4,5-dimethyl-5-(trifluoromethyl)tetrahydrofuran-2-carboxylate (1.0 kg, 2.82 mol) in acetonitrile (10 L) under nitrogen stirring at ambient temperature. After stirring overnight, additional iodomethane (120 mL, 2 mmol) was added. After stirring overnight, additional iodomethane (60 mL, 0.85 mmol) was added and the mixture was stirred for a further 3 days. The reaction mixture was diluted with MTBE (30 L), treated with celite (1 kg) and filtered through a bed of celite (1 kg) washing with MTBE (10 L). The filtrate was filtered a second time through celite (1 kg) washing with MTBE (4 L) and the filtrate concentrated in vacuo. The residue was dissolved in toluene (4 L) and concentrated in vacuo, and this process repeated. The residue was dried under vacuum at 40° C. overnight to give methyl (2S,3S,4S,5R)-3-(3,4-difluoro-2-methoxyphenyl)-4,5-dimethyl-5-(trifluoromethyl)tetrahydrofuran-2-carboxylate (0.99 kg at 90% purity, 95%) as a brown solid. ¹H NMR (400 MHz, DMSO-d₆) 7.14-7.00 (m, 2H), 5.14 (d, J=6.0 Hz, 1H), 4.15 (dd, J=6.2, 8.4 Hz, 1H), 3.88 (d, J=1.7 Hz, 3H), 2.97 (quin, J=7.8 Hz, 1H), 1.48 (s, 3H), 0.72 (br d, J=6.6 Hz, 3H) ppm.

Steps 10 and 11:

Sodium methoxide (25% in methanol, 65 mL, 0.28 mol) was added to a solution of methyl (2S,3S,4S,5R)-3-(3,4-difluoro-2-methoxyphenyl)-4,5-dimethyl-5-(trifluoromethyl) tetrahydrofuran-2-carboxylate (0.98 kg, 2.66 mol) in THF (10 L) stirring at ambient temperature under nitrogen. After 5 h, MeOH (1 L), water (1 L) and lithium hydroxide monohydrate (0.168 kg, 4.0 mol) were sequentially added and the mixture was stirred overnight. The reaction mixture was poured into 1M HCl (4.4 L, 4.4 mol) then extracted with MTBE (20 L). The aqueous layer was further extracted with MTBE (2×5 L), and the combined organic layers were washed with brine (2 L), dried (Na₂SO₄), filtered, and then treated with activated carbon (50 g, 5% w/w) with stirring for 1 h. The mixture was filtered through celite, washing with MTBE (2×4 L), and the filtrate was concentrated in vacuo. The residue was dissolved in toluene (4 L) and concentrated in vacuo, then dissolved in MTBE (4 L) and concentrated in vacuo again to give (2R,3S,4S,5R)-3-(3,4-difluoro-2-methoxyphenyl)-4,5-dimethyl-5-(trifluoromethyl)tetrahydrofuran-2-carboxylic acid (1.06 kg at 77.7% purity) as an amber oil, which was used without further purification.

Step 12:

Crude (2R,3S,4S,5R)-3-(3,4-difluoro-2-methoxyphenyl)-4,5-dimethyl-5-(trifluoromethyl)tetrahydrofuran-2-carboxylic acid (2.09 kg at 77% purity, 4.54 mol) was dissolved in MTBE (25 L) in a 100 L Chemglass reactor then stirred at 84 rpm at ambient temperature. A mixture of (R)-1-phenylethylamine (0.704 kg, 5.81 mol) and MTBE (2 L) was added to the reactor, followed by additional MTBE to give a total volume of 30 L in the reactor. After 2 h, additional MTBE (2 L) was added to the reaction. After a total of 3.5 h, the mixture was filtered, washing with MTBE (2 L). The reactor was rinsed with MTBE (4 L), which was used to rinse the solids, which were then compressed and dried on the Buchner funnel for 2 h. The solid product cake was loosened then dried under a stream of nitrogen and under vacuum overnight on the Buchner funnel. The isolated solids were dried in a convection oven at 40° C. for 24 h to give (2R,3S,4S,5R)-3-(3,4-Difluoro-2-methoxyphenyl)-4,5-dimethyl-5-(trifluoromethyl)tetrahydrofuran-2-carboxylic acid (R)-1-phenylethan-1-amine salt (1.86 kg at 95.7% purity, 74% over 3 steps) as an off-white solid. ¹H NMR, 400 MHz, DMSO-d₆) 8.34 (br s, 2H), 7.46-7.41 (m, 2H), 7.36-7.27 (m, 3H), 7.16-7.11 (m, 1H), 7.10-7.03 (m, 1H), 4.58 (d, J=9.9 Hz, 1H), 4.23 (q, J=6.7 Hz, 1H), 3.99 (dd, J=7.8, 9.8 Hz, 1H), 3.90 (d, J=2.0 Hz, 3H), 2.60 (quin, J=7.5 Hz, 1H), 1.50 (s, 3H), 1.40 (d, J=6.7 Hz, 3H), 0.71-0.59 (m, 3H) ppm.

Step 13:

To a suspension of (2R,3S,4S,5R)-3-(3,4-difluoro-2-methoxy-phenyl)-4,5-dimethyl-5-(trifluoromethyl)tetrahydrofuran-2-carboxylic acid (1R)-1-phenylethanamine salt (10.6 g, 22.29 mmol) in MTBE (250 mL) was added HCl (200 mL of 2 M, 400.0 mmol). The layers were separated, and the organic layer was washed with water (200 mL), dried (MgSO₄), filtered, and concentrated in vacuo to give (2R,3S,4S,5R)-3-(3,4-difluoro-2-methoxy-phenyl)-4,5-dimethyl-5-(trifluoromethyl)tetrahydrofuran-2-carboxylic acid (8.4 g, 99%) as an oil. ¹H NMR (400 MHz, Chloroform-d) δ 6.96 (ddd, J=7.9, 5.6, 2.0 Hz, 1H), 6.88 (td, J=9.2, 7.3 Hz, 1H), 4.96 (d, J=10.5 Hz, 1H), 4.15 (dd, J=10.5, 8.0 Hz, 1H), 4.02 (d, J=2.8 Hz, 3H), 2.74 (p, J=7.6 Hz, 1H), 1.64 (t, J=1.2 Hz, 3H), 0.79 (dq, J=7.4, 2.3 Hz, 3H) ppm.

Steps 14 and 15:

Oxalyl chloride (738 μL, 8.460 mmol) was added dropwise to a solution of (2R,3S,4S,5R)-3-(3,4-difluoro-2-methoxy-phenyl)-4,5-dimethyl-5-(trifluoromethyl)tetrahydrofuran-2-carboxylic acid (1.5 g, 4.234 mmol) and DMF (31 μL, 0.4004 mmol) in dichloromethane (10 mL). After stirring for 30 min at ambient temperature, the solution was concentrated in vacuo. The residue was re-dissolved in dichloromethane (10 mL), and a mixture of rac-6-(2,2-Dimethyl-1,3-dioxolan-4-yl)pyridin-3-amine (904 mg, 4.654 mmol) and triethylamine (706 μL, 5.065 mmol) was. The mixture was stirred at ambient temperature for 1 h. The reaction mixture was partitioned between ethyl acetate (30 mL) and water (30 mL). The aqueous layer was further extracted with EtOAc (50 mL). The combined organic extracts were washed with brine (1×20 mL), dried (MgSO$_4$), filtered, and concentrated in vacuo. Purification by reverse phase preparative HPLC (Waters Sunfire C18, 10 μM, 100 Å column, 0% to 100% MeCN in water containing 0.10% ammonia) gave after freeze-drying a mixture of the 2 diastereoisomers of (2R,3S,4S,5R)-3-(3,4-difluoro-2-methoxyphenyl)-N-(6-(2,2-dimethyl-1,3-dioxolan-4-yl)pyridin-3-yl)-4,5-dimethyl-5-(trifluoromethyl)tetrahydrofuran-2-carboxamide.

The mixture of the 2 diastereoisomers of (2R,3S,4S,5R)-3-(3,4-difluoro-2-methoxyphenyl)-N-(6-(2,2-dimethyl-1,3-dioxolan-4-yl)pyridin-3-yl)-4,5-dimethyl-5-(trifluoromethyl)tetrahydrofuran-2-carboxamide was separated by chiral SFC using a Chiralcel OJ-H column, 5 m particle size, 25 cm×10 mm from Daicel (Mobile phase: 12% MeOH (containing 20 mM Ammonia), 88% CO$_2$. Flow: 10 mL/min.) on a Minigram SFC instrument from Berger Instruments:

First Eluting Isomer (rt=2.99 min): (2R,3S,4S,5R)-3-(3,4-difluoro-2-methoxyphenyl)-N-(6-((R)-2,2-dimethyl-1,3-dioxolan-4-yl)pyridin-3-yl)-4,5-dimethyl-5-(trifluoromethyl)tetrahydrofuran-2-carboxamide (700 mg, 60%). ESI-MS m/z calc. 530.184, found 531.2 (M+1)$^+$; Retention time: 3.56 minutes.

Second Eluting Isomer (rt=3.63 min): (2R,3S,4S,5R)-3-(3,4-difluoro-2-methoxyphenyl)-N-(6-((S)-2,2-dimethyl-1,3-dioxolan-4-yl)pyridin-3-yl)-4,5-dimethyl-5-(trifluoromethyl)tetrahydrofuran-2-carboxamide (700 mg, 60%). ESI-MS m/z calc. 530.184, found 531.2 (M+1)$^+$; Retention time: 3.56 minutes.

Step 16:

TFA (1.743 mL, 22.62 mmol) was added to a solution of (2R,3S,4S,5R)-3-(3,4-difluoro-2-methoxyphenyl)-N-(6-((R)-2,2-dimethyl-1,3-dioxolan-4-yl)pyridin-3-yl)-4,5-dimethyl-5-(trifluoromethyl)tetrahydrofuran-2-carboxamide (600 mg, 1.112 mmol) (First Eluting Isomer from SFC separation) in DCM (20 mL) and the mixture stirred for 2 h at ambient temperature. The mixture was concentrated in vacuo and freeze-dried from MeCN and water to give a white solid. Purification by reverse phase preparative HPLC (Waters Sunfire C18, 10 μM, 100 Å column, 0% to 100% MeCN in water containing 0.1% ammonia) gave after freeze-drying (2R,3S,4S,5R)-3-(3,4-difluoro-2-methoxyphenyl)-N-(6-((R)-1,2-dihydroxyethyl)pyridin-3-yl)-4,5-dimethyl-5-(trifluoromethyl)tetrahydrofuran-2-carboxamide (1, 304 mg, 55%). $^1$H NMR (500 MHz, DMSO-d$_6$) δ 10.48 (s, 1H), 8.73 (s, 1H), 8.10 (d, J=8.4 Hz, 1H), 7.52 (d, J=8.6 Hz, 1H), 7.23-7.13 (m, 2H), 5.11 (d, J=10.3 Hz, 1H), 4.61 (s, 1H), 4.25 (dd, J=10.3, 7.6 Hz, 1H), 3.95 (d, J=2.1 Hz, 3H), 3.63 (dd, J=11.0, 4.4 Hz, 2H), 3.48 (dd, J=11.0, 6.5 Hz, 2H), 2.77 (p, J=7.6 Hz, 1H), 1.61 (s, 3H), 0.79-0.69 (m, 3H) ppm. ESI-MS m/z calc. 490.1527, found 491.6 (M+1)$^+$; Retention time: 2.98 minutes.

(2R,3S,4S,5R)-3-(3,4-difluoro-2-methoxyphenyl)-N-(6-((S)-2,2-dimethyl-1,3-dioxolan-4-yl)pyridin-3-yl)-4,5-dimethyl-5-(trifluoromethyl)tetrahydrofuran-2-carboxamide (600 mg, 1.106 mmol) (Second Eluting Isomer from SFC separation) was treated in the same way to give after freeze-drying (2R,3S,4S,5R)-3-(3,4-difluoro-2-methoxyphenyl)-N-(6-((S)-1,2-dihydroxyethyl)pyridin-3-yl)-4,5-dimethyl-5-(trifluoromethyl)tetrahydrofuran-2-carboxamide (2, 340 mg, 61%). $^1$H NMR (500 MHz, DMSO-d$_6$) δ 10.36 (s, 1H), 8.67 (dd, J=2.5, 0.7 Hz, 1H), 7.98 (dd, J=8.5, 2.6 Hz, 1H), 7.43 (d, J=8.5 Hz, 1H), 7.17 (dd, J=9.4, 6.3 Hz, 2H), 5.32 (d, J=4.9 Hz, 1H), 5.09 (d, J=10.3 Hz, 1H), 4.63 (t, J=5.9 Hz, 1H), 4.54 (dt, J=6.7, 4.4 Hz, 1H), 4.24 (dd, J=10.3, 7.7 Hz, 1H), 3.95 (d, J=2.1 Hz, 3H), 3.63 (ddd, J=11.0, 6.0, 4.1 Hz, 1H), 3.45 (ddd, J=11.0, 6.9, 5.8 Hz, 1H), 2.77 (p, J=7.5 Hz, 1H), 1.61 (s, 3H), 0.82-0.65 (m, 3H) ppm. ESI-MS m/z calc. 490.1527, found 491.6 (M+1)$^+$; Retention time: 2.99 minutes.

The absolute stereochemistry of 1 and 2 was determined by single-crystal X-ray crystallography analysis of 1.

Compound 1 was analyzed by X-ray powder diffraction analysis Method A and determined to be amorphous (see FIG. 1).

The following compounds were made using the method described in Example 1, except that rac-6-((4R,5R)-2,2,5-trimethyl-1,3-dioxolan-4-yl)pyridin-3-amine was used in place of rac-6-(2,2-Dimethyl-1,3-dioxolan-4-yl)pyridin-3-amine in the amide coupling step 14. In step 15, purification was performed by chiral SFC using a Chiralcel OD-H column, 5 m particle size, 25 cm×10 mm from Daicel Corporation (Mobile phase: 12% MeOH (containing 20 mM Ammonia), 88% CO$_2$. Flow: 10 mL/min.) on a Minigram SFC instrument from Berer Instruments:

| Cmpd No. | Compound Name | LC/MS | NMR (shifts in ppm) |
| --- | --- | --- | --- |
| 3 | rel-(2R*,3S*,4S*,5R*)-3-(3,4-difluoro-2-methoxyphenyl)-N-(6-((1R,2R)-1,2-dihydroxypropyl)pyridin-3-yl)-4,5-dimethyl-5-(trifluoromethyl)tetrahydrofuran-2-carboxamide (Precursor was the first eluting peak by SFC on Chiralcel OD-H column, rt = 4.36 min) | ESI-MS m/z calc. 504.16837, found 505.0 (M + 1)$^+$; 503.1 (M − 1)$^−$; Retention time: 3.08 minutes | $^1$H NMR (500 MHz, DMSO-d$_6$) δ 10.37 (s, 1H), 8.68 (d, J = 2.2 Hz, 1H), 7.97 (dd, J = 8.5, 2.5 Hz, 1H), 7.40 (d, J = 8.5 Hz, 1H), 7.20-7.13 (m, 2H), 5.20 (d, J = 5.3 Hz, 1H), 5.09 (d, J = 10.3 Hz, 1H), 4.46 (d, J = 5.5 Hz, 1H), 4.30 (t, J = 5.2 Hz, 1H), 4.25 (dd, J= 10.1, 7.8 Hz, 1H), 3.95 (d, J = 2.1 Hz, 3H), 3.81-3.75 (m, 1H), 2.77 (p, J = 7.2 Hz, 1H), 1.61 (s, 3H), 0.94 (d, J = 6.4 Hz, 3H), 0.74 (d, J = 7.3 Hz, 3H) ppm. |
| 4 | rel-(2R*,3S*,4S*,5R*)-3-(3,4-difluoro-2-methoxyphenyl)-N-(6-((1S,2S)-1,2-dihydroxypropyl)pyridin-3-yl)-4,5-dimethyl-5- | ESI-MS m/z calc. 504.16837, found 505.0 (M + 1)$^+$; 503.1 (M − 1)$^−$; Retention time: 3.08 minutes | $^1$H NMR (500 MHz, DMSO-d$_6$) δ 10.37 (s, 1H), 8.65 (d, J = 2.5 Hz, 1H), 7.99 (dd, J = 8.6, 2.5 Hz, 1H), 7.40 (d, J = 8.5 |

| Cmpd No. | Compound Name | LC/MS | NMR (shifts in ppm) |
|---|---|---|---|
|  | (trifluoromethyl)tetrahydrofuran-2-carboxamide (Precursor was the second eluting peak by SFC on Chiralcel OD-H column, rt = 5.28 min) |  | Hz, 1H), 7.20-7.13 (m, 2H), 5.20 (d, J = 5.3 Hz, 1H), 5.09 (d, J = 10.3 Hz, 1H), 4.45 (d, J = 5.5 Hz, 1H), 4.30 (t, J = 5.2 Hz, 1H), 4.25 (dd, J = 10.4, 7.6 Hz, 1H), 3.95 (d, J = 2.0 Hz, 3H), 3.81-3.75 (m, 1H), 2.80-2.73 (m, 1H), 1.61 (s, 3H), 0.94 (d, J = 6.4 Hz, 3H), 0.73 (d, J = 6.5 Hz, 3H) ppm. |

The following compound was made using the method described in Example 1, except that (1R,2S)-6,7-difluoro-1,2-dimethyl-2-(trifluoromethyl)-1,2-dihydro-4H-furo[2,3-c]chromen-4-one was used in place of (1S,2R)-6,7-Difluoro-1,2-dimethyl-2-(trifluoromethyl)-1,2-dihydro-4H-furo[2,3-c]chromen-4-one in the hydrogenation step 8 and (S)-6-(2,2-dimethyl-1,3-dioxolan-4-yl)pyridin-3-amine was used as the coupling partner in step 14. The SFC separation step 15 was not required:

| Cmpd No. | Compound Name | LC/MS | NMR (shifts in ppm) |
|---|---|---|---|
| 5 | (2S,3R,4R,5S)-3-(3,4-difluoro-2-methoxyphenyl)-N-(6-((S)-1,2-dihydroxyethyl)pyridin-3-yl)-4,5-dimethyl-5-(trifluoromethyl)tetrahydrofuran-2-carboxamide | ESI-MS m/z calc. 490.1527, found 491.2 (M + 1)⁺; 489.2 (M − 1)⁻; Retention time: 2.97 minutes | ¹H NMR (400 MHz, DMSO-d₆) δ 10.39 (s, 1H), 8.65 (dd, J = 2.5, 0.7 Hz, 1H), 8.00 (dd, J = 8.6, 2.5 Hz, 1H), 7.43 (d, J = 8.5 Hz, 1H), 7.17 (dd, J = 8.6, 5.2 Hz, 2H), 5.33 (d, J = 4.9 Hz, 1H), 5.10 (d, J = 10.3 Hz, 1H), 4.63 (t, J = 5.9 Hz, 1H), 4.54 (dt, J = 6.9, 4.5 Hz, 1H), 4.24 (dd, J = 10.3, 7.6 Hz, 1H), 3.95 (d, J = 2.2 Hz, 3H), 3.63 (ddd, J = 10.9, 6.0, 4.1 Hz, 1H), 3.44 (ddd, J = 10.9, 6.8, 5.8 Hz, 1H), 2.77 (t, J = 7.5 Hz, 1H), 1.61 (s, 3H), 0.80-0.68 (m, 3H) ppm. |

The following compounds were made using the method described in Example 1, except that ethyl iodide was used in place of methyl iodide in the alkylation step 9. The conditions used for the epimenization/hydrolysis steps 10 and 11 followed the first part of the conditions described in Example 5 step 4. In step 14, (S)-6-(2,2-dimethyl-1,3-dioxolan-4-yl)pyridin-3-amine and (R)-6-(2,2-dimethyl-1,3-dioxolan-4-yl)pyridin-3-amine were respectively used as the coupling partner for compounds 6 and 7. The SFC separation step 15 was not required:

| Cmpd No. | Compound Name | LC/MS | NMR (shifts in ppm) |
|---|---|---|---|
| 6 | (2R,3S,4S,5R)-N-(6-((S)-1,2-dihydroxyethyl)pyridin-3-yl)-3-(2-ethoxy-3,4-difluorophenyl)-4,5-dimethyl-5-(trifluoromethyl)tetrahydrofuran-2-carboxamide | ESI-MS m/z calc. 504.16837, found 505.4 (M + 1)⁺; 503.5 (M − 1)⁻; Retention time: 3.12 minutes | ¹H NMR (500 MHz, DMSO-d₆) δ 10.36 (s, 1H), 8.65 (s, 1H), 7.97 (d, J = 9.2 Hz, 1H), 7.42 (d, J = 8.6 Hz, 1H), 7.16 (dd, J = 8.5, 4.6 Hz, 2H), 5.31 (s, 1H), 5.08 (d, J= 10.6 Hz, 1H), 4.62 (t, J = 5.7 Hz, 1H), 4.53 (s, 1H), 4.27 (dd, J = 10.5, 7.5 Hz, 1H), 4.24-4.09 (m, 2H), 3.62 (s, 1H), 3.44 (d, J = 9.8 Hz, 1H), 2.74 (p, J = 7.4 Hz, 1H), 1.60 (s, 3H), 1.35 (t, J = 7.0 Hz, 3H), 0.73 (d, J = 7.3 Hz, 3H) ppm. |

| Cmpd No. | Compound Name | LC/MS | NMR (shifts in ppm) |
|---|---|---|---|
| 7 | (2R,3S,4S,5R)-N-(6-((R)-1,2-dihydroxyethyl)pyridin-3-yl)-3-(2-ethoxy-3,4-difluorophenyl)-4,5-dimethyl-5-(trifluoromethyl)tetrahydrofuran-2-carboxamide | ESI-MS m/z calc. 504.16837, found 505.4 (M + 1)$^+$; 503.5 (M − 1)$^-$; Retention time: 3.11 minutes | $^1$H NMR (500 MHz, DMSO-$d_6$) δ 10.36 (s, 1H), 8.63 (dd, J = 2.5, 0.8 Hz, 1H), 7.99 (dd, J = 8.5, 2.6 Hz, 1H), 7.42 (d, J = 8.5 Hz, 1H), 7.21-7.08 (m, 2H), 5.31 (d, J = 4.9 Hz, 1H), 5.08 (d, J = 10.5 Hz, 1H), 4.62 (t, J = 5.9 Hz, 1H), 4.53 (dt, J = 6.8, 4.5 Hz, 1H), 4.27 (dd, J = 10.5, 7.5 Hz, 1H), 4.24-4.08 (m, 2H), 3.62 (ddd, J = 10.9, 6.0, 4.1 Hz, 1H), 3.44 (ddd, J = 11.0, 6.8, 5.8 Hz, 1H), 2.74 (p, J = 7.5 Hz, 1H), 1.60 (s, 3H), 1.35 (t, J = 7.0 Hz, 3H), 0.77-0.67 (m, 3H) ppm. |

Figure 2:
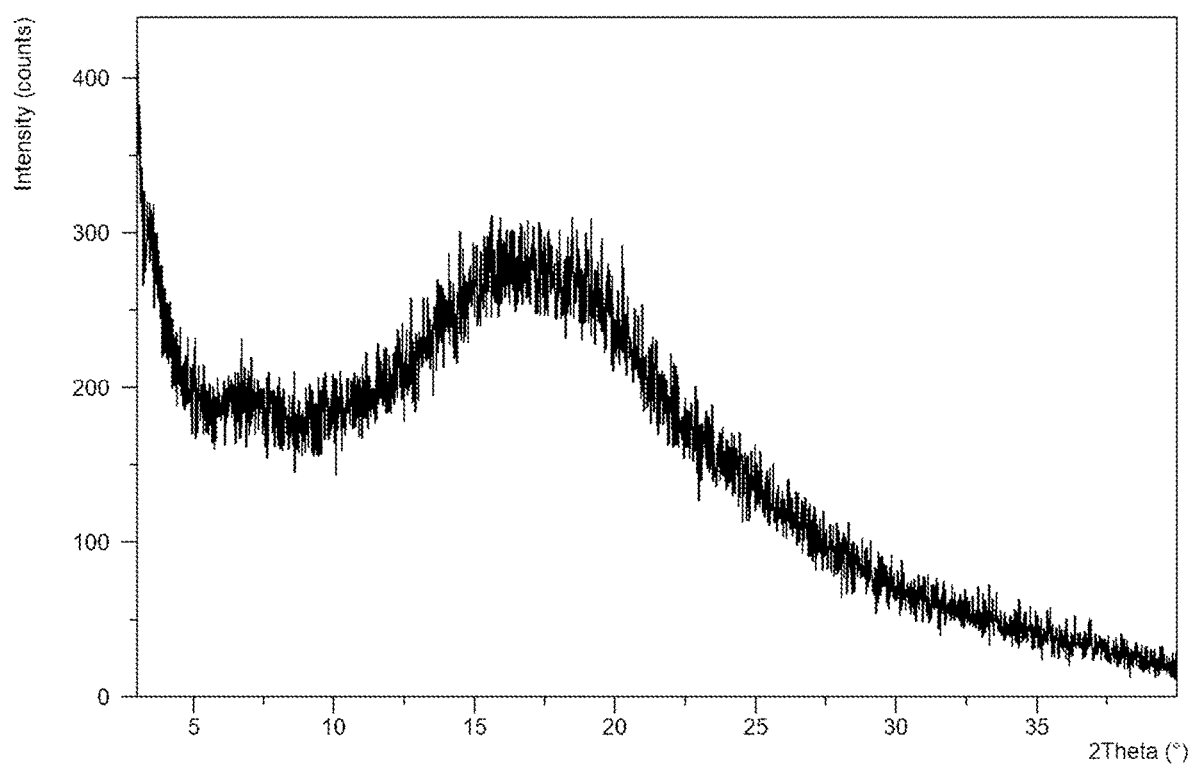
FIG. 2 depicts an XRPD pattern characteristic of amorphous Compound 7.

Compound 7 was analyzed by X-ray powder diffraction analysis Method B and determined to be amorphous (see FIG. 2).

The following compound was made using a method similar to that described in Example 1 except that iodomethane-$d_3$ was used in place of methyl iodide in the alkylation step 9 and the conditions carried out for the amide coupling step 14 followed the conditions described in Example 2 step 1 using (R)-6-(2,2-dimethyl-1,3-dioxolan-4-yl)pyridin-3-amine as the coupling partner. The SFC separation step 15 was not required:

| Cmpd No. | Compound Name | LC/MS | NMR (shifts in ppm) |
|---|---|---|---|
| 8 | (2R,3S,4S,5R)-3-(3,4-difluoro-2-(methoxy-$d_3$)phenyl)-N-(6-((R)-1,2-dihydroxyethyl)pyridin-3-yl)-4,5-dimethyl-5-(trifluoromethyl)tetrahydrofuran-2-carboxamide | ESI-MS m/z calc. 493.17154, found 494.3 (M + 1)$^+$; 492.3 (M − 1)$^-$; Retention time: 2.99 minutes | $^1$H NMR (500 MHz, DMSO-$d_6$) δ 10.37 (s, 1H), 8.65 (dd, J = 2.6, 0.7 Hz, 1H), 8.00 (dd, J = 8.5, 2.5 Hz, 1H), 7.43 (d, J = 8.5 Hz, 1H), 7.18-7.13 (m, 2H), 5.32 (d, J = 4.9 Hz, 1H), 5.09 (d, J = 10.3 Hz, 1H), 4.62 (t, J = 5.9 Hz, 1H), 4.54 (dt, J = 6.8, 4.5 Hz, 1H), 4.24 (dd, J = 10.3, 7.6 Hz, 1H), 3.63 (ddd, J = 11.0, 6.1, 4.2 Hz, 1H), 3.48-3.42 (m, 1H), 2.77 (t, J = 7.5 Hz, 1H), 1.61 (s, 3H), 0.76-0.71 (m, 3H) ppm. |

Figure 3:
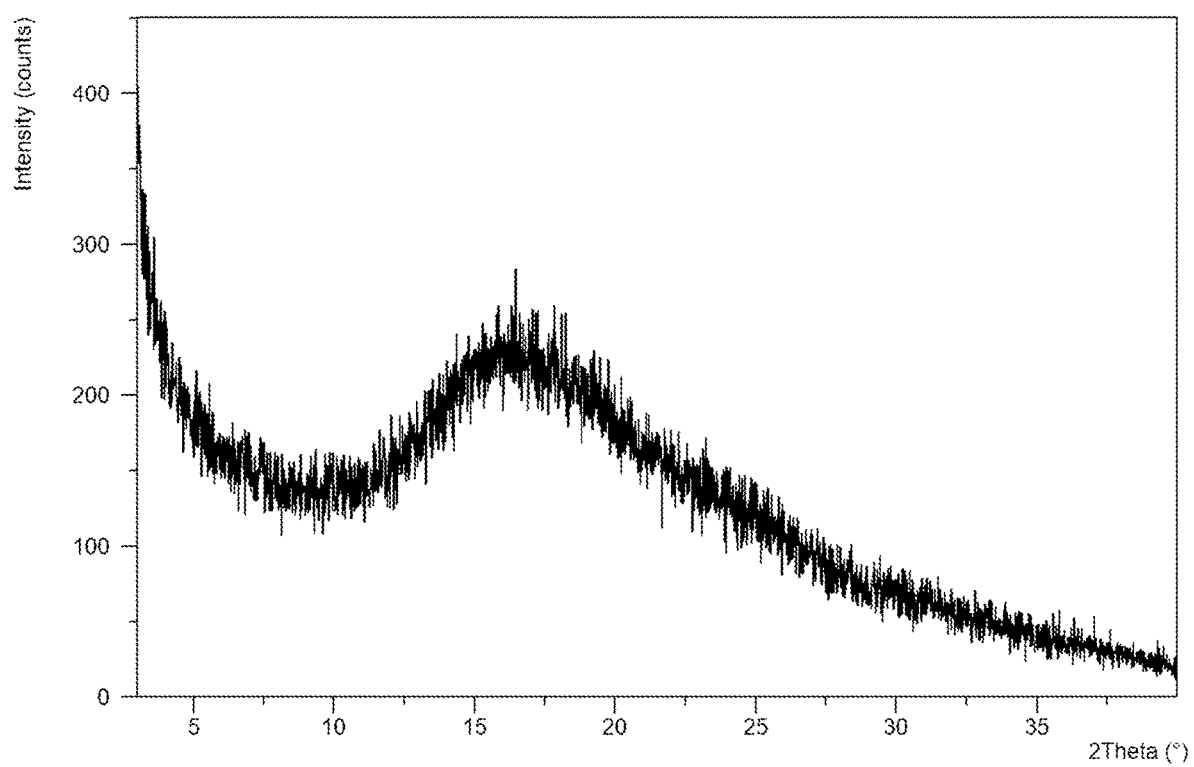
FIG. 3 depicts an XRPD pattern characteristic of amorphous Compound 8.

Compound 8 was analyzed by X-ray powder diffraction analysis Method B and determined to be amorphous (see FIG. 3).

The following compounds were made using the method described in Example 1, except that 2-iodopropane was used in place of methyl iodide in step 9 and the reaction was carried out at 75° C. The epimerization/hydrolysis steps 10 and 11 were carried out in one step following the conditions described in Example 6 step 3. Steps 12 and 13 were omitted and, in the amide coupling step 14, 2-(2,2-dimethyl-1,3-dioxolan-4-yl)pyrimidin-5-amine was used as the coupling partner. In step 15, purification was performed by chiral SFC using a Chiralpak IB column, 5 um particle size, 25 cm×20 mm from Daicel Corporation (Mobile phase: 20% MeOH (containing 20 mM Ammonia), 80% $CO_2$. Flow: 100 mL/min.) on a Minigram SFC instrument from Berger Instruments:

| Cmpd No. | Compound Name | LC/MS | NMR (shifts in ppm) |
|---|---|---|---|
| 9 | rel-(2R*,3S*,4S*,5R*)-3-(3,4-difluoro-2-isopropoxyphenyl)-N-(2-(1,2-dihydroxyethyl)pyrimidin-5-yl)-4,5-dimethyl-5-(trifluoromethyl)tetrahydrofuran-2-carboxamide (Precursor was the first eluting peak by SFC on Chiralpak IB column, rt = 0.80 min) | ESI-MS m/z calc. 519.17926, found 520.3 (M + 1)$^+$; 518.2 (M − 1)$^-$; Retention time: 3.2 minutes | $^1$H NMR (400 MHz, Methanol-$d_4$) δ 9.02 (s, 2H), 7.14 (ddd, J = 8.4, 5.6, 2.1Hz, 1H), 6.97 (ddd, J = 9.9, 8.9, 7.5 Hz, 1H), 5.08 (d, J = 10.7 Hz, 1H), 4.78 (dd, J = 6.0, 4.6 Hz, 1H), 4.66 (pd, J = 6.1, 1.2 Hz, 1H), 4.37 (dd, J = 10.7, 7.9 Hz, 1H), 3.94- |

| Cmpd No. | Compound Name | LC/MS | NMR (shifts in ppm) |
|---|---|---|---|
| 10 | rel-(2R*,3S*,4S*,5R*)-3-(3,4-difluoro-2-isopropoxyphenyl)-N-(2-(1,2-dihydroxyethyl)pyrimidin-5-yl)-4,5-dimethyl-5-(trifluoromethyl)tetrahydrofuran-2-carboxamide (Precursor was the second eluting peak by SFC on Chiralpak IB column, rt = 0.95 min) | ESI-MS m/z calc. 519.17926, found 520.3 (M + 1)$^+$; 518.2 (M − 1)$^−$; Retention time: 3.19 minutes | $^1$H NMR (400 MHz, Methanol-d$_4$) δ 9.02 (s, 2H), 7.14 (ddd, J = 8.3, 5.6, 2.1Hz, 1H), 6.97 (ddd, J = 9.9, 8.9, 7.6 Hz, 1H), 5.08 (d, J = 10.7 Hz, 1H), 4.78 (dd, J = 6.0, 4.6 Hz, 1H), 4.66 (pd, J = 6.2, 1.3 Hz, 1H), 4.37 (dd, J = 10.7, 7.9 Hz, 1H), 3.94-3.77 (m, 2H), 2.78 (p, J = 7.6 Hz, 1H), 1.67 (d, J = 1.1 Hz, 3H), 1.40 (dd, J = 6.1, 0.9 Hz, 3H), 1.25 (d, J = 6.1 Hz, 3H), 0.80 (dt, J = 7.6, 2.3 Hz, 3H) ppm; alcohols OH and amide NH not observed. |

The following compounds were made using the method described in Example 1, except that steps 12 and 13 were omitted and, in the amide coupling step 14, 2-(2,2-dimethyl-1,3-dioxolan-4-yl)pyrimidin-5-amine was used as the coupling partner. In step 15, purification was performed by chiral SFC using a Chiralcel OD-H column, 5um particle size, 25 cm×10 mm from Daicel Corporation (Mobile phase: 22% MeOH (containing 20 mM Ammonia), 78% CO$_2$. Flow: 10 mL/min.) on a Minigram SFC instrument from Berger Instruments:

| Cmpd No. | Compound Name | LC/MS | NMR (shifts in ppm) |
|---|---|---|---|
| 11 | rel-(2R*,3S*,4S*,5R*)-3-(3,4-difluoro-2-methoxyphenyl)-N-(2-(1,2-dihydroxyethyl)pyrimidin-5-yl)-4,5-dimethyl-5-(trifluoromethyl)tetrahydrofuran-2-carboxamide (Precursor was the first eluting peak by SFC on Chiralcel OD-H column, rt = 2.91 min) | ESI-MS m/z calc. 491.14795, found 492.0 (M + 1)$^+$; 490.1 (M − 1)$^−$; Retention time: 2.94 minutes | $^1$H NMR (500 MHz, DMSO-d$_6$) δ 10.50 (s, 1H), 8.99 (s, 2H), 7.19-7.16 (m, 2H), 5.17 (d, J = 6.0 Hz, 1H), 5.14 (d, J = 10.4 Hz, 1H), 4.59 (dt, J = 12.6, 6.0 Hz, 2H), 4.25 (dd, J = 10.3, 7.7 Hz, 1H), 3.95 (d, J = 2.1 Hz, 3H), 3.71 (dt, J = 11.5, 6.0 Hz, 1H), 3.65-3.61 (m, 1H), 2.80-2.75 (m, 1H), 1.62 (s, 3H), 0.74 (d, J = 7.4 Hz, 3H) ppm. |
| 12 | rel-(2R*,3S*,4S*,5R*)-3-(3,4-difluoro-2-methoxyphenyl)-N-(2-(1,2-dihydroxyethyl)pyrimidin-5-yl)-4,5-dimethyl-5-(trifluoromethyl)tetrahydrofuran-2-carboxamide (Precursor was the second eluting peak by SFC on Chiralcel OD-H column, rt = 3.79 min) | ESI-MS m/z calc. 491.14795, found 492.0 (M + 1)$^+$; 490.1 (M − 1)$^−$; Retention time: 2.94 minutes | $^1$H NMR (500 MHz, DMSO-d$_6$) δ 10.50 (s, 1H), 8.99 (s, 2H), 7.19-7.14 (m, 2H), 5.17 (br s, 1H), 5.15 (d, J = 10.2 Hz, 1H), 4.61-4.58 (m, 2H), 4.25 (dd, J = 10.3, 7.6 Hz, 1H), 3.95 (d, J = 2.0 Hz, 3H), 3.73-3.70 (m, 1H), 3.65-3.61 (m, 1H), 2.80-2.74(m, 1H), 1.62 (s, 3H), 0.74 (d, J = 7.4 Hz, 3H) ppm. |

The following compound was made using the method described in Example 1, except that (3-fluoro-2-methoxyphenyl)boronic acid was used in place of (3,4-difluoro-2-methoxyphenyl)boronic acid in the Suzuki step 5. In the amide coupling step 14, (R)-6-(2,2-dimethyl-1,3-dioxolan-4-yl)pyridin-3-amine was used in place of 6-(2,2-dimethyl-1,3-dioxolan-4-yl)pyridin-3-amine and the coupling conditions were those used in Example 2 step 1. The compound did not require the chiral SFC separation step 15:

| Cmpd No. | Compound Name | LC/MS | NMR (shifts in ppm) |
|---|---|---|---|
| 13 | (2R,3S,4S,5R)-N-(6-((R)-1,2-dihydroxyethyl)pyridin-3-yl)-3-(3-fluoro-2-methoxyphenyl)-4,5-dimethyl-5-(trifluoromethyl)tetrahydrofuran-2-carboxamide | | $^1$H NMR (400 MHz, DMSO-d$_6$) δ 10.40 (s, 1H), 8.63 (d, J = 2.0 Hz, 1H), 7.99 (dd, J = 2.0, 6.8 Hz, 1H), 7.42 (d, J = 6.8 Hz, 1H), 7.24-7.06 (m, 3H), 5.31 (d, J = 4.0 Hz, 1H), 5.08 (d, J = 8.4 Hz, 1H), 4.61 (t, J = 4.8 Hz, 1H), 4.52 (m, 1H), 4.29 (dd, J = 4.8, 8.4 Hz, 1H), 3.86 (s, 3H), 3.60 (m, 1H), 3.43 (m, 1H), 2.76 (qint, J = 6.0 Hz, 1H), 1.59 (s, 3H), 0.71 (d, J = 5.2 Hz, 3H) ppm. |

The following compound was made using the method described in Example 1, except that 6-(((tert-butyldimethylsilyl)oxy)methyl)pyridin-3-amine was used as the coupling partner in the amide coupling step 14. The SFC separation step 15 was not required and the deprotection step 16 was carried out at ambient temperature over 3 days using an excess of HCl (37% w/v) in MeOH as the solvent:

| Cmpd No. | Compound Name | LC/MS | NMR (shifts in ppm) |
|---|---|---|---|
| 14 | (2R,3S,4S,5R)-3-(3,4-difluoro-2-methoxyphenyl)-N-(6-(hydroxymethyl)pyridin-3-yl)- | ESI-MS m/z calc. 460.14215, | $^1$H NMR (500 MHz, DMSO-d$_6$) δ 10.37 (s, 1H), |

| Cmpd No. | Compound Name | LC/MS | NMR (shifts in ppm) |
|---|---|---|---|
| | 4,5-dimethyl-5-(trifluoromethyl)tetrahydrofuran-2-carboxamide | found 461.7 (M + 1)⁺; 459.6 (M − 1)⁻; Retention time: 3.11 minutes | 8.68 (d, J = 2.5 Hz, 1H), 8.03 (dd, J = 8.5, 2.5 Hz, 1H), 7.42 (d, J = 8.5 Hz, 1H), 7.18 (dd, J = 9.9, 6.5 Hz, 2H), 5.36 (t, J = 5.8 Hz, 1H), 5.10 (d, J = 10.3 Hz, 1H), 4.52 (d, J = 5.8 Hz, 2H), 4.26 (dd, J = 10.3, 7.7 Hz, 1H), 3.97 (d, J = 2.0 Hz, 3H), 2.78 (t, J = 7.5 Hz, 1H), 1.62 (s, 3H), 0.77-0.73 (m, 3H) ppm. |

The following compound was made using the method described in Example 1, except that (5-aminopyrimidin-2-yl)methyl benzoate was used as the coupling partner in the amide coupling step 14. The SFC separation step 15 was not required and the deprotection step 16 was carried out overnight at ambient temperature using a 2 M solution of sodium hydroxide in excess and 1,4-dioxane as the solvent:

| Cmpd No. | Compound Name | LC/MS | NMR (shifts in ppm) |
|---|---|---|---|
| 15 | (2R,3S,4S,5R)-3-(3,4-difluoro-2-methoxyphenyl)-N-(2-(hydroxymethyl)pyrimidin-5-yl)-4,5-dimethyl-5-(trifluoromethyl)tetrahydrofuran-2-carboxamide | ESI-MS m/z calc. 461.1374, found 462.6 (M + 1)⁺; 460.5 (M − 1)⁻; Retention time: 3.09 minutes | $^1$H NMR (500 MHz, DMSO-d$_6$) δ 10.47 (s, 1H), 8.98 (s, 2H), 7.20-7.13 (m, 2H), 5.25 (t, J = 6.3 Hz, 1H), 5.14 (d, J = 10.3 Hz, 1H), 4.55 (d, J = 6.1Hz, 2H), 4.25 (dd, J = 10.3, 7.5 Hz, 1H), 3.95 (d, J = 2.0 Hz, 3H), 2.77 (dq, J = 7.5, 7.5 Hz, 1H), 1.62 (s, 3H), 0.73 (d, J = 6.2 Hz, 3H) ppm. |

Figure 4:
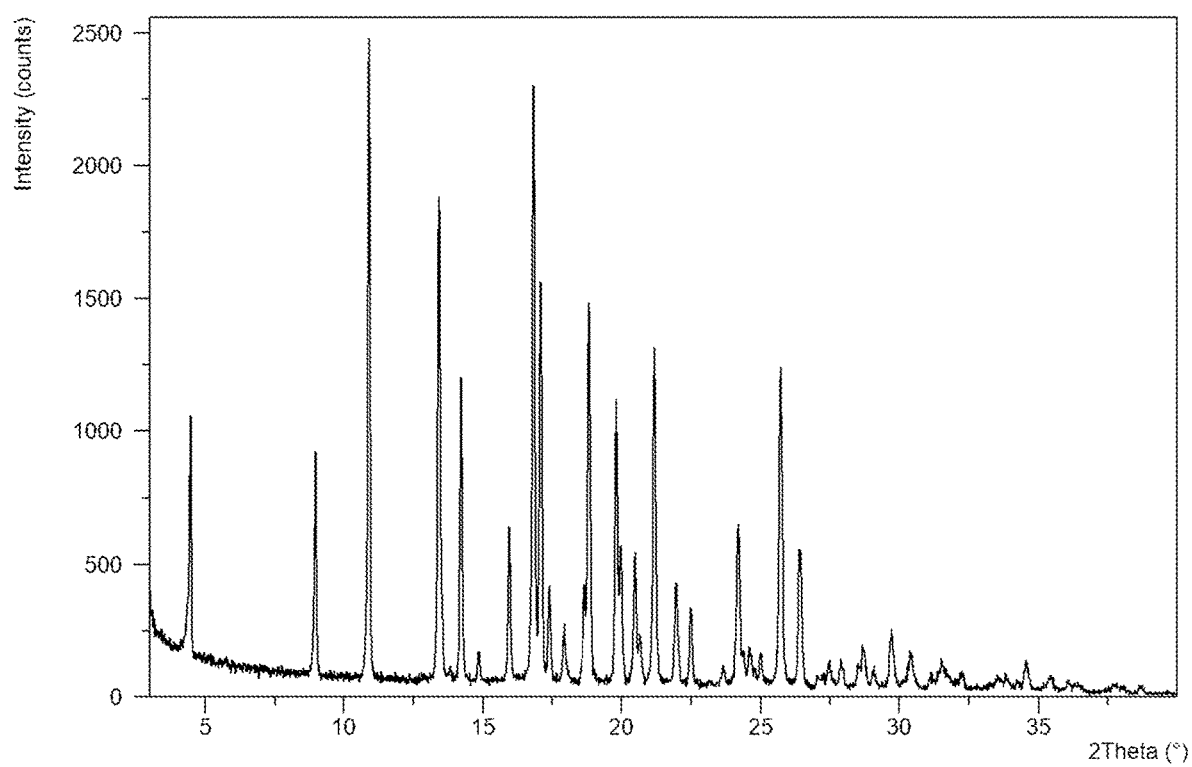
FIG. 4 depicts an XRPD pattern characteristic of Compound 16 in crystalline form.

The following compounds were made using the method described in Example 1, except that 6-(1-((tert-butyldimethylsilyl)oxy)-2-fluoroethyl)pyridin-3-amine was used as the coupling partner in the amide coupling step 14. The chiral SFC separation step 15 was carried out using a Chiralpak IB column, 5 m particle size, 25 cm×20 mm from Daicel (Mobile phase: 5% IPA (containing 20 mM Ammonia), 95% CO$_2$. Flow: 100 mL/min.) on a Prep-100 SFC instrument from Waters. The conditions used for the deprotection step 16 were those described in Example 2 step 3 utilizing THF as the solvent rather than 2-MeTHF:

Compound 16 was analyzed by X-ray powder diffraction analysis Method B and determined to be crystalline (see FIG. 4).

| Cmpd No. | Compound Name | LC/MS | NMR (shifts in ppm) |
|---|---|---|---|
| 16 | rel-(2R*,3S*,4S*,5R*)-3-(3,4-difluoro-2-methoxyphenyl)-N-(6-(2-fluoro-1-hydroxyethyl)pyridin-3-yl)-4,5-dimethyl-5-(trifluoromethyl)tetrahydrofuran-2-carboxamide (Precursor was the first eluting peak by SFC on Chiralpak IB column, rt = 0.46 min) | ESI-MS m/z calc. 492.1484, found 493.3 (M + 1)⁺; 491.3 (M − 1)⁻; Retention time: 3.28 minutes | $^1$H NMR (500 MHz, DMSO-d$_6$) δ 10.41 (s, 1H), 8.70 (d, J = 2.4 Hz, 1H), 8.06 (dd, J = 8.6, 2.5 Hz, 1H), 7.50 (d, J = 8.5 Hz, 1H), 7.23-7.07 (m, 2H), 5.86 (d, J = 5.2 Hz, 1H), 5.10 (d, J = 10.2 Hz, 1H), 4.81 (dtd, J = 20.5, 5.8, 3.3 Hz, 1H), 4.73-4.55 (m, 1H), 4.55-4.36 (m, 1H), 4.25 (dd, J = 10.3, 7.7 Hz, 1H), 3.95 (d, J = 2.0 Hz, 3H), 2.77 (p, J = 7.5 Hz, 1H), 1.61 (s, 3H), 0.74 (dd, J = 7.4, 2.5 Hz, 3H) ppm. |
| 17 | rel-(2R*,3S*,4S*,5R*)-3-(3,4-difluoro-2-methoxyphenyl)-N-(6-(2-fluoro-l-hydroxyethyl)pyridin-3-yl)-4,5-dimethyl-5-(trifluoromethyl)tetrahydrofuran-2-carboxamide (Precursor was the second eluting peak by SFC on Chiralpak IB column, rt = 0.75 min) | ESI-MS m/z calc. 492.1484, found 493.3 (M + 1)⁺; 491.3 (M − 1)⁻; Retention time: 3.28 minutes | $^1$H NMR (500 MHz, DMSO-d$_6$) δ 10.37 (s, 1H), 8.67 (d, J = 2.4 Hz, 1H), 7.99 (dd, J = 8.5, 2.5 Hz, 1H), 7.45 (d, J = 8.5 Hz, 1H), 7.19-7.05 (m, 2H), 5.82 (s, 1H), 5.05 (d, J = 10.3 Hz, 1H), 4.76 (ddd, J = 20.5, 6.3, 3.2 Hz, 1H), 4.59 (ddd, J = 47.6, 9.4, 3.3 Hz, 1H), 4.45 (ddd, J = 47.9, 9.3, 6.3 Hz, 1H), 4.20 (dd, J = 10.3, 7.6 Hz, 1H), 3.91 (d, J = 2.0 Hz, 3H), 2.73 (q, J = 7.5 Hz, 1H), 1.56 (s, 3H), 0.69 (dd, J = 7.3, 2.5 Hz, 3H) ppm. |

Example 2 rel-(2R*,3S*,4S*,5R*)-3-(3,4-difluoro-2-methoxyphenyl)-N-(6-(1-hydroxy-2-methoxyethyl)pyridin-3-yl)-4,5-dimethyl-5-(trifluoromethyl)tetrahydrofuran-2-carboxamide (20) and rel-(2R*,3S*,4S*,5R*)-3-(3,4-difluoro-2-methoxyphenyl)-N-(6-(1-hydroxy-2-methoxyethyl)pyridin-3-yl)-4,5-dimethyl-5-(trifluoromethyl)tetrahydrofuran-2-carboxamide (21)

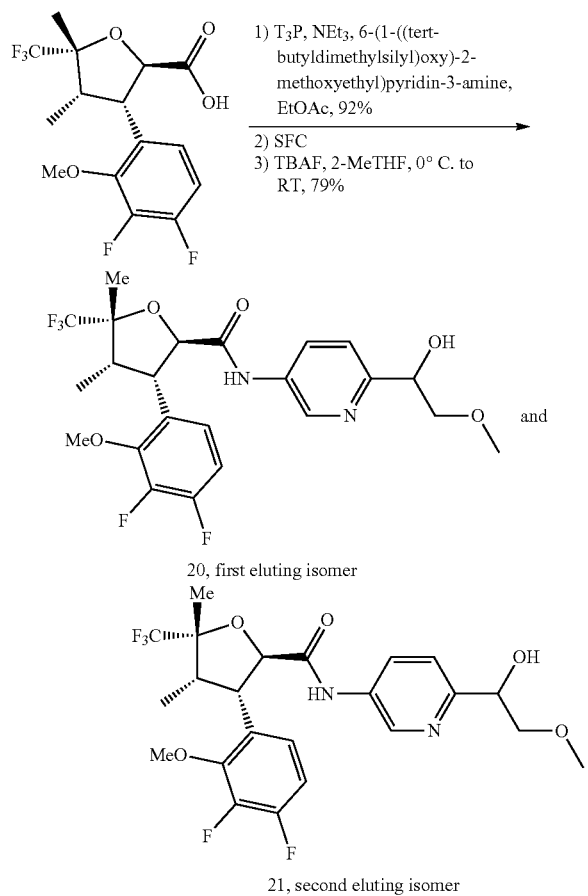

Step 1:

T3P (1000 µL of 50% w/v, 1.571 mmol) was added to a mixture of (2R,3S,4S,5R)-3-(3,4-difluoro-2-methoxyphenyl)-4,5-dimethyl-5-(trifluoromethyl)tetrahydrofuran-2-carboxylic acid (130 mg, 0.3486 mmol), rac-6-(1-((tert-butyldimethylsilyl)oxy)-2-methoxyethyl)pyridin-3-amine (108 mg, 0.3824 mmol) and Et3N (100 µL, 0.7175 mmol) in EtOAc (1.5 mL). The clear mixture was stirred at ambient temperature for 2 h. The mixture was partitioned between EtOAc and water and passed through a phase separation cartridge. The organic filtrates were concentrated in vacuo to give a clear oil. Purification by silica gel chromatography (12 g SiO$_2$, 0 to 30% EtOAc in hexanes) gave a mixture of the 2 diastereoisomers of (2R,3S,4S,5R)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (211 mg, 92%) as a clear oil. ESI-MS m/z calc. 618.2548, found 619.0 (M+1)$^+$; 617.0 (M−1)$^-$; Retention time: 4.3 minutes.

Step 2:

The 2 diastereoisomers of (2R,3S,4S,5R)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (210 mg, 0.3191 mmol) were separated by using a Chiralcel OD-H column, 5 m particle size, 25 cm×10 mm from Daicel (Mobile phase: 15% MeOH (containing 20 mM Ammonia), 85% CO$_2$. Flow: 10 mL/min.) on a Minigram SFC instrument from Berger Instruments:

First Eluting Isomer (rt=2.24 min): rel-(2R*,3S*,4S*,5R*)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (83 mg, 84%). ESI-MS m/z calc. 618.2548, found 619.0 (M+1)$^+$; 617.0 (M−1)$^-$; Retention time: 4.3 minutes.

Second Eluting Isomer (rt=3.01 min): rel-(2R*,3S*,4S*,5R*)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (82 mg, 83%). ESI-MS m/z calc. 618.2548, found 619.0 (M+1)$^+$; 617.0 (M−1)$^-$; Retention time: 4.3 minutes.

Step 3:

A THF solution of TBAF (650 µL of 1 M, 0.6500 mmol) was added to a stirred solution of rel-(2R*,3S*,4S*,5R*)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (80 mg, 0.1293 mmol) (First Eluting Isomer from SFC separation) in 2-MeTHF (4 mL) at 0° C. The reaction was stirred at ambient temperature over the weekend (convenience). The reaction mixture was quenched with saturated aqueous NaHCO$_3$ (10 mL), stirred for 10 min and extracted with ethyl acetate (2×10 mL). The combined organic extracts were dried (MgSO4), filtered and concentrated in vacuo. Purification by reverse phase preparative HPLC (Waters Sunfire C18, 10 µM, 100 Å column, 0% to 100% MeCN in water containing 0.1% ammonia) gave after freeze-drying rel-(2R*,3S*,4S*,5R*)-3-(3,4-difluoro-2-methoxyphenyl)-N-(6-(1-hydroxy-2-methoxyethyl)pyridin-3-yl)-4,5-dimethyl-5-(trifluoromethyl)tetrahydrofuran-2-carboxamide (20, 52 mg, 79%). $^1$H NMR (400 MHz, DMSO-d$_6$) δ 10.38 (s, 1H), 8.66 (dd, J=2.5, 0.7 Hz, 1H), 8.01 (dd, J=8.5, 2.5 Hz, 1H), 7.44 (d, J=8.5 Hz, 1H), 7.21-7.13 (m, 2H), 5.47 (d, J=5.0 Hz, 1H), 5.09 (d, J=10.3 Hz, 1H), 4.73-4.64 (m, 1H), 4.29-4.19 (m, 1H), 3.95 (d, J=2.2 Hz, 3H), 3.57 (dd, J=10.0, 3.9 Hz, 1H), 3.44 (dd, J=10.1, 7.0 Hz, 1H), 3.24 (s, 3H), 2.78 (q, J=7.5 Hz, 1H), 1.61 (s, 3H), 0.74 (d, J=6.7 Hz, 3H) ppm. ESI-MS m/z calc. 504.16837, found 505.0 (M+1)$^+$; 503.0 (M−1)$^-$; Retention time: 3.16 minutes.

rel-(2R*,3S*,4S*,5R*)—N-(6-(1-((tert-butyldimethylsilyl)oxy)-2-methoxyethyl)pyridin-3-yl)-3-(3,4-difluoro-2-methoxyphenyl)-4,5-dimethyl-5-(trifluoromethyl)tetrahydrofuran-2-carboxamide (80 mg, 0.1293 mmol) (Second Eluting Isomer from SFC separation) was treated in the same way to give after freeze-drying rel-(2R*,3S*,4S*,5R*)-3-(3,4-difluoro-2-methoxyphenyl)-N-(6-(1-hydroxy-2-methoxyethyl)pyridin-3-yl)-4,5-dimethyl-5-(trifluoromethyl)tetrahydrofuran-2-carboxamide (21, 54 mg, 82%). $^1$H NMR (400 MHz, DMSO-d$_6$) δ 10.38 (s, 1H), 8.68 (dd, J=2.5, 0.7 Hz, 1H), 7.99 (dd, J=8.5, 2.5 Hz, 1H), 7.44 (d, = 8.5 Hz, 1H), 7.21-7.13 (i, 2H), 5.47 (d, J=4.4 Hz, 1H), 5.09 (d, J=10.3 Hz, 1H), 4.69 (d, J=6.2 Hz, 1H), 4.24 (dd, J=10.3, 7.7 Hz, 1H), 3.95 (d, J=2.2 Hz, 3H), 3.57 (dd, J=10.0, 3.9 Hz, 1H), 3.44 (dd, =10.0, 6.9 Hz, 1H), 3.24 (s, 3H), 2.77 (p, M=7.6 Hz, 1H), 1.61 (s, 3H), 0.74 (d, 7=7.0 Hz, 3H) ppm. ESI-MS m/z calc. 504.16837, found 505.0 (M+1)$^+$; 503.0 (M−1)$^-$; Retention time: 3.16 minutes.

Figure 5:
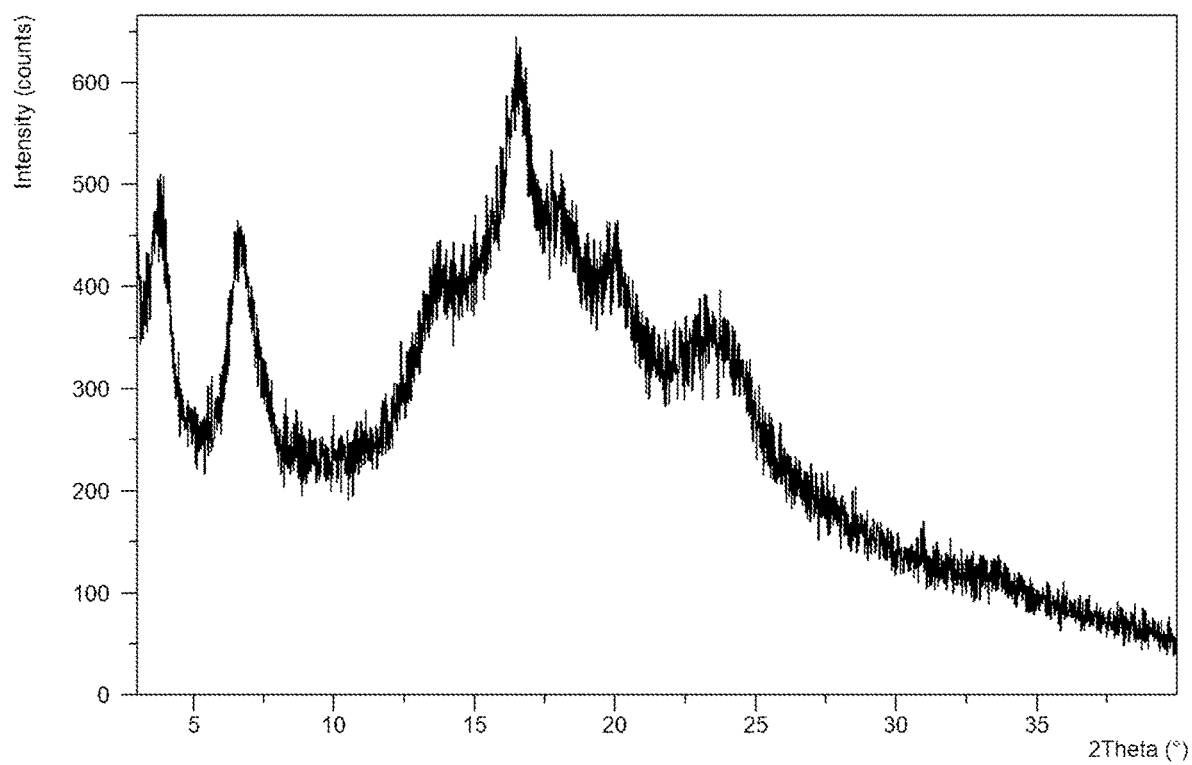
FIG. 5 depicts an XRPD pattern characteristic of amorphous Compound 21.

Compound 21 was analyzed by X-ray powder diffraction analysis Method B and determined to be amorphous (see FIG. 5).

The following compounds were made using the method described in Example 2, except that 6-(1-((tert-butyldimethylsilyl)oxy)-3-methoxypropyl)pyridin-3-amine was used as the coupling partner in the amide coupling step 1. In step 2, purification was performed by chiral SFC using a Chiralpak IB column, b m particle size, 25 cm×20 mm from Daicel (Mobile phase: 5% MeOH (containing 20 mM Ammonia), 95% $CO_2$. Flow: 100 mL/min.) on a Prep-100 SFC instrument from Waters:

| Cmpd No. | Compound Name | LC/MS | NMR (shifts in ppm) |
|---|---|---|---|
| 22 | rel-(2R*,3S*,4S*,5R*)-3-(3,4-difluoro-2-methoxyphenyl)-N-(6-(1-hydroxy-3-methoxypropyl)pyridin-3-yl)-4,5-dimethyl-5-(trifluoromethyl)tetrahydrofuran-2-carboxamide (Precursor was the first eluting peak by SFC on Chiralpak IB column, rt = 0.37 min) | ESI-MS m/z calc. 518.184, found 519.0 $(M + 1)^+$; 517.0 $(M - 1)^-$; Retention time: 3.20 minutes | $^1$H NMR (400 MHz, DMSO-$d_6$) δ 10.37 (s, 1H), 8.64 (dd, J = 2.6, 0.7 Hz, 1H), 8.01 (dd, J = 8.5, 2.5 Hz, 1H), 7.43 (d, J = 8.5 Hz, 1H), 7.17 dd, J = 9.0, 6.3 Hz, 2H), 5.32 (d, J = 5.2 Hz, 1H), 5.09 (d, J = 10.4 Hz, 1H), 4.61 (dt, J = 9.0, 4.7 Hz, 1H), 4.25 (dd, J = 10.3, 7.6 Hz, 1H), 3.95 (d, J = 2.2 Hz, 3H), 3.46 (ddd, J = 9.4, 7.5, 6.7 Hz, 1H), 3.38-3.33 (m, 1H), 3.20 (s, 3H), 2.77 (p, J = 7.5 Hz, 1H), 1.96 (dtd, J = 14.4, 7.4, 4.3 Hz, 1H), 1.73 (dddd, J = 13.6, 8.6, 6.7, 5.1 Hz, 1H), 1.61 (s, 3H), 0.77-0.70 (m, 3H) ppm. |
| 23 | rel-(2R*,3S*,4S*,5R*)-3-(3,4-difluoro-2-methoxyphenyl)-N-(6-(1-hydroxy-3-methoxypropyl)pyridin-3 -yl)-4,5-dimethyl-5-(trifluoromethyl)tetrahydrofuran-2-carboxamide (Precursor was the second eluting peak by SFC on Chiralpak IB column, rt = 0.75 min) | ESI-MS m/z calc. 518.184, found 519.0 $(M + 1)^+$; 517.0 $(M - 1)^-$; Retention time: 3.20 minutes | $^1$H NMR (400 MHz, DMSO-$d_6$) δ 10.36 (s, 1H), 8.67 (dd, J = 2.6, 0.7 Hz, 1H), 7.99 (dd, J = 8.5, 2.5 Hz, 1H), 7.43 (d, J = 8.5 Hz, 1H), 7.22-7.13 (m, 2H), 5.32 (d, J = 5.2 Hz, 1H), 5.09 (d, J = 10.3 Hz, 1H),4.61 (dt, J = 9.0, 4.7 Hz, 1H), 4.25 (dd, J = 10.3, 7.6 Hz, 1H), 3.95 (d, J = 2.2 Hz, 3H), 3.46 (dt, J = 9.4, 7.2 Hz, 1H), 3.39-3.32 (m, 1H), 3.21 (s, 3H), 2.77 (p, J = 7.5 Hz, 1H), 1.96 (dtd, J = 14.2, 7.4, 4.2 Hz, 1H), 1.80-1.67 (m, 1H), 1.61 (s, 3H), 0.77-0.70 (m, 3H) ppm. |

Example 3 rel-(2R,3S,5R)-3-(3,4-difluoro-2-methoxyphenyl)-N-(6-((R*)-1,2-dihydroxyethyl)pyridin-3-yl)-5-methyl-5-(trifluoromethyl)tetrahydrofuran-2-carboxamide (24) and rel-(2S,3R,5S)-3-(3,4-difluoro-2-methoxyphenyl)-N-(6-((R*)-1,2-dihydroxyethyl)pyridin-3-yl)-5-methyl-5-(trifluoromethyl)tetrahydrofuran-2-carboxamide (25)

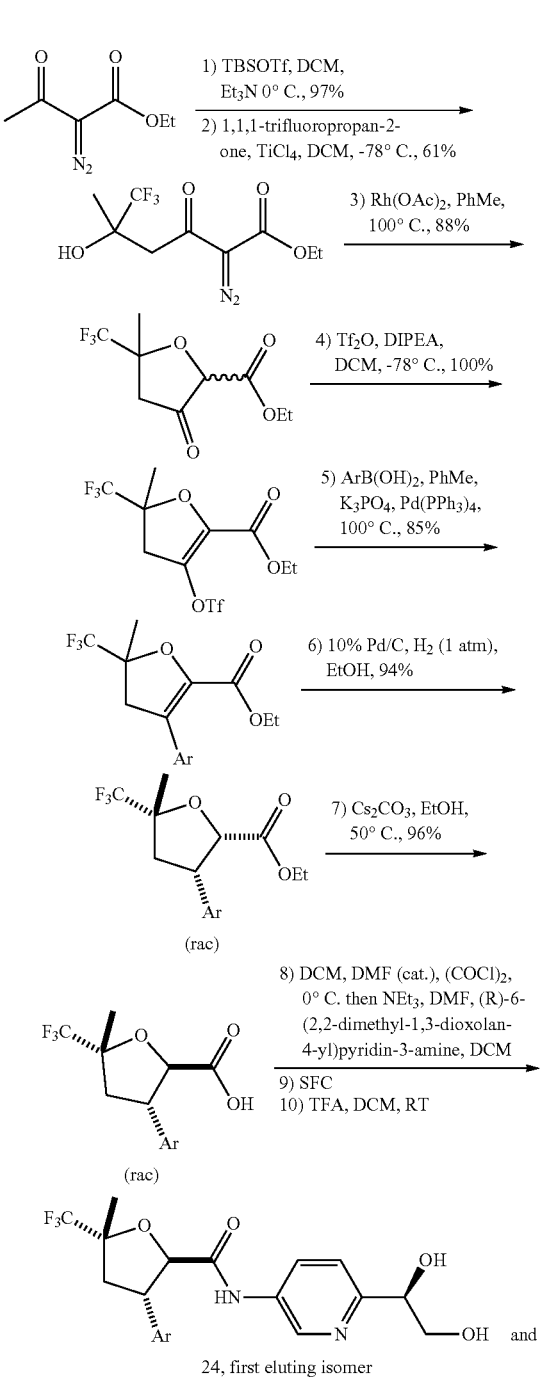

24, first eluting isomer

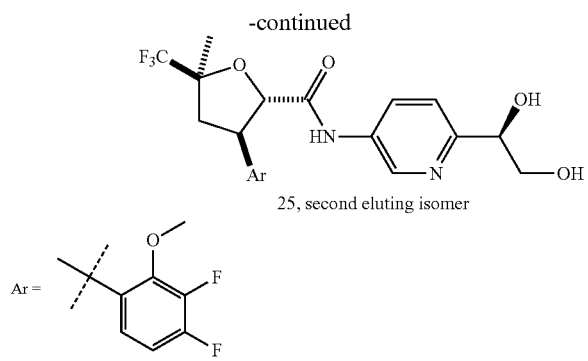

25, second eluting isomer

Step 1:

Triethylamine (8.05 g, 11.2 mL, 78.8 mmol) was added to a stirred solution of ethyl 2-diazo-3-oxobutanoate (5.0 g, 31.4 mmol) in DCM (50 mL) at 0° C. TBSOTf (9.24 g, 8.2 mL, 34.3 mmol) was added slowly and the reaction mixture was stirred for 30 min at 0° C. The reaction mixture was washed with a 30% NaHCO$_3$ solution (200 mL). The organic layer was separated, washed with water (500 mL), dried (MgSO$_4$), filtered and concentrated in vacuo to give ethyl 3-((tert-butyldimethylsilyl)oxy)-2-diazobut-3-enoate (8.22 g, 97%), which was used in the next step without further purification.

Step 2:

A solution of 1,1,1-trifluoropropan-2-one (33.8 g, 27 mL, 301.2 mmol) in DCM (150 mL) was cooled down to −78° C. TiCl$_4$ (56.8 g, 33 mL, 299.2 mmol) was added dropwise to the stirred reaction mixture. The reaction was kept at −78° C. for 10 min before a solution of ethyl 3-((tert-butyldimethylsilyl)oxy)-2-diazobut-3-enoate (64 g, 236.7 mmol) in DCM (150 mL) was added dropwise. The reaction was kept at −78° C. for 1 h. A saturated solution of NaHCO$_3$ was added and the mixture was diluted with DCM. The organic layer was separated, dried (MgSO$_4$), filtered and concentrated in vacuo. Purification by silica gel chromatography (SiO$_2$, 0 to 30% EtOAc in hexane) gave ethyl 2-diazo-6,6,6-trifluoro-5-hydroxy-5-methyl-3-oxohexanoate (39 g, 61%) as a pale yellow liquid. $^1$H NMR (400 MHz, Chloroform-d) δ 4.92 (s, 1H), 4.32 (q, J=7.1 Hz, 2H), 3.63 (d, J=15.5 Hz, 1H), 2.84 (d, J=15.5 Hz, 1H), 1.41 (s, 3H), 1.33 (t, J=7.1 Hz, 3H) ppm.

Step 3:

Rhodium (II) acetate (643 mg, 1.45 mmol) was charged into an oven dried two necked flask. Toluene (970 mL) was added and the solution was stirred at 100° C. for 10 min. The solution was briefly lifted out of the oil bath whilst a solution of ethyl 2-diazo-6,6,6-trifluoro-5-hydroxy-5-methyl-3-oxohexanoate (39 g, 145.4 mmol) in a toluene (200 mL) was added dropwise. The reaction mixture was heated at reflux for 1 h. The mixture was filtered through filter paper and the filtrate was concentrated in vacuo to give ethyl 5-methyl-3-oxo-5-(trifluoromethyl)tetrahydrofuran-2-carboxylate (30.89 g, 88%) as a mixture of epimers at the position next to the ester. $^1$H NMR (400 MHz, Chloroform-d) δ 4.68 (s, 1H), 4.35-4.17 (m, 2H), 2.89 (d, J=18.8, 1H), 2.58 (d, J=18.8, 1H), 1.70 (s, 3H), 1.30 (t, J=7.2, Hz, 3H) ppm.

Step 4:

Trifluoromethanesulfonic anhydride (6.0 mL, 35.7 mmol) was added dropwise to a solution of ethyl 5-methyl-3-oxo-5-(trifluoromethyl)tetrahydrofuran-2-carboxylate (6.5 g, 27.1 mmol) and DIPEA (14 mL, 80.4 mmol) in DCM (150 mL) at −78° C. The reaction mixture was stirred for 2.5 h before saturated aqueous NH$_4$Cl (75 mL) was added. The mixture was warmed up to ambient temperature. The aqueous layer was extracted with DCM (2×30 mL). The combined organic extracts were dried (MgSO$_4$), filtered and concentrated in vacuo to give ethyl 5-methyl-5-(trifluoromethyl)-3-(((trifluoromethyl)sulfonyl)oxy)-4,5-dihydrofuran-2-carboxylate (10.1 g), which was used directly in the next reaction.

Step 5:

K$_3$PO$_4$ (13 mL of 2 M aq., 26.0 mmol) was added to a stirred solution of (3,4-difluoro-2-methoxyphenyl)boronic acid (2.0 g, 10.6 mmol) and ethyl 5-methyl-5-(trifluoromethyl)-3-(((trifluoromethyl)sulfonyl)oxy)-4,5-dihydrofuran-2-carboxylate (3 g, 7.90 mmol) in toluene (80 mL). The mixture was degassed by bubbling nitrogen through the solution for 20 min. Pd(PPh$_3$)$_4$ (466 mg, 0.40 mmol) was added and the reaction was heated to 100° C. for 1 h. The mixture was filtered through a pad of celite. The filtrates were diluted with water (50 mL) and the phases were separated. The aqueous layer was extracted with EtOAc (50×2 mL). The combined organic extracts were dried (MgSO$_4$), filtered and concentrated in vacuo. Purification by silica gel chromatography (SiO$_2$, 0 to 2% EtOAc in hexane) gave ethyl 3-(3,4-difluoro-2-methoxyphenyl)-5-methyl-5-(trifluoromethyl)-4,5-dihydrofuran-2-carboxylate (2.5 g, 85%) as a light-yellow liquid. $^1$H NMR (400 MHz, Chloroform-d) δ 6.87 (pd, J=8.8, 6.2 Hz, 2H), 4.15 (q, J=7.1 Hz, 2H), 3.89 (s, 3H), 3.42 (d, J=17.4 Hz, 1H), 2.93 (d, J=17.4 Hz, 1H), 1.65 (s, 3H), 1.14 (t, J=7.1 Hz, 3H) ppm. ESI-MS m/z calc. 366.08905, found 367.4 (M+1)$^+$; Retention time: 1.01 minutes.

Step 6:

EtOH (200 mL) was added to a mixture of ethyl 3-(3,4-difluoro-2-methoxyphenyl)-5-methyl-5-(trifluoromethyl)-4,5-dihydrofuran-2-carboxylate (5.51 g, 15.0 mmol) and Pd/C (10 wt. % loading, 2.2 g, 2.067 mmol). The mixture was degassed and stirred under a balloon of H$_2$ for 96 h. The catalyst was removed by filtration and the solids washed with EtOH (50 mL). The filtrates were concentrated in vacuo. A further portion of Pd/C (10 wt. % loading, 2.2 g, 2.07 mmol) was added to the residue followed by EtOH (200 mL). The reaction mixture was stirred under a balloon of H$_2$ at ambient temperature for 24 h. The catalyst was removed by filtration and the solids washed with EtOH (50 mL). The filtrates were concentrated in vacuo. A further portion of Pd/C (10 wt. % loading, 2.2 g, 2.07 mmol) was added to the residue followed by EtOH (200 mL) and the reaction mixture stirred under a balloon of H$_2$ at ambient temperature for 4 days. The catalyst was removed by filtration and the solids washed with EtOH (50 mL). The filtrates were concentrated in vacuo to give ethyl rac-(2S,3S,5R)-3-(3,4-difluoro-2-methoxyphenyl)-5-methyl-5-(trifluoromethyl)tetrahydrofuran-2-carboxylate (5.19 g, 94%) as a white solid, and as a single diastereomer. $^1$H NMR (500 MHz, Chloroform-d) δ 6.89-6.86 (m, 1H), 6.82-6.77 (m, 1H), 4.93 (d, J=8.9 Hz, 1H), 4.23 (dt, J=13.0, 7.6 Hz, 1H), 4.08 (d, J=2.9 Hz, 3H), 3.85-3.71 (m, 2H), 2.82 (t, J=12.5 Hz, 1H), 2.04 (dd, J=12.0, 6.7 Hz, 1H), 1.53 (s, 3H), 0.94 (t, J=7.1 Hz, 3H) ppm; $^{19}$F NMR (471 MHz, Chloroform-d) δ −80.15, −136.84 (d, J=19.4 Hz), −154.77 (d, J=19.6 Hz) ppm.

Step 7:

Ethyl rac-(2S,3S,5R)-3-(3,4-difluoro-2-methoxyphenyl)-5-methyl-5-(trifluoromethyl)tetrahydrofuran-2-carboxylate (5.19 g, 14.09 mmol) was dissolved in ethanol (100 mL). $Cs_2CO_3$ (7.1 g, 21.79 mmol) was added and the suspension stirred at 50° C. for 2 h. The reaction mixture was concentrated in vacuo and the residue partitioned between 1M HCl and MTBE. The aqueous layer was extracted twice with MTBE. The combined organic extracts were dried ($MgSO_4$), filtered and concentrated in vacuo to give rac-(2R,3S,5R)-3-(3,4-difluoro-2-methoxyphenyl)-5-methyl-5-(trifluoromethyl)tetrahydrofuran-2-carboxylic acid (5.1063 g, 96%) as a colourless oil. $^1$H NMR (500 MHz, Chloroform-d) δ 6.99-6.96 (m, 1H), 6.92-6.87 (m, 1H), 4.68 (d, J=10.5 Hz, 1H), 4.00 (d, J=2.7 Hz, 3H), 3.90 (ddd, J=12.0, 10.6, 8.2 Hz, 1H), 2.58 (t, J=12.5 Hz, 1H), 2.31 (dd, J=13.0, 8.2 Hz, 1H), 1.60 (s, 3H) ppm; $^{19}$F NMR (471 MHz, Chloroform-d) δ −81.56, −136.40 (d, J=19.6 Hz), −153.60 (d, J=19.5 Hz) ppm. ESI-MS m/z calc. 340.0734, found 339.5 (M−1)$^-$; Retention time: 0.52 minutes.

Step 8:

Oxalyl chloride (70 μL, 0.8024 mmol) was carefully added to an ice cooled solution of rac-(2R,3S,5R)-3-(3,4-difluoro-2-methoxyphenyl)-5-methyl-5-(trifluoromethyl)tetrahydrofuran-2-carboxylic acid (150 mg, 0.3968 mmol) and DMF (2-methyl-THF solution, 50 μL of 0.86 M, 0.04300 mmol) in 2-methyltetrahydrofuran (5 mL). The reaction mixture was stirred and warmed to room temperature over 45 min. The reaction mixture was concentrated in vacuo and the residue dissolved in 2-methyltetrahydrofuran (5 mL). This solution was added to an ice cooled solution of (R)-6-(2,2-dimethyl-1,3-dioxolan-4-yl)pyridin-3-amine (90 mg, 0.4634 mmol) and TEA (250 μL, 1.794 mmol) in 2-methyltetrahydrofuran (5 mL). The resulting mixture was stirred and warmed to ambient temperature over 1 h. The reaction mixture was quenched with water (2 mL) and the layers separated. The aqueous phase was extracted with EtOAc (2×5 mL). The combined organic extracts were dried (MgSO4), filtered and concentrated in vacuo. Purification by silica gel chromatography (24 g $SiO_2$, 0 to 100% EtOAc in heptane, loaded from DCM) gave rel-(2R,3S,5R)-3-(3,4-difluoro-2-methoxyphenyl)-N-(6-((R*)-2,2-dimethyl-1,3-dioxolan-4-yl)pyridin-3-yl)-5-methyl-5-(trifluoromethyl)tetrahydrofuran-2-carboxamide (120.4 mg, 59%) as a white solid and as a mixture of 2 diastereoisomers. $^1$H NMR (500 MHz, DMSO-$d_6$) δ 10.15 (s, 1H), 8.70-8.69 (m, 1H), 8.03 (dt, J=8.4, 2.6 Hz, 1H), 7.45 (d, J=8.5 Hz, 1H), 7.22-7.15 (m, 2H), 5.07 (t, J=6.8 Hz, 1H), 4.65 (d, J=10.1 Hz, 1H), 4.33 (dd, J=8.2, 6.7 Hz, 1H), 4.05 (q, J=10.0 Hz, 1H), 3.87 (d, J=2.0 Hz, 3H), 3.83 (ddd, J=8.0, 6.7, 1.2 Hz, 1H), 2.46 (d, J=10.5 Hz, 2H), 1.57 (s, 3H), 1.43 (s, 3H), 1.40 (s, 3H) ppm; 19F NMR (471 MHz, DMSO-$d_6$) δ −80.12, −138.13 (d, J=21.1 Hz), −154.77 (d, J=21.2 Hz) ppm. ESI-MS m/z calc. 516.16833, found 517.5 (M+1)$^+$; 515.6 (M−1)$^-$; Retention time: 0.99 minutes.

Step 9:

The 2 diastereoisomers of rel-(2R,3S,5R)-3-(3,4-difluoro-2-methoxyphenyl)-N-(6-((R*)-2,2-dimethyl-1,3-dioxolan-4-yl)pyridin-3-yl)-5-methyl-5-(trifluoromethyl)tetrahydrofuran-2-carboxamide were separated by chiral SFC using a Chiralpak IA column, 5 m particle size, 25 cm×20 mm from Daicel (Mobile phase: 15% MeOH (containing 20 mM Ammonia), 85% $CO_2$. Flow: 100 mL/min.) on a Prep-100 SFC instrument from Waters:

First Eluting Isomer (rt=0.73 min): rel-(2R,3S,5R)-3-(3,4-difluoro-2-methoxyphenyl)-N-(6-((R*)-2,2-dimethyl-1,3-dioxolan-4-yl)pyridin-3-yl)-5-methyl-5-(trifluoromethyl)tetrahydrofuran-2-carboxamide (42 mg, 60%) as a white solid. ESI-MS m/z calc. 516.16833, found 517.2 (M+1)$^+$; 515.3 (M−1)$^-$; Retention time: 3.41 minutes.

Second Eluting Isomer (rt=0.95 min): rel-(2S,3R,5S)-3-(3,4-difluoro-2-methoxyphenyl)-N-(6-((R*)-(2,2-dimethyl-1,3-dioxolan-4-yl)pyridin-3-yl)-5-methyl-5-(trifluoromethyl)tetrahydrofuran-2-carboxamide (51 mg, 73%) as a white solid. ESI-MS m/z calc. 516.16833, found 517.2 (M+1)$^+$; 515.3 (M−1)$^-$; Retention time: 3.41 minutes.

Step 10:

TFA (225 μL, 2.920 mmol) was added to a solution of rel-(2R,3S,5R)-3-(3,4-difluoro-2-methoxyphenyl)-N-(6-((R*)-(2,2-dimethyl-1,3-dioxolan-4-yl)pyridin-3-yl)-5-methyl-5-(trifluoromethyl)tetrahydrofuran-2-carboxamide (42 mg, 0.081 mmol) (First Eluting Isomer from SFC separation) in DCM (5 mL) and the mixture stirred for 18 h at ambient temperature. The mixture was concentrated in vacuo and azeotroped twice with DCM. Purification by reverse phase preparative HPLC (Waters Sunfire C18, 10 μM, 100 Å column, 0% to 100% MeCN in water containing 0.1% ammonia) gave after freeze-drying rel-(2R,3S,5R)-3-(3,4-difluoro-2-methoxyphenyl)-N-(6-((R*)-1,2-dihydroxyethyl)pyridin-3-yl)-5-methyl-5-(trifluoromethyl)tetrahydrofuran-2-carboxamide (24, 24.6 mg, 62%) as a white solid. $^1$H NMR (500 MHz, DMSO-$d_6$) δ 10.09 (s, 1H), 8.64 (d, J=2.2 Hz, 1H), 7.97 (dd, J=8.5, 2.5 Hz, 1H), 7.42 (d, J=8.5 Hz, 1H), 7.22-7.15 (m, 2H), 5.32 (d, J=4.9 Hz, 1H), 4.66-4.62 (m, 2H), 4.54 (dt, J=6.6, 4.5 Hz, 1H), 4.05 (q, J=10.1 Hz, 1H), 3.88 (d, J=1.9 Hz, 3H), 3.63 (ddd, J=10.3, 6.0, 4.2 Hz, 1H), 3.48-3.43 (m, 1H), 2.47 (s, 1H), 2.45 (s, 1H), 1.56 (s, 3H) ppm; $^{19}$F NMR (471 MHz, DMSO-$d_6$) δ −80.12, −138.14 (d, J=21.0 Hz), −154.77 (d, J=21.0 Hz) ppm. ESI-MS m/z calc. 476.13705, found 474.4 (M+1)$^+$; 475.5 (M−1)$^-$; Retention time: 2.77 minutes.

rel-(2S,3R,5S)-3-(3,4-difluoro-2-methoxyphenyl)-N-(6-((R*)-(2,2-dimethyl-1,3-dioxolan-4-yl)pyridin-3-yl)-5-methyl-5-(trifluoromethyl)tetrahydrofuran-2-carboxamide (51 mg, 0.099 mmol) (Second Eluting Isomer from SFC separation) was treated in the same way to give after freeze-drying rel-(2S,3R,5S)-3-(3,4-difluoro-2-methoxyphenyl)-N-(6-((R*)-1,2-dihydroxyethyl)pyridin-3-yl)-5-methyl-5-(trifluoromethyl)tetrahydrofuran-2-carboxamide (25, 32.0 mg, 66%) as a white solid. $^1$H NMR (500 MHz, DMSO-$d_6$) δ 10.08 (s, 1H), 8.65 (d, J=2.5 Hz, 1H), 7.96 (dd, J=8.5, 2.5 Hz, 1H), 7.42 (d, J=8.5 Hz, 1H), 7.22-7.15 (m, 2H), 5.32 (d, J=4.9 Hz, 1H), 4.66-4.62 (m, 2H), 4.54 (dt, = 6.7, 4.5 Hz, 1H), 4.05 (q, J=10.0 Hz, 1H), 3.88 (d, J=1.9 Hz, 3H), 3.64 (ddd, J=10.4, 6.0, 4.2 Hz, 1H), 3.45 (ddd, J=11.0, 6.7, 5.9 Hz, 1H), 2.47 (s, 1H), 2.45 (s, 1H), 1.57 (s, 3H) ppm; $^{19}$F NMR (471 MHz, DMSO-$d_6$) δ −80.12, −138.14 (d, J=21.1 Hz), −154.77 (d, i=21.1 Hz) ppm. ESI-MS m/z calc. 476.13705, found 477.4 (M+1)$^+$; 475.4 (M−1)$^-$; Retention time: 2.77 minutes.

The following compounds were made using the method described in Example 3, except that (S)-6-(2,2-dimethyl-1,3-dioxolan-4-yl)pyridin-3-amine was used in place of (R)-6-(2,2-dimethyl-,3-dioxolan-4-yl)pyridin-3-amine in the amide coupling step 8. In step 9, purification was performed by chiral SFC using a Chiralpak IA column, 5 μm particle size, 25 cm×20 mm from Daicel Corporation on a Prep-100 SFC instrument from Waters:

| Cmpd No. | Compound Name | LC/MS | NMR (shifts in ppm) |
|---|---|---|---|
| 26 | rel-(2R,3S,5R)-3-(3,4-difluoro-2-methoxyphenyl)-N-(6-((S*)-1,2-dihydroxyethyl)pyridin-3-yl)-5-methyl-5-(trifluoromethyl)tetrahydrofuran-2-carboxamide (Precursor was the first eluting peak by SFC on Chiralpak IA column, rt = 0.70 min) | ESI-MS m/z calc. 476.13705, found 477.4 (M + 1)$^+$; 475.5 (M − 1)$^−$; Retention time: 2.78 minutes | $^1$H NMR (500 MHz, DMSO-d$_6$) δ 10.08 (s, 1H), 8.65 (d, J = 2.3 Hz, 1H), 7.96 (dd, J = 8.5, 2.5 Hz, 1H), 7.42 (d, J = 8.5 Hz, 1H), 7.21-7.15 (m, 2H), 5.32 (d, J = 4.9 Hz, 1H), 4.66-4.62 (m, 2H), 4.54 (dt, J = 6.7, 4.5 Hz, 1H), 4.08-4.02 (m, 1H), 3.87 (d, J = 1.8 Hz, 3H), 3.64 (ddd, J = 10.5, 6.0, 4.4 Hz, 1H), 3.48-3.43 (m, 1H), 2.47 (s, 1H), 2.45 (s, 1H), 1.57 (s, 3H) ppm. |
| 27 | rel-(2S,3R,5S)-3-(3,4-difluoro-2-methoxyphenyl)-N-(6-((S*)-1,2-dihydroxyethyl)pyridin-3-yl)-5-methyl-5-(trifluoromethyl)tetrahydrofuran-2-carboxamide (Precursor was the second eluting peak by SFC on Chiralpak IA column, rt = 0.87 min) | ESI-MS m/z calc. 476.13705, found 477.3 (M + 1)$^+$; 475.5 (M − 1)$^−$; Retention time: 2.78 minutes | $^1$H NMR (500 MHz, DMSO-d$_6$) δ 10.09 (s, 1H), 8.64 (d, J = 2.3 Hz, 1H), 7.97 (dd, J = 8.5, 2.5 Hz, 1H), 7.42 (d, J = 8.5 Hz, 1H), 7.22-7.15 (m, 2H), 5.32 (d, J = 4.9 Hz, 1H), 4.66-4.62 (m, 2H), 4.54 (dt, J = 6.7, 4.5 Hz, 1H), 4.05 (q, J = 10.1 Hz, 1H), 3.88 (d, J = 1.9 Hz, 3H), 3.63 (ddd, J = 10.4, 6.0, 4.2 Hz, 1H), 3.45 (ddd, J = 11.0, 6.9, 5.8 Hz, 1H), 2.47 (s, 1H), 2.45 (s, 1H), 1.57 (s, 3H) ppm. |
| 28 | rel-(2S,3R,5S)-3-(3,4-difluoro-2-methoxyphenyl)-N-(2-(1,2-dihydroxyethyl)pyrimidin-5-yl)-5-methyl-5-(trifluoromethyl)tetrahydrofuran-2-carboxamide (Precursor was the first eluting peak by SFC on Chiralcel OJ column, rt = 4.75 min) | ESI-MS m/z calc. 477.13232, found 478.0 (M + 1)$^+$; 476.0 (M − 1)$^−$; Retention time: 2.78 minutes | $^1$H NMR (500 MHz, DMSO-d$_6$) δ 10.25 (s, 1H), 8.96 (s, 2H), 7.23-7.15 (m, 2H), 5.17 (d, J = 6.0 Hz, 1H), 4.68 (d, J = 10.1 Hz, 1H), 4.60 (dt, J = 10.2, 5.9 Hz, 2H), 4.04 (q, J = 10.3 Hz, 1H), 3.88 (d, J = 2.0 Hz, 3H), 3.72 (dt, J = 11.6, 6.0 Hz, 1H), 3.64 (dt, J = 11.2, 6.0 Hz, 1H), 1.58 (s, 3H) ppm. 2 protons hidden by DMSO signal. |
| 29 | rel-(2R,3S,5R)-3-(3,4-difluoro-2-methoxy phenyl)-N-(2-(1,2-dihydroxyethyl)pyrimidin-5-yl)-5-methyl-5-(trifluoromethyl)tetrahydrofuran-2-carboxamide (Precursor was the second eluting peak by SFC on Chiralcel OJ column, rt = 5.42 min) | ESI-MS m/z calc. 477.13232, found 478.0 (M + 1)$^+$; 476.0 (M − 1)$^−$; Retention time: 2.78 minutes | $^1$H NMR (500 MHz, DMSO-d$_6$) δ 10.25 (s, 1H), 8.96 (s, 2H), 7.23-7.15 (m, 2H), 5.17 (d, J = 6.0 Hz, 1H), 4.68 (d, J = 10.2 Hz, 1H), 4.60 (dt, J = 11.4, 5.9 Hz, 2H), 4.04 (q, J = 10.1 Hz, 1H), 3.89 (d, J = 2.0 Hz, 3H), 3.72 (dt, J = 11.5, 6.0 Hz, 1H), 3.64 (dt, J = 11.0, 5.9 Hz, 1H), 1.58 (s, 3H) ppm. 2 protons hidden by DMSO signal. |
| 30 | rel-(2S,3R,5S)-3-(3,4-difluoro-2-methoxyphenyl)-N-(2-(1,2-dihydroxyethyl)pyrimidin-5-yl)-5-methyl-5-(trifluoromethyl)tetrahydrofuran-2-carboxamide (Precursor was the third eluting peak by SFC on Chiralcel OJ column, rt = 10.45 min) | ESI-MS m/z calc. 477.13232, found 477.8 (M + 1)$^+$; 476.0 (M − 1)$^−$; Retention time: 2.78 minutes | $^1$H NMR (500 MHz, DMSO-d$_6$) δ 10.25 (s, 1H), 8.96 (s, 2H), 7.23-7.15 (m, 2H), 5.17 (d, J = 6.0 Hz, 1H), 4.68 (d, J = 10.1 Hz, 1H), 4.62-4.57 (m, 2H), 4.04 (q, J = 11.0, 10.5 Hz, 1H), 3.88 (d, J = 1.9 Hz, 3H), 3.72 (dt, J = 11.5, 6.0 Hz, 1H), 3.64 (dt, J = 11.1, 6.0 Hz, 1H), 1.58 (s, 3H) ppm. 2 protons hidden by DMSO signal. |
| 31 | rel-(2R,3S,5R)-3-(3,4-difluoro-2-methoxyphenyl)-N-(2-(1,2-dihydroxyethyl)pyrimidin-5-yl)-5-methyl-5-(trifluoromethyl)tetrahydrofuran-2-carboxamide (Precursor was the fourth eluting peak by SFC on Chiralcel OJ column, rt = 12.17 min) | ESI-MS m/z calc. 477.13232, found 478.0 (M + 1)$^+$; 476.0 (M − 1)$^−$; Retention time: 2.78 minutes | $^1$H NMR (500 MHz, DMSO-d$_6$) δ 10.25 (s, 1H), 8.96 (s, 2H), 7.23-7.15 (m, 2H), 5.17 (d, J = 6.0 Hz, 1H), 4.68 (d, J = 10.1 Hz, 1H), 4.62-4.57 (m, 2H), 4.04 (q, J = 10.2 Hz, 1H), 3.88 (d, J = 1.9 Hz, 3H), 3.72 (dt, J = 11.5, 5.9 Hz, 1H), 3.64 (dt, J = 11.0, 5.9 Hz, 1H), 1.58 (s, 3H) ppm. |

The following compounds were made using the method described in Example 3, except that rac-2-(2,2-dimethyl-1,3-dioxolan-4-yl)pyrimidin-5-amine was used in place of (R)-6-(2,2-dimethyl-1,3-dioxolan-4-yl)pyridin-3-amine in the amide coupling step 8. In the Suzuki coupling step 5, Pd(PPh$_3$)$_4$ was used as the catalyst together with Na$_2$CO$_3$ as the base and a mixture of toluene, water and methanol as the solvent and the reaction was carried out at 80° C. over 16 h. In step 9, a mixture of four stereoisomers of rel-(2R,3S,5R)-3-(3,4-difluoro-2-methoxyphenyl)-N-(2-(1,2-dihydroxyethyl)pyrimidin-5-yl)-5-methyl-S-(trifluoromethyl)tetrahydrofuran-2-carboxamide, which had known relative stereochemistry about the THF ring (i.e., (2R,3S,5R)), but unknown relative stereochemistry between the THF ring and the dihydroxyethyl substituent, was performed by chiral SFC using a Chiralcel OJ column, 5 μm particle size, 25 cm×21.2 mm from Daicel Corporation (40° C.; Mobile Phase: 6% MeOH (20 mM NH3), 94% CO2; Flow: 70 mL/min.) on a Prep-100 SFC instrument from Waters:

-continued

| Cmpd No. | Compound Name | LC/MS | NMR (shifts in ppm) |
|---|---|---|---|
| | | | 2 protons hidden by DMSO signal. |

The following compounds were made using the method described in Example 3, except that 2-(2-ethoxy-3,4-difluoro-phenyl)-4,4,5,5-tetramethyl-1,3,2-dioxaborolane was used in place of (3,4-difluoro-2-methoxyphenyl)boronic acid in the Suzuki coupling of step 5. In the case of compounds 32 and 33, (S)-6-(2,2-dimethyl-1,3-dioxolan-4-yl)pyridin-3-amine was used in place of (R)-6-(2,2-dimethyl-1,3-dioxolan-4-yl)pyridin-3-amine in the amide coupling step 8. In the Suzuki coupling step 5, Pd(PPh₃)₄ was used as the catalyst together with Na₂CO₃ as the base and a mixture of toluene, water and methanol as the solvent and the reaction was carried out at 80° C. over 16 h. In step 9, purification was performed by chiral SFC using a (R,R)-Whelk-1 column, 5 um particle size, 25 cm×21.1 mm from Daicel (Mobile phase: 30% MeOH (containing 20 mM Ammonia), 70% CO₂. Flow: 100 mL/min.) on a Minigram SFC instrument from Berger Instruments. The deprotection step 10 was carried out at ambient temperature over 1.5 h using 12 M HCl in THF as the solvent:

| Cmpd No. | Compound Name | LC/MS | NMR (shifts in ppm) |
|---|---|---|---|
| 32 | rel-(2S,3R,5S)-N-(6-((S*)-1,2-dihydroxyethyl)pyridin-3-yl)-3-(2-ethoxy-3,4-difluorophenyl)-5-methyl-5-(trifluoromethyl)tetrahydrofuran-2-carboxamide (Precursor was the first eluting peak by SFC on (R,R)-Whelk-O1 column, rt = 3.62 min) | ESI-MS m/z calc. 490.1527, found 491.4 (M + 1)⁺; 489.5 (M − 1)⁻; Retention time: 2.93 minutes | |
| 33 | rel-(2R,3S,5R)-N-(6-((S*)-1,2-dihydroxyethyl)pyridin-3-yl)-3-(2-ethoxy-3,4-difluorophenyl)-5-methyl-5-(trifluoromethyl)tetrahydrofuran-2-carboxamide (Precursor was the second eluting peak by SFC on (R,R)-Whelk-O1 column, rt = 4.18 min) | ESI-MS m/z calc. 490.1527, found 491.4 (M + 1)⁺; 489.5 (M − 1)⁻; Retention time: 2.92 minutes | |
| 34 | rel-(2S,3R,5S)-N-(6-((R*)-1,2-dihydroxyethyl)pyridin-3-yl)-3-(2-ethoxy-3,4-difluorophenyl)-5-methyl-5-(trifluoromethyl)tetrahydrofuran-2-carboxamide (Precursor was the first eluting peak by SFC on (R,R)-Whelk-O1 column, rt = 3.62 min) | ESI-MS m/z calc. 490.1527, found 491.4 (M + 1)⁺; 489.5 (M − 1)⁻; Retention time: 2.93 minutes | |
| 35 | rel-(2R,3S,5R)-N-(6-((R*)-1,2-dihydroxyethyl)pyridin-3-yl)-3-(2-ethoxy-3,4-difluorophenyl)-5-methyl-5-(trifluoromethyl)tetrahydrofuran-2-carboxamide (Precursor was the second eluting peak by SFC on (R,R)-Whelk-O1 column, rt = 4.18 min) | ESI-MS m/z calc. 490.1527, found 491.4 (M + 1)⁺; 489.5 (M − 1)⁻; Retention time: 2.92 minutes | |

Figure 6:
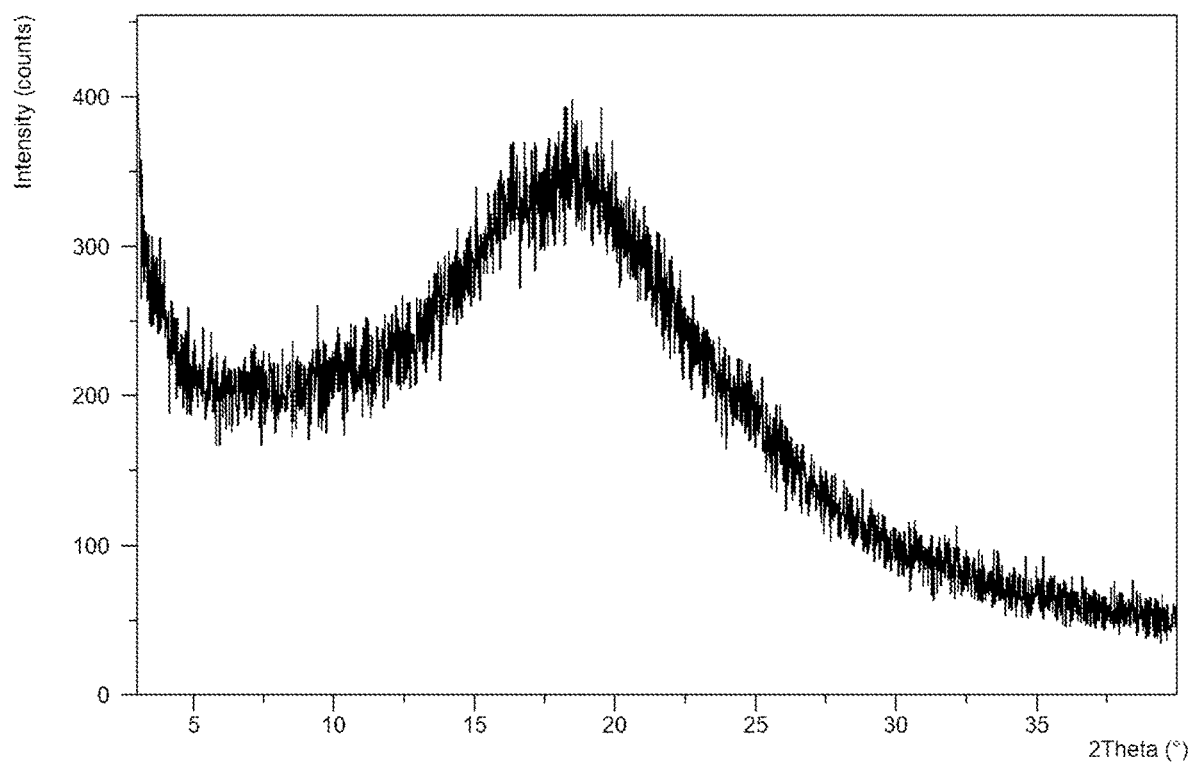
FIG. 6 depicts an XRPD pattern characteristic of amorphous Compound 35.

Compound 35 was analyzed by X-ray powder diffraction analysis Method B and determined to be amorphous (see FIG. 6).

Example 4

(2R,3S,4S,5R)-3-(3,4-difluoro-2-hydroxyphenyl)-N-(6-((R)-1,2-dihydroxyethyl)pyridin-3-yl)-4,5-dimethyl-5-(trifluoromethyl)tetrahydrofuran-2-carboxamide (36) and (2R,3S,4S,5R)-3-(3,4-difluoro-2-(2-fluoroethoxy)phenyl)-N-(6-((R)-1,2-dihydroxyethyl)pyridin-3-yl)-4,5-dimethyl-5-(trifluoromethyl)tetrahydrofuran-2-carboxamide (37)

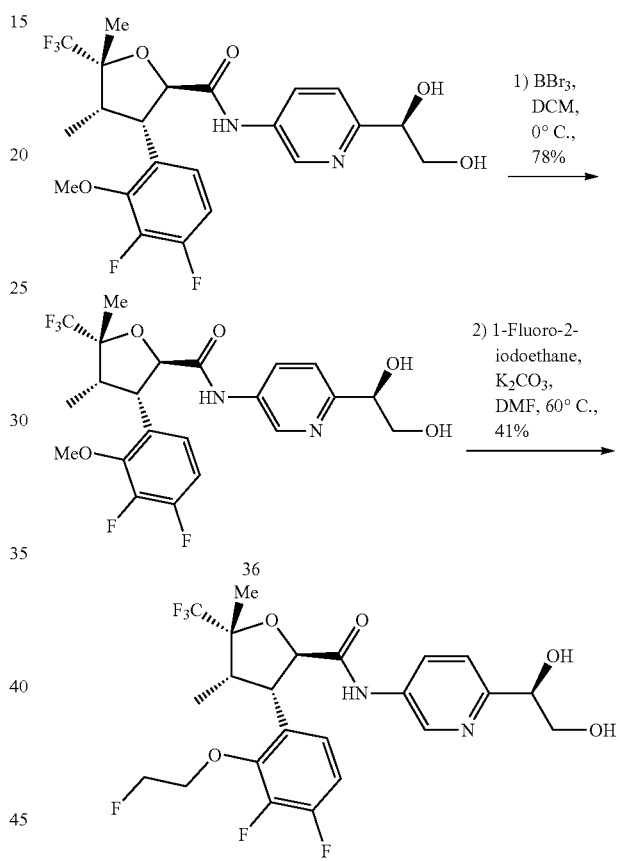

Step 1:

A stirred solution of (2R,3S,4S,5R)-3-(3,4-difluoro-2-methoxyphenyl)-N-(6-((R)-1,2-dihydroxyethyl)pyridin-3-yl)-4,5-dimethyl-5-(trifluoromethyl)tetrahydrofuran-2-carboxamide (1, 343.7 mg, 0.7008 mmol) in DCM (9 mL) was placed under a nitrogen atmosphere and cooled down with an ice bath. Boron tribromide (in DCM) (2.2 mL of 1 M, 2.200 mmol) was added and the reaction mixture was stirred for 2 h. The reaction was quenched by addition of MeOH (2 mL) and stirred overnight at ambient temperature. The mixture was concentrated in vacuo. The residue was dissolved in MeOH (3 mL) and the pH was adjusted to pH 9 with a 2M aqueous sodium hydroxide solution. Purification by reverse phase preparative HPLC (Waters Sunfire C18, 10 μM, 100 Å column, 0% to 100% MeCN in water containing 0.1% ammonia) gave (2R,3S,4S,5R)-3-(3,4-difluoro-2-hydroxyphenyl)-N-(6-((R)-1,2-dihydroxyethyl)pyridin-3-yl)-4,5-dimethyl-5-(trifluoromethyl)tetrahydrofuran-2-carboxamide (36, 259.8 mg, 78%). $^1$H NMR (500 MHz, DMSO-d$_6$) δ 10.45 (s, 1H), 10.40 (s, 1H), 8.65 (d, J=2.2 Hz, 1H), 8.00 (dd, J=8.7, 2.3 Hz, 1H), 7.42 (d, J=8.6 Hz, 1H), 7.03 (t, J=6.8 Hz, 1H), 6.85 (q, J=8.6 Hz, 1H), 5.33 (d, J=4.9 Hz, 1H), 5.09 (d, J=10.3 Hz, 1H), 4.64 (t, J=5.9 Hz, 1H), 4.57-4.50 (m, 1H), 4.28-4.19 (m, 1H), 3.66-3.57 (m, 1H), 3.49-3.38 (m, 1H), 2.83 (p, J=7.4 Hz, 1H), 1.58 (s, 3H), 0.70 (d, J=6.4 Hz, 3H) ppm. ESI-MS m/z calc. 476.13705, found 477.3 (M+1)$^+$; Retention time: 2.46 minutes.

Step 2:

K$_2$CO$_3$ (18 mg, 0.1302 mmol) was added to a mixture of 1-fluoro-2-iodoethane (10 µL, 0.1230 mmol) and (2R,3S, 4S,5R)-3-(3,4-difluoro-2-hydroxyphenyl)-N-(6-((R)-1,2-dihydroxyethyl)pyridin-3-yl)-4,5-dimethyl-5-(trifluoromethyl)tetrahydrofuran-2-carboxamide (36, 40 mg, 0.08396 mmol) in DMF (2 mL). The mixture was stirred at 60° C. for 6 h30. The mixture was diluted with MeOH and purified by reverse phase preparative HPLC (Waters Sunfire C18, 10 µM, 100 Å column, 0% to 100% MeCN in water containing 0.1% ammonia) to give (2R,3S,4S,5R)-3-(3,4-difluoro-2-(2-fluoroethoxy)phenyl)-N-(6-((R)-1,2-dihydroxyethyl)pyridin-3-yl)-4,5-dimethyl-5-(trifluoromethyl)tetrahydrofuran-2-carboxamide (37, 18.48 mg, 41%). $^1$H NMR (500 MHz, DMSO-d$_6$) δ 10.35 (s, 1H), 8.64 (dd, J=2.5, 0.8 Hz, 1H), 8.00 (dd, J=8.5, 2.5 Hz, 1H), 7.42 (d, J=8.6 Hz, 1H), 7.27-7.09 (m, 2H), 5.32 (d, J=4.9 Hz, 1H), 5.11 (d, J=10.6 Hz, 1H), 4.79 (dt, J=4.9, 2.4 Hz, 1H), 4.69 (dt, J=5.0, 2.4 Hz, 1H), 4.63 (t, J=5.9 Hz, 1H), 4.54 (dt, J=6.8, 4.5 Hz, 1H), 4.49-4.27 (m, 3H), 3.70-3.59 (m, 1H), 3.45 (ddd, J=10.9, 6.8, 5.7 Hz, 1H), 2.78 (p, J=7.4 Hz, 1H), 1.59 (s, 3H), 0.81-0.68 (m, 3H) ppm. ESI-MS m/z calc. 522.15894, found 523.3 (M+1)$^+$; Retention time: 3.0 minutes.

The following compound was made using the method described in Example 4, except that 2-bromo-1,1-difluoroethane was used in place of 1-fluoro-2-iodoethane in the alkylation step 2:

| Cmpd No. | Compound Name | LC/MS | NMR (shifts in ppm) |
|---|---|---|---|
| 38 | (2R,3S,4S,5R)-3-(2-(2,2-difluoroethoxy)-3,4-difluorophenyl)-N-(6-((R)-1,2-dihydroxyethyl)pyridin-3-yl)-4,5-dimethyl-5-(trifluoromethyl)tetrahydrofuran-2-carboxamide | ESI-MS m/z calc. 540.14954, found 541.2 (M + 1)$^+$; 539.1 (M − 1)$^-$; Retention time: 3.07 minutes | $^1$H NMR (500 MHz, DMSO-d$_6$) δ 10.35 (s, 1H), 8.64 (dd, J = 2.5, 0.8 Hz, 1H), 8.00 (dd, J = 8.6, 2.5 Hz, 1H), 7.42 (d, J = 8.5 Hz, 1H), 7.32-6.98 (m, 2H), 6.39 (tt, J = 53.9, 2.9 Hz, 1H), 5.32 (d, J = 4.9 Hz, 1H), 5.11 (d, J = 10.6 Hz, 1H), 4.63 (t, J = 5.9 Hz, 1H), 4.58-4.34 (m, 3H), 4.29 (dd, J = 10.6, 7.3 Hz, 1H), 3.63 (ddd, J = 10.6, 6.1, 4.2 Hz, 1H), 3.44 (ddd, J = 11.0, 6.9, 5.8 Hz, 1H), 2.78 (p, J = 7.4 Hz, 1H), 1.59 (s, 3H), 0.73 (d, J = 7.3 Hz, 3H) ppm. |

The following compound was made using the method described in Example 4 step 1, except that (2R,3S,4S,5R)-3-(3,4-difluoro-2-methoxyphenyl)-N-(2-(hydroxymethyl)pyrimidin-5-yl)-4,5-dimethyl-5-(trifluoromethyl)tetrahydrofuran-2-carboxamide (15) was used as the starting material:

| Cmpd No. | Compound Name | LC/MS | NMR (shifts in ppm) |
|---|---|---|---|
| 39 | (2R,3S,4S,5R)-3-(3,4-difluoro-2-hydroxyphenyl)-N-(2-(hydroxymethyl)pyrimidin-5-yl)-4,5-dimethyl-5-(trifluoromethyl)tetrahydrofuran-2-carboxamide | ESI-MS m/z calc. 447.12173, found 448.6 (M + 1)$^+$; 446.5 (M − 1)$^-$; Retention time: 2.46 minutes | $^1$H NMR (500 MHz, DMSO-d$_6$) δ 10.53 (s, 1H), 10.40 (s, 1H), 8.99 (s, 2H), 7.05 (ddd, J = 8.3, 5.7, 1.9 Hz, 1H), 6.87-6.78 (m, 1H), 5.26 (t, J = 6.5 Hz, 1H), 5.15 (d, J = 10.3 Hz, 1H), 4.56 (d, J = 5.4 Hz, 2H), 4.25 (dd, J = 10.3, 7.6 Hz, 1H), 2.84 (t, J = 7.5 Hz, 1H), 1.61 (s, 3H), 0.77-0.65 (m, 3H) ppm. |

Example 5 rel-(2R,3S,4S,5R)—N-(6-((R*)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide (40) and rel-(2S,3R,4R,5S)—N-(6-((R*)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide (41)

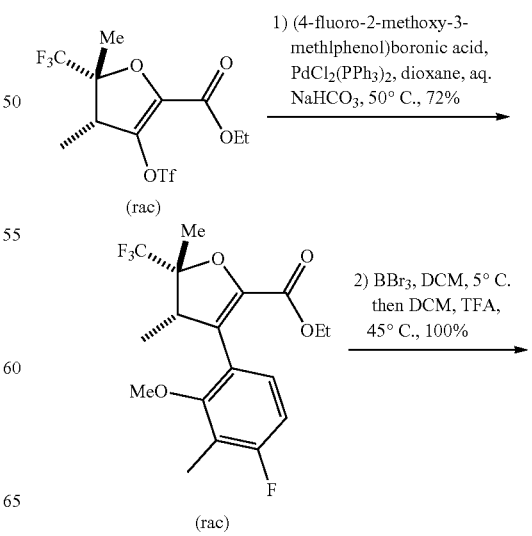

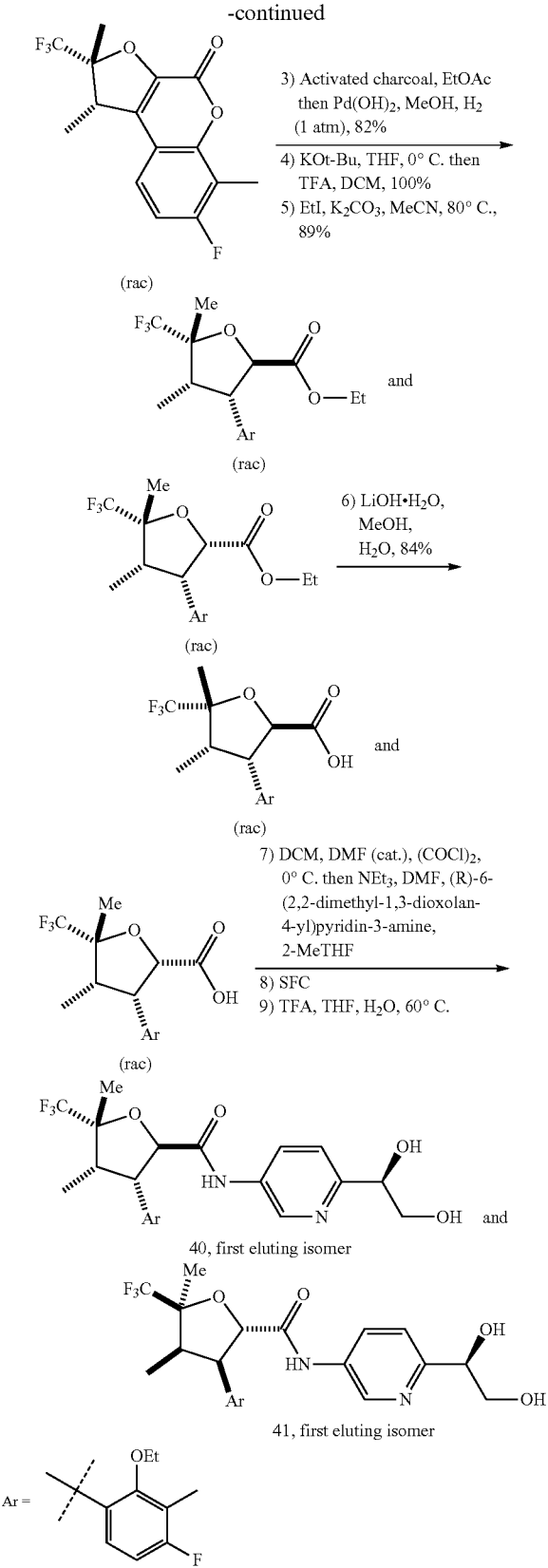

Step 1:

To a 2 L three necked round bottom flask, flanked with a thermometer, was added a mixture of ethyl rac-(4R,5R)-4, 5-dimethyl-5-(trifluoromethyl)-3-(((trifluoromethyl)sulfonyl)oxy)-4,5-dihydrofuran-2-carboxylate (39.05 g, 101.1 mmol), (4-fluoro-2-methoxy-3-methylphenyl)boronic acid (20.4 g, 110.9 mmol) and $PdCl_2(PPh_3)_2$(1.4 g, 1.995 mmol) in a saturated solution of $NaHCO_3$ (120 mL) and dioxane (400 mL). The orange mixture was heated to 50° C. internally for 20 min. The reaction mixture was cooled to ambient temperature and diluted with EtOAc (100 mL) and water (100 mL). The layers were separated and the aqueous phase was extracted with EtOAc (4×100 mL). The combined organic extracts were washed with brine (1×50 mL), dried ($MgSO_4$), filtered and concentrated in vacuo to an approximative volume of 100 mL. Charcoal (10 g) was added and the mixture was stirred for 2 h. The mixture was filtered and the residual cake was washed further with EtOAc. The filtrates were collected and concentrated in vacuo to give 50 g of crude product. Purification by flash chromatography (330 g $SiO_2$, 0 to 30% EtOAc in heptane) gave ethyl rac-(4S,5R)-3-(4-fluoro-2-methoxy-3-methylphenyl)-4,5-dimethyl-5-(trifluoromethyl)-4,5-dihydrofuran-2-carboxylate (27.348 g, 72%) as a pale yellow oil. $^1$H NMR (500 MHz, Chloroform-d) δ 6.98-6.88 (m, 1H), 6.81 (t, J=8.7 Hz, 1H), 4.20-4.07 (m, 2H), 3.66 (s, 3H), 3.58-3.49 (m, 1H), 2.21 (d, J=2.1 Hz, 3H), 1.7 (s, 3H), 1.12 (t, J=7.1 Hz, 3H), 1.06 (dq, J=7.2, 2.3 Hz, 3H) ppm. ESI-MS m/z calc. 376.12976, found 377.5 (M+1)$^+$; Retention time: 1.09 minutes.

Step 2:

To a 1 L three necked flask, fitted with a thermometer, was added ethyl rac-(4S,5R)-3-(4-fluoro-2-methoxy-3-methylphenyl)-4,5-dimethyl-5-(trifluoromethyl)-4,5-dihydrofuran-2-carboxylate (27.35 g, 72.67 mmol) followed by DCM (200 mL). The reaction mixture was cooled to 5° C. with an ice bath. Boron tribromide (112 mL, 1 M solution in DCM, 112.0 mmol) was added via cannula over 30 min, keeping the internal temperature around 5° C. The reaction mixture was stirred for 1 h. The mixture was quenched by slow addition of water (100 mL) causing effervescence and of a saturated sodium bicarbonate solution (100 mL). The mixture was stirred for 30 min. The aqueous phase was collected and washed with DCM (3×50 mL). The combined organic extracts were washed with a saturated sodium bicarbonate solution (5×100 mL), dried ($MgSO_4$), filtered and concentrated in vacuo to give a yellow waxy solid. The waxy solid was re-dissolved in EtOAc (100 mL). Charcoal (15 g) was added and the mixture was stirred at ambient temperature overnight. The mixture was filtered through a pad of celite. The filtrates were collected, dried ($MgSO_4$), filtered and concentrated in vacuo to give a ~1:1 mixture of rac-(1S,2R)-7-fluoro-1,2,6-trimethyl-2-(trifluoromethyl)-1,2-dihydro-4H-furo[2,3-c]chromen-4-one and ethyl rac-(4S,5R)-3-(4-fluoro-2-hydroxy-3-methylphenyl)-4,5-dimethyl-5-(trifluoromethyl)-4,5-dihydrofuran-2-carboxylate (27.7 g) as a waxy solid.

The mixture was dissolved in DCM (200 mL) and TFA (9.8 mL, 127.2 mmol) was added at ambient temperature under stirring. The reaction mixture was heated at reflux and stirred for 2.5 h. The mixture was cooled to ambient temperature and quenched with a saturated aqueous sodium bicarbonate solution (100 mL). The organic phase was washed with saturated aqueous sodium bicarbonate solution (4×100 mL), dried ($Na_2SO_4$) and concentrated in vacuo to give a waxy solid. The waxy solid was re-dissolved in EtOAc (200 mL) and activated charcoal (10 g) was added. The mixture was stirred at ambient temperature overnight. The mixture was filtered through a celite cartridge, washing with EtOAc (3×100 mL). The filtrates were concentrated in vacuo to give a waxy solid. Purification by flash chromatography (120 g SiO$_2$, 50% EtOAc in heptane) gave rac-(1S,2R)-7-fluoro-1,2,6-trimethyl-2-(trifluoromethyl)-1,2-dihydro-4H-furo[2,3-c]chromen-4-one (24.18 g, 100%). $^1$H NMR (500 MHz, Chloroform-d) δ 7.25-7.23 (m, 1H), 7.05 (t, J=8.7 Hz, 1H), 3.65 (q, J=7.4 Hz, 1H), 2.39 (d, J=2.0 Hz, 3H), 1.67 (q, J=1.0 Hz, 3H), 1.58 (t, J=2.2 Hz, 3H) ppm. ESI-MS m/z calc. 316.07227, found 317.4 (M+1)$^+$; 315.4 (M−1)$^-$; Retention time: 0.94 minutes.

Step 3:

rac-(1S,2R)-7-fluoro-1,2,6-trimethyl-2-(trifluoromethyl)-1,2-dihydro-4H-furo[2,3-c]chromen-4-one (1.5 g, 3.273 mmol) was dissolved in EtOAc (20 mL) and stirred with activated charcoal (300 mg, 24.98 mmol) for 18 h. The mixture was filtered through a pad of celite. The liquors were concentrated in vacuo to give a yellow solid. The solid was dissolved in methanol (20 mL) and added to a 100 mL flask containing dihydroxypalladium (460 mg of 20% w/w, 0.6551 mmol). The resulting mixture was stirred under an atmospheric pressure of hydrogen for 120 h. The mixture was filtered through a celite cartridge washing with MeOH. The filtrates were concentrated in vacuo to an approximate volume of 20 mL and added to a flask containing dihydroxypalladium (230 mg of 20% w/w, 0.3276 mmol). The resulting mixture was stirred under a ballon atmosphere of hydrogen for 12 h. The reaction mixture was filtered through a celite cartridge, washing with MeOH. The filtrates were concentrated in vacuo to give a mixture of isomers of methyl 3-(4-fluoro-2-hydroxy-3-methylphenyl)-4,5-dimethyl-5-(trifluoromethyl)tetrahydrofuran-2-carboxylate (939.3 mg, 82%) as an off-white solid, of which methyl rac-(2S,3S,4S,5R)-3-(4-fluoro-2-hydroxy-3-methylphenyl)-4,5-dimethyl-5-(trifluoromethyl)tetrahydrofuran-2-carboxylate was the major isomer. $^1$H NMR (500 MHz, Chloroform-d) δ 7.20 (t, J=7.7 Hz, 1H), 6.57 (t, J=8.9 Hz, 1H), 4.88 (d, J=6.1 Hz, 2H), 4.28 (dd, J=8.4, 6.1 Hz, 1H), 3.56 (s, 3H), 2.81 (p, J=7.8 Hz, 1H), 2.14 (d, J=1.6 Hz, 3H), 1.4 (3H), 0.92 (dq, J=7.6, 1.9 Hz, 3H) ppm; alcohol OH not observed. ESI-MS m/z calc. 350.11414, found 349.0 (M−1)$^-$; Retention time: 0.95 minutes.

Step 4:

Potassium tert-butoxide (11.40 g, 101.6 mmol) was added to a stirred solution of a mixture of isomers of methyl 3-(4-fluoro-2-hydroxy-3-methylphenyl)-4,5-dimethyl-5-(trifluoromethyl)tetrahydrofuran-2-carboxylate (8.896 g, 25.39 mmol), of which methyl rac-(2S,3S,4S,5R)-3-(4-fluoro-2-hydroxy-3-methylphenyl)-4,5-dimethyl-5-(trifluoromethyl)tetrahydrofuran-2-carboxylate was the major isomer, in tetrahydrofuran (125 mL) at 0° C. After 15 minutes, the mixture was quenched by the addition of 1M HCl (350 mL) and diluted with saturated brine (100 mL) and DCM (100 mL). The aqueous layer was extracted with DCM (3×100 mL). The combined organic extracts were dried (MgSO$_4$), filtered and concentrated in vacuo. The residue was dissolved in DCM (71 mL) and treated with TFA (26.62 g, 17.99 mL, 233.5 mmol). The reaction mixture was stirred at ambient temperature for 2 h. The mixture was concentrated in vacuo and the residue azeotroped with DCM (2×50 mL). The residue was partitioned between DCM (100 mL) and water (50 mL) and the layers separated. The organic layer was washed with water (3×50 mL) and the organic extracts dried (MgSO4), filtered and concentrated in vacuo to give a mixture of rac-(2R,3S,4S,5R)-3-(4-fluoro-2-hydroxy-3-methylphenyl)-4,5-dimethyl-5-(trifluoromethyl)tetrahydrofuran-2-carboxylic acid and rac-(2S,3S,4S,5R)-3-(4-fluoro-2-hydroxy-3-methylphenyl)-4,5-dimethyl-5-(trifluoromethyl)tetrahydrofuran-2-carboxylic acid (9.753 g, 100%) as a brown oil, which was used as is in the next step. ESI-MS m/z calc. 336.09848, found 335.5 (M−1)$^-$; Retention time: 0.56 minutes.

Step 5:

K$_2$CO$_3$ (1.65 g, 11.94 mmol) and iodoethane (1 mL, 12.50 mmol) were added to a solution of a mixture of rac-(2R,3S,4S,5R)-3-(4-fluoro-2-hydroxy-3-methylphenyl)-4,5-dimethyl-5-(trifluoromethyl)tetrahydrofuran-2-carboxylic acid and rac-(2S,3S,4S,5R)-3-(4-fluoro-2-hydroxy-3-methylphenyl)-4,5-dimethyl-5-(trifluoromethyl)tetrahydrofuran-2-carboxylic acid (1 g, 2.974 mmol) in acetonitrile (10 mL) in a sealed vial. The vial was sealed and heated to 80° C. for 5 h. The reaction mixture was cooled down to ambient temperature and diluted with DCM. The mixture was filtered and the solid washed further with DCM. The filtrates were collected and concentrated in vacuo to give a mixture of ethyl rac-(2R,3S,4S,5R)-3-(2-ethoxy-4-fluoro-3-methylphenyl)-4,5-dimethyl-5-(trifluoromethyl)tetrahydrofuran-2-carboxylate and ethyl rac-(2S,3S,4S,5R)-3-(2-ethoxy-4-fluoro-3-methylphenyl)-4,5-dimethyl-5-(trifluoromethyl)tetrahydrofuran-2-carboxylate (1.038 g, 89%). ESI-MS m z calc. 392.16107, found 393.6 (M+1)$^+$; Retention time: 0.99 minutes.

Step 6:

LiOH (3.3 mL of 2 M, 6.600 mmol) was added to a stirred solution of a mixture of ethyl rac-(2R,3S,4S,5R)-3-(2-ethoxy-4-fluoro-3-methylphenyl)-4,5-dimethyl-5-(trifluoromethyl)tetrahydrofuran-2-carboxylate and rac-(2S,3S,4S,5R)-3-(2-ethoxy-4-fluoro-3-methylphenyl)-4,5-dimethyl-5-(trifluoromethyl)tetrahydrofuran-2-carboxylate (1 g, 2.549 mmol) in methanol (15 mL) and water (4 mL). The mixture was stirred at ambient temperature for 18 h. The MeOH was removed in vacuo and diluted with 1M HCl to pH 1. The mixture was extracted with DCM (2×10 mL). The combined organic extracts were dried by passing through a phase separating cartridge and concentrated in vacuo to give a mixture of rac-(2R,3S,4S,5R)-3-(2-ethoxy-4-fluoro-3-methylphenyl)-4,5-dimethyl-5-(trifluoromethyl)tetrahydrofuran-2-carboxylic acid and rac-(2S,3S,4S,5R)-3-(2-ethoxy-4-fluoro-3-methylphenyl)-4,5-dimethyl-5-(trifluoromethyl)tetrahydrofuran-2-carboxylic acid (778.9 mg, 84%). ESI-MS m/z calc. 364.12976, found 363.6 (M−1)$^-$; Retention time: 0.62 minutes.

Step 7:

DMF (2.5 µL, 0.0323 mmol) and oxalyl chloride (27.5 µL, 0.315 mmol) were added to a solution of a mixture of rac-(2R,3S,4S,5R)-3-(2-ethoxy-4-fluoro-3-methylphenyl)-4,5-dimethyl-5-(trifluoromethyl)tetrahydrofuran-2-carboxylic acid and rac-(2S,3S,4S,5R)-3-(2-ethoxy-4-fluoro-3-methylphenyl)-4,5-dimethyl-5-(trifluoromethyl)tetrahydrofuran-2-carboxylic acid (76 mg, 0.209 mmol) in DCM (2 mL) cooled to 0° C. After the end of the addition, the mixture was stirred at ambient temperature for 2 h. The reaction mixture was concentrated in vacuo. The residue was taken in 2-MeTHF (2 mL) and added dropwise to a solution of (R)-6-(2,2-dimethyl-1,3-dioxolan-4-yl)pyridin-3-amine (48.8 mg, 0.2512 mmol) and TEA (90 µL, 0.6457 mmol). The reaction mixture was stirred at ambient temperature for 2 h. The mixture was concentrated in vacuo and loaded onto solid support. Purification by flash chromatography (SiO$_2$, 0 to 100% EtOAc in heptane) gave a mixture of isomers:

First Eluting Isomers: mixture of rel-(2R,3S,4S,5R)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide and rel-(2S,3R,4R,5S)—N-(6-((R*)-2,2-dimethyl-1,3-dioxolan-4-yl)pyridin-3-yl)-3-(2-ethoxy-4-fluoro-3-methylphenyl)-4,5- dimethyl-5-(trifluoromethyl)tetrahydrofuran-2-carboxamide (23 mg, 41%). ¹H NMR (400 MHz, Chloroform-d) δ 8.54 (dd, J=2.6, 0.7 Hz, 1H), 8.35 (s, 1H), 8.12 (dd, J=8.6, 2.6 Hz, 1H), 7.47 (d, J=8.5 Hz, 1H), 7.19 (dd, J=8.7, 6.3 Hz, 1H), 6.86 (t, J=8.7 Hz, 1H), 5.16 (t, J=6.7 Hz, 1H), 5.00 (d, J=11.1 Hz, 1H), 4.42 (ddd, J=8.0, 6.8, 1.1 Hz, 1H), 4.13 (dd, J=11.0, 7.9 Hz, 1H), 3.95-3.75 (m, 3H), 2.76 (p, J=7.7 Hz, 1H), 2.20 (d, J=2.1 Hz, 3H), 1.69 (s, 3H), 1.51 (dd, J=1.5, 0.7 Hz, 3H), 1.48 (t, J=0.7 Hz, 3H), 1.39 (t, J=7.0 Hz, 3H), 0.83-0.76 (m, 3H) ppm. ESI-MS m/z calc. 540.22473, found 541.2 (M+1)⁺; 539.3 (M−1)⁻; Retention time: 1.09 minutes.

Second Eluting Isomers: mixture of rel-(2S,3S,4S,5R)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide and rel-(2R,3R,4R,5S)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (13.3 mg, 24%). ¹H NMR (400 MHz, Chloroform-d) δ 8.45 (ddd, J=18.1, 2.6, 0.7 Hz, 1H), 8.22 (d, J=2.8 Hz, 1H), 7.85 (ddd, J=24.6, 8.5, 2.6 Hz, 1H), 7.44 (dd, J=8.6, 1.1 Hz, 1H), 7.12 (dd, J=8.7, 6.7 Hz, 1H), 6.63 (td, J=8.8, 1.7 Hz, 1H), 5.15 (t, J=6.7 Hz, 1H), 4.92 (d, J=6.6 Hz, 1H), 4.41 (ddd, J=8.3, 6.7, 1.5 Hz, 1H), 4.36 (dd, J=8.8, 6.6 Hz, 1H), 4.01-3.79 (m, 3H), 2.90 (p, J=7.8 Hz, 1H), 2.17 (d, J=2.1 Hz, 3H), 1.59 (d, J=1.1 Hz, 4H), 1.50 (s, 3H), 1.48 (d, J=0.7 Hz, 3H), 1.44 (t, J=7.0 Hz, 3H), 0.88-0.82 (m, 3H) ppm. ESI-MS m/z calc. 540.22473, found 541.2 (M+1)⁺; 539.3 (M−1)⁻; Retention time: 1.06 minutes. These isomers were not separated by chiral SFC.

Step 8:

The mixture of rel-(2R,3S,4S,5R)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide and rel-(2S,3R,4R,5S)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (23 mg, 0.042 mmol) (First Eluting Isomers from Step 7) were separated by chiral SFC using a Lux i-Cellulose-5 column, 5 um particle size, 25 cm×20 mm from Phenomenex, Inc. (Mobile phase: 15% MeOH (containing 20 mM Ammonia), 85% CO₂. Flow: 100 mL/min.) on a Minigram SFC instrument from Berger Instruments to give:

First Eluting Isomer (rt=3.41 min): rel-(2R,3S,4S,5R)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (10 mg, 87%). ESI-MS m/z calc. 540.22473, found 541.2 (M+1)⁺; 539.3 (M−1)⁻; Retention time: 3.73 minutes.

Second Eluting Isomer (rt=4.48 min): rel-(2S,3R,4R,5S)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (9 mg, 78%). ESI-MS m/z calc. 540.22473, found 541.2 (M+1)⁺; 539.3 (M−1)⁻; Retention time: 3.73 minutes.

Step 9:

TFA (10 μL, 0.130 mmol) was added to a solution of ref-(2R,3S,4S,5R)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (10 mg, 0.0185 mmol) (First Eluting Isomer from SFC separation) in THF (800 μL) and water (200 μL). The reaction mixture was stirred at 60° C. for 6 h and for a further 16 h at 40° C. The mixture was concentrated in vacuo. Purification by reversed phase HPLC-MS using a X-bridge C18 OBD column (150×19 mm, 5 mm particle size) from Waters gave rel-(2R,3S,4S,5R)—N-(6-((R*)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide (40, 2.5 mg, 27%). ¹H NMR (400 MHz, Methanol-d₄) δ 8.67 (dd, J=2.5, 0.7 Hz, 1H), 8.04 (dd, J=8.6, 2.5 Hz, 1H), 7.52 (dt, J=8.5, 0.7 Hz, 1H), 7.20 (dd, J=8.7, 6.3 Hz, 1H), 6.86 (t, J=8.8 Hz, 1H), 5.03 (d, J=10.8 Hz, 1H), 4.71 (dd, J=6.7, 4.2 Hz, 1H), 4.34 (dd, J=10.8, 7.9 Hz, 1H), 3.96-3.82 (m, 2H), 3.79 (dd, J=11.3, 4.2 Hz, 1H), 3.65 (dd, J=11.3, 6.7 Hz, 1H), 2.77 (p, J=7.6 Hz, 1H), 2.19 (d, J=2.1 Hz, 3H), 1.67 (d, J=1.1 Hz, 3H), 1.43 (t, J=7.0 Hz, 3H), 0.80 (dq, J=7.4, 2.3 Hz, 3H) ppm; alcohols OH and amide NH not observed. ESI-MS m z calc. 500.19342, found 501.2 (M+1)⁺; 499.2 (M−1)⁻; Retention time: 3.17 minutes.

rel-(2S,3R,4R,5S)—N-(6-((R*)-2,2-dimethyl-1,3-dioxolan-4-yl)pyridin-3-yl)-3-(2-ethoxy-4-fluoro-3-methylphenyl)-4,5-dimethyl-5-(trifluoromethyl)tetrahydrofuran-2-carboxamide (9 mg, 0.01665 mmol) (Second Eluting Isomer from SFC separation) was treated in the same way to give rel-(2S,3R,4R,5S)—N-(6-((R*)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide (41, 2.2 mg, 26%). ¹H NMR (400 MHz, Methanol-d₄) δ 8.67 (dd, J=2.5, 0.7 Hz, 1H), 8.04 (dd, J=8.5, 2.5 Hz, 1H), 7.52 (dt, J=8.6, 0.7 Hz, 1H), 7.20 (dd, J=8.7, 6.3 Hz, 1H), 6.86 (t, J=8.8 Hz, 1H), 5.03 (d, J=10.8 Hz, 1H), 4.71 (dd, J=6.6, 4.2 Hz, 1H), 4.35 (dd, J=10.8, 7.9 Hz, 1H), 3.98-3.82 (m, 2H), 3.79 (dd, J=11.3, 4.2 Hz, 1H), 3.65 (dd, J=11.3, 6.7 Hz, 1H), 2.77 (p, J=7.6 Hz, 1H), 2.19 (d, J=2.1 Hz, 3H), 1.67 (d, J=1.1 Hz, 3H), 1.43 (t, J=7.0 Hz, 3H), 0.80 (dt, J=7.2, 2.4 Hz, 3H) ppm; alcohols OH and amide NH not observed. ESI-MS m/z calc. 500.19342, found 501.3 (M+1)⁺; 499.3 (M−1)⁻; Retention time: 3.19 minutes.

The following compound was made using the method described in Example 5, except that (S)-6-(2,2-dimethyl-1,3-dioxolan-4-yl)pyridine-3-amine was used in place of (R)-6-(2,2-dimethyl-1,3-dioxolan-4-yl)pyridin-3-amine in step 7. In step 8, purification was performed by chiral SFC using a Lux i-Cellulose-5 column, 5 mm particle size, 25 cm×20 mm from Daicel Corporation (Mobile phase: 15% MeOH (containing 20 mM Ammonia), 85% CO₂. Flow: 100 mL/min.) on a Prep-100 SFC instrument from Waters:

| Cmpd No. | Compound Name | LC/MS | NMR (shifts in ppm) |
|---|---|---|---|
| 42 | rel-(2R,3S,4S,5R)-N-(6-((S*)-1,2-dihydroxyethyl)pyridine-3-yl)-3-(2-ethoxy-4-fluoro-3-methylphenyl)-4,5-dimethyl-5-(trifluoromethyl)tetrahydrofuran-2-carboxamide (Precursor was the first eluting peak by SFC on Chiralpak IC column, rt = 0.85 min) | ESI-MS m/z calc. 500.19342, found 501.3 (M + 1)⁺; 499.3 (M − 1)⁻; Retention time: 3.19 minutes | ¹H NMR (400 MHz, Methanol-d₄) δ 8.67 (dd, J = 2.6, 0.7 Hz, 1H), 8.04 (dd, J = 8.6, 2.5 Hz, 1H), 7.52 (dt, J = 8.6, 0.7 Hz, 1H), 7.20 (dd, J = 8.7, 6.3 Hz, 1H), 6.86 (t, J = 8.8 Hz, 1H), 5.02 (d, J = 10.8 Hz, 1H), 4.71 (dd, J = 6.6, 4.2 Hz, 1H), 4.34 (dd, J = 10.8, 7.9 Hz, 1H), 3.96-3.82 (m, 2H), 3.79 (dd, J = 11.3, 4.2 Hz, 1H), 3.65 (dd, J = 11.3, 6.7 Hz, 1H), 2.77 (p, J = 7.6 Hz, 1H), 2.19 (d, J = 2.1 Hz, 3H), 1.67 (d, |

| Cmpd No. | Compound Name | LC/MS | NMR (shifts in ppm) |
|---|---|---|---|
| 43 | rel-(2S,3R,4R,5S)-N-(6-((S*)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide (Precursor was the second eluting peak by SFC on Chiralpak IC column, rt = 1.00 min) | ESI-MS m/z calc. 500.19342, found 501.3 (M + 1)⁺; 499.2 (M − 1)⁻; Retention time: 3.19 minutes | ¹H NMR (400 MHz, Methanol-d₄) δ 8.67 (dd, J = 2.5, 0.7 Hz, 1H), 8.04 (dd, J = 8.6, 2.5 Hz, 1H), 7.52 (dt, J = 8.6, 0.7 Hz, 1H), 7.20 (dd, J = 8.8, 6.3 Hz, 1H), 6.86 (t, J = 8.8 Hz, 1H), 5.03 (d, J = 10.8 Hz, 1H), 4.71 (dd, J = 6.6, 4.2 Hz, 1H), 4.34 (dd, J = 10.8, 7.9 Hz, 1H), 3.96-3.82 (m, 2H), 3.79 (dd, J = 11.3, 4.2 Hz, 1H), 3.65 (dd, J = 11.3, 6.6 Hz, 1H), 2.77 (p, J = 7.6 Hz, 1H), 2.19 (d, J = 2.1 Hz, 3H), 1.67 (d, J = 1.2 Hz, 3H), 1.43 (t, J = 7.0 Hz, 3H), 0.80 (dt, J = 7.5, 2.4 Hz, 3H) ppm; alcohols OH and amide NH not observed. J = 1.1 Hz, 3H), 1.43 (t, J = 7.0 Hz, 3H), 0.80 (dt, J = 7.4, 2.4 Hz, 3H) ppm; alcohols OH and amide NH not observed. |

The following compounds were made using the method described in Example 5, except that the hydrogenation step 3 was carried out using 60 psi of hydrogen. In step 5, methyl iodide was used in place of ethyl iodide as the alkylating agent. In step 7, in the case of compounds 44 and 45, (s)-6-(2,2-dimethyl-1,3-dioxolan-4-yl)pyridine-3-amine was used in place of (R)-6-(2,2-dimethyl-1,3-dioxolan-4-yl)pyridine-3-amine. In step 8, purification was performed by chiral SFC using a (R,R)-Whelk-81 column, 5 um particle size, 25 cm×21.1 mm from Daicel (Mobile phase: 5 to 25% MeOH (containing 20 mM Ammonia), 95 to 75% CO₂. Flow: 100 mL/min.) on a Minigram SFC instrument from Berger Instruments. In step 9, DCM was used as the solvent rather than a mixture of TH and water:

| Cmpd No. | Compound Name | LC/MS | NMR (shifts in ppm) |
|---|---|---|---|
| 44 | rel-(2S,3R,4R,5S)-N-(6-((S*)-1,2-dihydroxyethyl)138yridine-3-yl)-3-(4-fluoro-2-methoxy-3-methylphenyl)-4,5-dimethyl-5-(trifluoromethyl)tetrahydrofuran-2-carboxamide (Precursor was the first eluting peak by SFC on (R,R)-Whelk-O1 column, rt = 1.31 min) | ESI-MS m/z calc. 486.1778, found 487.6 (M + 1)⁺; 485.6 (M − 1)⁻; Retention time: 3.02 minutes | ¹H NMR (500 MHz, DMSO-d₆) δ 10.40 (s, 1H), 8.65 (d, J = 2.4 Hz, 1H), 8.01 (dd, J = 8.6, 2.6 Hz, 1H), 7.44 (d, J = 8.5 Hz, 1H), 7.25-7.06 (m, 2H), 7.01-6.94 (m, 1H), 5.05 (d, J = 10.6 Hz, 1H), 4.55 (dd, J = 6.8, 4.2 Hz, 1H), 4.28 (dd, J = 10.7, 7.6 Hz, 1H), 3.72 (s, 3H), 3.62 (dd, J = 11.0, 4.2 Hz, 1H), 3.44 (dd, J = 11.0, 6.8 Hz, 2H), 2.73 (p, J = 7.4 Hz, 1H), 2.16 (d, J = 2.0 Hz, 3H), 1.62 (s, 3H), 0.73 (d, J = 7.4 Hz, 3H) ppm. |
| 45 | rel-(2R,3S,4S,5R)-N-(6-((S*)-1,2-dihydroxyethyl)pyridin-3-yl)-3-(4-fluoro-2-methoxy-3-methylphenyl)-4,5-dimethyl-5-(trifluoromethyl)tetrahydrofuran-2-carboxamide (Precursor was the second eluting peak by SFC on (R,R)-Whelk-O1 column, rt = 2.20 min) | ESI-MS m/z calc. 486.1778, found 487.6 (M + 1)⁺; 485.6 (M − 1)⁻; Retention time: 3.02 minutes | ¹H NMR (500 MHz, DMSO-d₆) δ 10.36 (s, 1H), 8.68-8.59 (m, 1H), 7.95 (dd, J = 8.5, 2.5 Hz, 1H), 7.40 (d, J = 8.5 Hz, 1H), 7.19 (dd, J = 8.7, 6.5 Hz, 1H), 6.97 (t, J = 8.8 Hz, 1H), 5.30 (d, J = 4.9 Hz, 1H), 5.03 (d, J = 10.6 Hz, 1H), 4.61 (t, J = 5.9 Hz, 1H), 4.52 (dt, J = 6.7, 4.5 Hz, 1H), 4.27 (dd, J = 10.7, 7.6 Hz, 1H), 3.71 (s, 3H), 3.61 (ddd, J = 10.4, 6.0, 4.1 Hz, 1H), 3.43 (ddd, J = 10.9, 6.9, 5.8 Hz, 1H), 2.71 (p, J = 7.5 Hz, 1H), 2.14 (d, J = 2.0 Hz, 3H), 1.60 (s, 3H), 0.77-0.68 (m, 3H) ppm. |
| 46 | rel-(2S,3R,4R,5S)-N-(6-((R*)-1,2-dihydroxyethyl)pyridin-3-yl)-3-(4-fluoro-2-methoxy-3-methylphenyl)-4,5-dimethyl-5-(trifluoromethyl)tetrahydrofuran-2-carboxamide (Precursor was the first eluting peak by SFC on (R,R)-Whelk-O1 column, rt = 1.26 min) | ESI-MS m/z calc. 486.1778, found 487.6 (M + 1)⁺; 485.6 (M − 1)⁻; Retention time: 3.02 minutes | |
| 47 | rel-(2R,3S,4S,5R)-N-(6-((R*)-1,2-dihydroxyethyl)pyridin-3-yl)-3-(4-fluoro-2-methoxy-3-methylphenyl)-4,5-dimethyl-5-(trifluoromethyl)tetrahydrofuran-2-carboxamide (Precursor was the second eluting peak by SFC on (R,R)-Whelk-O1 column, rt = 2.10 min) | ESI-MS m/z calc. 486.1778, found 487.6 (M + 1)⁺; 485.6 (M − 1)⁻; Retention time: 3.02 minutes | ¹H NMR (500 MHz, DMSO-d₆) δ 10.37 (s, 1H), 8.63 (d, J = 2.5 Hz, 1H), 7.99 (dd, J = 8.6, 2.6 Hz, 1H), 7.41 (d, J = 8.5 Hz, 1H), 7.20 (dd, J = 8.7, 6.5 Hz, 1H), 6.98 (t, J = 8.8 Hz, 1H), 5.31 (d, J = 4.9 Hz, 1H), 5.04 (d, J = 10.6 Hz, 1H), 4.62 (t, J = 5.9 Hz, 1H), 4.53 (dt, J = 7.0, 4.5 Hz, 1H), 4.28 (dd, J = 10.6, 7.5 Hz, 1H), 3.72 (s, 3H), 3.62 (ddd, J = 10.5, 6.1, 4.2 Hz, 1H), |

| Cmpd No. | Compound Name | LC/MS | NMR (shifts in ppm) |
|---|---|---|---|
| | | | 3.49-3.39 (m, 1H), 2.72 (p, J = 7.5 Hz, 1H), 2.15 (d, J = 2.0 Hz, 3H), 1.61 (s, 3H), 0.73 (d, J = 7.0 Hz, 3H) ppm. |

Example 6 rel-(2S,3R,4R,5S)-3-(3-(difluoromethyl)-4-fluoro-2-methoxyphenyl)-N-(6-((S*)-1,2-dihydroxyethyl)pyridin-3-yl)-4,5-dimethyl-5-(trifluoromethyl)tetrahydrofuran-2-carboxamide (48) and rel-(2R,3S,4S,5R)-3-(3-(difluoromethyl)-4-fluoro-2-methoxyphenyl)-N-(6-((S*)-1,2-dihydroxyethyl)pyridin-3-yl)-4,5-dimethyl-5-(trifluoromethyl)tetrahydrofuran-2-carboxamide (49)

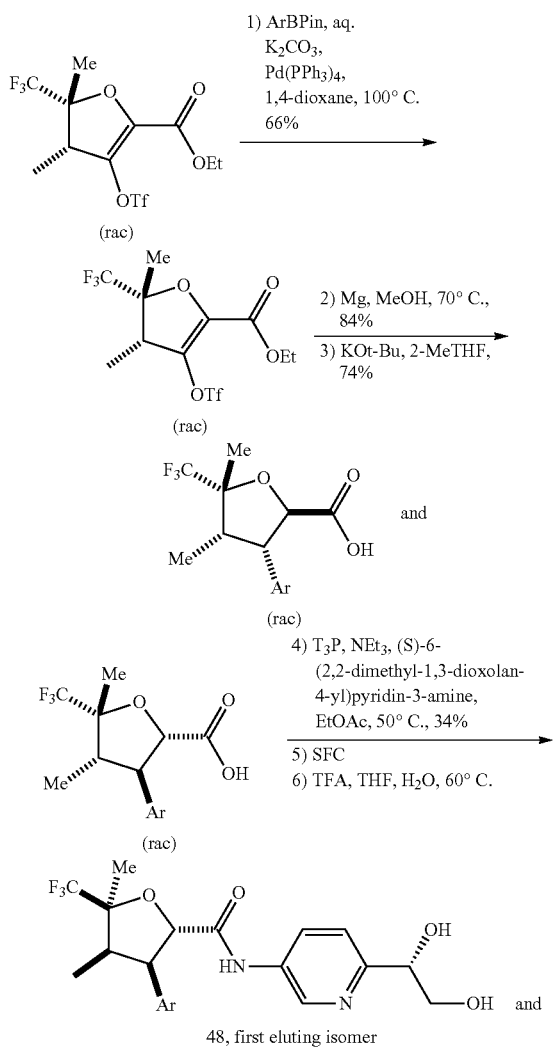

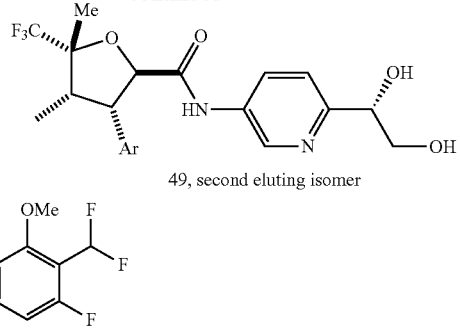

49, second eluting isomer

Step 1:

A mixture of ethyl rac-(4R,5R)-4,5-dimethyl-5-(trifluoromethyl)-3-(((trifluoromethyl)sulfonyl)oxy)-4,5-dihydrofuran-2-carboxylate (1.44 g, 3.169 mmol), 2-(3-(difluoromethyl)-4-fluoro-2-methoxyphenyl)-4,4,5,5-tetramethyl-1,3,2-dioxaborolane (900 mg, 2.592 mmol), Pd(PPh₃)₄ (148 mg, 0.1281 mmol) and aqueous K₂CO₃ (2.6 mL of 2 M, 5.200 mmol) in 1,4-dioxane (25 mL) was heated at 100° C. for 2 h. The mixture was concentrated in vacuo and loaded onto solid support. Purification by flash chromatography (SiO₂, 0 to 25% EtOAc in heptane) gave ethyl rac-(4S,5R)-3-(3-(difluoromethyl)-4-fluoro-2-methoxyphenyl)-4,5-dimethyl-5-(trifluoromethyl)-4,5-dihydrofuran-2-carboxylate (708 mg, 66%) as a colourless oil. $^1$H NMR (400 MHz, Chloroform-d) δ 7.25 (ddt, J=7.3, 6.2, 1.2 Hz, 1H), 6.95 (td, J=53.6, 0.7 Hz, 1H), 6.94 (tt, J=8.7, 0.9 Hz, 1H), 4.17 (qd, J=7.1, 1.3 Hz, 2H), 3.77 (s, 3H), 3.62-3.53 (m, 1H), 1.71 (q, J=1.0 Hz, 3H), 1.15 (t, J=7.1 Hz, 3H), 1.07 (dq, J=7.1, 2.2 Hz, 3H) ppm. ESI-MS m/z calc. 412.11093, found 413.2 (M+1)⁺; Retention time: 1.05 minutes.

Step 2:

A solution of ethyl rac-(4S,5R)-3-(3-(difluoromethyl)-4-fluoro-2-methoxyphenyl)-4,5-dimethyl-5-(trifluoromethyl)-4,5-dihydrofuran-2-carboxylate (3.5 g, 8.488 mmol) in MeOH (100 mL) was added to a two necked flask containing magnesium (2.07 g, 85.17 mmol). The reaction mixture was heated at 70° C. for 3 h. The mixture was concentrated in vacuo and partitioned between aqueous AcOH and EtOAc. The aqueous layer was separated and extracted twice with EtOAc. The combined organic phases were washed with aqueous NaHCO₃ and twice with water. The organic phase was dried (MgSO₄) and concentrated in vacuo to give a mixture of methyl rac-(2S,3S,4S,5R)-3-(3-(difluoromethyl)-4-fluoro-2-methoxyphenyl)-4,5-dimethyl-5-(trifluoromethyl)tetrahydrofuran-2-carboxylate and methyl rac-(2R,3R,4S,5R)-3-(3-(difluoromethyl)-4-fluoro-2-methoxyphenyl)-4,5-dimethyl-5-(trifluoromethyl)tetrahydrofuran-2-carboxylate (2.87 g, 84%) as an orange oil. $^1$H NMR (400 MHz, Chloroform-d) δ 7.43-7.32 (m, 1H), 7.01-6.95 (m, 1H), 7.09-6.80 (m, 1H), 4.89 (d, J=10.2 Hz, 1H), 4.21-4.15 (m, 1H), 3.84 (s, 3H), 3.71 (s, 3H), 2.73 (p, J=7.7 Hz, 1H), 1.63 (q, J=1.2 Hz, 3H), 0.78 (ddq, J=7.2, 4.7, 2.3 Hz, 3H) ppm.

Step 3:

Potassium tert-butoxide (1.66 g, 14.79 mmol) was added to a solution of a mixture of methyl rac-(2S,3S,4S,5R)-3-(3-(difluoromethyl)-4-fluoro-2-methoxyphenyl)-4,5-dimethyl-5-(trifluoromethyl)tetrahydrofuran-2-carboxylate and methyl rac-(2R,3R,4S,5R)-3-(3-(difluoromethyl)-4-fluoro-2-methoxyphenyl)-4,5-dimethyl-5-(trifluoromethyl)tetrahydrofuran-2-carboxylate (2.87 g, 7.169 mmol) in 2-MeTHF (35 mL) in a water bath at ambient temperature. During addition, a ~3° exotherm was observed. The reaction mixture was stirred for 2 h, after which time a further portion of potassium tert-butoxide (860 mg) was added. The mixture was stirred at ambient temperature for a further 1 h. The reaction was quenched with a diluted HCl solution. The aqueous layer was separated and washed with EtOAc, dried (MgSO$_4$) and concentrated in vacuo to give a mixture of rac-(2R,3S,4S,5R)-3-(3-(difluoromethyl)-4-fluoro-2-methoxyphenyl)-4,5-dimethyl-5-(trifluoromethyl)tetrahydrofuran-2-carboxylic acid and rac-(2S,3R,4S,5R)-3-(3-(difluoromethyl)-4-fluoro-2-methoxyphenyl)-4,5-dimethyl-5-(trifluoromethyl)tetrahydrofuran-2-carboxylic acid (3.32 g, 74%) as an orange oil. $^1$H NMR (400 MHz, Chloroform-d) δ 7.43-7.35 (m, 1H), 6.98 (ddd, J=13.4, 9.3, 4.2 Hz, 1H), 6.93 (t, J=53.6 Hz, 1H), 4.93 (d, J=10.3 Hz, 1H), 4.18-4.14 (m, 1H), 3.84 (s, 3H), 2.76 (p, J=7.7 Hz, 1H), 1.67-1.62 (m, 3H), 0.82-0.75 (m, 3H) ppm; OH acid not observed. ESI-MS m/z calc. 386.09528, found 385.1 (M−1)$^-$; Retention time: 0.57 minutes.

Step 4:

T3P (310 µL of 50% w/w, 0.5208 mmol) was added to a solution of a mixture of rac-(2R,3S,4S,5R)-3-(3-(difluoromethyl)-4-fluoro-2-methoxyphenyl)-4,5-dimethyl-5-(trifluoromethyl)tetrahydrofuran-2-carboxylic acid and rac-(2S,3R,4S,5R)-3-(3-(difluoromethyl)-4-fluoro-2-methoxyphenyl)-4,5-dimethyl-5-(trifluoromethyl)tetrahydrofuran-2-carboxylic acid (100 mg, 0.2589 mmol), (S)-6-(2,2-dimethyl-1,3-dioxolan-4-yl)pyridin-3-amine (78 mg, 0.4016 mmol) and triethylamine (110 µL, 0.7892 mmol) in ethyl acetate (2 mL). The reaction mixture was stirred at 50° C. for 30 min and then at ambient temperature overnight. The reaction mixture was partitioned between EtOAc and water and passed through a Whatmann phase separation filter paper. The organic phase was concentrated concentrated in vacuo and loaded onto to silica. Purification by flash chromatography (SiO$_2$, 0 to 75% EtOAc in heptane) gave a mixture of rel-(2R,3S,4S,5R)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide and rel-(2S,3R,4R,5S)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (50 mg, 34%). $^1$H NMR (400 MHz, Chloroform-d) δ 8.56 (t, J=2.5 Hz, 1H), 8.38 (s, 1H), 8.13 (dt, J=8.7, 2.9 Hz, 1H), 7.50 (d, J=8.5 Hz, 1H), 7.11-6.76 (m, 2H), 5.18 (t, J=6.7 Hz, 1H), 5.01 (d, J=10.6 Hz, 1H), 4.43 (ddd, J=8.4, 6.7, 0.8 Hz, 1H), 4.16-4.08 (m, 1H), 3.98-3.88 (m, 1H), 3.84 (d, J=0.6 Hz, 4H), 2.78 (p, J=7.7 Hz, 1H), 1.69 (s, 3H), 1.50-1.45 (m, 6H), 0.84-0.75 (m, 3H) ppm; NH amide not observed. ESI-MS m/z calc. 562.19025, found 563.2 (M+1)$^+$; 561.3 (M−1)$^-$; Retention time: 1.02 minutes.

Step 5:

The mixture of rel-(2R,3S,4S,5R)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide and rel-(2S,3R,4R,5S)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (50 mg, 0.089 mmol) were separated by chiral SFC using a Chiralpak AS-H column, 5 um particle size, 25 cm×10 mm from Daicel Corporation (Mobile phase: 15% MeOH (containing 20 mM Ammonia), 85% CO$_2$. Flow: 10 mL/min.) on a Minigram SFC instrument from Berger Instruments to give:

First Eluting Isomer (rt=2.14 min): rel-(2S,3R,4R,5S)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (15 mg, 60%). ESI-MS m/z calc. 562.19025, found 563.2 (M+1)$^+$; 561.2 (M−1)$^-$; Retention time: 3.5 minutes.

Second Eluting Isomer (rt=3.60 min): rel-(2R,3S,4S,5R)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (12 mg, 48%). ESI-MS m/z calc. 562.19025, found 563.2 (M+1)$^+$; 561.2 (M−1)$^-$; Retention time: 3.49 minutes.

Step 6:

TFA (10 µL, 0.1298 mmol) was added to a solution of rel-(2S,3R,4R,5S)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (15 mg, 0.02667 mmol) (First Eluting Isomer from SFC separation) in THF (800 µL) and water (200 µL). The reaction mixture was stirred overnight at 60° C. The mixture was concentrated in vacuo. Purification by reversed phase HPLC-MS using a X-bridge C18 OBD column (150×19 mm, 5 mm particle size) from Waters gave rel-(2S,3R,4R,5S)-3-(3-(difluoromethyl)-4-fluoro-2-methoxyphenyl)-N-(6-((S*)-1,2-dihydroxyethyl)pyridin-3-yl)-4,5-dimethyl-5-(trifluoromethyl)tetrahydrofuran-2-carboxamide (48, 6 mg, 41%). $^1$H NMR (400 MHz, Methanol-d$_4$) δ 8.71 (dd, J=2.6, 0.8 Hz, 1H), 8.08 (dd, J=8.5, 2.5 Hz, 1H), 7.64-7.58 (m, 1H), 7.55 (dt, J=8.6, 0.7 Hz, 1H), 7.21-6.89 (m, 2H), 5.09 (d, J=10.4 Hz, 1H), 4.74 (dd, J=6.6, 4.2 Hz, 1H), 4.36 (dd, J=10.4, 8.1 Hz, 1H), 3.87 (s, 3H), 3.86-3.62 (m, 2H), 2.83 (p, J=7.7 Hz, 1H), 1.70 (d, J=1.2 Hz, 3H), 0.90-0.82 (m, 3H) ppm; alcohols OH and amide NH not observed. ESI-MS m/z calc. 522.15894, found 522.9 (M+1)$^+$; 521.0 (M−1)$^-$; Retention time: 3.04 minutes.

rel-(2R,3S,4S,5R)-3-(3-(difluoromethyl)-4-fluoro-2-methoxyphenyl)-N-(6-((S*)-2,2-dimethyl-1,3-dioxolan-4-yl)pyridin-3-yl)-4,5-dimethyl-5-(trifluoromethyl)tetrahydrofuran-2-carboxamide (12 mg, 0.02133 mmol) (Second Eluting Isomer from SFC separation) was treated in the same way to give rel-(2R,3S,4S,5R)-3-(3-(difluoromethyl)-4-fluoro-2-methoxyphenyl)-N-(6-((S*)-1,2-dihydroxyethyl)pyridin-3-yl)-4,5-dimethyl-5-(trifluoromethyl)tetrahydrofuran-2-carboxamide (49, 4 mg, 34%). $^1$H NMR (400 MHz, Methanol-d$_4$) δ 8.69 (dd, J=2.6, 0.8 Hz, 1H), 8.06 (dd, J=8.5, 2.5 Hz, 1H), 7.63-7.57 (m, 1H), 7.53 (dt, J=8.6, 0.7 Hz, 1H), 7.20-6.87 (m, 2H), 5.08 (d, J=10.4 Hz, 1H), 4.72 (dd, J=6.6, 4.2 Hz, 1H), 4.34 (dd, J=10.4, 8.1 Hz, 1H), 3.86 (s, 3H), 3.84-3.61 (m, 2H), 2.82 (p, J=7.7 Hz, 1H), 1.69 (d, J=1.2 Hz, 3H), 0.88-0.80 (m, 3H) ppm; alcohols OH and amide NH not observed. ESI-MS m/z calc. 522.15894, found 522.9 (M+1)$^+$; 521.0 (M−1)$^-$; Retention time: 3.01 minutes.

The following compounds were made using the method described in Example 6, except that (R)-6-(2,2-dimethyl-1,3-dioxolan-4-yl)pyridine-3-amine was used in place of (S)-6-(2,2-dimethyl-1,3-dioxolan-4-yl)pyridine-3-amine in the amide coupling step 4. In step 5, purification was performed by chiral SFC using a (R,R)-Whelk-1 column, 5 um particle size, 25 cm×21.1 mm from Daicel (Mobile phase: 5 to 55% MeOH, 95 to 45% CO$_2$. Flow: 100 mL/min.) on a Minigram SFC instrument from Berger Instruments. The conditions used in step 6 were similar to those described in Example 1 step 16:

| Cmpd No. | Compound Name | LC/MS | NMR (shifts in ppm) |
|---|---|---|---|
| 50 | rel-(2S,3R,4R,5S)-3-(3-(difluoromethyl)-4-fluoro-2-methoxyphenyl)-N-(6-((R*)-1,2-dihydroxyethyl)pyridin-3-yl)-4,5-dimethyl-5-(trifluoromethyl)tetrahydrofuran-2-carboxamide (Precursor was the first eluting peak by SFC on (R,R)-Whelk-O1 column, rt = 1.16 min) | ESI-MS m/z calc. 522.15894, found 523.2 (M + 1)⁺; 521.1 (M − 1)⁻; Retention time: 2.97 minutes | ¹H NMR (500 MHz, Chloroform-d) δ 8.67 (s, 1H), 8.57 (s, 1H), 8.18 (d, J = 8.6 Hz, 1H), 7.59-7.49 (m, 1H), 7.37 (d, J = 8.5 Hz, 1H), 7.10-6.80 (m, 2H), 5.02 (d, J = 10.6 Hz, 1H), 4.83 (s, 1H), 4.15 (dd, J = 10.6, 8.4 Hz, 1H), 3.92 (dd, J = 11.3, 3.7 Hz, 1H), 3.84 (s, 3H), 3.76 (dd, J = 11.4, 5.3 Hz, 1H), 2.78 (p, J = 7.7 Hz, 1H), 1.69 (s, 3H), 0.81 (dd, J = 7.6, 2.4 Hz, 3H) ppm; alcohols OH not observed. |
| 51 | rel-(2R,3S,4S,5R)-3-(3-(difluoromethyl)-4-fluoro-2-methoxyphenyl)-N-(6-((R*)-1,2-dihydroxyethyl)pyridin-3-yl)-4,5-dimethyl-5-(trifluoromethyl)tetrahydrofuran-2-carboxamide (Precursor was the second eluting peak by SFC on (R,R)-Whelk-O1 column, rt = 1.78 min) | ESI-MS m/z calc. 522.15894, found 523.2 (M + 1)⁺; 521.1 (M − 1)⁻; Retention time: 2.97 minutes | ¹H NMR (500 MHz, Chloroform-d) δ 8.69 (s, 1H), 8.23 (dd, J = 8.6, 2.3 Hz, 1H), 7.53 (dd, J = 8.9, 5.8 Hz, 1H), 7.39 (d, J = 8.6 Hz, 1H), 7.05-6.79 (m, 2H), 5.02 (d, J = 10.6 Hz, 1H), 4.85 (t, J = 4.6 Hz, 1H), 4.15 (dt, J = 10.8, 7.9 Hz, 1H), 3.92 (dd, J = 11.5, 3.8 Hz, 1H), 3.84 (s, 3H), 3.76 (dd, J = 11.4, 5.4 Hz, 1H), 2.78 (p, J = 7.7 Hz, 1H), 1.70 (d, J = 3.6 Hz, 3H), 0.81 (dt, J = 7.8, 2.1 Hz, 3H) ppm; alcohols OH and amide NH not observed. |

The following compounds were made using the method described in Example 6, except that the product of step 1 was prepared in 3 steps using the conditions described in Example 11 steps 1, 2 and 3 and the coupling partner was 1-bromo-3-(difluoromethyl)-4-fluoro-2-methoxybenzene. In the amide coupling step 4, methyl 5-aminopicolinate was used as the amine coupling partner. The ester formed in step 4 was reduced overnight at 50° C. using an excess of NaBH₄ in MeOH as the solvent, conditions well known in the art. The deprotection step 6 was not required:

| Cmpd No. | Compound Name | LC/MS | NMR (shifts in ppm) |
|---|---|---|---|
| 52 | rel-(2S,3R,4R,5S)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide (First eluting peak by SFC on Chiralpak AS-H column, 10 × 250 mm (Mobile phase: 20% MeOH (containing 20 mM Ammonia), 80% CO₂. Flow: 10 mL/min.), rt = 1.99 min) | ESI-MS m/z calc. 492.14838, found 493.4 (M + 1)⁺; 491.3 (M − 1)⁻; Retention time: 2.76 minutes | ¹H NMR (500 MHz, Methanol-d₄) δ 9.03 (d, J = 2.4 Hz, 1H), 8.37 (dd, J = 8.8, 2.3 Hz, 1H), 7.74 (d, J = 8.8 Hz, 1H), 7.60 (dd, J = 8.8, 6.1 Hz, 1H), 7.19-6.88 (m, 2H), 5.12 (d, J = 10.4 Hz, 1H), 4.81 (s, 2H), 4.36 (dd, J = 10.5, 8.2 Hz, 1H), 3.86 (s, 3H), 2.83 (p, J = 7.7 Hz, 1H), 1.69 (d, J = 1.2 Hz, 3H), 0.84 (dt, J = 7.6, 2.4 Hz, 3H) ppm; alcohol OH and amide NH not observed. |
| 53 | rel-(2R,3S,4S,5R)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide (Second eluting peak by SFC on Chiralpak AS-H column, 10 × 250 mm (Mobile phase: 20% MeOH (containing 20 mM Ammonia), 80% CO₂. Flow: 10 mL/min.), rt = 3.05 min) | ESI-MS m/z calc. 492.14838, found 493.4 (M + 1)⁺; Retention time: 2.77 minutes | ¹H NMR (500 MHz, Methanol-d₄) δ 8.67 (d, J = 2.5 Hz, 1H), 8.07 (dd, J = 8.5, 2.5 Hz, 1H), 7.59 (dd, J = 8.8, 6.0 Hz, 1H), 7.50 (d, J = 8.5 Hz, 1H), 7.15-6.90 (m, 2H), 5.08 (d, J = 10.4 Hz, 1H), 4.64 (s, 2H), 4.34 (dd, J = 10.5, 8.2 Hz, 1H), 3.86 (s, 3H), 2.82 (p, J = 7.7 Hz, 1H), 1.68 (d, J = 1.2 Hz, 3H), 0.83 (dt, J = 7.5, 2.3 Hz, 3H) ppm; alcohol OH and amide NH not observed. |

The following compounds were made using the method described in Example 6, except that the product of step 1 was prepared in 3 steps using the conditions described in Example 11 steps 1, 2 and 3 and the coupling partner was 1-bromo-3-(difluoromethyl)-4-fluoro-2-methoxybenzene. In the amide coupling step 4, (5-aminopyrimidin-2-yl)methyl benzoate was used as the amine coupling partner. The chiral SFC separation step 5 was carried out using a Chiralpak IG column, 5 μm particle size, 25 cm×20 mm from Daicel (Mobile phase: 17% MeOH (containing 20 mM Ammonia), 83% $CO_2$. Flow: 100 mL/min.) on a Prep-100 SFC instrument from Waters. The deprotection step 6 was carried out at 30° C. over 16 h using a 2M LiOH solution in excess in MeOH as the solvent, conditions well known in the art:

| Cmpd No. | Compound Name | LC/MS | NMR (shifts in ppm) |
| --- | --- | --- | --- |
| 54 | rel-(2R,3S,4S,5R)-3-(3-(difluoromethyl)-4-fluoro-2-methoxyphenyl)-N-(2-(hydroxymethyl)pyrimidin-5-yl)-4,5-dimethyl-5-(trifluoromethyl)tetrahydrofuran-2-carboxamide (Precursor was the first eluting peak by SFC on Chiralpak IG column, rt = 1.31 min) | ESI-MS m/z calc. 493.14362, found 494.6 (M + 1)$^+$; 492.5 (M − 1)$^-$; Retention time: 3.06 minutes | $^1$H NMR (500 MHz, Methanol-d$_4$) δ 9.04 (s, 2H), 7.60 (dd, J = 8.9, 6.1 Hz, 1H), 7.27-6.80 (m, 2H), 5.11 (d, J = 10.4 Hz, 1H), 4.72 (s, 2H), 4.35 (dd, J = 10.4, 8.2 Hz, 1H), 3.86 (s, 3H), 2.83 (p, J = 7.7 Hz, 1H), 1.69 (d, J = 1.2 Hz, 3H), 0.83 (dq, J = 7.5, 2.3 Hz, 3H) ppm; alcohol OH and amide NH not observed. |
| 55 | rel-(2S,3R,4R,5S)-3-(3-(difluoromethyl)-4-fluoro-2-methoxyphenyl)-N-(2-(hydroxymethyl)pyrimidin-5-yl)-4,5-dimethyl-5-(trifluoromethyl)tetrahydrofuran-2-carboxamide (Precursor was the second eluting peak by SFC on Chiralpak IG column, rt = 1.47 min) | ESI-MS m/z calc. 493.14362, found 494.6 (M + 1)$^+$; 492.5 (M − 1)$^-$; Retention time: 3.06 minutes | $^1$H NMR (500 MHz, Methanol-d$_4$) δ 9.04 (s, 2H), 7.60 (dd, J = 8.8, 6.0 Hz, 1H), 7.21-6.86 (m, 2H), 5.11 (d, J = 10.4 Hz, 1H), 4.72 (s, 2H), 4.35 (dd, J = 10.4, 8.2 Hz, 1H), 3.86 (s, 3H), 2.83 (p, J = 7.7 Hz, 1H), 1.69 (d, J = 1.4 Hz, 3H), 0.83 (dt, J = 7.5, 2.4 Hz, 3H) ppm; alcohol OH and amide NH not observed. |

The following compounds were made using the method described in Example 6, except that the product of step 1 was prepared in 3 steps using the conditions described in Example 11 steps 1, 2 and 3 and the coupling partner was 1-bromo-3-(difluoromethyl)-4-fluoro-2-methoxybenzene. In the amide coupling step 4, 1-(5-aminopyridin-2-yl)ethan-1-one was used as the amine coupling partner. The chiral SFC separation step 5 was carried out using a Chiralpak IG column, 5 μm particle size, 25 cm×10 mm from Daicel (Mobile phase: 25% IPA (containing 20 mM Ammonia), 75% $CO_2$. Flow: 10 mL/min.) on a Minigram SFC instrument from Berger Instruments. The deprotection step 6 was replaced by a ketone reduction step taking place at ambient temperature over 30 min and using 3 eq of NaBH$_4$ in MeOH as the solvent, conditions well known in the art. The first eluting isomers in the SFC separation (step 5) was a mixture of epimers at the hydroxyethyl position, which was not further separated and is referred to herein as compound 56. The second eluting isomers in the SFC separation (step 5) was a mixture of epimers at the hydroxyethyl position, compounds 57 and 58, which were further separated by chiral SFC using a Chiralpak IG column, 5 μm particle size, 25 cm×10 mm from Daicel (Mobile phase: 25% IPA (containing 20 mM Ammonia), 75% $CO_2$. Flow: 10 mL/min.) on a Minigram SFC instrument from Berger Instruments:

| Cmpd No. | Compound Name | LC/MS | NMR (shifts in ppm) |
| --- | --- | --- | --- |
| 56 | rel-(2R,3S,4S,5R)-3-(3-(difluoromethyl)-4-fluoro-2-methoxyphenyl)-N-(6-(1-hydroxyethyl)pyridin-3-yl)-4,5-dimethyl-5-(trifluoromethyl)tetrahydrofuran-2-carboxamide (mixture of epimers at hydroxyethyl position) (Precursor was the first eluting peak by SFC on Chiralpak IG | ESI-MS m/z calc. 506.16403, found 507.6 (M + 1)$^+$; 505.5 (M − 1)$^-$; Retention time: 3.23 minutes | $^1$H NMR (500 MHz, Methanol-d$_4$) δ 8.66 (dt, J = 2.6, 0.8 Hz, 1H), 8.06 (ddd, J = 8.5, 2.5, 0.9 Hz, 1H), 7.62-7.57 (m, 1H), 7.53-7.48 (m, 1H), 7.14-6.91 (m, 2H), 5.07 (d, J = 10.4 Hz, 1H), 4.82 (q, J = 6.6 Hz, 1H), 4.34 (dd, J = 10.4, 8.2 Hz, 1H), 3.86 (s, 3H), 2.82 (p, J = 7.6 Hz, 1H), 1.68 (d, J = 1.2 |

| Cmpd No. | Compound Name | LC/MS | NMR (shifts in ppm) |
|---|---|---|---|
| | column, rt = 2.51 min; epimers not separated) | | Hz, 3H), 1.43 (d, J = 6.5 Hz, 3H), 0.86-0.80 (m, 3H) ppm; alcohol OH and amide NH not observed. |
| 57 | rel-(2S,3R,4R,5S)-3-(3-(difluoromethyl)-4-fluoro-2-methoxyphenyl)-N-(6-(1-hydroxyethyl)pyridin-3-yl)-4,5-dimethyl-5-(trifluoromethyl)tetrahydrofuran-2-carboxamide (Precursor was the second eluting peak by SFC on Chiralpak IG column, rt = 3.51 min; first eluting peak by SFC on Chiralpak IG column in the final step, rt = 3.44 min) | ESI-MS m/z calc. 506.16403, found 507.4 (M + 1)$^+$; 505.3 (M − 1)$^-$; Retention time: 3.21 minutes | $^1$H NMR (500 MHz, Methanol-d$_4$) δ 8.66 (d, J = 2.5 Hz, 1H), 8.05 (dd, J = 8.5, 2.5 Hz, 1H), 7.59 (dd, J = 8.9, 6.1Hz, 1H), 7.51 (d, J = 8.6 Hz, 1H), 7.16-6.91 (m, 2H), 5.07 (d, J = 10.4 Hz, 1H), 4.86-4.79 (m, 1H), 4.34 (dd, J = 10.4, 8.2 Hz, 1H), 3.86 (s, 3H), 2.82 (p, J = 7.7 Hz, 1H), 1.68 (d, J = 1.3 Hz, 3H), 1.43 (d, J = 6.6 Hz, 3H), 0.83 (dq, J = 7.4, 2.4 Hz, 3H) ppm; alcohol OH and amide NH not observed. |
| 58 | rel-(2S,3R,4R,5S)-3-(3-(difluoromethyl)-4-fluoro-2-methoxyphenyl)-N-(6-(1-hydroxyethyl)pyridin-3-yl)-4,5-dimethyl-5-(trifluoromethyl)tetrahydrofuran-2-carboxamide (Precursor was the second eluting peak by SFC on Chiralpak IG column, rt = 3.51 min; second eluting peak by SFC on Chiralpak IG column in the final step, rt = 4.33 min) | ESI-MS m/z calc. 506.16403, found 507.4 (M + 1)$^+$; 505.3 (M − 1)$^-$; Retention time: 3.21 minutes | $^1$H NMR (500 MHz, Methanol-d$_4$) δ 8.66 (d, J = 2.5 Hz, 1H), 8.05 (dd, J = 8.5, 2.5 Hz, 1H), 7.59 (dd, J = 8.8, 6.0 Hz, 1H), 7.51 (d, J = 8.6 Hz, 1H), 7.14-6.91 (m, 2H), 5.07 (d, J = 10.4 Hz, 1H), 4.86-4.79 (m, 1H), 4.34 (dd, J = 10.4, 8.2 Hz, 1H), 3.86 (s, 3H), 2.82 (p, J = 7.7 Hz, 1H), 1.68 (d, J = 1.2 Hz, 3H), 1.43 (d, J = 6.6 Hz, 3H), 0.83 (dq, J = 7.4, 2.3 Hz, 3H) ppm; alcohol OH and amide NH not observed. |

Example 7 rel-2-((S*)-1,2-dihydroxyethyl)-5-((2R,3S,4S,5R)-3-(4-fluoro-2-methoxy-3-methylphenyl)-4,5-dimethyl-5-(trifluoromethyl)tetrahydrofuran-2-carboxamido)pyridine 1-oxide (59)

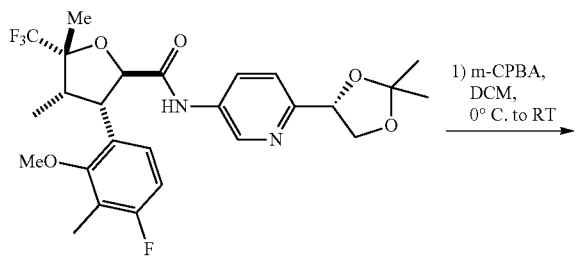

1) m-CPBA, DCM, 0° C. to RT

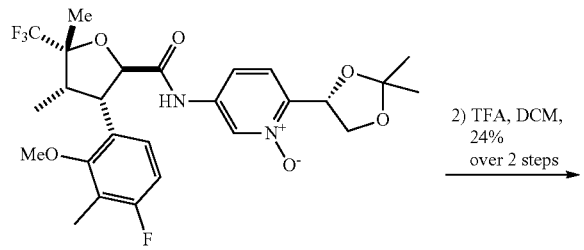

2) TFA, DCM, 24% over 2 steps

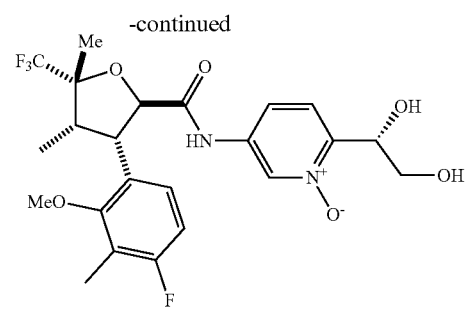

59

Step 1:

A solution of rel-(2R,3S,4S,5R)—N-(6-((S*)-2,2-dimethyl-1,3-dioxolan-4-yl)pyridin-3-yl)-3-(4-fluoro-2-methoxy-3-methylphenyl)-4,5-dimethyl-5-(trifluoromethyl)tetrahydrofuran-2-carboxamide (11.5 mg, 0.02184 mmol), which is prepared as described for the precursor of compound 45 in Example 5, in DCM (2 mL) was cooled down in an ice bath. m-CPBA (19.9 mg, 0.08072 mmol) was added in one portion and the mixture was allowed to warm up slowly with the ice bath in place. The reaction mixture was stirred for 24 h. The reaction mixture was quenched with saturated bicarbonate (2 ml). The aqueous layer was washed with DCM (3×2 ml). The organic phases were combined and passed through a phase separator cartridge. The liquors were concentrated in vacuo to give rel-2-((S*)-2,2-dimethyl-1,3-dioxolan-4-yl)-5-((2R,3S,4S,5R)-3-(4-fluoro-2-methoxy-3-methylphenyl)-4,5-dimethyl-5-(trifluoromethyl)tetrahydrofuran-2-carboxamido)pyridine 1-oxide (15.4 mg, 100%) as a yellow solid, which was used as is in the next step. ESI-MS m/z calc. 542.204, found 543.7 (M+1)⁺; 541.6 (M−1)⁻; Retention time: 0.97 minutes.

Step 2:

TFA (25 μL, 0.3245 mmol) was added to a stirred solution of rel-2-((S*)-2,2-dimethyl-1,3-dioxolan-4-yl)-5-((2R,3S,4S,5R)-3-(4-fluoro-2-methoxy-3-methylphenyl)-4,5-dimethyl-5-(trifluoromethyl)tetrahydrofuran-2-carboxamido)pyridine 1-oxide (15.4 mg, 0.02441 mmol) in DCM (500 μL). The reaction mixture was stirred at ambient temperature for 24 h. Purification by reverse phase preparative HPLC (basic eluent) gave rel-2-((S*)-1,2-dihydroxyethyl)-5-((2R,3S,4S,5R)-3-(4-fluoro-2-methoxy-3-methylphenyl)-4,5-dimethyl-5-(trifluoromethyl)tetrahydrofuran-2-carboxamido)pyridine 1-oxide (3.2 mg, 24%) as a white solid. ¹H NMR (500 MHz, Methanol-d₄) δ 8.96 (d, J=1.9 Hz, 1H), 7.78-7.73 (m, 1H), 7.69 (d, J=8.8 Hz, 1H), 7.22 (dd, J=8.7, 6.4 Hz, 1H), 6.91 (t, J=8.8 Hz, 1H), 5.28 (dd, J=5.4, 3.5 Hz, 1H), 5.06 (d, J=10.6 Hz, 1H), 4.38 (dd, J=10.6, 8.0 Hz, 1H), 3.93 (dd, J=11.3, 3.4 Hz, 1H), 3.83-3.72 (m, 4H), 2.81 (p, J=7.6 Hz, 1H), 2.25 (d, J=2.0 Hz, 3H), 1.70 (s, 3H), 0.84 (dd, J=6.9, 2.6 Hz, 3H) ppm; alcohols OH and amide NH not observed. ¹⁹F NMR (471 MHz, Methanol-d₄) δ −75.62, −117.82 ppm. ESI-MS m/z calc. 502.1727, found 503.6 (M+1)⁺; 501.6 (M−1)⁻; Retention time: 2.9 minutes.

The following compound was made using the method described in Example 7, using 1 as the starting material:

Example 8 rel-(2S,3R,5S)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide (61) and rel-(2R,3S,5R)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide (62)

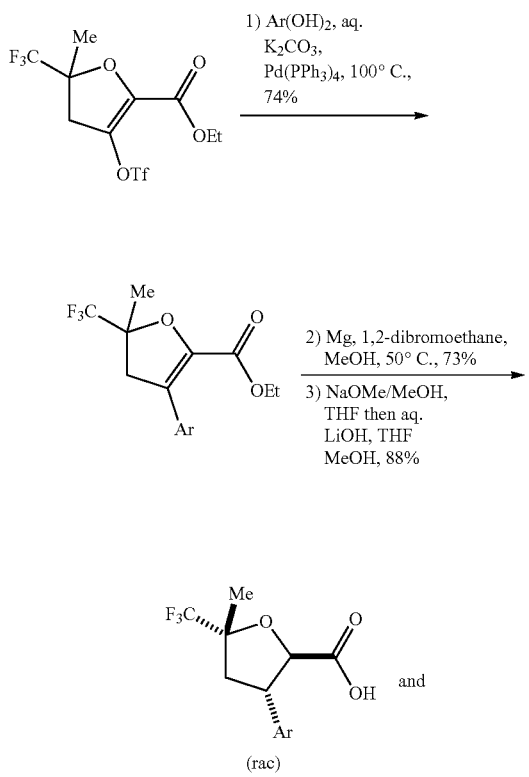

| Cmpd No. | Compound Name | LC/MS | NMR (shifts in ppm) |
|---|---|---|---|
| 60 | 5-((2R,3S,4S,5R)-3-(3,4-difluoro-2-methoxyphenyl)-4,5-dimethyl-5-(trifluoromethyl)tetrahydrofuran-2-carboxamido)-2-((R)-1,2-dihydroxyethyl)pyridine 1-oxide | ESI-MS m/z calc. 506.1476, found 507.3 (M + 1)⁺; 505.3 (M − 1)⁻; Retention time: 2.84 minutes | ¹H NMR (500 MHz, DMSO-d₆) δ 10.46 (s, 1H), 8.66 (d, J = 1.9 Hz, 1H), 7.54 (dd, J = 8.8, 2.0 Hz, 1H), 7.47 (d, J = 8.7 Hz, 1H), 7.17 (dd, J = 11.2, 6.6 Hz, 2H), 5.64 (d, J = 5.4 Hz, 1H), 5.08 (d, J = 10.1 Hz, 1H), 5.03-4.98 (m, 1H), 4.77 (t, J = 6.0 Hz, 1H), 4.24 (dd, J = 10.1, 7.7 Hz, 1H), 3.95 (d, J = 2.1 Hz, 3H), 3.66 (ddd, J = 10.9, 6.0, 3.4 Hz, 1H), 3.46 (dt, J = 10.9, 6.0 Hz, 1H), 2.76 (q, J = 7.6 Hz, 1H), 1.60 (s, 3H), 0.73 (d, J = 7.1 Hz, 3H) ppm. |

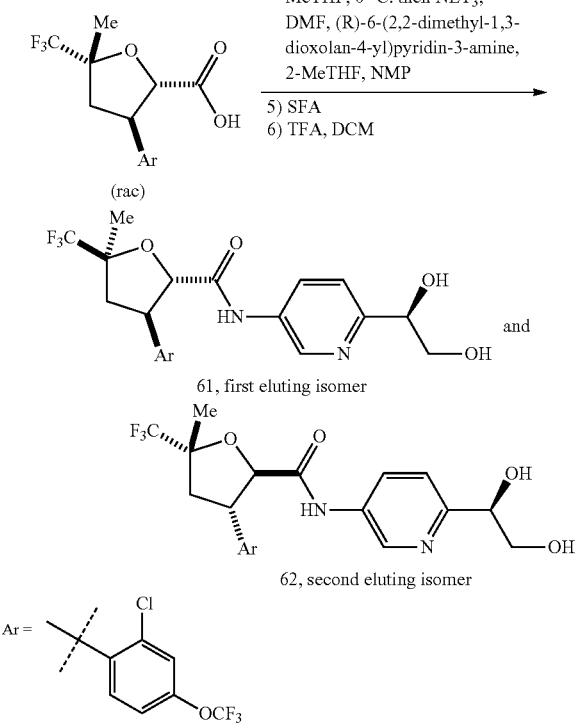

Step 1:

Tetrakis(triphenylphosphine)palladium (0) (1.3 g, 1.125 mmol) was added to a mixture of (2-chloro-4-(trifluoromethoxy)phenyl)boronic acid (5 g, 20.80 mmol), ethyl 5-methyl-5-(trifluoromethyl)-3-(((trifluoromethyl)sulfonyl)oxy)-4,5-dihydrofuran-2-carboxylate (8 g, 21.49 mmol) and aqueous sodium carbonate (28.2 mL of 2 M, 56.40 mmol) in dioxane (85 mL). The reaction mixture was heated at 100° C. for 3 h. The mixture was partitioned between EtOAc and water. The organic layer was washed with brine, dried (MgSO$_4$), filtered and concentrated in vacuo. Purification by flash chromatography (120 g SiO$_2$, 0 to 40% EtOAc in heptane) gave ethyl 3-(2-chloro-4-(trifluoromethoxy)phenyl)-5-methyl-5-(trifluoromethyl)-4,5-dihydrofuran-2-carboxylate (6.46 g, 74%). $^1$H NMR (500 MHz, Chloroform-d) δ 7.34 (dd, J=2.3, 1.0 Hz, 1H), 7.32-7.24 (m, 1H), 7.16 (dtd, J=8.5, 2.0, 0.9 Hz, 1H), 4.14 (q, J=7.2 Hz, 2H), 3.43 (d, J=17.5 Hz, 1H), 3.07-2.96 (m, 1H), 1.71 (d, J=1.0 Hz, 3H), 1.08 (t, J=7.1 Hz, 3H) ppm. ESI-MS m/z calc. 418.04065, found 418.8 (M+1)$^+$; Retention time: 1.13 minutes.

Step 2:

A pressure tube was loaded with magnesium powder (2.35 g, 96.69 mmol) and purged with nitrogen. To the reaction vessel was added MeOH (20 mL) followed by a solution of ethyl 3-(2-chloro-4-(trifluoromethoxy)phenyl)-5-methyl-5-(trifluoromethyl)-4,5-dihydrofuran-2-carboxylate (2 g, 4.777 mmol) in MeOH (20 mL). The reaction mixture was degassed with nitrogen before adding a few drops of 1,2-dibromoethane (80 mg, 0.4258 mmol). The reaction mixture was stirred vigorously and heated at 50° C. for 5 h. The mixture was cooled down to ambient temperature and quenched by pouring it slowly onto cooled 1M solution of HCl. The mixture was stirred for 30 min until a clear solution was obtained. The mixture was partitioned with TBME. The separated aqueous layer was washed with TBME (×3). The combined organic phases were passed through a phase separator cartridge. The filtrate was concentrated in vacuo to give a mixture of diastereoisomers, the 2 major ones being methyl rac-(2S,3S,5R)-3-(2-chloro-4-(trifluoromethoxy)phenyl)-5-methyl-5-(trifluoromethyl)tetrahydrofuran-2-carboxylate and methyl rac-(2R,3R,5R)-3-(2-chloro-4-(trifluoromethoxy)phenyl)-5-methyl-5-(trifluoromethyl)tetrahydrofuran-2-carboxylate (2.85 g, 73%) which was used as is in the next step. ESI-MS m/z calc. 406.04065, Retention times: 1.09 and 1.11 minutes for the 2 main diastereoisomers.

Step 3:

Sodium methoxide (310 μL of 25% w/v in MeOH, 1.435 mmol) was added to a stirred solution containing a mixture of methyl rac-(2S,3S,5R)-3-(2-chloro-4-(trifluoromethoxy)phenyl)-5-methyl-5-(trifluoromethyl)tetrahydrofuran-2-carboxylate and methyl rac-(2R,3R,5R)-3-(2-chloro-4-(trifluoromethoxy)phenyl)-5-methyl-5-(trifluoromethyl)tetrahydrofuran-2-carboxylate (3.8 g, 9.343 mmol) in THF (40 mL) at ambient temperature under nitrogen. After 5 h, methanol (0.2 ml) and LiOH (7.3 mL of 2 M aqueous solution, 14.60 mmol) were added and the reaction mixture was stirred overnight at ambient temperature. The reaction was poured into a 1M HCl solution. The mixture was extracted with TBME (2×30 ml). The combined organic layers were washed with brine, dried (Na$_2$SO$_4$), filtered and concentrated in vacuo to give a mixture containing 2 major diastereoisomers, rac-(2R,3S,5R)-3-(2-chloro-4-(trifluoromethoxy)phenyl)-5-methyl-5-(trifluoromethyl)tetrahydrofuran-2-carboxylic acid and rac-(2S,3R,5R)-3-(2-chloro-4-(trifluoromethoxy)phenyl)-5-methyl-5-(trifluoromethyl)tetrahydrofuran-2-carboxylic acid (3.244 g, 88%). ESI-MS m/z calc. 392.025, found 391.0 (M−1)$^−$; Retention times: 0.63 and 0.66 minutes for the 2 main diastereoisomers.

Step 4:

Dimethylformamide (0.3 μL, 0.003874 mmol) and oxalyl chloride (78 μL, 0.8941 mmol) were added to an ice cold stirring solution of a mixture of diastereoisomers containing rac-(2R,3S,5R)-3-(2-chloro-4-(trifluoromethoxy)phenyl)-5-methyl-5-(trifluoromethyl)tetrahydrofuran-2-carboxylic acid and rac-(2S,3R,5R)-3-(2-chloro-4-(trifluoromethoxy)phenyl)-5-methyl-5-(trifluoromethyl)tetrahydrofuran-2-carboxylic acid (167 mg, 0.4253 mmol) in 2-methyltetrahydrofuran (2 mL). The reaction mixture was stirred and warmed up to ambient temperature over 1.5 h. The reaction mixture was concentrated in vacuo. The residue was taken up in 2-methyltetrahydrofuran (2 mL) and added to an ice cooled solution of (R)-6-(2,2-dimethyl-1,3-dioxolan-4-yl)pyridin-3-amine (90 mg, 0.4634 mmol) and TEA (178 μL, 1.277 mmol) in a mixture of 2-methyltetrahydrofuran (2 mL) and NMP (0.1 mL). The resulting mixture was stirred and warmed up to ambient temperature over 18 h. The reaction mixture was quenched with water (5 mL) and the layers separated. The aqueous phase was extracted with EtOAc (2×10 mL). The combined organic extracts were washed with brine (5 mL), dried (MgSO$_4$), filtered and concentrated in vacuo. Purification by column chromatography (12 g SiO$_2$, 0 to 50% EtOAc in heptane) gave a mixture of isomers:

First Eluting Isomers: mixture of rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide and rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (95 mg, 28%) as a white solid and as a ~3:1 mixture with the dechlorinated side product. ESI-MS m/z calc. 568.12, found 570.1 (M+1)+; Retention time: 1.09 minutes.

Second Eluting Isomers: mixture of rel-(2S,3R,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide and rel-(2R,3S,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (59 mg, 21%) as a white solid. $^1$H NMR (500 MHz, Chloroform-d) δ 8.58 (dd, J=22.6, 2.5 Hz, 1H), 8.32 (d, J=2.9 Hz, 1H), 8.12 (ddd, J=25.0, 8.6, 2.6 Hz, 1H), 7.54 (d, J=8.5 Hz, 1H), 7.49 (d, J=8.6 Hz, 1H), 7.33 (dd, J=2.5, 1.0 Hz, 1H), 7.24-7.16 (m, 1H), 5.22 (t, J=6.7 Hz, 1H), 4.97 (dd, J=9.5, 1.3 Hz, 1H), 4.46 (dd, J=8.4, 6.7 Hz, 1H), 4.22 (dt, J=11.4, 8.9 Hz, 1H), 3.96 (dd, J=8.3, 6.7 Hz, 1H), 2.95 (dd, J=13.9, 8.4 Hz, 1H), 2.27-2.15 (m, 1H), 1.69-1.62 (m, 3H), 1.54 (s, 3H), 1.51 (s, 3H) ppm. ESI-MS m/z calc. 568.12, found 570.1 (M+1)+; Retention time: 1.09 minutes. The SFC separation and the deprotection of these Second Eluting Isomers will be exemplified in the table following Example 8.

Step 5:

The mixture of rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide and rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (95 mg, 0.120 mmol) (First Eluting Isomers from Step 4) were separated by chiral SFC using a (R,R)-Whelk-O1 column, 5 um particle size, 25 cm×21.1 mm from Daicel (Mobile phase: 30% MeOH (containing 20 mM Ammonia), 70% $CO_2$. Flow: 100 mL/min.) on a Minigram SFC instrument from Berger Instruments:

First Eluting Isomer (rt=2.66 min): rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (28 mg, 36%) as a colourless oil. $^1$H NMR (500 MHz, Chloroform-d) δ 8.55 (d, J=2.5 Hz, 1H), 8.27 (s, 1H), 8.14 (dd, J=8.6, 2.6 Hz, 1H), 7.54-7.49 (m, 2H), 7.32 (dd, J=2.5, 1.0 Hz, 1H), 7.22 (ddd, J=8.7, 2.5, 1.1 Hz, 1H), 5.19 (t, J=6.7 Hz, 1H), 4.83 (d, J=10.6 Hz, 1H), 4.45 (dd, J=8.3, 6.7 Hz, 1H), 4.12 (td, J=11.2, 8.2 Hz, 1H), 3.94 (dd, J=8.3, 6.7 Hz, 1H), 2.55 (dd, J=13.2, 8.2 Hz, 1H), 2.46 (dd, J=13.2, 11.7 Hz, 1H), 1.69 (s, 3H), 1.54 (s, 3H), 1.51 (s, 3H) ppm. ESI-MS m/z calc. 568.12, found 569.2 (M+1)+; 567.1 (M−1)−; Retention time: 1.12 minutes.

Second Eluting Isomer (rt=3.76 min): rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (27 mg, 38%) as a colourless oil. $^1$H NMR (500 MHz, Chloroform-d) δ 8.46 (d, J=2.4 Hz, 1H), 8.18 (s, 1H), 8.04 (dd, J=8.6, 2.6 Hz, 1H), 7.42 (dd, J=8.7, 1.8 Hz, 2H), 7.22 (dd, J=2.5, 1.0 Hz, 1H), 7.13 (ddd, J=8.6, 2.5, 1.1 Hz, 1H), 5.10 (t, J=6.7 Hz, 1H), 4.74 (d, J=10.5 Hz, 1H), 4.35 (dd, J=8.3, 6.7 Hz, 1H), 4.03 (td, J=11.2, 8.2 Hz, 1H), 3.84 (dd, J=8.3, 6.8 Hz, 1H), 2.46 (dd, J=13.3, 8.2 Hz, 1H), 2.36 (dd, J=13.2, 11.7 Hz, 1H), 1.59 (s, 3H), 1.44 (s, 3H), 1.41 (s, 3H) ppm. ESI-MS m/z calc. 568.12, found 569.2 (M+1)+; 567.1 (M−1)−; Retention time: 1.12 minutes.

Step 6:

TFA (200 µL, 2.596 mmol) was added to a solution of rel-(2S,3R,5S)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (32 mg, 0.04950 mmol) (First Eluting Isomer from SFC separation) in DCM (3 mL). The reaction mixture was stirred at ambient temperature for 18 h. The mixture was concentrated in vacuo. Purification by reverse phase preparative HPLC (Waters Sunfire C18, M, 100 Å column, 0% to 100% MeCN in water containing 0.1% ammonia) gave rel-(2S,3R,5S)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide (61, 7.9 mg, 26%). $^1$H NMR (500 MHz, DMSO-$d_6$) δ 10.09 (s, 1H), 8.62 (d, J=2.5 Hz, 1H), 7.94 (dd, J=8.5, 2.6 Hz, 1H), 7.72 (d, J=8.8 Hz, 1H), 7.62-7.57 (m, 1H), 7.48-7.44 (m, 1H), 7.43 (d, J=8.5 Hz, 1H), 5.32 (d, J=4.9 Hz, 1H), 4.73 (d, J=9.9 Hz, 1H), 4.64 (t, J=5.9 Hz, 1H), 4.56-4.51 (m, 1H), 4.28-4.18 (m, 1H), 3.64 (ddd, J=10.5, 6.0, 4.2 Hz, 1H), 3.45 (dt, J=11.0, 6.2 Hz, 1H), 2.59 (dd, J=13.0, 8.1 Hz, 1H), 2.44 (t, J=12.3 Hz, 1H), 1.59 (s, 3H) ppm; $^{19}$F NMR (471 MHz, DMSO-$d_6$) δ −56.96, −79.96 ppm. ESI-MS m/z calc. 528.0887, found 529.2 (M+1)+; 527.1 (M−1)−; Retention time: 3.15 minutes.

rel-(2R,3S,5R)-3-(2-chloro-4-(trifluoromethoxy)phenyl)-N-(6-((R*)-2,2-dimethyl-1,3-dioxolan-4-yl)pyridin-3-yl)-5-methyl-5-(trifluoromethyl)tetrahydrofuran-2-carboxamide (27 mg, 0.04604 mmol) (Second Eluting Isomer from SFC separation) was treated in the same way to give rel-(2R,3S,5R)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide (62, 8.1 mg, 33%). $^1$H NMR (500 MHz, DMSO-$d_6$) δ 10.10 (s, 1H), 8.61 (d, J=2.5 Hz, 1H), 7.95 (dd, J=8.5, 2.5 Hz, 1H), 7.72 (d, J=8.8 Hz, 1H), 7.59 (d, J=2.6 Hz, 1H), 7.52-7.44 (m, 1H), 7.43 (d, J=8.5 Hz, 1H), 5.33 (d, J=4.5 Hz, 1H), 4.73 (d, J=9.9 Hz, 1H), 4.64 (t, J=5.9 Hz, 1H), 4.54 (dt, J=7.4, 4.0 Hz, 1H), 4.24 (dt, J=10.7, 10.2, 8.2 Hz, 1H), 3.68-3.58 (m, 1H), 3.45 (dt, J=11.4, 5.9 Hz, 1H), 2.59 (dd, J=13.0, 8.1 Hz, 1H), 2.48-2.39 (m, 1H), 1.59 (s, 3H) ppm; $^{19}$F NMR (471 MHz, DMSO-$d_6$) δ −56.96, −79.96 ppm. ESI-MS m/z calc. 528.0887, found 529.2 (M+1)+; 527.1 (M−1)−; Retention time: 3.15 minutes.

The following compounds were made using the method described in Example 8, using the second eluting isomers obtained from the column chromatography of the amide coupling step 4. In step 5, purification was performed by chiral SFC using a Chiralcel OD-H column, 5 um particle size, 25 cm×10 mm from Daicel (Mobile phase: 15% MeOH (containing 20 mM Ammonia), 85% $CO_2$. Flow: 10 mL/min.) on a Minigram SFC instrument from Berger Instruments:

| Cmpd No. | Compound Name | LC/MS | NMR (shifts in ppm) |
| --- | --- | --- | --- |
| 63 | rel-(2R,3S,5S)-3-(2-chloro-4-(trifluoromethoxy)phenyl)-N-(6-((R*)-1,2-dihydroxyethyl)pyridin-3-yl)-5-methyl-5-(trifluoromethyl) | ESI-MS m/z calc. 528.0887, found 529.2 (M + 1)+; 527.1 (M − 1)−; Retention time: 3.1 minutes | $^1$H NMR (500 MHz, DMSO-$d_6$) δ 10.05 (s, 1H), 8.62 (d, J = 2.5 Hz, 1H), 7.96 (dd, J = 8.5, 2.5 Hz, 1H), 7.87 (d, J = 8.7 Hz, 1H), 7.62-7.54 (m, |

-continued

| Cmpd No. | Compound Name | LC/MS | NMR (shifts in ppm) |
|---|---|---|---|
| | tetrahydrofuran-2-carboxamide (Precursor was the first eluting peak by SFC on Chiralcel OD-H column, rt = 3.33 min) | | 1H), 7.48-7.43 (m, 1H), 7.41 (d, J = 8.5 Hz, 1H), 5.31 (d, J = 4.8 Hz, 1H), 4.92 (d, J = 9.3 Hz, 1H), 4.63 (t, J = 5.8 Hz, 1H), 4.54 (q, J = 4.8 Hz, 1H), 4.30-4.15 (m, 1H), 3.67-3.58 (m, 1H), 3.45 (dt, J = 11.1, 6.2 Hz, 1H), 2.81 (dd, J = 13.7, 8.2 Hz, 1H), 2.25 (dd, J = 13.8, 11.7 Hz, 1H), 1.59 (s, 3H) ppm. |
| 64 | rel-(2S,3R,5R)-3-(2-chloro-4-(trifluoromethoxy)phenyl)-N-(6-((R*)-1,2-dihydroxyethyl)pyridin-3-yl)-5-methyl-5-(trifluoromethyl)tetrahydrofuran-2-carboxamide (Precursor was the second eluting peak by SFC on Chiralcel OD-H column, rt = 4.17 min) | ESI-MS m/z calc. 528.0887, found 529.2 (M + 1)⁺; 527.1 (M − 1)⁻; Retention time: 3.1 minutes | $^1$H NMR (500 MHz, DMSO-d$_6$) δ 10.04 (s, 1H), 8.62 (d, J = 2.5 Hz, 1H), 7.96 (dd, J = 8.6, 2.6 Hz, 1H), 7.87 (d, J = 8.8 Hz, 1H), 7.58 (dd, J = 2.6, 0.9 Hz, 1H), 7.48-7.43 (m, 1H), 7.41 (d, J = 8.5 Hz, 1H), 5.31 (d, J = 4.9 Hz, 1H), 4.92 (d, J = 9.5 Hz, 1H), 4.63 (t, J = 5.9 Hz, 1H), 4.54 (dt, J = 6.8, 4.6 Hz, 1H), 4.24 (q, J = 10.1, 9.7 Hz, 1H), 3.63 (ddd, J = 10.5, 6.1, 4.2 Hz, 1H), 3.45 (ddd, J = 11.0, 6.9, 5.8 Hz, 1H), 2.81 (dd, J = 13.8, 8.2 Hz, 1H), 2.32-2.19 (m, 1H), 1.59 (s, 3H) ppm. |

Example 9 rel-(2S,3R,4S,5R)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (65)

rel-(2R,3S,4S,5R)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (66)

rel-(2R,3S,4R,5S)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (67) and rel-(2S,3R,4R,5S)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (68)

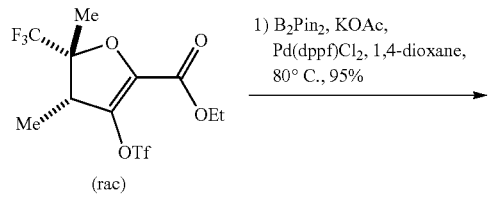

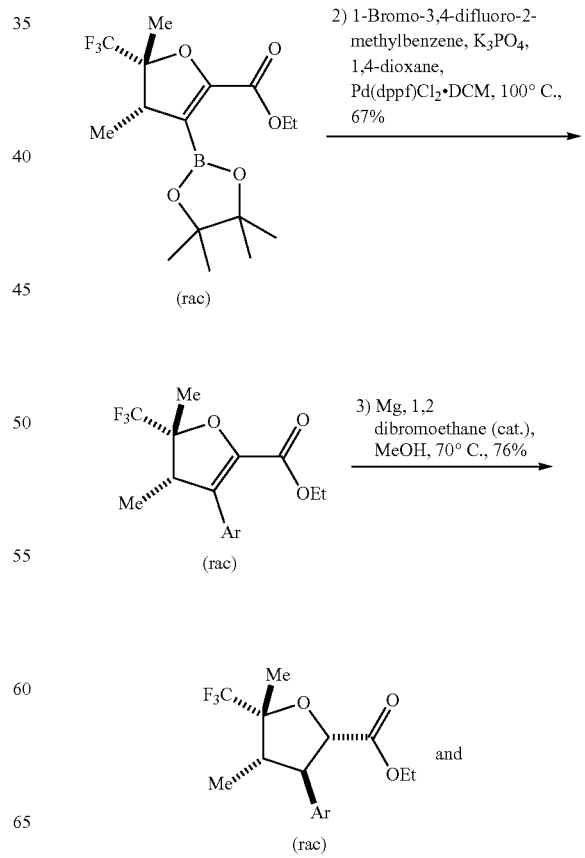

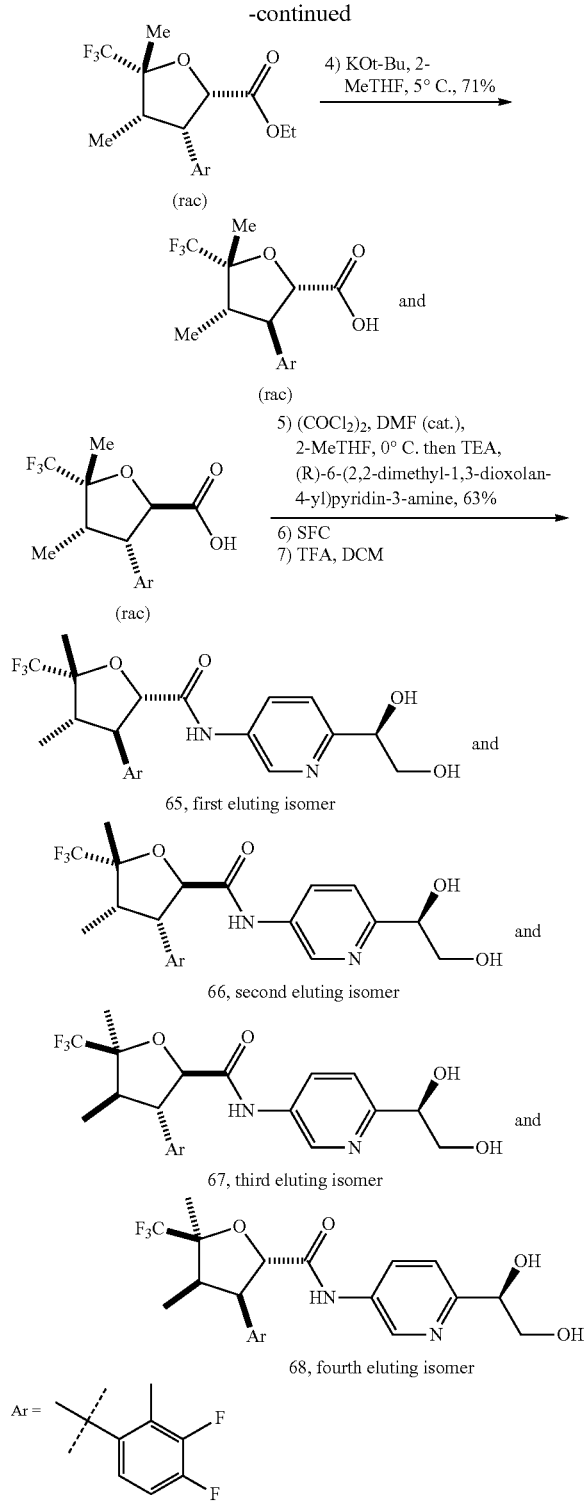

Step 1:

To a 3 neck 1 litre flask flanked with a thermometer and air condenser is added ethyl rac-(4R,5R)-4,5-dimethyl-5-(trifluoromethyl)-3-(((trifluoromethyl)sulfonyl)oxy)-4,5-dihydrofuran-2-carboxylate (42 g, 108.7 mmol) and 1,4-dioxane (500 mL). The stirred mixture is degassed and flushed with nitrogen. KOAc (32 g, 326.1 mmol) was added followed by bis(pinacolato)diboron (32 g, 126.0 mmol). The reaction mixture was evacuated and back filled with nitrogen (×3). Pd(dppf)Cl$_2$ (4 g, 5.467 mmol) was added and the mixture was heated to 80° C. for 20 h. The reaction mixture was cooled down to ambient temperature and partitioned between ethyl acetate (300 mL) and water (100 mL). The mixture was filtered through a pad of celite, washing with ethyl acetate (5×100 ml) until no more product came off. The filtrate phases were separated. The aqueous layer was extracted with ethyl acetate (100 mL×2). The combined organic layers were passed through a Whatmann phase separation filter paper. The filtrates were concentrated in vacuo to give 47 g of a brown oil. Purification by flash chromatography (Florisil, 100% heptane) gave ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g, 95%) as a thick viscous yellow oil. $^1$H NMR (500 MHz, Chloroform-d) δ 4.33-4.23 (m, 2H), 3.27-3.18 (m, 1H), 1.55 (d, J=1.1 Hz, 3H), 1.32 (s, 12H), 1.28 (d, J=2.3 Hz, 3H), 1.24 (s, 3H) ppm. ESI-MS m/z calc. 364.1669, found 365.3 (M+1)$^+$; Retention time: 1.1 minutes.

Step 2:

An aqueous solution of K$_3$PO$_4$ (8 mL of 2 M, 16.00 mmol) was added to a solution of rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (3 g, 7.414 mmol), 1-bromo-3,4-difluoro-2-methylbenzene (1.4 g, 6.763 mmol) and Pd(dppf)Cl$_2$·CH$_2$Cl$_2$ (350 mg, 0.4286 mmol) in 1,4-dioxane (60 mL). The mixture was degassed and placed under a nitrogen atmosphere. The reaction was stirred at 100° C. for 2 h. The mixture was partitioned between water and ethyl acetate. The aqueous layer was extracted 3 times with ethyl acetate. The organic phases were combined and passed through a Whatmann phase separation filter paper. The filtrates were concentrated in vacuo to give a brown oil. Purification by flash chromatography (24 g SiO$_2$, 0 to 100% EtOAc in heptane) gave ethyl rac-(4S,5R)-3-(3,4-difluoro-2-methylphenyl)-4,5-dimethyl-5-(trifluoromethyl)-4,5-dihydrofuran-2-carboxylate (2.213 g, 67%) as a pale yellow oil. $^1$H NMR (500 MHz, Methanol-d$_4$) δ 7.10 (dt, J=10.3, 8.4 Hz, 1H), 6.90 (s, 1H), 4.14-4.00 (m, 2H), 3.54 (d, J=8.2 Hz, 1H), 2.19 (d, J=2.7 Hz, 3H), 1.70 (d, J=1.2 Hz, 3H), 1.09 (dq, J=7.5, 2.4 Hz, 3H), 1.05 (t, J=7.1 Hz, 3H) ppm. ESI-MS m/z calc. 364.10977, found 365.2 (M+1)$^+$; Retention time: 1.08 minutes.

Step 3:

A pressure tube was loaded with magnesium powder (200 mg, 8.229 mmol) and purged with nitrogen. To the reaction vessel was added a solution of ethyl rac-(4S,5R)-3-(3,4-difluoro-2-methylphenyl)-4,5-dimethyl-5-(trifluoromethyl)-4,5-dihydrofuran-2-carboxylate (2.02 g, 5.545 mmol) in MeOH (30 mL). The mixture was degassed and placed under a nitrogen atmosphere. A few drops of 1,2-dibromoethane (5 μL, 0.058 mmol) were added. The reaction mixture was stirred vigorously and heated at 70° C. for 6 h. A further 3 consecutive portions of magnesium powder (200 mg, 8.229 mmol) were added followed by a drop of 1,2-dibromoethane (5 μL, 0.058 mmol). The mixture was stirred overnight at 70° C. for 88 h. The reaction mixture was cooled down to 0° C. prior to opening the pressure vessel. The cooled mixture was added dropwise to an ice cold 1M solution of HCl. The reaction was stirred at 0° C. for 30 min until all Mg solids dissolved. The mixture was concentrated in vacuo to remove the MeOH. The resulting aqueous solution was extracted with ethyl acetate (×3). The combined organic extracts were passed through a Whatmann phase separation filter paper. The filtrate was concentrated in vacuo to give a mixture of methyl rac-(2R,3R,4S,5R)-3-(3,4-difluoro-2-methylphenyl)-4,5-dimethyl-5-(trifluoromethyl)tetrahydrofuran-2-carboxylate and methyl rac-(2S,3S,4S,5R)-3-(3,4-difluoro-2-methylphenyl)-4,5-dimethyl-5-(trifluoromethyl)tetrahydrofuran-2-carboxylate (1.487 g, 76%) as a colourless oil. ESI-MS m/z calc. 352.10977, found 353.3 (M+1)$^+$; Retention times: 0.94, 1.00, 1.01 and 1.04 minutes.

Step 4:

To a cooled solution of a mixture of methyl rac-(2R,3R,4S,5R)-3-(3,4-difluoro-2-methylphenyl)-4,5-dimethyl-5-(trifluoromethyl)tetrahydrofuran-2-carboxylate and methyl rac-(2S,3S,4S,5R)-3-(3,4-difluoro-2-methylphenyl)-4,5-dimethyl-5-(trifluoromethyl)tetrahydrofuran-2-carboxylate (1.487 g, 4.221 mmol) in 2-MeTHF (20 mL) was added potassium tert-butoxide (1.4 g, 12.48 mmol), causing a −5° C. increase in temperature. The reaction mixture turned yellow on addition of potassium t-butoxide. The reaction was stirred for 1 h at ambient temperature. The reaction was diluted with ethyl acetate and 1N NaOH. The aqueous layer was separated. The organic layer was washed further with 1M NaOH (×2). The combined organic layers were passed through a Whatmann phase separation filter paper. The filtrate was concentrated in vacuo to give a mixture of 2 major diastereoisomers, rac-(2S,3R,4S,5R)-3-(3,4-difluoro-2-methylphenyl)-4,5-dimethyl-5-(trifluoromethyl)tetrahydrofuran-2-carboxylic acid and rac-(2R,3S,4S,5R)-3-(3,4-difluoro-2-methylphenyl)-4,5-dimethyl-5-(trifluoromethyl)tetrahydrofuran-2-carboxylic acid (1.01 g, 71%) as a colourless oil. ESI-MS m/z calc. 338.09415, found 337.0 (M−1)$^-$; Retention times: 1.20 and 1.27 minutes for the 2 main diastereoisomers.

Step 5:

DMF (2 µL, 0.026 mmol) and oxalyl chloride (154.2 mg, 106.0 µL, 1.215 mmol) were carefully added to an ice cold stirring solution of a mixture of rac-(2S,3R,4S,5R)-3-(3,4-difluoro-2-methylphenyl)-4,5-dimethyl-5-(trifluoromethyl)tetrahydrofuran-2-carboxylic acid and rac-(2R,3S,4S,5R)-3-(3,4-difluoro-2-methylphenyl)-4,5-dimethyl-5-(trifluoromethyl)tetrahydrofuran-2-carboxylic acid (200 mg, 0.591 mmol) in 2-MeTHF (5 mL). The mixture was warmed up to ambient temperature over 30 min. The reaction mixture was concentrated in vacuo. The residue was taken in 2-MeTHF (5 mL) and added to an ice cold solution of (R)-6-(2,2-dimethyl-1,3-dioxolan-4-yl)pyridin-3-amine (155 mg, 0.710 mmol) and triethylamine (384 µL, 2.755 mmol) in 2-methyltetrahydrofuran (5 mL). The resulting mixture was stirred and warmed to ambient temperature over 18 h. The reaction mixture was quenched by addition of water (5 mL) and the layers were separated. The aqueous layer was extracted with EtOAc (2×10 mL). The combined organic extracts were passed through a Whatmann phase separation filter paper. The filtrate was concentrated in vacuo to give an oil. Purification by flash chromatography (4 g SiO$_2$, 0 to 50% EtOAc:EtOH (3:1) containing 2% NH$_4$OH in heptane) gave a mixture of diastereoisomers, including rel-(2S,3R,4S,5R)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide, rel-(2R,3S,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide, rel-(2R,3S,4S,5R)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide, and rel-(2S,3R,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (191.4 mg, 63%). ESI-MS m/z calc. 514.1891, found 515.3 (M+1)$^+$; 513.4 (M−1)$^-$; Retention times: 3.60 and 3.67 minutes.

Step 6:

T mixture of diastereoisomers obtained in Step 5 was separated by chiral SFC using a (R,R)-Whelk-01 column, 5 um particle size, 25 cm×21 mm Mobile phase: 5 to 45% MeOH (containing 20 mM Ammonia), 95 to 55% CO$_2$. Flow: 100 mL/min.) on a Minigram SFC instrument from Berger Instruments:

First Eluting Isomer (rt=3.43 min): rel-(2S,3R,4S,5R)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (16 mg, 26%). ESI-MS m/z calc. 514.1891, found 515.0 (M+1)$^+$; 513.2 (M−1)$^-$; Retention time: 3.66 minutes.

Second Eluting Isomer (rt=3.98 min): rel-(2R,3S,4S,5R)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (23 mg, 41%). ESI-MS m/z calc. 514.1891, found 515.1 (M+1)$^+$; 513.2 (M−1)$^-$; Retention time: 3.59 minutes.

Third Eluting Isomer (rt=5.29 min): rel-(2R,3S,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (14 mg, 27%). ESI-MS m/z calc. 514.1891, found 515.1 (M+1)$^+$; 513.2 (M−1)$^-$; Retention time: 3.66 minutes.

Fourth Eluting Isomer (rt=6.44 min): rel-(2S,3R,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (35 mg, 50%). ESI-MS m/z calc. 514.1891, found 515.2 (M+1)$^+$; 513.2 (M−1)$^-$; Retention time: 3.59 minutes.

Step 7:

TFA (100 µL, 1.298 mmol) was added to a stirred solution of rel-(2S,3R,4S,5R)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (16 mg, 0.025 mmol) (First Eluting Isomer from SFC separation) in DCM (5 mL). The reaction mixture was stirred overnight at ambient temperature. The mixture was concentrated in vacuo. The residue was azeotroped twice with DCM, quenched with a 1M NaOH solution and partitioned with DCM. The aqueous layer was extracted with DCM (×3). The combined organic phases were passed through a phase separator cartridge and concentrated in vacuo. Purification by reverse phase HPLC-MS using a X-bridge C18 OBD column (150×19 mm, 5 mm particle size) from Waters to give of rel-(2S,3R,4S,5R)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (65, 6.4 mg, 51%) as a white solid. $^1$H NMR (400 MHz, DMSO-d$_6$) δ 10.04 (s, 1H), 8.61 (dd, J=2.5, 0.8 Hz, 1H), 7.96 (dd, J=8.5, 2.5 Hz, 1H), 7.48-7.38 (m, 2H), 7.32 (q, J=9.1 Hz, 1H), 5.32 (d, J=4.7 Hz, 1H), 4.68-4.59 (m, 2H), 4.56-4.49 (m, 1H), 3.83-3.73 (m, 1H), 3.62 (dt, J=10.3, 4.9 Hz, 1H), 3.44 (dt, J=11.9, 6.3 Hz, 1H), 2.78-2.58 (m, 1H), 2.25 (d, J=1.8 Hz, 3H), 1.60 (s, 3H), 0.95 (d, J=7.0 Hz, 3H) ppm. ESI-MS m/z calc. 474.1578, found 475.2 (M+1)$^+$; 473.2 (M−1)$^-$; Retention time: 2.93 minutes.

rel-(2R,3S,4S,5R)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (23 mg, 0.038 mmol) (Second Eluting Isomer from SFC separation) was treated in the same way to give rel-(2R,3S,4S,5R)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (66, 10.6 mg, 55%) as a white solid. $^1$H NMR (400 MHz, DMSO-d$_6$) δ 10.39 (s, 1H), 8.65 (dd, J=2.5, 0.8 Hz, 1H), 7.99 (dd, J=8.5, 2.5 Hz, 1H), 7.45-7.38 (m, 1H), 7.26 (q, J=9.0 Hz, 1H), 7.17 (dd, J=8.8, 3.5 Hz, 1H), 5.33 (d, J=4.8 Hz, 1H), 5.16 (d, J=10.4 Hz, 1H), 4.63 (t, J=5.9 Hz, 1H), 4.58-4.50 (m, 1H), 4.17 (dd, J=10.5, 7.5 Hz, 1H), 3.67-3.57 (m, 1H), 3.49-3.38 (m, 1H), 2.85 (p, J=7.5 Hz, 1H), 2.28 (d, J=1.9 Hz, 3H), 1.63 (s, 3H), 0.68 (d, J=7.4 Hz, 3H) ppm. ESI-MS m/z calc. 474.1578, found 475.2 (M+1)$^+$; 473.2 (M−1)$^−$; Retention time: 3.02 minutes.

rel-(2R,3S,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (14 mg, 0.025 mmol) (Third Eluting Isomer from SFC separation) was treated in the same way to give rel-(2R,3S,4R,5S)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (67, 7.5 mg, 63%) as a white solid. $^1$H NMR (400 MHz, DMSO-d$_6$) δ 10.05 (s, 1H), 8.61 (dd, J=2.6, 0.7 Hz, 1H), 7.97 (dd, J=8.5, 2.5 Hz, 1H), 7.48-7.37 (m, 2H), 7.32 (q, J=9.1 Hz, 1H), 5.32 (s, 1H), 4.64 (d, J=9.3 Hz, 2H), 4.53 (s, 1H), 3.83-3.73 (m, 1H), 3.66-3.59 (m, 1H), 3.44 (dt, J=11.1, 5.8 Hz, 1H), 2.58 (m, 1H), 2.25 (d, J=1.9 Hz, 3H), 1.60 (s, 3H), 0.95 (d, J=7.0 Hz, 3H) ppm. ESI-MS m/z calc. 474.1578, found 475.2 (M+1)$^+$; 473.2 (M−1)$^−$; Retention time: 2.93 minutes.

rel-(2S,3R,4R,5S)-3-(3,4-difluoro-2-methylphenyl)-N-(6-((R*)-2,2-dimethyl-1,3-dioxolan-4-yl)pyridin-3-yl)-4,5-dimethyl-5-(trifluoromethyl)tetrahydrofuran-2-carboxamide (35 mg, 0.047 mmol) (Fourth Eluting Isomer from SFC separation) was treated in the same way to give rel-(2S,3R,4R,5S)-3-(3,4-difluoro-2-methylphenyl)-N-(6-((R*)-1,2-dihydroxyethyl)pyridin-3-yl)-4,5-dimethyl-5-(trifluoromethyl)tetrahydrofuran-2-carboxamide (68, 9.6 mg, 42%) as a white solid. $^1$H NMR (400 MHz, DMSO-d$_6$) δ 10.37 (s, 1H), 8.67 (dd, J=2.6, 0.7 Hz, 1H), 7.97 (dd, J=8.5, 2.5 Hz, 1H), 7.42 (d, J=8.5 Hz, 1H), 7.26 (q, J=9.1 Hz, 1H), 7.17 (dd, J=8.8, 3.5 Hz, 1H), 5.32 (d, J=4.9 Hz, 1H), 5.16 (d, J=10.5 Hz, 1H), 4.63 (t, J=5.9 Hz, 1H), 4.54 (dt, J=6.8, 4.5 Hz, 1H), 4.17 (dd, J=10.5, 7.5 Hz, 1H), 3.62 (ddd, J=10.5, 6.0, 4.1 Hz, 1H), 3.44 (ddd, J=10.9, 6.9, 5.8 Hz, 1H), 2.85 (p, J=7.5 Hz, 1H), 2.28 (d, J=1.9 Hz, 3H), 1.63 (s, 3H), 0.68 (d, J=6.6 Hz, 3H) ppm. ESI-MS m/z calc. 474.1578, found 475.2 (M+1)$^+$; 473.2 (M−1)$^−$; Retention time: 3.01 minutes.

The following compounds were made using the method described in Example 9, except that the product of step 2 was prepare by reaction of ethyl rac-(4R,5R)-4,5-dimethyl-5-(trifluoromethyl)-3-(((trifluoromethyl)sulfonyl)oxy)-4,5-dihydrofuran-2-carboxylate and (2-methoxy-3-(trifluoromethyl)phenyl)boronic acid using the Suzuki condition of step 2 with K$_2$CO$_3$ as the base. In step 6, purification was performed by chiral SFC using a (R,R)-Whelk-O1 column, 5 um particle size, 25 cm×21.1 mm from Daicel (Mobile phase: 5 to 20% MeOH (containing 20 mM Ammonia), 95 to 80% CO$_2$. Flow: 100 mL/min.) on a Minigram SFC instrument from Berger Instruments:

| Cmpd No. | Compound Name | LC/MS | NMR (shifts in ppm) |
|---|---|---|---|
| 69 | rel-(2S,3R,4R,5S)-N-(6-((R*)-1,2-dihydroxyethyl)pyridin-3-yl)-3-(2-methoxy-3-(trifluoromethyl)phenyl)-4,5-dimethyl-5-(trifluoromethyl)tetrahydrofuran-2-carboxamide (Precursor was the first eluting peak by SFC on (R,R)-Whelk-O1 column, rt = 1.08 min) | ESI-MS m/z calc. 522.15894, found 523.1 (M + 1)$^+$; 521.2 (M − 1)$^−$; Retention time: 3.14 minutes | $^1$H NMR (500 MHz, DMSO-d$_6$) δ 10.35 (s, 1H), 8.66 (d, J = 2.4 Hz, 1H), 7.97 (dd, J = 8.5, 2.6 Hz, 1H), 7.71 (d, J = 7.8 Hz, 1H), 7.64 (d, J = 7.9 Hz, 1H), 7.42 (d, J = 8.6 Hz, 1H), 7.37 (t, J = 7.9 Hz, 1H), 5.31 (d, J = 4.9 Hz, 1H), 5.13 (d, J = 10.3 Hz, 1H), 4.62 (t, J = 5.9 Hz, 1H), 4.57-4.50 (m, 1H), 4.36 (dd, J = 10.3, 7.8 Hz, 1H), 3.83 (s, 3H), 3.63 (ddd, J = 10.5, 6.0, 4.1 Hz, 1H), 3.48-3.40 (m, 1H), 2.85 (p, J = 7.6 Hz, 1H), 1.65 (s, 3H), 0.74 (d, J = 7.3 Hz, 3H) ppm. |
| 70 | rel-(2R,3S,4S,5R)-N-(6-((R*)-1,2-dihydroxyethyl)pyridin-3-yl)-3-(2-methoxy-3-(trifluoromethyl)phenyl)-4,5-dimethyl-5-(trifluoromethyl)tetrahydrofuran-2-carboxamide (Precursor was the second eluting peak by SFC on (R,R)-Whelk-O1 column, rt = 1.62 min) | ESI-MS m/z calc. 522.15894, found 523.1 (M + 1)$^+$; 521.2 (M − 1)$^−$; Retention time: 3.14 minutes | $^1$H NMR (500 MHz, DMSO-d$_6$) δ 10.36 (s, 1H), 8.64 (d, J = 2.6 Hz, 1H), 7.99 (dd, J = 8.6, 2.6 Hz, 1H), 7.73-7.68 (m, 1H), 7.65-7.60 (m, 1H), 7.41 (d, J = 8.5 Hz, 1H), 7.36 (t, J = 7.9 Hz, 1H), 5.31 (d, J = 4.7 Hz, 1H), 5.13 (d, J = 10.3 Hz, 1H), 4.62 (t, J = 5.9 Hz, 1H), 4.53 (q, J = 5.3, 4.2 Hz, 1H), 4.35 (dd, J = 10.3, 7.8 Hz, 1H), 3.82 (s, 3H), 3.65-3.58 (m, 1H), 3.43 (dt, J = 11.5, 6.2 Hz, 1H), 2.85 (p, J = 7.6 Hz, 1H), 1.64 (s, 3H), 0.73 (d, J = 7.4 Hz, 3H) ppm. |

The following compounds were made using the method described in Example 9, except that the product of step 2 was prepared by reaction of ethyl rac-(4R,5R)-4,5-dimethyl-5-(trifluoromethyl)-3-(((trifluoromethyl)sulfonyl)oxy)-4,5-dihydrofuran-2-carboxylate and (2-methoxy-3-(trifluoromethyl)phenyl)boronic acid using the Suzuki condition of step 2 with $K_2CO_3$ as the base. In the amide coupling step 5, 2-(2,2-dimethyl-1,3-dioxolan-4-yl)pyrimidin-5-amine was used as the coupling partner. In step 6, purification was performed by chiral SFC using a Chiralcel O1 column, 5 urn particle size, 25 cm×20 mm from Daicel (Mobile phase: 2 to 7% MeOH (containing 20 mM Ammonia), 98 to 93% $CO_2$. Flow: 75 mL/min.) on a Prep-100 SFC instrument from Waters:

| Cmpd No. | Compound Name | LC/MS | NMR (shifts in ppm) |
|---|---|---|---|
| 71 | rel-(2R,3S,4S,5R)-N-(2-(1,2-dihydroxyethyl)pyrimidin-5-yl)-3-(2-methoxy-3-(trifluoromethyl)phenyl)-4,5-dimethyl-5-(trifluoromethyl)tetrahydrofuran-2-carboxamide (Precursor was the first eluting peak by SFC on Chiralcel OJ column, rt = 2.01 min) | ESI-MS m/z calc. 523.1542, found 524.2 (M + 1)$^+$; 522.2 (M − 1)$^-$; Retention time: 3.07 minutes | $^1$H NMR (400 MHz, Methanol-d$_4$) δ 9.09 (s, 2H), 7.72 (d, J = 8.0 Hz, 1H), 7.62 (d, J = 7.5 Hz, 1H), 7.34 (t, J = 7.9 Hz, 1H), 5.18 (d, J = 10.4 Hz, 1H), 4.85-4.77 (m, 1H), 4.45 (dd, J = 10.4, 8.3 Hz, 1H), 3.93 (dd, J = 11.3, 4.7 Hz, 1H), 3.89 (s, 3H), 3.85 (dd, J = 11.4, 5.9 Hz, 1H), 2.91 (p, J = 7.6 Hz, 1H), 1.72 (d, J = 1.1 Hz, 3H), 0.87-0.78 (m, 3H) ppm; amide NH and alcohols OH not observed. |
| 72 | rel-(2S,3R,4R,5S)-N-(2-(1,2-dihydroxyethyl)pyrimidin-5-yl)-3-(2-methoxy-3-(trifluoromethyl)phenyl)-4,5-dimethyl-5-(trifluoromethyl)tetrahydrofuran-2-carboxamide (Precursor was the second eluting peak by SFC on Chiralcel OJ column, rt = 2.21 min) | ESI-MS m/z calc. 523.1542, found 524.2 (M + 1)$^+$; 522.2 (M − 1)$^-$; Retention time: 3.07 minutes | $^1$H NMR (400 MHz, Methanol-d$_4$) δ 9.03 (s, 2H), 7.69 (d, J = 7.7 Hz, 1H), 7.59 (d, J = 7.8 Hz, 1H), 7.31 (t, J = 7.8 Hz, 1H), 5.15 (d, J = 10.3 Hz, 1H), 4.77 (s, 1H), 4.46-4.36 (m, 1H), 3.92 (s, 1H), 3.86 (s, 3H), 3.82 (d, J = 6.5 Hz, 1H), 2.88 (t, J = 7.7 Hz, 1H), 1.69 (s, 3H), 0.84-0.74 (m, 3H) ppm; amide NH and alcohols OH not observed. |
| 73 | rel-(2R,3S,4S,5R)-N-(2-(1,2-dihydroxyethyl)pyrimidin-5-yl)-3-(2-methoxy-3-(trifluoromethyl)phenyl)-4,5-dimethyl-5-(trifluoromethyl)tetrahydrofuran-2-carboxamide (Precursor was the third eluting peak by SFC on Chiralcel OJ column, rt = 2.39 min) | ESI-MS m/z calc. 523.1542, found 524.2 (M + 1)$^+$; 522.2 (M − 1)$^-$; Retention time: 3.07 minutes | $^1$H NMR (400 MHz, Methanol-d$_4$) δ 9.03 (s, 2H), 7.69 (d, J = 7.7 Hz, 1H), 7.59 (d, J = 7.8 Hz, 1H), 7.31 (t, J = 7.8 Hz, 1H), 5.15 (d, J = 10.3 Hz, 1H), 4.77 (s, 1H), 4.46-4.36 (m, 1H), 3.92 (s, 1H), 3.86 (s, 3H), 3.82 (d, J = 6.5 Hz, 1H), 2.88 (t, J = 7.7 Hz, 1H), 1.69 (s, 3H), 0.84-0.74 (m, 3H) ppm; amide NH and alcohols OH not observed. |
| 74 | rel-(2S,3R,4R,5S)-N-(2-(1,2-dihydroxyethyl)pyrimidin-5-yl)-3-(2-methoxy-3-(trifluoromethyl)phenyl)-4,5-dimethyl-5-(trifluoromethyl)tetrahydrofuran-2-carboxamide (Precursor was the fourth eluting peak by SFC on Chiralcel OJ column, rt = 2.55 min) | ESI-MS m/z calc. 523.1542, found 524.2 (M + 1)$^+$; 522.2 (M − 1)$^-$; Retention time: 3.13 minutes | $^1$H NMR (400 MHz, Methanol-d$_4$) δ 9.03 (s, 2H), 7.69 (d, J = 7.9 Hz, 1H), 7.59 (d, J = 7.3 Hz, 1H), 7.31 (t, J = 7.8 Hz, 1H), 5.15 (d, J = 10.4 Hz, 1H), 4.80-4.73 (m, 2H), 4.42 (dd, J = 10.3, 8.2 Hz, 1H), 3.92-3.88 (m, 1H), 3.87 (d, J = 3.9 Hz, 3H), 3.81 (dd, J = 11.3, 6.0 Hz, 1H), 2.93-2.84 (m, 1H), 1.69 (d, J = 1.2 Hz, 3H), 0.85-0.76 (m, 3H) ppm; amide NH and alcohols OH not observed. |

The following compounds were made using the method described in Example 9, except that 4-bromo-2,2,7-trifluorobenzo[d][1,3]dioxole was used in place of 1-bromo-3,4-difluoro-2-methylbenzene in the Suzuki coupling step 2. The conditions used for the reduction step 3 were those described in Example 5 step 3. In the deprotection step 7, 2-MeTHF was used as the solvent rather than DCM and the reaction was carried out in a sealed tube at 60° C. over 72 h:

| Cmpd No. | Compound Name | LC/MS | NMR (shifts in ppm) |
|---|---|---|---|
| 75 | rel-(2R,3S,4S,5R)-N-(6-((R*)-1,2-dihydroxyethyl)pyridin-3-yl)-3-(7-ethoxy-2,2-difluorobenzo[d][1,3]dioxol-4-yl)-4,5-dimethyl-5-(trifluoromethyl)tetrahydrofuran-2-carboxamide (Precursor was the first eluting peak by SFC on Lux i-Cellulose-5 column, 20 × 250 mm (Mobile phase: 25% MeOH (containing 20 mM Ammonia), 75% $CO_2$. Flow: 10 mL/min.), rt = 2.66 min) | ESI-MS m/z calc. 548.1582, found 549.2 $(M + 1)^+$; 547.1 $(M - 1)^-$; Retention time: 3.38 minutes | |
| 76 | rel-(2S,3R,4R,5S)-N-(6-((R*)-1,2-dihydroxyethyl)pyridin-3-yl)-3-(7-ethoxy-2,2-difluorobenzo[d][1,3]dioxol-4-yl)-4,5-dimethyl-5-(trifluoromethyl)tetrahydrofuran-2-carboxamide (Precursor was the second eluting peak by SFC on Lux i-Cellulose-5 column, 20 × 250 mm (Mobile phase: 25% MeOH (containing 20 mM Ammonia), 75% $CO_2$. Flow: 10 mL/min.), rt = 3.18 min) | ESI-MS m/z calc. 548.1582, found 549.2 $(M + 1)^+$; 547.1 $(M - 1)^-$; Retention time: 3.38 minutes | $^1$H NMR (400 MHz, Methanol-$d_4$) δ 8.70 (dd, J = 2.6, 0.8 Hz, 1H), 8.07 (dd, J = 8.6, 2.5 Hz, 1H), 7.53 (dt, J = 8.6, 0.7 Hz, 1H), 7.07 (d, J = 8.9 Hz, 1H), 6.86 (d, J = 8.9 Hz, 1H), 5.15 (d, J = 9.8 Hz, 1H), 4.72 (dd, J = 6.7, 4.1 Hz, 1H), 4.26-4.11 (m, 3H), 3.80 (dd, J = 11.3, 4.2 Hz, 1H), 3.66 (dd, J = 11.3, 6.7 Hz, 1H), 2.80 (p, J = 7.6 Hz, 1H), 1.66 (s, 3H), 1.41 (t, J = 7.0 Hz, 3H), 0.92 (dd, J = 7.7, 2.1 Hz, 3H) ppm; amide NH and alcohols OH not observed. |

The following compounds were made using the method described in Example 9, except that 6-(((tert-butyldimethylsilyl)oxy)methyl)pyridin-3-amine was used as the coupling partner in the amide coupling step 5. In step 6, purification was performed by chiral SFC using a (R,R)-Whelk-O1 column, 5 μm particle size, 25 cm×21.1 mm from Daicel (Mobile phase: 5 to 15% IPA (containing 20 mM Ammonia), 95 to 85% $CO_2$. Flow: 100 mL/min.) on a Minigram SFC instrument from Berger Instruments:

| Cmpd No. | Compound Name | LC/MS | NMR (shifts in ppm) |
|---|---|---|---|
| 77 | rel-(2R,3S,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (Precursor was the first eluting peak by SFC on (R,R)-Whelk-O1 column, rt = 1.80 min) | ESI-MS m/z calc. 444.14725, found 445.1 $(M + 1)^+$; 443.1 $(M - 1)^-$; Retention time: 3.07 minutes | $^1$H NMR (400 MHz, DMSO-$d_6$) δ 10.09 (s, 1H), 8.62 (d, J = 2.4 Hz, 1H), 7.99 (dd, J = 8.5, 2.5 Hz, 1H), 7.48-7.27 (m, 3H), 6.94 (s, 1H), 5.35 (t, J = 5.8 Hz, 1H), 4.65 (d, J = 9.5 Hz, 1H), 4.49 (d, J = 5.7 Hz, 2H), 3.82-3.71 (m, 1H), 2.25 (d, J = 2.0 Hz, 3H), 1.60 (s, 3H), 0.95 (d, J = 6.9 Hz, 3H) ppm. |
| 78 | rel-(2S,3R,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (Precursor was the second eluting peak by SFC on (R,R)-Whelk-O1 column, rt = 1.89 min) | ESI-MS m/z calc. 444.14725, found 445.2 $(M + 1)^+$; 443.1 $(M - 1)^-$; Retention time: 3.12 minutes | $^1$H NMR (400 MHz, DMSO-$d_6$) δ 10.40 (s, 1H), 8.67 (d, J = 2.4 Hz, 1H), 8.01 (dd, J = 8.5, 2.5 Hz, 1H), 7.40 (d, J = 8.5 Hz, 1H), 7.25 (t, J = 9.2 Hz, 1H), 7.18 (dd, J = 8.8, 3.5 Hz, 1H), 5.35 (t, J = 5.8 Hz, 1H), 5.17 (d, J = 10.5 Hz, 1H), 4.50 (d, J = 5.8 Hz, 2H), 4.18 (dd, J = 10.5, 7.5 Hz, 1H), 2.85 (t, J = 7.5 Hz, 1H), 2.28 (d, J = 1.9 Hz, 3H), 1.63 (s, 3H), 0.68 (d, J = 7.2 Hz, 3H) ppm. |

| Cmpd No. | Compound Name | LC/MS | NMR (shifts in ppm) |
| --- | --- | --- | --- |
| 79 | rel-(2S,3R,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (Precursor was the third eluting peak by SFC on (R,R)-Whelk-O1 column, rt = 2.42 min) | ESI-MS m/z calc. 444.14725, found 445.2 (M + 1)⁺; 443.1 (M − 1)⁻; Retention time: 3.07 minutes | ¹H NMR (400 MHz, DMSO-d₆) δ 10.06 (s, 1H), 8.61 (dd, J = 2.6, 0.8 Hz, 1H), 7.99 (dd, J = 8.5, 2.5 Hz, 1H), 7.48-7.27 (m, 3H), 5.34 (s, 1H), 4.64 (d, J = 9.5 Hz, 1H), 4.49 (s, 2H), 3.83-3.73 (m, 1H), 2.54 (br s, 1H), 2.25 (d, J = 1.9 Hz, 3H), 1.60 (s, 3H), 0.95 (d, J = 7.0 Hz, 3H) ppm. |
| 80 | rel-(2R,3S,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide (Precursor was the fourth eluting peak by SFC on (R,R)-Whelk-O1 column, rt = 2.68 min) | ESI-MS m/z calc. 444.14725, found 445.2 (M + 1)⁺; 443.1 (M − 1)⁻; Retention time: 3.12 minutes | ¹H NMR (400 MHz, DMSO-d₆) δ 10.37 (s, 1H), 8.66 (dd, J = 2.5, 0.8 Hz, 1H), 8.01 (dd, J = 8.5, 2.5 Hz, 1H), 7.40 (dd, J = 8.5, 0.7 Hz, 1H), 7.27 (q, J = 9.1 Hz, 1H), 7.17 (dd, J = 8.9, 3.4 Hz, 1H), 5.34 (t, J = 5.8 Hz, 1H), 5.16 (d, J = 10.5 Hz, 1H), 4.50 (d, J = 5.6 Hz, 2H), 4.18 (dd, J = 10.5, 7.5 Hz, 1H), 2.85 (p, J = 7.3 Hz, 1H), 2.28 (d, J = 1.8 Hz, 3H), 1.63 (s, 3H), 0.71-0.65 (m, 3H) ppm. |

The following compounds were made using the method described in Example 9, except that the product of step 2 was prepared by reaction of ethyl rac-(4R,5R)-4,5-dimethyl-5-(trifluoromethyl)-3-(((trifluoromethyl)sulfonyl)oxy)-4,5-dihydrofuran-2-carboxylate and (2-methoxy-3-(trifluoromethyl)phenyl)boronic acid using the Suzuki conditions of step 2 with $K_2CO_3$ as the base. The amine used in the amide coupling step 5 was 6-(((tert-butyldimethylsilyl)oxy)methyl)pyridin-3-amine. In step 6, purification was performed by chiral SFC using a (R,R)-Whelk-1 column, 5 m particle size, 25 cm×21.1 mm from Daicel (Mobile phase: 40% MeOH (containing 20 mM Ammonia), 60% $CO_2$. Flow: 100 mL/min.) on a Minigram SFC instrument from Berger Instruments:

| Cmpd No. | Compound Name | LC/MS | NMR (shifts in ppm) |
| --- | --- | --- | --- |
| 81 | rel-(2S,3R,4R,5S)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide (Precursor was the first eluting peak by SFC on (R,R)-Whelk-O1 column, rt = 2.05 min) | ESI-MS m/z calc. 492.14838, found 493.1 (M + 1)⁺; 491.1 (M − 1)⁻; Retention time: 3.24 minutes | ¹H NMR (400 MHz, DMSO-d₆) δ 10.37 (s, 1H), 8.65 (dd, J = 2.6, 0.7 Hz, 1H), 8.01 (dd, J = 8.5, 2.6 Hz, 1H), 7.74-7.67 (m, 1H), 7.64 (dd, J = 8.0, 1.5 Hz, 1H), 7.44-7.33 (m, 2H), 5.35 (d, J = 5.4 Hz, 1H), 5.13 (d, J = 10.4 Hz, 1H), 4.50 (d, J = 4.8 Hz, 2H), 4.37 (dd, J = 10.3, 7.8 Hz, 1H), 3.83 (s, 3H), 2.85 (p, J = 7.6 Hz, 1H), 1.64 (s, 3H), 0.73 (d, J = 7.3 Hz, 3H) ppm. |
| 82 | rel-(2R,3S,4S,5R)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide (Precursor was the second eluting peak by SFC on (R,R)-Whelk-O1 column, rt = 3.15 min) | ESI-MS m/z calc. 492.14838, found 493.1 (M + 1)⁺; 491.1 (M − 1)⁻; Retention time: 3.24 minutes | ¹H NMR (400 MHz, DMSO-d₆) δ 10.37 (s, 1H), 8.66 (dd, J = 2.6, 0.7 Hz, 1H), 8.01 (dd, J = 8.5, 2.5 Hz, 1H), 7.71 (d, J = 7.8 Hz, 1H), 7.64 (d, J = 7.5 Hz, 1H), 7.44-7.33 (m, 2H), 5.35 (s, 1H), 5.13 (d, J = 10.3 Hz, 1H), 4.50 (s, 2H), 4.37 (dd, J = 10.4, 7.8 Hz, 1H), 3.83 (s, 3H), 2.86 (t, J = 7.6 Hz, 1H), 1.65 (s, 3H), 0.74 (d, J = 7.3 Hz, 3H) ppm. |

Example 10

(2R,3S,4S,5R)-3-(3,4-difluoro-2-methoxyphenyl)-N-(5-fluoro-6-(hydroxymethyl)pyridin-3-yl)-4,5-dimethyl-5-(trifluoromethyl)tetrahydrofuran-2-carboxamide (83)

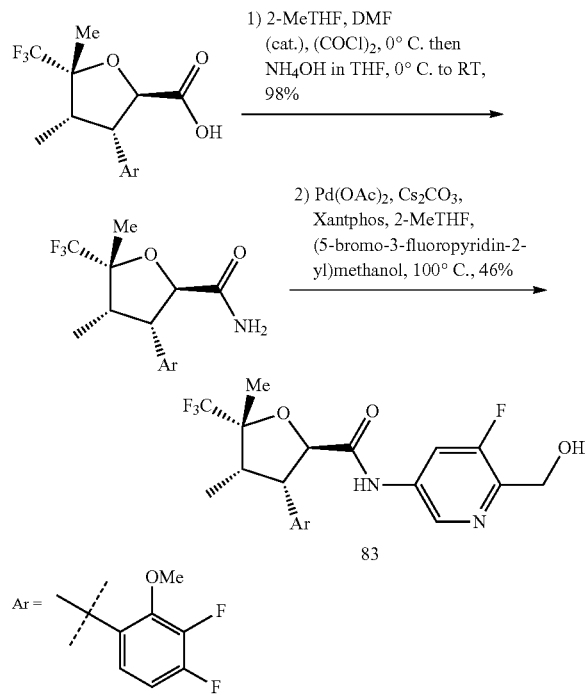

Step 1:

To an ice cold solution of (2R,3S,4S,5R)-3-(3,4-difluoro-2-methoxyphenyl)-4,5-dimethyl-5-(trifluoromethyl)tetrahydrofuran-2-carboxylic acid (2390 mg, 6.409 mmol) (see Example 1, step 13) in 2-methyltetrahydrofuran (20 mL) was added DMF (60 µL, 0.775 mmol) followed by careful addition of oxalyl chloride (1.1 mL, 12.61 mmol). The reaction mixture warmed to room temperature and stirred for 90 min. The reaction mixture was concentrated in vacuo and the residue dissolved in 2-methyltetrahydrofuran (10 mL). This solution was added to an ice cooled solution of ammonium hydroxide (10 mL of 28% w/v, 79.90 mmol) in 2-methyltetrahydrofuran (10 mL). The resulting mixture was stirred at room temperature for 1.5 h. The reaction mixture was quenched with water (15 mL) and partitioned with ethyl acetate (15 mL). The layers were separated and the organic phase was washed with brine (15 mL), passed through a phase separation cartridge and concentrated under reduced pressure to give (2R,3S,4S,5R)-3-(3,4-difluoro-2-methoxyphenyl)-4,5-dimethyl-5-(trifluoromethyl)tetrahydrofuran-2-carboxamide (2.34 g, 98%) as a pale yellow oil. $^1$H NMR (400 MHz, DMSO-d$_6$) δ 7.51 (s, 1H), 7.33 (s, 1H), 7.23-7.04 (m, 2H), 4.83 (d, J=10.7 Hz, 1H), 4.11-3.97 (m, 1H), 3.94 (d, J=2.2 Hz, 3H), 2.66 (p, J=7.5 Hz, 1H), 1.56 (d, J=1.2 Hz, 3H), 0.75-0.63 (m, 3H) ppm. ESI-MS m/z calc. 353.10504, found 354.0 (M+1)$^+$; Retention time: 0.87 minutes.

Step 2:

(5-bromo-3-fluoropyridin-2-yl)methanol (42.8 mg, 0.2078 mmol), Pd(OAc)$_2$ (4.92 mg, 0.02191 mmol), Xantphos (21.2 mg, 0.03664 mmol) and cesium carbonate (117.6 mg, 0.3609 mmol) were added to a solution of (2R,3S,4S,5R)-3-(3,4-difluoro-2-methoxyphenyl)-4,5-dimethyl-5-(trifluoromethyl)tetrahydrofuran-2-carboxamide (64 mg, 0.1812 mmol) in 1,4-dioxane (2 mL). The reaction mixture was degassed (N$_2$/vac cycles×5) and heated at 90° C. for 2 h. The mixture was concentrated in vacuo. Purification by reversed phase HPLC-MS using a X-bridge C18 OBD column (150×19 mm, 5 m particle size) from Waters gave (2R,3S,4S,5R)-3-(3,4-difluoro-2-methoxyphenyl)-N-(5-fluoro-6-(hydroxymethyl)pyridin-3-yl)-4,5-dimethyl-5-(trifluoromethyl)tetrahydrofuran-2-carboxamide (83, 41.3 mg, 46%). $^1$H NMR (500 MHz, DMSO-d$_6$) δ 10.58 (s, 1H), 8.67-8.49 (m, 1H), 8.00 (dd, J=11.9, 2.0 Hz, 1H), 7.23-7.09 (m, 2H), 5.23 (t, J=5.9 Hz, 1H), 5.11 (d, J=10.3 Hz, 1H), 4.53 (dd, J=5.9, 2.1 Hz, 2H), 4.25 (dd, J=10.2, 7.7 Hz, 1H), 3.95 (d, J=2.0 Hz, 3H), 2.78 (p, J=7.5 Hz, 1H), 1.61 (s, 3H), 0.79-0.68 (m, 3H) ppm. ESI-MS m/z calc. 478.13272, found 479.3 (M+1)$^+$; 477.2 (M−1)$^-$; Retention time: 3.27 minutes.

The following compounds were made using a method similar to that described in Example 10, except that different coupling partners were used in the Buchwald coupling step 2:

| Cmpd No. | Compound Name | LC/MS | NMR (shifts in ppm) |
|---|---|---|---|
| 84 | (2R,3S,4S,5R)-3-(3,4-difluoro-2-methoxyphenyl)-N-(6-((R)-1-hydroxyethyl)pyridin-3-yl)-4,5-dimethyl-5-(trifluoromethyl)tetrahydrofuran-2-carboxamide | ESI-MS m/z calc. 474.1578, found 475.4 (M + 1)$^+$; 473.4 (M − 1)$^-$; Retention time: 3.23 minutes | $^1$H NMR (500 MHz, DMSO-d$_6$) δ 10.35 (s, 1H), 8.66 (d, J = 2.5 Hz, 1H), 7.99 (dd, J = 8.5, 2.5 Hz, 1H), 7.45 (d, J = 8.5 Hz, 1H), 7.17 (dd, J = 9.3, 6.3 Hz, 2H), 5.28 (d, J = 4.7 Hz, 1H), 5.09 (d, J = 10.3 Hz, 1H), 4.72-4.64 (m, 1H), 4.25 (dd, J = 10.3, 7.7 Hz, 1H), 3.95 (d, J = 2.0 Hz, 3H), 2.77 (p, J = 7.5 Hz, 1H), 1.61 (s, 3H), 1.32 (d, J = 6.5 Hz, 3H), 0.74 (d, J = 7.4 Hz, 3H) ppm. |
| 85 | (2R,3S,4S,5R)-3-(3,4-difluoro-2-methoxyphenyl)-N-(6-((S)-1-hydroxyethyl)pyridin-3-yl)-4,5-dimethyl-5-(trifluoromethyl)tetrahydrofuran-2-carboxamide | ESI-MS m/z calc. 474.1578, found 475.5 (M + 1)$^+$; 473.4 (M − 1)$^-$; Retention time: 3.23 minutes | $^1$H NMR (500 MHz, DMSO-d$_6$) δ 10.36 (s, 1H), 8.66-8.62 (m, 1H), 8.01 (dd, J = 8.5, 2.6 Hz, 1H), 7.44 (d, J = 8.5 Hz, 1H), 7.17 (dd, J = 9.6, 6.4 |

-continued

| Cmpd No. | Compound Name | LC/MS | NMR (shifts in ppm) |
|---|---|---|---|
| | | | Hz, 2H), 5.29 (d, J = 4.6 Hz, 1H), 5.09 (d, J = 10.4 Hz, 1H), 4.71-4.64 (m, 1H), 4.24 (dd, J = 10.3, 7.7 Hz, 1H), 3.95 (d, J = 2.0 Hz, 3H), 2.77 (p, J = 7.5 Hz, 1H), 1.61 (s, 3H), 1.32 (d, J = 6.5 Hz, 3H), 0.76-0.71 (m, 3H) ppm. |
| 86 | (2R,3S,4S,5R)-3-(3,4-difluoro-2-methoxyphenyl)-N-(5-(hydroxymethyl)pyrazin-2-yl)-4,5-dimethyl-5-(trifluoromethyl)tetrahydrofuran-2-carboxamide | ESI-MS m/z calc. 461.1374, found 462.4 (M + 1)+; 460.4 (M − 1)−; Retention time: 3.19 minutes | $^1$H NMR (400 MHz, DMSO-$d_6$) δ 10.95 (s, 1H), 9.18 (d, J = 1.5 Hz, 1H), 8.45 (dd, J = 1.5, 0.8 Hz, 1H), 7.26-7.09 (m, 2H), 5.53 (t, J = 5.8 Hz, 1H), 5.25 (d, J = 10.5 Hz, 1H), 4.59 (d, J = 5.7 Hz, 2H), 4.27 (dd, J = 10.5, 7.6 Hz, 1H), 3.95 (d, J = 2.2 Hz, 3H), 2.78 (p, J = 7.5 Hz, 1H), 1.61 (s, 3H), 0.75-0.69 (m, 3H) ppm. |
| 87 | (2R,3S,4S,5R)-N-(5,6-bis(hydroxymethyl)pyridin-3-yl)-3-(3,4-difluoro-2-methoxyphenyl)-4,5-dimethyl-5-(trifluoromethyl)tetrahydrofuran-2-carboxamide | ESI-MS m/z calc. 490.1527, found 491.3 (M + 1)+; 489.3 (M − 1)−; Retention time: 3.04 minutes | $^1$H NMR (500 MHz, DMSO-$d_6$) δ 10.40 (s, 1H), 8.62 (d, J = 2.5 Hz, 1H), 8.09 (d, J = 2.4 Hz, 1H), 7.17 (dd, J = 10.4, 6.6 Hz, 2H), 5.29 (t, J = 5.4 Hz, 1H), 5.09 (d, J = 10.4 Hz, 1H), 5.01 (t, J = 5.5 Hz, 1H), 4.61 (d, J = 5.4 Hz, 2H), 4.50 (d, J = 5.5 Hz, 2H), 4.25 (dd, J = 10.4, 7.6 Hz, 1H), 3.96 (d, J = 2.1 Hz, 3H), 2.77 (p, J = 7.5 Hz, 1H), 1.61 (s, 3H), 0.78-0.67 (m, 3H) ppm. |

Example 11 rel-(2R,3S,4S,5R)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (88) and rel-(2S,3R,4R,5S)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (89)

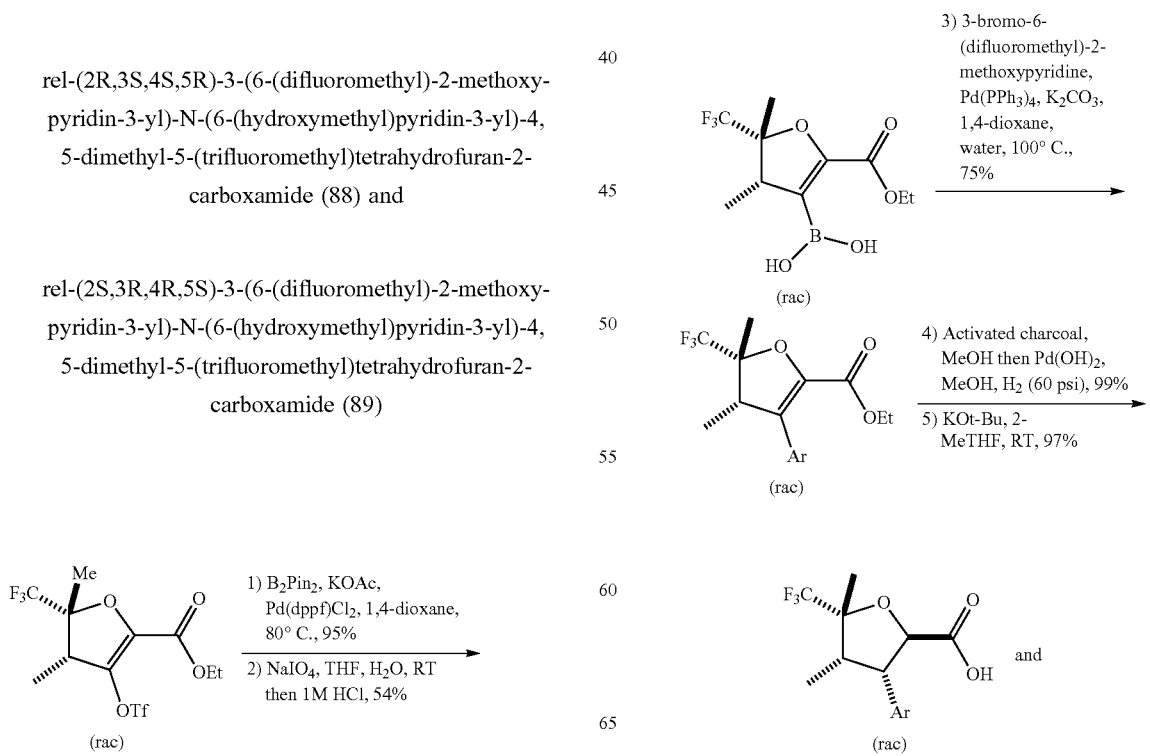

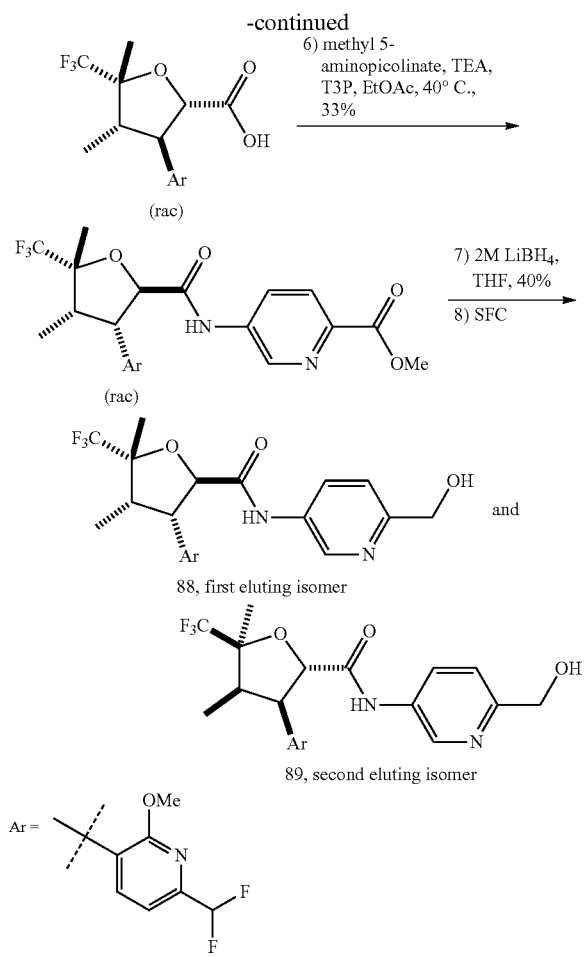

Step 1:

To a 3 neck 1 litre flask, flanked with a thermometer and air condenser, was added ethyl rac-(4R,5R)-4,5-dimethyl-5-(trifluoromethyl)-3-(((trifluoromethyl)sulfonyl)oxy)-4,5-dihydrofuran-2-carboxylate (42 g, 108.7 mmol) and 1,4-dioxane (500 mL). The mixture was stirred, degassed and flushed with nitrogen. KOAc (32 g, 326.1 mmol) was added followed by bis(pinacolato)diboron (32 g, 126.0 mmol). The reaction mixture was evacuated and back filled with nitrogen (×3 cycles). Pd(dppf)Cl$_2$ (4 g, 5.467 mmol) was added and the mixture was heated to 80° C. for 20 h. The reaction mixture was cooled down to ambient temperature and partitioned between ethyl acetate (300 mL) and water (100 mL). The mixture was filtered through a pad of celite, washing with ethyl acetate (5×100 mL) until no more product came off. The filtrate phases were separated. The aqueous layer was extracted with ethyl acetate (2×100 mL). The combined organic layers were passed through a Whatmann phase separation filter paper. The filtrate was concentrated in vacuo to give 47 g of a brown oil. Purification by flash chromatography (Florisil (magnesium silicate), 100% heptane) gave ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g, 95%) as a thick viscous yellow oil. $^1$H NMR (500 MHz, Chloroform-d) δ 4.33-4.23 (m, 2H), 3.27-3.18 (m, 1H), 1.55 (d, J=1.1 Hz, 3H), 1.32 (s, 12H), 1.28 (d, J=2.3 Hz, 2H), 1.24 (s, 3H) ppm. ESI-MS m/z calc. 364.1669, found 365.3 (M+1)$^+$; Retention time: 1.1 minutes.

Step 2:

Ethyl rac-(4S,5R)-4,5-dimethyl-3-(4,4,5,5-tetramethyl-1,3,2-dioxaborolan-2-yl)-5-(trifluoromethyl)-4,5-dihydrofuran-2-carboxylate (47 g) was dissolved in a mixture of water (50 mL) and THF (100 mL). Sodium periodate (50 g, 233.8 mmol) was added and the reaction was stirred for 1 h at ambient temperature. The reaction mixture was cooled with an ice bath. 1M HCl (60 mL) was added and reaction mixture was stirred for 1 h. The mixture was diluted with water (50 mL) and ethyl acetate (100 mL). A white solid was filtered and washed with ethyl acetate. The filtrate was washed with sodium thiosulphate (shaken vigorously at every wash to remove traces of iodine) (3×50 ml) followed by a brine solution. The combined organic layers were dried (Na$_2$SO$_4$) and concentrated in vacuo to give a cream solid (23 g), which was triturated further with cold heptane to afford rac-((4S,5R)-2-(ethoxycarbonyl)-4,5-dimethyl-5-(trifluoromethyl)-4,5-dihydrofuran-3-yl)boronic acid (16.66 g, 54%) as a white solid. $^1$H NMR (500 MHz, Chloroform-d) δ 6.84 (s, 2H), 4.38 (q, J=7.1 Hz, 2H), 3.18 (q, J=7.3 Hz, 1H), 1.51 (d, J 1.2 Hz, 3H), 1.39 (t, J 7.1 Hz, 3H), 1.32 (dq, J=7.2, 2.4 Hz, 3H) ppm. ESI-MS m/z calc. 282.08865, found 281.2 (M-1)$^-$; Retention time: 0.75 minutes.

Step 3:

Pd(PPh$_3$)$_4$ (82 mg, 0.07096 mmol) and an aqueous solution of K$_2$CO$_3$ (3.5 mL of 2 M, 7.000 mmol) were successively added to a solution of rac-((4S,5R)-2-(ethoxycarbonyl)-4,5-dimethyl-5-(trifluoromethyl)-4,5-dihydrofuran-3-yl)boronic acid (1 g, 3.546 mmol) and 3-bromo-6-(difluoromethyl)-2-methoxypyridine (902 mg, 3.789 mmol) in 1,4-dioxane (20 mL). The reaction was heated with stirring at 100° C. for 5 h. A further 30 mg of Pd(PPh$_3$)$_4$ was added and the mixture was stirred at reflux for 30 min. The reaction mixture was partitioned between water and ethyl acetate. Aqueous brine was added to help separate the layers. The aqueous phase was separated and extracted twice with EtOAc. The combined organic layers were washed with a brine, dried (MgSO$_4$) and concentrated in vacuo. Purification by flash chromatography (SiO$_2$, 0 to 25% EtOAc in heptane) gave ethyl rac-(4S,5R)-3-(6-(difluoromethyl)-2-methoxypyridin-3-yl)-4,5-dimethyl-5-(trifluoromethyl)-4,5-dihydrofuran-2-carboxylate (1.05 g, 75%) as a colourless oil. $^1$H NMR (500 MHz, Chloroform-d) δ 7.61 (d, J=7.5 Hz, 1H), 7.22 (d, J=7.4 Hz, 1H), 6.52 (t, J=55.6 Hz, 1H), 4.23-4.07 (m, 2H), 3.96 (s, 3H), 3.63 (q, J=7.4 Hz, 1H), 1.70 (d, J=1.1 Hz, 3H), 1.13 (t, J=7.1 Hz, 3H), 1.06 (dq, J=7.3, 2.2 Hz, 3H) ppm. ESI-MS m z calc. 395.1156, found 396.3 (M+1)$^+$; Retention time: 1.05 minutes.

Step 4:

A solution of ethyl rac-(4S,5R)-3-(6-(difluoromethyl)-2-methoxypyridin-3-yl)-4,5-dimethyl-5-(trifluoromethyl)-4,5-dihydrofuran-2-carboxylate (670 mg, 1.695 mmol) in MeOH (50 mL) was stirred with activated charcoal for 3 h. The mixture was filtered and added to Pd(OH)$_2$ (505 mg of 20% w/w, 0.7192 mmol) under nitrogen in a Parr bottle. The bottle was connected to the Parr shaker and agitated under hydrogen (60 psi, 4 bar) at ambient temperature over the weekend. The reaction mixture was filtered through a pad of celite and concentrated in vacuo to give a mixture of ethyl rac-(2S,3S,4S,5R)-3-(6-(difluoromethyl)-2-methoxypyridin-3-yl)-4,5-dimethyl-5-(trifluoromethyl)tetrahydrofuran-2-carboxylate and ethyl rac-(2R,3R,4S,5R)-3-(6-(difluoromethyl)-2-methoxypyridin-3-yl)-4,5-dimethyl-5-(trifluoromethyl)tetrahydrofuran-2-carboxylate (670 mg, 99%) as the 2 major diastereoisomers in a ~1:0.7 ratio. ESI-MS m/z calc. 397.13126, found 398.2 (M+1)$^+$; Retention time: 1.03 and 1.08 minutes.

Step 5:

Potassium tert-butoxide (398 mg, 3.547 mmol) was added to a solution of a mixture of ethyl rac-(2S,3S,4S,5R)-3-(6-(difluoromethyl)-2-methoxypyridin-3-yl)-4,5-dimethyl-5-(trifluoromethyl)tetrahydrofuran-2-carboxylate and ethyl rac-(2R,3R,4S,5R)-3-(6-(difluoromethyl)-2-methoxypyridin-3-yl)-4,5-dimethyl-5-(trifluoromethyl)tetrahydrofuran-2-carboxylate (700 mg, 1.762 mmol) in 2-MeTHF (20 mL). The reaction mixture was stirred for 30 min at ambient temperature. The reaction was quenched by addition of a 2M HCl solution and partitioned between water and EtOAc. The organic layer was separated and washed with brine, dried ($MgSO_4$) and concentrated in vacuo to give a mixture of rac-(2R,3S,4S,5R)-3-(6-(difluoromethyl)-2-methoxypyridin-3-yl)-4,5-dimethyl-5-(trifluoromethyl)tetrahydrofuran-2-carboxylic acid and rac-(2S,3R,4S,5R)-3-(6-(difluoromethyl)-2-methoxypyridin-3-yl)-4,5-dimethyl-5-(trifluoromethyl)tetrahydrofuran-2-carboxylic acid (630 mg, 97%) as a yellow oil and as the 2 major diastereoisomers in a ~1:0.8 ratio. ESI-MS m/z calc. 369.09995, found 368.1 (M−1)$^-$; Retention time: 0.56 and 0.58 minutes.

Step 6:

Triethylamine (225 μL, 1.614 mmol) and T3P (450 μL of 50% w/w, 0.7559 mmol) were successively added to a solution of methyl 5-aminopicolinate (102.5 mg, 0.6737 mmol) and a mixture of rac-(2R,3S,4S,5R)-3-(6-(difluoromethyl)-2-methoxypyridin-3-yl)-4,5-dimethyl-5-(trifluoromethyl)tetrahydrofuran-2-carboxylic acid and rac-(2S,3R,4S,5R)-3-(6-(difluoromethyl)-2-methoxypyridin-3-yl)-4,5-dimethyl-5-(trifluoromethyl)tetrahydrofuran-2-carboxylic acid (200 mg, 0.5416 mmol) in ethyl acetate (4 mL). The reaction mixture was stirred at 40° C. overnight. The mixture was partitioned between water and EtOAc. The aqueous layer was extracted with EtOAc. The combined organic phases were washed with brine, dried ($MgSO_4$), filtered and concentrated in vacuo. Purification by flash chromatography ($SiO_2$, 0 to 90% EtOAc in heptane) gave methyl rac-5-((2R,3S,4S,5R)-3-(6-(difluoromethyl)-2-methoxypyridin-3-yl)-4,5-dimethyl-5-(trifluoromethyl)tetrahydrofuran-2-carboxamido)picolinate (89 mg, 33%) as a yellow gum and containing small amounts of other stereoisomers. $^1$H NMR (500 MHz, Chloroform-d) δ 8.66 (d, J=2.5 Hz, 1H), 8.57 (s, 1H), 8.37 (dd, J=8.7, 2.5 Hz, 1H), 8.11 (d, J=8.6 Hz, 1H), 7.83 (d, J=7.6 Hz, 1H), 7.28 (s, 1H), 6.52 (t, J=55.6 Hz, 1H), 5.11 (d, J=11.0 Hz, 1H), 4.09-4.05 (m, 1H), 3.99 (s, 3H), 3.98 (s, 3H), 2.93 (p, J=7.7 Hz, 1H), 1.72 (s, 3H), 0.77 (dd, J=7.7, 2.3 Hz, 3H) ppm. ESI-MS m/z calc. 503.14795, found 504.3 (M+1)$^+$; 502.2 (M−1)$^-$; Retention time: 0.97 minutes.

Step 7:

$LiBH_4$ (75 μL, 2 M in THF solution, 0.1500 mmol) was added to a solution of methyl rac-5-((2R,3S,4S,5R)-3-(6-(difluoromethyl)-2-methoxypyridin-3-yl)-4,5-dimethyl-5-(trifluoromethyl)tetrahydrofuran-2-carboxamido)picolinate (40 mg, 0.07946 mmol) in THF (2 mL). The reaction mixture was stirred at ambient temperature overnight. A further 50 μl of a 2M $LiBH_4$ solution in THF was added and the mixture was stirred for a further 2 h. The reaction was quenched by addition of a 2M HCl solution. The mixture was concentrated in vacuo. Purification by reversed phase HPLC-MS gave rac-(2R,3S,4S,5R)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (15 mg, 40%). ESI-MS m/z calc. 475.15305, found 476.3 (M+1)$^+$; 474.3 (M−1)$^-$; Retention time: 3.11 minutes.

Step 8:

The enantiomers of rac-(2R,3S,4S,5R)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (15 mg, 0.032 mmol) were separated by chiral SFC using a Chiralcel OD-H column, 5 m particle size, 25 cm×10 mm from Daicel (Mobile phase: 25% IPA:MeCN 1:1 (containing 0.2% DMIPA), 75% $CO_2$. Flow: 10 mL/min.) on a Minigram SFC instrument from Berger Instruments:

First Eluting Isomer (rt=2.70 min): rel-(2R,3S,4S,5R)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (88, 5 mg, 54%). $^1$H NMR (500 MHz, DMSO-$d_6$) δ 10.37 (s, 1H), 8.74 (s, 1H), 8.14-8.05 (m, 1H), 7.91 (d, J=7.6 Hz, 1H), 7.49 (d, J=8.4 Hz, 1H), 7.31 (d, J=7.6 Hz, 1H), 6.87 (t, J=54.9 Hz, 1H), 5.22 (d, J=9.9 Hz, 1H), 4.55 (s, 2H), 4.24-4.15 (m, 1H), 3.95 (s, 3H), 2.94-2.83 (m, 1H), 1.62 (s, 3H), 0.70 (d, J=7.2 Hz, 3H) ppm; alcohol OH not observed. ESI-MS m/z calc. 475.15305, found 476.4 (M+1)$^+$; 474.4 (M−1)$^-$; Retention time: 3.11 minutes.

Second Eluting Isomer (rt=3.42 min): rel-(2S,3R,4R,5S)-3-(6-(difluoromethyl)-2-methoxypyridin-3-yl)-N-(6-(hydroxymethyl)pyridin-3-yl)-4,5-dimethyl-5-(trifluoromethyl)tetrahydrofuran-2-carboxamide (89, 6 mg, 65%). $^1$H NMR (500 MHz, DMSO-$d_6$) δ 10.36 (s, 1H), 8.73 (d, J=2.3 Hz, 1H), 8.08 (d, J=8.5 Hz, 1H), 7.90 (d, J=7.6 Hz, 1H), 7.47 (d, J=8.5 Hz, 1H), 7.31 (d, J=7.7 Hz, 1H), 6.86 (t, J=54.9 Hz, 1H), 5.21 (d, J=9.9 Hz, 1H), 4.54 (s, 2H), 4.24-4.12 (m, 1H), 3.94 (s, 3H), 2.90 (t, J=7.5 Hz, 1H), 1.62 (s, 3H), 0.69 (d, J=7.4 Hz, 3H) ppm; alcohol OH not observed. ESI-MS m/z calc. 475.15305, found 476.4 (M+1)$^+$; 474.4 (M−1)$^-$; Retention time: 3.11 minutes.

The following compounds were made using the method described in Example 11, except that the conditions used for the Suzuki coupling step 3 are those described in Example 9 step 2 and the coupling partner was 1-bromo-4-(difluoromethyl)-3-fluoro-2-methoxybenzene rather than 3-bromo-6-(difluoromethyl)-2-methoxypyridine. The reduction step 4 was carried out under an atmospheric pressure of hydrogen. The conditions for the amide coupling step 6 were those described in Example 9 step 5 using 6-(((tert-butyldimethylsilyl)oxy)methyl)pyridin-3-amine as the coupling partner. The $LiBH_4$ reduction step 7 was not required. The separation step 8 was carried by chiral SFC using a (R,R)-Whelk-01 column, 21×250 mm (Mobile phase: 10 to 25% IPA (containing 20 mM Ammonia), 90 to 75% $CO_2$. Flow: 100 mL/min.). A TBS deprotection step was carried out overnight at ambient temperature as a last step in the sequence, using TFA in excess and DCM as the solvent:

| Cmpd No. | Compound Name | LC/MS | NMR (shifts in ppm) |
|---|---|---|---|
| 90 | rel-(2S,3R,4R,5S)-3-(4-(difluoromethyl)-3-fluoro-2-methoxyphenyl)-N-(6-(hydroxymethyl)pyridin-3-yl)-4,5-dimethyl-5-(trifluoromethyl) | ESI-MS m/z calc. 492.14838, found 493.3 (M + 1)$^+$; 491.2 (M − 1)$^-$; Retention time: 3.16 minutes | $^1$H NMR (500 MHz, DMSO-$d_6$) δ 10.37 (s, 1H), 8.66 (d, J = 2.5 Hz, 1H), 8.01 (dd, J = 8.4, 2.5 Hz, 1H), 7.40 (d, J = 8.5 Hz, 1H), 7.39-7.06 (m, |

| Cmpd No. | Compound Name | LC/MS | NMR (shifts in ppm) |
|---|---|---|---|
|  | tetrahydrofuran-2-carboxamide (Precursor was the first eluting peak by SFC on (R,R)-Whelk-O1 column, rt = 1.06 min) |  | 3H), 5.34 (s, 1H), 5.13 (d, J = 10.2 Hz, 1H), 4.50 (s, 2H), 4.32 (dd, J = 10.3, 7.7 Hz, 1H), 3.93 (d, J = 1.8 Hz, 3H), 2.82 (p, J = 7.5 Hz, 1H), 1.62 (s, 3H), 0.74 (d, J = 7.2 Hz, 3H) ppm. |
| 91 | rel-(2R,3S,4S,5R)-3-(4-(difluoromethyl)-3-fluoro-2-methoxyphenyl)-N-(6-(hydroxymethyl)pyridin-3-yl)-4,5-dimethyl-5-(trifluoromethyl)tetrahydrofuran-2-carboxamide (Precursor was the second eluting peak by SFC on (R,R)-Whelk-O1 column, rt = 1.51 min) | ESI-MS m/z calc. 492.14838, found 493.3 (M + 1)⁺; 491.3 (M − 1)⁻; Retention time: 3.16 minutes |  |

Example 12

(2R,3S,4S,5R)-3-(4-(difluoromethoxy)-3-fluoro-2-methoxyphenyl)-N-(2-(hydroxymethyl)pyrimidin-5-yl)-4,5-dimethyl-5-(trifluoromethyl)tetrahydrofuran-2-carboxamide (19)

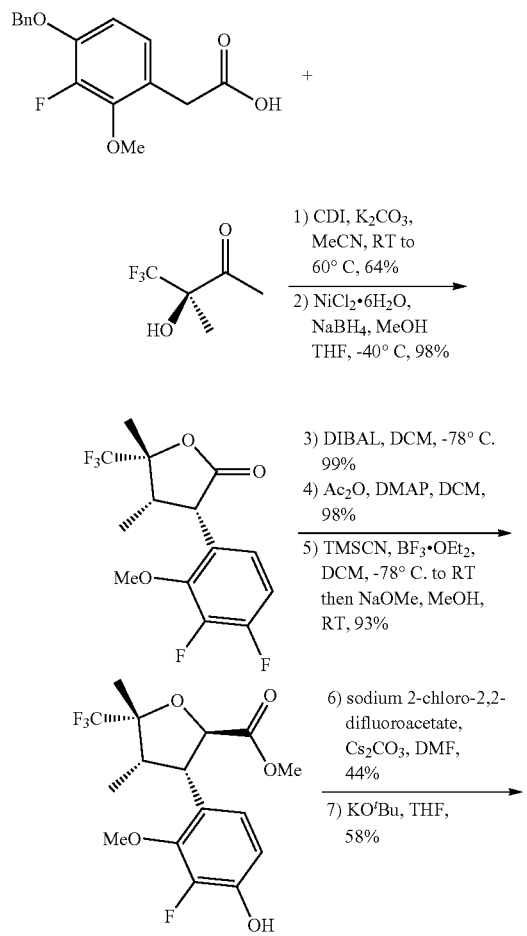

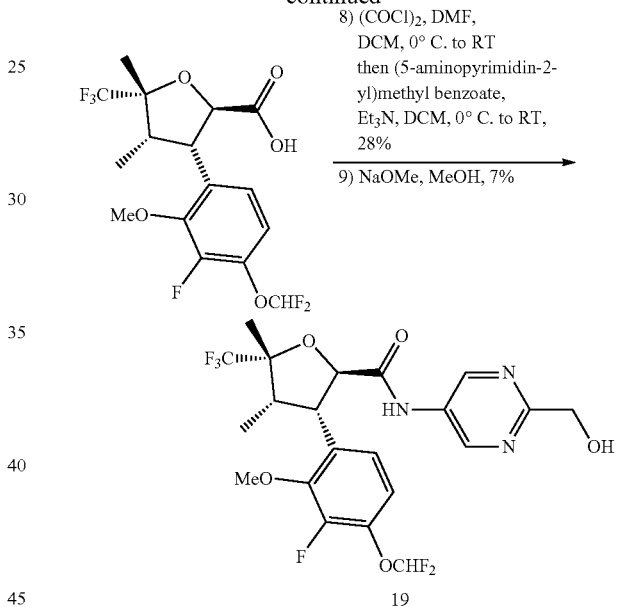

Step 1:

To a solution of 2-(4-(benzyloxy)-3-fluoro-2-methoxyphenyl)acetic acid (9.8 g, 32.072 mmol) in MeCN (100 mL) was added CDI (6 g, 37.003 mmol), and the reaction mixture was heated at 40° C. for 15 min. (R)-4,4,4-trifluoro-3-hydroxy-3-methylbutan-2-one (6 g, 38.436 mmol) and potassium carbonate (5.5 g, 39.796 mmol) were added and the reaction mixture was heated at 60° C. for 30 h. The reaction mixture was diluted with water (50 mL) and extracted with MTBE (2×100 mL). The combined organic extracts were washed with HCl (2×50 mL of 2 M aqueous solution), dried (Na$_2$SO$_4$), filtered and concentrated in vacuo. Purification by flash chromatography (120 g SiO$_2$, 0 to 100% EtOAc in heptane) gave (R)-3-(4-(benzyloxy)-3-fluoro-2-methoxyphenyl)-4,5-dimethyl-5-(trifluoromethyl)furan-2(5H)-one (9.17 g, 64%) as a yellow solid. $^1$H NMR (400 MHz, Chloroform-d) δ 7.46-7.34 (m, 5H), 6.91 (dd, J=8.7, 1.8 Hz, 1H), 6.80 (dd, J=8.7, 7.8 Hz, 1H), 5.16 (s, 2H), 3.85 (d, J=1.8 Hz, 3H), 2.03 (s, 3H), 1.73 (s, 3H) ppm. ESI-MS m/z calc. 410.1141, found 411.23 (M+1)⁺; Retention time: 2.97 minutes.

Step 2:

Nickel dichloride hexahydrate (1.8 g, 7.573 mmol) was added to a solution of (R)-3-(4-(benzyloxy)-3-fluoro-2-methoxyphenyl)-4,5-dimethyl-5-(trifluoromethyl)furan-2(5H)-one (3 g, 7.311 mmol) in MeOH (300 mL) and THF (60 mL) at −40° C. under nitrogen. NaBH$_4$ (1.4 g, 37.00 mmol) was added portion-wise and the reaction mixture was stirred −40° C. 6 further additions of NiCl$_2$·6H$_2$O (1.8 g, 7.573 mmol) and NaBH$_4$ (1.4 g, 37.00 mmol) were made over a 2 h period. NH$_4$Cl (100 mL of saturated aqueous solution) was added, and the mixture was extracted with DCM (100 mL). The organic extract was dried (MgSO$_4$), filtered and concentrated in vacuo to give (3S,4S,5R)-3-(3-fluoro-4-hydroxy-2-methoxyphenyl)-4,5-dimethyl-5-(trifluoromethyl)dihydrofuran-2(3H)-one (2.3 g, 98%). ESI-MS m/z calc. 322.08282, found 321.4 (M−1)$^-$; Retention time: 0.79 minutes.

Step 3:

To a stirred solution of (3S,4S,5R)-3-(3-fluoro-4-hydroxy-2-methoxyphenyl)-4,5-dimethyl-5-(trifluoromethyl)dihydrofuran-2(3H)-one (2.3 g, 7.137 mmol) in DCM (40 mL) at −78° C. under a nitrogen atmosphere was added DIBAL (15 mL of 1 M in DCM, 15 mmol) dropwise. The reaction mixture was stirred at −78° C. The reaction mixture was quenched by addition of NH$_4$Cl (100 mL of saturated aqueous solution) and Rochelle's salt (100 mL of 30% w/w aqueous solution). The resulting mixture was vigorously stirred at ambient temperature until a clear phase separation was achieved. The organic layer was dried (MgSO$_4$), filtered and concentrated in vacuo to give (3S,4S,5R)-3-(3-fluoro-4-hydroxy-2-methoxyphenyl)-4,5-dimethyl-5-(trifluoromethyl)tetrahydrofuran-2-ol (2.3 g, 99%). ESI-MS m z calc. 324.09848, found 323.4 (M−1)$^-$; Retention time: 0.73 minutes.

Step 4:

To a solution of (3S,4S,5R)-3-(3-fluoro-4-hydroxy-2-methoxyphenyl)-4,5-dimethyl-5-(trifluoromethyl)tetrahydrofuran-2-ol (380 mg, 1.172 mmol) in DCM (4 mL) was added DMAP (210 mg, 1.719 mmol) and acetic anhydride (700 µL, 7.419 mmol). The reaction mixture was stirred at ambient temperature. Upon reaction completion, the mixture was quenched by addition of NaHCO$_3$ (30 mL of saturated aqueous solution). The mixture was diluted with DCM (20 mL) and extracted with DCM (10 mL). The combined organic extracts were dried (MgSO$_4$), filtered and concentrated in vacuo. Purification by flash chromatography (24 g SiO$_2$, 0 to 100% EtOAc in heptane) gave (3S,4S,5R)-3-(4-acetoxy-3-fluoro-2-methoxyphenyl)-4,5-dimethyl-5-(trifluoromethyl)tetrahydrofuran-2-yl acetate (470 mg, 98%) as a mixture of epimers at the C$_2$ position. ESI-MS m/z calc. 408.1196, found 407.3 (M−1)$^-$; Retention time: 1.01 minutes.

Step 5:

TMSCN (400 µL, 3.000 mmol) and BF$_3$·OEt$_2$ (1000 µL, 8.103 mmol) were added successively to a solution of (3S,4S,5R)-3-(4-acetoxy-3-fluoro-2-methoxyphenyl)-4,5-dimethyl-5-(trifluoromethyl)tetrahydrofuran-2-yl acetate (470 mg, 1.151 mmol) in DCM (15 mL) at −78° C. The reaction mixture was stirred at −78° C. for 30 min and then allowed to warm to ambient temperature. Upon reaction completion, the mixture was quenched with NaHCO$_3$ (60 mL of saturated aqueous solution). The mixture was extracted with DCM (3×30 mL). The combined organic extracts were dried (Na$_2$SO$_4$), filtered and concentrated in vacuo to give 4-((3S,4S,5R)-2-cyano-4,5-dimethyl-5-(trifluoromethyl)tetrahydrofuran-3-yl)-2-fluoro-3-methoxyphenyl acetate (400 mg, 93%). ESI-MS m/z calc. 375.10938, found 374.5 (M−1)$^-$; Retention time: 1.0 minutes. To a solution of 4-((3S,4S,5R)-2-Cyano-4,5-dimethyl-5-(trifluoromethyl)tetrahydrofuran-3-yl)-2-fluoro-3-methoxyphenyl acetate in MeOH (7 mL) was added NaOMe solution (800 µL of 25% w/w in MeOH, 3.498 mmol) and the reaction mixture was stirred at ambient temperature overnight. A saturated citric acid solution was added and the reaction mixture was stirred at ambient temperature for 4 h. The mixture was extracted with DCM (2×30 mL). The combined organic extracts were dried (MgSO$_4$), filtered and concentrated in vacuo to give methyl (2R,3S,4S,5R)-3-(3-fluoro-4-hydroxy-2-methoxyphenyl)-4,5-dimethyl-5-(trifluoromethyl)tetrahydrofuran-2-carboxylate (380 mg, 90%). ESI-MS m/z calc. 366.10904, found 365.4 (M−1)$^-$; Retention time: 0.87 minutes.

Step 6:

Sodium 2-chloro-2,2-difluoroacetate (1.1 g, 7.168 mmol) was added to a mixture of methyl (2R,3S,4S,5R)-3-(3-fluoro-4-hydroxy-2-methoxyphenyl)-4,5-dimethyl-5-(trifluoromethyl)tetrahydrofuran-2-carboxylate (1.01 g, 2.757 mmol) and Cs$_2$CO$_3$ (2.7 g, 8.287 mmol) in DMF (10 mL). The reaction mixture was heated to 90° C. Upon reaction completion, the mixture was partitioned between DCM (20 mL) and water (50 mL). The organic extract was dried (MgSO$_4$), filtered and concentrated in vacuo. Purification by flash chromatography (12 g SiO$_2$, 0 to 100% EtOAc in heptane) gave methyl (2R,3S,4S,5R)-3-(4-(difluoromethoxy)-3-fluoro-2-methoxyphenyl)-4,5-dimethyl-5-(trifluoromethyl)tetrahydrofuran-2-carboxylate (500 mg, 44%). ESI-MS m/z calc. 416.10583, Retention time: 0.87 minutes; no mass ionisation.

Step 7:

To a solution of methyl (2R,3S,4S,5R)-3-(4-(difluoromethoxy)-3-fluoro-2-methoxyphenyl)-4,5-dimethyl-5-(trifluoromethyl)tetrahydrofuran-2-carboxylate (180 mg, 0.4324 mmol) in THF (3 mL) at ambient temperature was added KO-t-Bu (200 mg, 1.782 mmol). The reaction mixture was stirred at ambient temperature for 5 min. The reaction mixture was quenched by addition of NH$_4$Cl (3 mL of saturated aqueous solution) and diluted with DCM (3 mL). The organic layer was separated and the aqueous phase was washed with DCM (5 mL). The combined organic extracts were dried (MgSO$_4$), filtered and concentrated in vacuo to give (2R,3S,4S,5R)-3-(4-(difluoromethoxy)-3-fluoro-2-methoxyphenyl)-4,5-dimethyl-5-(trifluoromethyl)tetrahydrofuran-2-carboxylic acid (100 mg, 58%), which was used in the next step without further purification. ESI-MS m/z calc. 402.09018, found 401.4 (M−1)$^-$; Retention time: 0.6 minutes.

Step 8

Oxalyl chloride (25 µL, 0.287 mmol) was added to a solution of (2R,3S,4S,5R)-3-(4-(difluoromethoxy)-3-fluoro-2-methoxyphenyl)-4,5-dimethyl-5-(trifluoromethyl)tetrahydrofuran-2-carboxylic acid (50 mg, 0.124 mmol) and DMF (2 µL, 0.026 mmol) in DCM (500 µL). The reaction mixture was stirred at ambient temperature for 30 min. The reaction mixture was concentrated in vacuo then dissolved in DCM (1 mL) and treated with Et$_3$N (25 µL, 0.179 mmol) and (5-aminopyrimidin-2-yl)methyl benzoate. The mixture was stirred at ambient temperature for 1 h and then quenched by the addition of MeOH (100 µL). The mixture was concentrated in vacuo. Purification by flash chromatography gave [5-[[(2R,3S,4S,5R)-3-[4-(difluoromethoxy)-3-fluoro-2-methoxy-phenyl]-4,5-dimethyl-5-(trifluoromethyl)tetrahydrofuran-2-carbonyl]amino]pyrimidin-2-yl]methyl benzoate (23 mg, 29%) which was used immediately in the next step. ESI-MS m/z calc. 613.16473, found 614.7 (M+1)⁺; 612.6 (M−1)⁻; Retention time: 3.77 minutes.

Step 9:

A solution of [5-[[(2R,3S,4S,5R)-3-[4-(difluoromethoxy)-3-fluoro-2-methoxy-phenyl]-4,5-dimethyl-5-(trifluoromethyl)tetrahydrofuran-2-carbonyl]amino]pyrimidin-2-yl]methyl benzoate (23 mg) in MeOH (0.5 mL)/NaOMe (60 μL of 25% w/w, 0.2624 mmol) was stirred at ambient temperature. After complete reaction, the mixture was concentrated in vacuo. Purification by flash chromatography (4 g SiO₂, 0 to 100% EtOAc in heptane) gave (2R,3S,4S,5R)-3-(4-(difluoromethoxy)-3-fluoro-2-methoxyphenyl)-N-(2-(hydroxymethyl)pyrimidin-5-yl)-4,5-dimethyl-5-(trifluoromethyl)tetrahydrofuran-2-carboxamide (4.5 mg, 7%). ¹H NMR (500 MHz, DMSO-d₆) δ 10.48 (s, 1H), 8.99 (s, 2H), 7.33 (t, J=73.2 Hz, 1H), 7.20 (dd, J=8.8, 1.8 Hz, 1H), 7.12-7.05 (m, 1H), 5.14 (d, J=10.3 Hz, 1H), 4.55 (s, 2H), 4.26 (dd, J=10.3, 7.7 Hz, 1H), 3.92 (d, J=1.8 Hz, 3H), 2.78 (p, J=7.5 Hz, 1H), 1.62 (s, 3H), 0.73 (dd, J=7.4, 2.5 Hz, 3H) ppm. OH alcohol not observed. ESI-MS m/z calc. 509.13855, found 510.6 (M+1)⁺; 508.5 (M−1)⁻; Retention time: 3.15 minutes.

The following compound was made using the method described in Example 12, except that 6-[[tert-butyl(dimethyl)silyl]oxymethyl]pyridin-3-amine was used as the coupling partner in step 8. Step 9 was replaced by TBS deprotection using TFA/DCM/water (5 mL of 9:3:1 ratio) and heating at 50° C. for 30 min.

| Cmpd No. | Compound Name | LC/MS | NMR (shifts in ppm) |
|---|---|---|---|
| 18 | (2R,3S,4S,5R)-3-(4-(difluoromethoxy)-3-fluoro-2-methoxyphenyl)-N-(6-(hydroxymethyl)pyridin-3-yl)-4,5-dimethyl-5-(trifluoromethyl)tetrahydrofuran-2-carboxamide | ESI-MS m/z calc. 508.14328, found 509.6 (M + 1)⁺; 507.6 (M − 1)⁻; Retention time: 3.22 minutes. | ¹H NMR (500 MHz, DMSO-d₆) δ 10.36 (s, 1H), 8.66 (d, J = 2.5 Hz, 1H), 8.01 (dd, J = 8.5, 2.6 Hz, 1H), 7.43-131 (m, 1H), 7.24 (t, J = 74 Hz, 1H), 7.20-7.14 (m, 1H), 7.12-7.06 (m, 1H), 5.34 (t, J = 5.8 Hz, 1H), 5.09 (d, J = 10.4 Hz, 1H), 4.49 (d, J = 5.8 Hz, 2H), 4.26 (dd, J = 10.4, 7.6 Hz, 1H), 3.93 (d, J = 1.9 Hz, 3H), 2.77 (p, J = 7.5 Hz, 1H), 1.61 (s, 3H), 0.73 (d, J = 7.5 Hz, 3H) ppm. |

Intermediate A rac-6-(2,2-dimethyl-1,3-dioxolan-4-yl)pyridin-3-amine

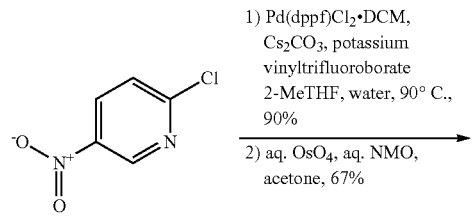

1) Pd(dppf)Cl₂·DCM, Cs₂CO₃, potassium vinyltrifluoroborate 2-MeTHF, water, 90° C., 90%
2) aq. OsO₄, aq. NMO, acetone, 67%

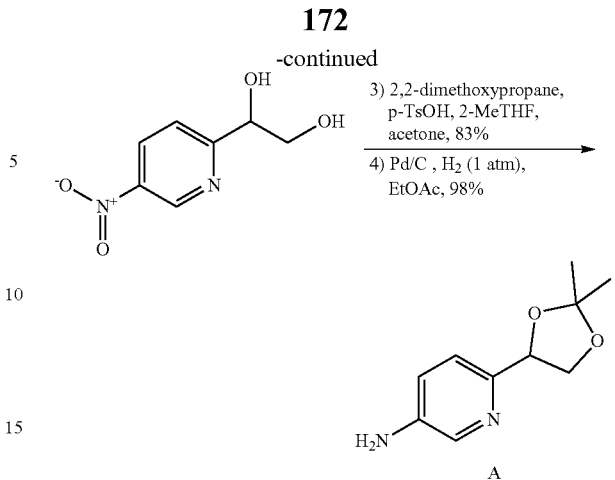

3) 2,2-dimethoxypropane, p-TsOH, 2-MeTHF, acetone, 83%
4) Pd/C, H₂ (1 atm), EtOAc, 98%

Step 1:

Cs₂CO₃ (100 g, 306.92 mmol) was added to a stirred solution of 2-chloro-5-nitro-pyridine (25 g, 157.69 mmol) and potassium vinyltrifluoroborate (25 g, 186.64 mmol) in 2-MeTHF (250 mL) and water (25 mL). The mixture was degassed for 5 min with argon. Pd(dppf)Cl₂·DCM (6.25 g, 7.65 mmol) was added and the reaction mixture was degassed again with argon. The reaction mixture was stirred for 6 h at 90° C. The mixture was concentrated in vacuo and partitioned between ethyl acetate (125 mL) and water (40 mL). The organic layer was separated, dried (MgSO₄), filtered and concentrated in vacuo. Purification by silica gel chromatography (SiO₂, 5 to 20% ethyl acetate in hexanes) gave 5-nitro-2-vinylpyridine (22 g, 90%) as a light brown solid. ¹H NMR (400 MHz, Chloroform-d) δ 9.38 (s, 1H), 8.42 (dd, J=2.1, 8.5 Hz, 1H), 7.46 (d, J=8.8 Hz, 1H), 6.93-6.86 (m, 1H), 6.44 (d, J=17.36 Hz, 1H), 5.74 (d, J=10.8 Hz, 1H) ppm. ESI-MS m/z calc. 150.0429, found 151.0 (M+1)⁺; Retention time: 1.59 minutes.

Step 2:

NMO (104 mL of 50% w/v aqueous solution, 443.89 mmol) and OsO₄ (19 mL of 4% w/v aqueous solution, 2.989 mmol) were added to a stirred solution of 5-nitro-2-vinylpyridine (22 g, 146.53 mmol) in acetone (250 mL). The reaction mixture was stirred for 3 h at ambient temperature. The acetone was removed in vacuo and the mixture was partitioned with ethyl acetate (150 mL). The organic layer was separated, dried (MgSO₄), filtered and concentrated in vacuo. Purification by silica gel chromatography (SiO₂, 20 to 80% ethyl acetate in hexanes) gave rac-1-(5-nitropyridin- 2-yl)ethane-1,2-diol (18 g, 67%) as an off-white solid. $^1$H NMR (400 MHz, DMSO-$d_6$) δ 9.29 (br s, 1H), 8.60-8.57 (m, 1H), 7.77 (d, J=8 Hz, 1H), 5.77 (d, J=8 Hz, 1H), 4.80 (t, J=5.6 Hz, 1H), 4.73-4.71 (m, 1H), 3.75-3.73 (m, 1H), 3.59-3.56 (m, 1H) ppm. ESI-MS m/z calc. 184.0484, found 185.1 (M+1)$^+$; Retention time: 1.46 minutes.

Step 3:

p-TsOH (30 mg, 0.028 mL, 0.174 mmol) and 2,2-dimethoxypropane (338.80 mg, 0.4 mL, 3.253 mmol) were added to a stirred solution of rac-1-(5-nitropyridin-2-yl)ethane-1,2-diol (295 mg, 1.602 mmol) in 2-MeTHF (5 mL) and acetone (5 mL). The reaction mixture was stirred at ambient temperature for 16 h. The reaction mixture was quenched with a solution of NaHCO$_3$ (7 mL). The mixture was concentrated in vacuo and ethyl acetate (50 mL) was added. The mixture was dried (MgSO$_4$), filtered and concentrated in vacuo. Purification by silica gel chromatography (SiO$_2$, 5 to 10% ethyl acetate in hexanes) gave rac-2-(2,2-dimethyl-1,3-dioxolan-4-yl)-5-nitropyridine (300 mg, 83%) as an off-white solid. $^1$H NMR (400 MHz, DMSO-$d_6$) δ 9.33 (br s, 1H), 8.63 (dd, J=2.4, 8.8 Hz, 1H), 7.76 (d, J=8 Hz, 1H), 5.27 (t, J=6.4 Hz, 1H), 4.45 (t, J=8 Hz, 1H), 3.93-3.89 (m, 1H), 1.46 (s, 3H), 1.43 (s, 3H) ppm. ESI-MS m/z calc. 224.0797, found 225.3 (M+1)$^+$; Retention time: 3.24 minutes.

Step 4:

Pd/C (10 wt % loading, wet, Degussa, 285 mg, 0.268 mmol) was added to a solution of rac-2-(2,2-dimethyl-1,3-dioxolan-4-yl)-5-nitropyridine (2 g, 8.920 mmol) in ethyl acetate (60 mL). The reaction mixture was degassed for 5 min with argon and stirred under a balloon atmosphere of hydrogen for 6 h. The reaction mixture was filtered through a pad of celite. The filtrates were concentrated in vacuo to give rac-6-(2,2-dimethyl-1,3-dioxolan-4-yl)pyridin-3-amine (1.7 g, 98%) as a light yellow gum. H NMR (400 MHz, DMSO-$d_6$) δ 7.86 (d, J=2 Hz, 1H), 7.12 (d, J=8.4 Hz, 1H), 6.92 (dd, J=2.4, 8.4 Hz, 1H), 5.30 (s, 2H), 4.92 (t, J=6.8 Hz, 1H), 4.20 (t, J=6.4 Hz, 1H), 3.78 (t, J=7.6 Hz, 1H), 1.39 (s, 3H), 1.35 (s, 3H) ppm. ESI-MS m/z calc. 194.1055, found 195.2 (M+1)$^+$; Retention time: 1.41 minutes.

The following intermediate was made using a method similar to that described in Intermediate A except that potassium (E)-trifluoro(prop-1-en-1-yl)borate was used in place of potassium vinyltrifluoroborate in Step 1 and the solvent used in the hydrogenation Step 4 was a mixture of EtOAc and EtOH in place of EtOAc:

| Compound Name | LC/MS | NMR (shifts in ppm) |
| --- | --- | --- |
| rac-6-((4R,5S)-2,2,5-trimethyl-1,3-dioxolan-4-yl)pyridin-3-amine | ESI-MS m/z calc. 208.1212, found 209.0 (M + 1)$^+$; Retention time: 1.39 minutes | $^1$H NMR (400 MHz, DMSO-$d_6$) δ 7.88 (d, J = 2.7 Hz, 1H), 7.13 (d, J = 8.4 Hz, 1H), 6.93 (dd, J = 8.4, 2.7 Hz, 1H), 5.30 (s, 2H), 4.35 (d, J = 8.4 Hz, 1H), 3.97-3.93 (m, 1H), 1.40 (s, 3H), 1.38 (s, 3H), 1.20 (d, J = 6.0 Hz, 3H) ppm. |

Intermediate B rac-6-(1-((tert-butyldimethylsilyl)oxy)-2-methoxyethyl)pyridin-3-amine

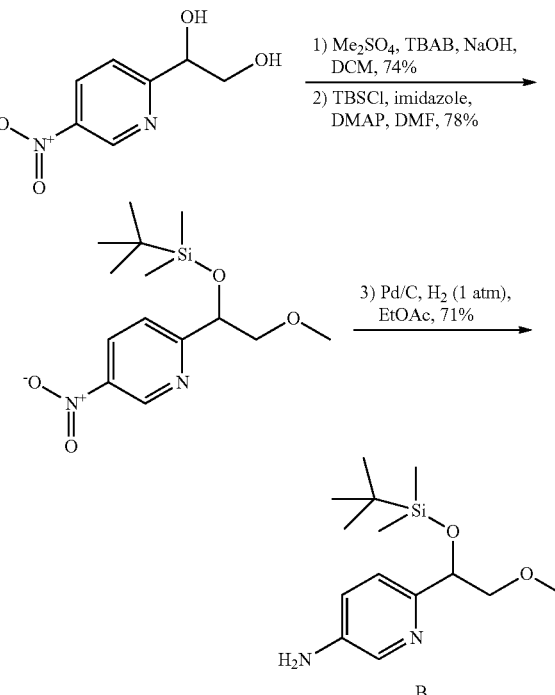

Step 1:

NaOH (3.3 mL of 1 M, 3.3000 mmol), dimethyl sulphate (266.00 mg, 0.2 mL, 2.1089 mmol) and TBAB (65 mg, 0.2016 mmol) were added sequentially to a stirred solution of rac-1-(5-nitro-2-pyridyl)ethane-1,2-diol (500 mg, 2.7152 mmol) in DCM (5 mL). The reaction mixture was stirred overnight at ambient temperature. The reaction mixture was diluted with DCM (30 mL) and washed with water (20 mL). The organic layer was dried (Na$_2$SO$_4$), filtered and concentrated in vacuo to give rac-2-methoxy-1-(5-nitropyridin-2-yl)ethan-1-ol (400 mg, 74%) as brown solid. ESI-MS m/z calc. 198.0641, found 199.1 (M+1)$^+$; Retention time: 1.36 minutes.

Step 2:

Imidazole (3 g, 44.068 mmol) and DMAP (360 mg, 2.9468 mmol) were added at ambient temperature to a stirred solution of rac-2-methoxy-1-(5-nitropyridin-2-yl)ethan-1-ol (2.86 g, 11.690 mmol) in DMF (30 mL). TBSCl (3.3 g, 21.895 mmol) was added portionwise at ambient temperature. The reaction mixture was stirred for 32 h at 60° C. The reaction mixture was diluted with water (50 mL) and extracted with ethyl acetate (120 mL). The organic layer was washed with saturated brine (120 mL), dried (MgSO$_4$), filtered and concentrated in vacuo. Purification by silica gel chromatography (SiO$_2$, 2 to 3% EtOAc in hexanes) gave rac-2-(1-((tert-butyldimethylsilyl)oxy)-2-methoxyethyl)-5-nitropyridine (2.86 g, 78%) as a colourless oil. $^1$H NMR (400 MHz, DMSO-$d_6$) δ 9.32 (s, 1H), 8.64 (d, J=8.64 Hz, 1H), 7.79 (d, J=8.64 Hz, 1H), 5.04 (s, 1H), 3.58-3.54 (m, 1H), 3.64-3.64 (m, 1H), 3.26 (s, 3H), 0.89 (s, 9H), 0.10 (s, 3H), 0.02 (s, 3H) ppm. ESI-MS m/z calc. 312.1505, found 313.0 (M+1)$^+$; Retention time: 1.88 minutes.

Step 3:

Pd/C (640 mg, 10 wt % loading, 0.601 mmol) was added to a solution of rac-2-(1-((tert-butyldimethylsilyl)oxy)-2-methoxyethyl)-5-nitropyridine (3.28 g, 10.498 mmol) in ethyl acetate (3 mL). The reaction mixture was degassed with nitrogen gas for 10 min and stirred overnight under a balloon atmosphere of hydrogen. The reaction mixture was filtered through a pad of celite, washing with ethyl acetate (50 mL). The filtrates were concentrated in vacuo. Purification by silica gel chromatography (basic $SiO_2$, 50 to 70% ethyl acetate in hexanes) gave rac-6-(1-((tert-butyldimethylsilyl)oxy)-2-methoxyethyl)pyridin-3-amine (2.1 g, 71%) as a solid. $^1$H NMR (400 MHz, DMSO-$d_6$) δ 7.83 (d, J=2.6 Hz, 1H), 7.09 (d, J=8.36 Hz, 1H), 6.91 (dd, J=8.3, 2.8 Hz, 1H), 5.21 (s, 2H), 4.71 (q, J=3.6 Hz, 1H), 3.48 (dd, J=10.2, 3.7 Hz, 1H), 3.35 (dd, J=10.2, 7.5 Hz, 1H), 3.25 (s, 3H), 0.84 (s, 9H), 0.02 (s, 3H), −0.07 (s, 3H) ppm. ESI-MS m/z calc. 282.1764, found 283.4 (M+1)$^+$; Retention time: 1.44 minutes.

Intermediates C and D (S)-6-(2,2-dimethyl-1,3-dioxolan-4-yl)pyridin-3-amine and (R)-6-(2,2-dimethyl-1,3-dioxolan-4-yl)pyridin-3-amine

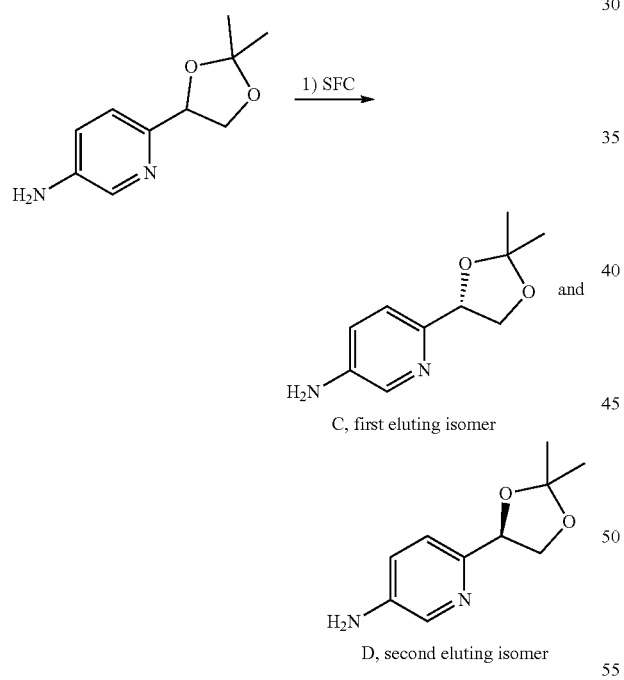

C, first eluting isomer

D, second eluting isomer

Step 1:

rac-6-(2,2-dimethyl-1,3-dioxolan-4-yl)pyridin-3-amine (9 g, 46.34 mmol) was separated by using a Chiralpak IB column, 5 m particle size, 25 cm×20 mm from Daicel (Mobile phase: 7% MeOH (containing 20 mM Ammonia), 93% $CO_2$. Flow: 100 mL/min.) on a Prep-100 SFC instrument from Waters:

First Eluting Isomer (rt=0.90 min): (S)-6-(2,2-dimethyl-1,3-dioxolan-4-yl)pyridin-3-amine (4.4 g, 49%). $^1$H NMR (400 MHz, DMSO-$d_6$) δ 7.86 (dd, J=2.8, 0.7 Hz, 1H), 7.12 (d, J=8.3 Hz, 1H), 6.92 (dd, J=8.3, 2.8 Hz, 1H), 5.29 (s, 2H), 4.92 (dd, J=7.4, 6.4 Hz, 1H), 4.21 (dd, J=8.0, 6.4 Hz, 1H), 3.79 (dd, J=8.0, 7.4 Hz, 1H), 1.40 (d, J=0.7 Hz, 3H), 1.36 (d, J=0.7 Hz, 3H) ppm. ESI-MS m/z calc. 194.10553, found 195.2 (M+1)$^+$; Retention time: 0.43 minutes.

Second Eluting Isomer (rt=1.09 min): (R)-6-(2,2-dimethyl-1,3-dioxolan-4-yl)pyridin-3-amine (4.6 g, 51%). $^1$H NMR (400 MHz, DMSO-$d_6$) δ 7.86 (dd, J=2.8, 0.7 Hz, 1H), 7.12 (d, J=8.3 Hz, 1H), 6.92 (dd, J=8.3, 2.7 Hz, 1H), 5.29 (s, 2H), 4.97-4.88 (m, 1H), 4.21 (dd, J=8.0, 6.4 Hz, 1H), 3.79 (dd, J=8.0, 7.4 Hz, 1H), 1.40 (d, J=0.7 Hz, 3H), 1.36 (d, J=0.7 Hz, 3H) ppm. ESI-MS m/z calc. 194.10553, found 195.2 (M+1)$^+$; Retention time: 0.43 minutes.

Intermediate E rac-2-(2,2-dimethyl-1,3-dioxolan-4-yl)pyrimidin-5-amine

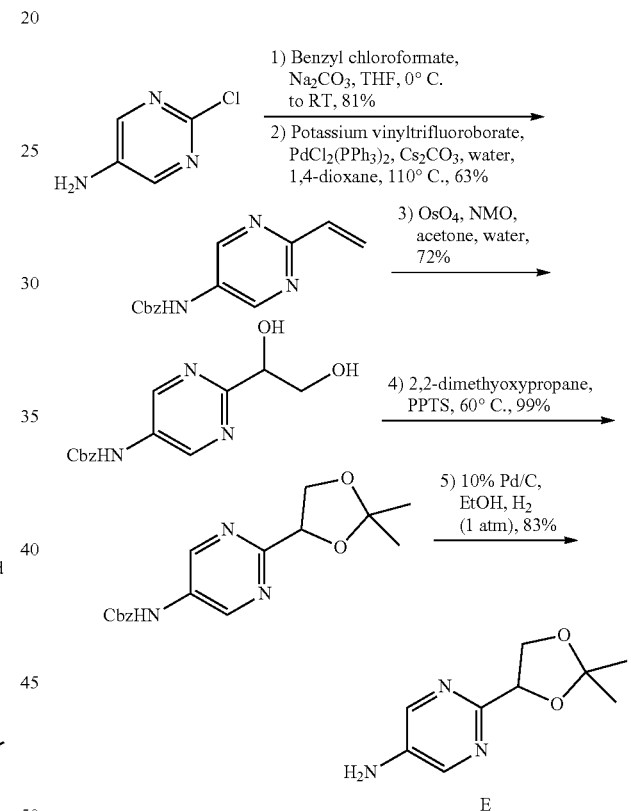

Step 1:

A solution of 2-chloropyrimidin-5-amine (4 g, 30.877 mmol) and $Na_2CO_3$ (9.818 g, 92.631 mmol) in THF (81 mL) was cooled down to 0° C. Benzyl chloroformate (7.374 g, 6.145 mL, 43.228 mmol) was added dropwise and the mixture was stirred at ambient temperature overnight. The mixture was partitioned between EtOAc and water. The aqueous layer was collected and extracted with EtOAc. The combined organic layers were concentrated in vacuo. The residue was triturated with 20% DCM in hexanes. The solid was collected and dried in vacuo to give benzyl (2-chloropyrimidin-5-yl)carbamate (7 g, 81%) as a yellow solid. $^1$H NMR (250 MHz, DMSO-$d_6$) δ 10.42 (s, 1H), 8.82 (s, 2H), 7.29-7.44 (m, 5H), 5.21 (s, 2H) ppm. ESI-MS m/z calc. 263.0462, found 263.9 (M+1)$^+$; Retention time: 2.57 minutes.

Step 2:

Benzyl (2-chloropyrimidin-5-yl)carbamate (25 g, 94.81 mmol), potassium vinyltrifluoroborate (40 g, 298.62 mmol) and $Cs_2CO_3$ (92.5 g, 283.90 mmol) were added to an oven dried 2-neck round bottom flask containing 1,4-dioxane (150 mL) and water (150 mL). The flask was flanked with a reflux condenser and the apparatus was degassed and purged with nitrogen gas for 15 min. $PdCl_2(PPh_3)_2$ (6.25 g, 8.90 mmol) was added. The mixture was heated to 110° C. overnight. The reaction mixture was filtered over a bed of celite. The filtrate was diluted with water (200 mL). The aqueous phase was separated and extracted with EtOAc (3×200 mL). The combined organic layers were dried ($Na_2SO_4$), filtered and concentrated in vacuo. The residue was recrystallized from EtOAc to give benzyl (2-vinylpyrimidin-5-yl)carbamate (15.61 g, 63%) as a yellow solid. $^1$H NMR (250 MHz, Chloroform-d) δ 8.81 (s, 1H), 7.50-7.32 (m, 5H), 6.85 (dd, J=17.3, 10.6 Hz, 1H), 6.78 (bs, 1H), 6.51 (dd, J=17.4, 1.7 Hz, 1H), 5.66 (dd, J=10.6, 1.7 Hz, 1H), 5.24 (s, 2H) ppm; NH carbamate not observed. ESI-MS m/z calc. 255.1008, found 256.4 (M+1)$^+$; Retention time: 2.43 minutes.

Step 3:

To a solution of benzyl (2-vinylpyrimidin-5-yl)carbamate (6 g, 23.504 mmol) in acetone (380 mL) and water (60 mL), was successively added NMO (3 g, 25.609 mmol) and osmium tetroxide in tert-butanol (5 mL of 2.5% w/w, 0.4917 mmol). The reaction mixture was stirred overnight at ambient temperature. The reaction mixture was concentrated in vacuo. The residue was poured on saturated aqueous $NH_4Cl$ (100 mL) and extracted with EtOAc (3×100 mL). The combined organic layers were washed with brine, dried ($Na_2SO_4$), filtered and concentrated in vacuo. The residue was triturated from DCM. The solid was collected by filtration, dried in vacuo to give benzyl rac-(2-(1,2-dihydroxyethyl)pyrimidin-5-yl)carbamate (4.87 g, 72%). $^1$H NMR (400 MHz, DMSO-$d_6$) δ 10.15 (br s, 1H), 8.83 (s, 2H), 7.45-7.35 (m, 5H), 5.19 (s, 2H), 5.15 (d, J=5.9 Hz, 1H), 4.60-4.56 (m, 2H), 3.74-3.68 (m, 1H), 3.65-3.59 (m, 1H) ppm. ESI-MS m/z calc. 289.1063, found 290.0 (M+1)$^+$; Retention time: 2.46 minutes.

Step 4:

PPTS (2.42 g, 9.6298 mmol) was added to a solution of benzyl rac-(2-(1,2-dihydroxyethyl)pyrimidin-5-yl)carbamate (13.80 g, 45.318 mmol) in 2,2-dimethoxypropane (100 mL). The reaction mixture was stirred at 60° C. overnight. The mixture was diluted with water (200 mL) and extracted with EtOAc (3×150 mL). The combined organic layers were dried ($Na_2SO_4$), filtered and concentrated in vacuo. Purification by flash chromatography (220 g $SiO_2$, 0 to 100% EtOAc in hexanes) gave benzyl (2-(2,2-dimethyl-1,3-dioxolan-4-yl)pyrimidin-5-yl)carbamate (15.1 g, 99%) as white solid. ESI-MS m/z calc. 329.1376, found 330.2 (M+1)$^+$; Retention time: 2.38 minutes.

Step 5:

A solution of benzyl rac-(2-(2,2-dimethyl-1,3-dioxolan-4-yl)pyrimidin-5-yl)carbamate (15.6 g, 44.998 mmol) in ethanol (600 mL) was extensively degassed and purged with nitrogen. The reaction was placed under a hydrogen atmosphere (balloon) and stirred for 5 h. The mixture was filtered over a bed of celite. The filtrates were concentrated in vacuo. The cream solid was washed with cold $Et_2O$ and dried in vacuo to give rac-2-(2,2-dimethyl-1,3-dioxolan-4-yl)pyrimidin-5-amine (7.58 g, 83%). $^1$H NMR (500 MHz, DMSO-$d_6$) δ 8.08 (s, 2H), 5.57 (s, 2H), 4.94 (dd, J=7.7, 6.5 Hz, 1H), 4.20 (dd, J=7.9, 6.5 Hz, 1H), 4.05 (t, J=7.8, 7.8 Hz, 1H), 1.36 (s, 3H), 1.34 (s, 3H) ppm. ESI-MS m/z calc. 195.1008, found 195.9 (M+1)$^+$; Retention time: 0.77 minutes.

Intermediate F

4-Fluoro-2-methoxy-3-methylphenyl)boronic acid

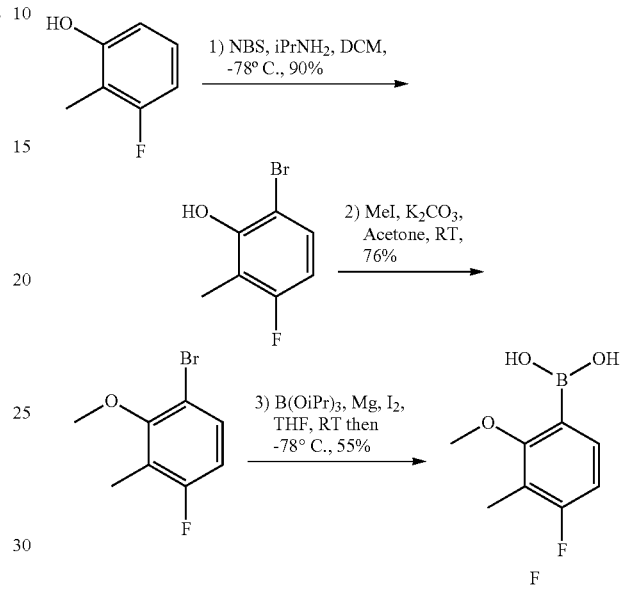

Step 1:

Isopropylamine (23.460 g, 34.5 mL, 396.89 mmol) was slowly added to a stirred solution of 3-fluoro-2-methyl-phenol (50 g, 396.42 mmol) in DCM (2.5 L). The reaction mixture was cooled to −78° C. NBS (70 g, 393.29 mmol) was added portion wise over 2 h 10 min and the mixture was stirred for a further 30 min. The mixture was warmed up to 25° C. 2N HCl (500 ml) was added and the mixture was stirred for 15 min. The organic layer was separated and concentrated in vacuo, keeping the water bath at 15° C. Hexane (500 ml) was added to the residue and the mixture was stirred for 10 min. The mixture was filtered and the liquors were concentrated in vacuo, keeping the water bath at 15° C. to give 6-bromo-3-fluoro-2-methyl-phenol (73 g, 90%) as a light brown oil. $^1$H NMR (400 MHz, Chloroform-d) δ 7.24-7.21 (m, 1H), 6.55 (t, J=8.8 Hz, 1H), 5.61 (s, 1H), 2.20 (s, 3H) ppm.

Step 2:

To a stirred solution of 6-bromo-3-fluoro-2-methylphenol (40 g, 195.10 mmol) in acetone (400 mL) at ambient temperature was added potassium carbonate (135 g, 976.80 mmol). The reaction mixture was stirred for 10 min at 25° C. Methyl iodide (39 g, 17.105 mL, 274.77 mmol) was added dropwise over 10 min and the mixture was stirred for 16 h at 25° C. The reaction mixture was filtered and the solid residues washed with acetone (50 ml). The mother liquors were concentrated at 15° C. under reduced pressure. Hexane (200 ml) was added and the mixture was stirred for 15 min. The solid was collected and washed with hexane (8 ml). The mother liquors were concentrated under reduced pressure at 15° C. Purification by distillation (520 mm Hg, 192-196° C.) gave 1-bromo-4-fluoro-2-methoxy-3-methylbenzene (32.4 g, 76%). $^1$H NMR (400 MHz, Chloroform-d) δ 7.33-7.30 (m, 1H), 6.72 (t, J=8.7 Hz, 1H), 3.80 (s, 3H), 2.23 (s, 3H) ppm.

Step 3:

Iodine (50 mg, 0.1970 mmol) was added at 25° C. to a stirred mixture of Mg turnings (5 g, 205.72 mmol) in THF (50 ml). The mixture was stirred until the reaction turned into a clear pale yellow colour. 1-bromo-4-fluoro-2-methoxy-3-methylbenzene (2.5 g, 11.4 mmol) was added dropwise at ambient temperature. When reaction initiation was observed, the remaining solution of 1-bromo-4-fluoro-2-methoxy-3-methylbenzene (22.5 g, 102.71 mmol) in THF (200 ml) was added dropwise. The mixture was stirred for 40 min. Reaction was cooled down to −78° C. and triisopropylborate (64.385 g, 79 mL, 342.34 mmol) was added dropwise. The mixture was warmed up to ambient temperature and stirred for 16 h. The reaction was quenched by addition of a 2N aqueous solution of HCl (25 ml) and stirred for 15 min. The mixture was diluted with water (125 ml) and extracted with ethyl acetate (2×250 ml). The organic layer was separated, washed with water (250 ml), dried (Na$_2$SO$_4$) and concentrated in vacuo. Hexane (25 ml) was added to the residue at 0° C. and the mixture was stirred for 5 min. The resulting solid was filtered, washed with 10 ml of chilled hexane and dried to give (4-fluoro-2-methoxy-3-methylphenyl)boronic acid (11.5 g, 55%). $^1$H NMR (400 MHz, DMSO-d$_6$) δ 7.96 (br s, 2H), 7.32 (t, J=8.0 Hz, 1H), 6.88 (t, J=8.7 Hz, 1H), 3.75 (s, 3H), 2.11 (s, 3H) ppm.

Intermediate G 2-(3-(Difluoromethyl)-4-fluoro-2-methoxyphenyl)-4,4,5,5-tetramethyl-1,3,2-dioxaborolane

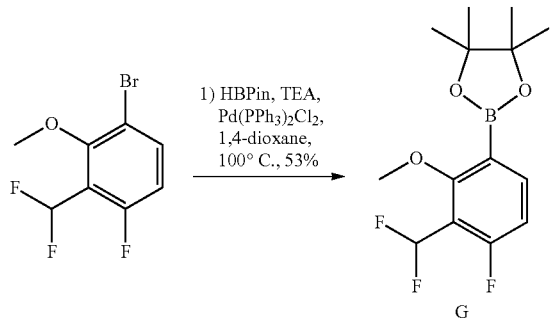 [SMILES: COc1c(Br)ccc(F)c1C(F)F ; COc1c(B2OC(C)(C)C(C)(C)O2)ccc(F)c1C(F)F]

Step 1:

To a solution of 1-bromo-3-(difluoromethyl)-4-fluoro-2-methoxybenzene (1.60 g, 6.274 mmol) and Pd(PPh$_3$)$_2$Cl$_2$ (200 mg, 0.2849 mmol) in 1,4-dioxane (25 mL) was added 4,4,5,5-tetramethyl-1,3,2-dioxaborolane (1.6 mL, 11.03 mmol) and TEA (2.5 mL, 17.94 mmol). The mixture was degassed by bubbling nitrogen through for 5 min. The reaction was heated at 100° C. in a sealed vial for 3 h. The reaction was concentrated in vacuo and loaded onto solid support. Purification by flash chromatography (0 to 25% EtOAc in heptane) gave 2-[3-(difluoromethyl)-4-fluoro-2-methoxy-phenyl]-4,4,5,5-tetramethyl-1,3,2-dioxaborolane (1.15 g, 53%) as a white solid. $^1$H NMR (400 MHz, Chloroform-d) δ 7.84 (ddt, J=8.2, 6.9, 1.2 Hz, 1H), 6.99 (td, J=53.9, 1.1 Hz, 1H), 6.91 (dd, J=9.7, 8.5 Hz, 1H), 3.90 (s, 3H), 1.36 (s, 12H) ppm. ESI-MS m/z calc. 302.1301, Retention time: 1.03 minutes.

Intermediate H 2-(2-ethoxy-3,4-difluorophenyl)-4,4,5,5-tetramethyl-1,3,2-dioxaborolane

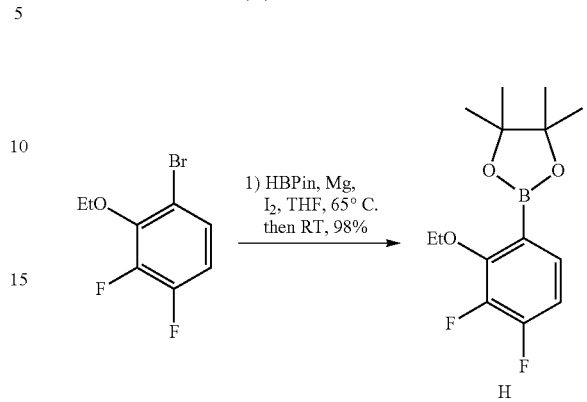

Step 1:

An oven dried 250 ml three necked flask was flanked with an air condenser, an additional funnel and a thermometer. Magnesium (1.8 g, 74.06 mmol) turnings were added. The flask was evacuated three times with vac/N$_2$ and then left under vacuum for 10 min while the flask was heated to 65° C. Using a nitrogen flushed needle, THF (35 mL) was added to the flask and the mixture was flushed once again with nitrogen. Iodine (5 mg, 0.01970 mmol) was added to the reaction. The mixture was stirred at 65° C. until the reaction turned into a clear pale yellow colour (~30 min). The mixture was taken off the heat. Pinacolborane (5.5 mL, 37.91 mmol) was added dropwise. A solution of 1-bromo-2-ethoxy-3,4-difluorobenzene (6.8 g, 28.69 mmol) in THF (35 mL) was added dropwise via additional funnel. The reaction mixture was left to cool overnight to ambient temperature. The reaction mixture was added carefully dropwise over 30 min to a stirred solution of 1 M HCl (50 ml) (vigorous effervescence observed) and left to stand for 1 h until all the Mg solids had dissolved. The mixture was diluted with TBME (100 mL). The aqueous layer was separated and extracted twice with TBME. The combined organic extracts were dried (MgSO$_4$), filtered and concentrated in vacuo to give 2-(2-ethoxy-3,4-difluorophenyl)-4,4,5,5-tetramethyl-1,3,2-dioxaborolane (8 g, 98%). ESI-MS m/z calc. 284.13953, found 285.4 (M+1)$^+$; Retention time: 1.12 minutes. $^1$H NMR (400 MHz, Chloroform-d) δ 7.38 (ddd, J=8.6, 6.5, 2.2 Hz, 1H), 6.87 (ddd, J=9.6, 8.5, 6.6 Hz, 1H), 4.14 (qd, J=7.0, 1.0 Hz, 2H), 1.40 (td, J=7.0, 0.6 Hz, 3H), 1.34 (s, 12H) ppm.

Intermediate I 4-bromo-2,2,7-trifluorobenzo[d][1,3]dioxole

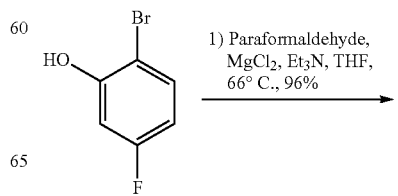

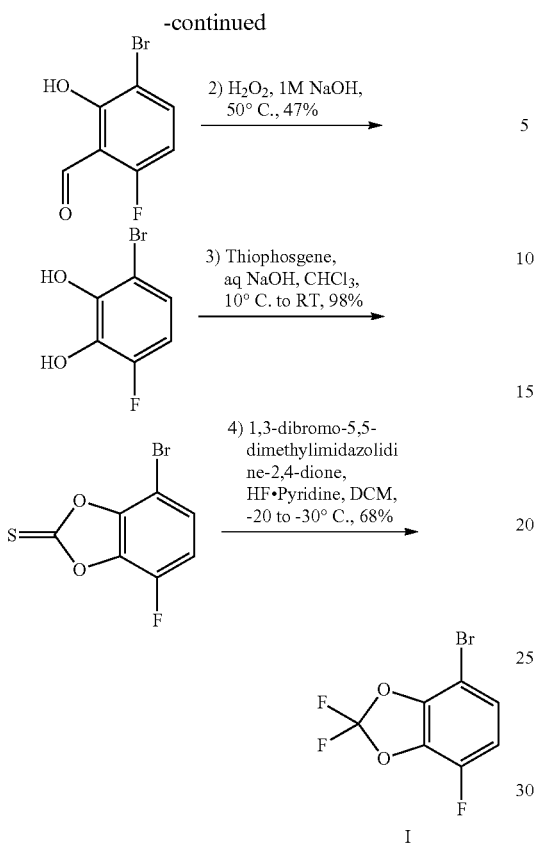

Step 1:

Triethylamine (23.232 g, 32 mL, 229.59 mmol) was added to a mixture of paraformaldehyde (20 g, 322.23 mmol) and MgCl$_2$ (20 g, 210.06 mmol) in THF (500 mL) under argon. The reaction mixture was stirred at room temperature for 10 min before adding 2-bromo-5-fluorophenol (20 g, 104.71 mmol). The reaction was heated to reflux for 2 h then allowed to cool to ambient temperature. Diethyl ether (700 mL) was added and the organic phase was washed with a 1N HCl solution (3×400 mL), dried (Na$_2$SO$_4$), filtered and concentrated in vacuo to give 3-bromo-6-fluoro-2-hydroxybenzaldehyde (22 g, 96%), which was used as is in the next step.

Step 2:

H$_2$O$_2$ (25.530 g, 23 mL of 30% w/v, 750.56 mmol) was added to a solution of 3-bromo-6-fluoro-2-hydroxybenzaldehyde (22 g, 100.45 mmol) in NaOH (120 mL of 1 M, 120.00 mmol) while applying external cooling to keep the temperature below 50° C. The reaction mixture was stirred for 2 hr. The reaction was quenched by pouring the mixture in a NaHSO$_3$ solution (120 ml). The resulting mixture was extracted with ethyl acetate (500 ml). The organic phase was washed with a saturated NaCl solution (100 ml), dried (Na$_2$SO$_4$) and concentrated in vacuo. Purification by flash chromatography (SiO$_2$, 0 to 5% ethyl acetate in hexane) gave 3-bromo-6-fluorobenzene-1,2-diol (9.8 g, 47%) as a yellow/orange oil. $^1$H NMR (400 MHz, DMSO-d$_6$) δ 9.82 (d, J=8.6 Hz, 1H), 9.65 (s, 1H), 6.94 (dd, J=9.0, 5.7 Hz, 1H), 6.64 (t, J=9.6 Hz, 1H) ppm.

Step 3:

A mixture of 3-bromo-6-fluorobenzene-1,2-diol (2.3 g, 11.111 mmol) and thiophosgene (1.5 g, 1 mL, 13.046 mmol) in chloroform (15 mL) was cooled down to 10° C. NaOH (10 mL of 10% w/v, 25.002 mmol) was added dropwise over 30 min under vigorous stirring. The reaction mixture was stirred for 2 hr at ambient temperature. The mixture was concentrated in vacuo. The residue was dissolved in ethyl acetate (200 mL). The organic solution was washed with water (30 mL) and a saturated NaCl solution (30 mL), dried (Na$_2$SO$_4$), filtered and concentrated in vacuo to give 4-bromo-7-fluorobenzo[d][1,3]dioxole-2-thione (2.7 g, 98%) as an off-white solid. $^1$H NMR (400 MHz, Chloroform-d) δ 7.66 (dd, J=9.2, 4.2 Hz, 1H), 7.1 (t, J=9.6 Hz, 1H) ppm.

Step 4:

Pyridine hydrofluoride (9 mL of 70% w/v, 63.568 mmol) was added to a solution of 4-bromo-7-fluorobenzo[d][1,3]dioxole-2-thione (3.3 g, 13.250 mmol) in DCM (35 mL) cooled down to −30° C. 1,3-Dibromo-5,5-dimethylimidazolidine-2,4-dione (4.6 g, 16.088 mmol) was added portionwise over 30 min. The mixture was stirred for 2 hr between −20 to −30° C. The reaction mixture was quenched by pouring the mixture in a 5% NaHSO$_3$ solution (9 ml). The mixture was stirred for 10 min. The organic layer was separated, dried (Na$_2$SO$_4$) and concentrated in vacuo. Purification by flash chromatography (SiO$_2$, 100% hexane) gave 4-bromo-2,2,7-trifluorobenzo[d][1,3]dioxole (2.3 g, 68%) as a colourless oil. H NMR (400 MHz, Chloroform-d) δ 7.16 (dd, J=9.2, 4.0 Hz, 1H), 6.84 (t, J=9.2 Hz, 1H) ppm.

Intermediate J 6-(((tert-butyldimethylsilyl)oxy)methyl)pyridin-3-amine

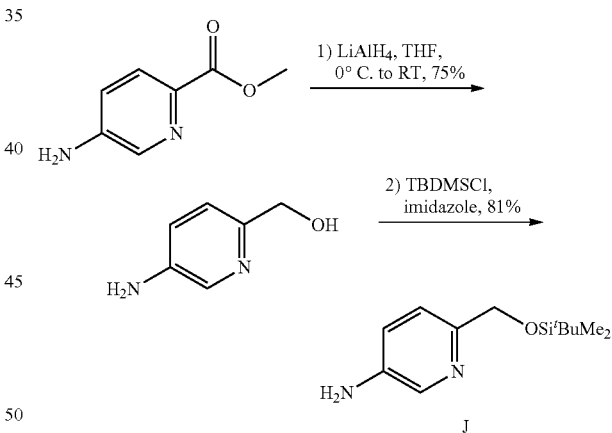

Step 1:

Lithium aluminium hydride (120 mL of 2 M, 240.00 mmol) was added at 0° C. under argon to a stirred suspension of methyl 5-aminopicolinate (21.05 g, 138.35 mmol) in dry THF (400 mL). The suspension was stirred at ambient temperature overnight then heated at 90° C. for 6 h. The reaction was left standing at room temperature for 30 h, after which time it was cooled back down to 0° C. The reaction was quenched by successive addition of water (9.3 mL, dropwise), 15% NaOH in water (9.3 mL) and then more water (28 mL). A white precipitate was filtered off, washing with additional THF (300 mL). The filtrate was concentrated in vacuo to give (5-aminopyridin-2-yl)methanol (16.1 g, 75%) as a brown liquid, which was used in the next step without additional purification. $^1$H NMR (400 MHz, DMSO-d$_6$) δ 7.81 (d, J=2.7 Hz, 1H), 7.06 (d, J=8.2 Hz, 1H), 6.89 (dd, J=8.5, 2.5 Hz, 1H), 5.11 (s, 2H), 4.34 (s, 2H) ppm; alcohol OH not observed.

Step 2:

Imidazole (1.97 g, 28.938 mmol) was added to a mixture of (5-aminopyridin-2-yl)methanol (3.65 g, 18.641 mmol) and tert-butylchlorodimethylsilane (3.41 g, 22.624 mmol) in THF (60 mL). The mixture was stirred at room temperature for 17 h. The THF layer was decanted off and the oily lower phase was dissolved in water (20 mL) and extracted with ethyl acetate (2×20 mL). The combined organic phases were washed with brine (10 mL), dried (Na$_2$SO$_4$), filtered and concentrated in vacuo. The oily residue (5.8 g) was taken up in a 1 to 1 mixture of ethyl acetate and heptane (30 mL). The precipitate was removed by filtration. The filtrate was concentrated in vacuo. Purification by flash chromatography (SiO$_2$, 25 to 75% ethyl acetate in heptane) gave 6-(((tert-butyldimethylsilyl)oxy)methyl)pyridin-3-amine (3.92 g, 81%) as a low-melting white solid. $^1$H NMR (400 MHz, Chloroform-d) δ 8.00 (d, J=2.7 Hz, 1H), 7.27-7.25 (d, 1H), 7.02 (d, J=2.7 Hz, 1H), 4.72 (s, 2H), 3.82-2.92 (br s, 2H), 0.93 (s, 9H), 0.08 (s, 6H) ppm. ESI-MS m/z calc. 238.1501, found 239.5 (M+1)$^+$; Retention time: 0.86 minutes.

Intermediate K (5-aminopyrimidin-2-yl)methyl benzoate

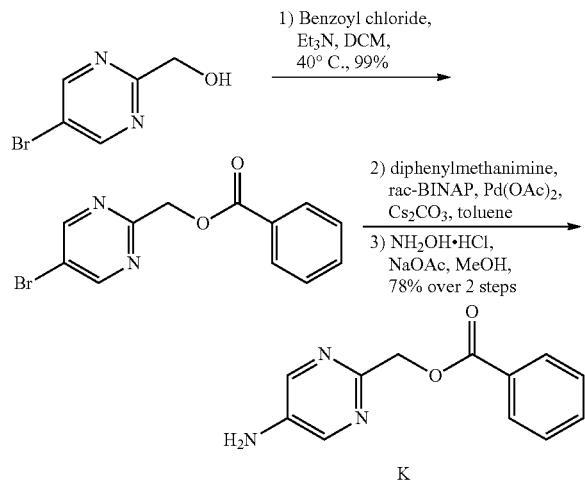

Step 1:

Benzoyl chloride (4.62 mL, 39.80 mmol) was added dropwise to a mixture of (5-bromopyrimidin-2-yl)methanol (7.2 g, 38.09 mmol) and triethylamine (7 mL, 50.22 mmol) in DCM (40 mL). The mixture was stirred under nitrogen at ambient temperature until reaction completion. The reaction mixture was washed with NaOH 0.5 M. The organic layer was separated, dried (MgSO4) and concentrated in vacuo to give (5-bromopyrimidin-2-yl)methyl benzoate (11.05 g, 99%). ESI-MS m/z calc. 291.9847, found 293.0 (M+1)$^+$; Retention time: 0.82 minutes.

Step 2:

Diphenylmethanimine (8.6 g, 47.45 mmol), rac-BINAP (2.41 g, 3.870 mmol) and Cs$_2$CO$_3$ (15.8 g, 48.49 mmol) were added to the stirred solution of (5-bromopyrimidin-2-yl)methyl benzoate (11.60 g, 39.57 mmol) in toluene (100 mL). The reaction mixture was purged with nitrogen gas for 5 min. Pd(OAc)$_2$ (440.9 mg, 1.964 mmol) was added and the reaction mixture was stirred for 22 h at reflux. Ethyl acetate and NaOH (1M) solution were added. The organic layer was separated, dried (MgSO$_4$), filtered and concentrated in vacuo. Purification by flash chromatography (220 g SiO$_2$, 5 to 35% ethyl acetate in heptane) gave (5-((diphenylmethylene)amino)pyrimidin-2-yl)methyl benzoate (11.60 g, 39.57 mmol), which was used as is in the next step. ESI-MS m/z calc. 393.1477, found 394.0 (M+1)$^+$; Retention time: 1.04 minutes.

Step 3:

(5-((diphenylmethylene)amino)pyrimidin-2-yl)methyl benzoate was dissolved in MeOH (100 mL) and treated with sodium acetate (14.31 g, 174.4 mmol) and hydroxylamine hydrochloride (8.471 g, 121.9 mmol). The mixture was stirred at ambient temperature for 7 h. The reaction was concentrated in vacuo. The residue was dissolved in DCM, washed with water, dried (MgSO$_4$), filtered and concentrated in vacuo. Purification by flash chromatography (80 g SiO$_2$, 0 to 100% ethyl acetate in heptane) gave (5-aminopyrimidin-2-yl)methyl benzoate (7.0338 g, 78%, over 2 steps). ESI-MS m/z calc. 229.0851, found 230.1 (M+1)$^+$; Retention time: 0.55 minutes.

Intermediate L 6-(1-((tert-butyldimethylsilyl)oxy)-2-fluoroethyl)pyridin-3-amine

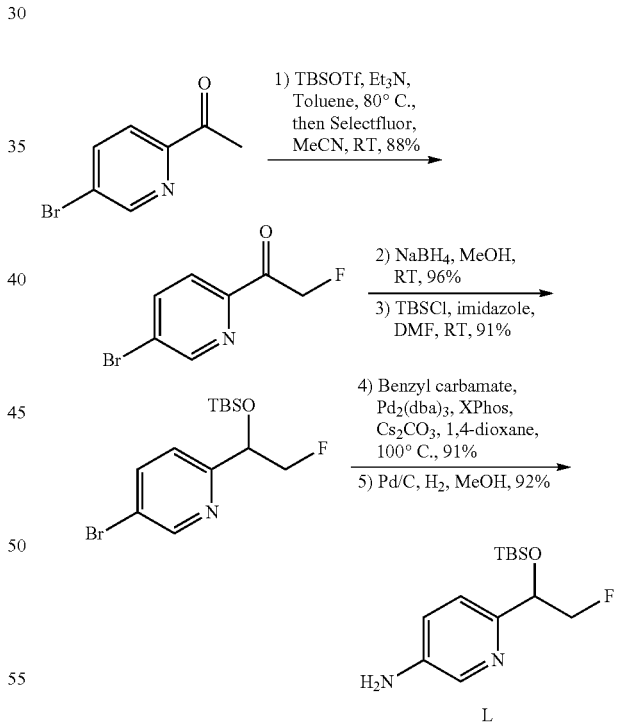

Step 1:

TBSOTf (10.005 g, 8.7 mL, 37.849 mmol) was added to a stirred solution of 1-(5-bromopyridin-2-yl)ethan-1-one (5 g, 24.996 mmol) and Et$_3$N (5.372 g, 7.4 mL, 53.092 mmol) in toluene (80 mL) under nitrogen. The reaction was heated to 80° C. for 2 h. The upper toluene phase was separated and concentrated under reduced pressure to give a yellow oil. Selectfluor (8.9 g, 25.123 mmol) was added at ambient temperature to the oil redissolved in acetonitrile (80 mL).

After stirring for 1 h, the reaction mixture was concentrated in vacuo. The residue was partitioned between water and EtOAc. The aqueous phase was extracted with EtOAc (2×150 mL). The combined organic layers were dried (Na$_2$SO$_4$), filtered and concentrated in vacuo. Purification by flash chromatography (SiO$_2$, 0 to 10% ethyl acetate in hexanes) gave 1-(5-bromopyridin-2-yl)-2-fluoroethan-1-one (4.8 g, 88%) as a white solid. $^1$H NMR (400 MHz, DMSO-d$_6$) δ 8.59 (d, J=5.2 Hz, 1H), 8.12 (d, J=1.4 Hz, 1H), 8.01 (dd, J=5.2, 1.8 Hz, 1H), 5.91 (d, J=46.8 Hz, 2H) ppm.

Step 2:

Sodium borohydride (2.3 g, 60.794 mmol) was added portionwise to a stirred solution of 1-(5-bromopyridin-2-yl)-2-fluoroethan-1-one (6.5 g, 29.813 mmol) in MeOH (80 mL) at 0° C. under nitrogen. The reaction mixture was stirred for 1 h at ambient temperature. The reaction mixture was concentrated in vacuo. The residue was partitioned between ethyl acetate and water. The aqueous phase was extracted with ethyl acetate (2×150 mL). The combined organic extracts were washed with brine, dried (Na$_2$SO$_4$), filtered and concentrated in vacuo to give 1-(5-bromopyridin-2-yl)-2-fluoroethan-1-ol (6.3 g, 96%) as a light yellow oil which was used without further purification in the next step. $^1$H NMR (400 MHz, DMSO-d$_6$) δ 8.64 (d, J=2.1 Hz, 1H), 8.07 (dd, J=8.4, 2.2 Hz, 1H), 7.52 (d, J=8.4 Hz, 1H), 6.01 (d, J=5.1 Hz, 1H), 4.87-4.46 (m, 3H) ppm.

Step 3:

Imidazole (4.2 g, 61.695 mmol) and TBSCl (5.45 g, 36.159 mmol) were successively added under nitrogen to a stirred solution of 1-(5-bromopyridin-2-yl)-2-fluoroethan-1-ol (4.2 g, 19.088 mmol) in DMF (25 mL). The reaction mixture was stirred at room temperature for 2 h. The reaction mixture was partitioned with ethyl acetate and ice cold water. The aqueous layer was extracted with EtOAc (2×150 mL). The combined organic layers was washed with brine, dried (Na$_2$SO$_4$), filtered and concentrated in vacuo. Purification by flash chromatography (SiO$_2$, 0 to 5% ethyl acetate in hexanes) gave 5-bromo-2-(1-((tert-butyldimethylsilyl)oxy)-2-fluoroethyl)pyridine (5.8 g, 91%) as a colourless oil. $^1$H NMR (400 MHz, DMSO-d$_6$) δ 8.67 (d, J=2.1 Hz, 1H), 8.12 (dd, J=8.4, 2.3 Hz, 1H), 7.48 (d, J=8.4 Hz, 1H), 5.02 (ddd, J=19.0, 6.2, 2.8 Hz, 1H), 4.69-4.40 (m, 2H), 0.88 (s, 9H), 0.09 (s, 3H), 0.02 (s, 3H) ppm. ESI-MS m/z calc. 333.056, found 335.0 (M+1)$^+$; Retention time: 2.58 minutes.

Step 4:

A solution of 5-bromo-2-(1-((tert-butyldimethylsilyl)oxy)-2-fluoroethyl)pyridine (200 mg, 0.598 mmol) in 1,4-dioxane (7 mL) was degassed by bubbling nitrogen through for 15 min. Cesium carbonate (403 mg, 1.237 mmol), benzyl carbamate (140 mg, 0.926 mmol), Xphos (45 mg, 0.094 mmol) and Pd$_2$(dba)$_3$ (40 mg, 0.044 mmol) were successively added under nitrogen. The reaction mixture was heated in a preheated oil bath to 100° C. The reaction mixture was stirred at 100° C. for 16 h. The reaction was filtered through a pad of celite. The filtrate was concentrated in vacuo. Purification by flash chromatography (SiO$_2$, 15 to 100% ethyl acetate in hexanes) gave benzyl (6-(1-((tert-butyldimethylsilyl)oxy)-2-fluoroethyl)pyridin-3-yl)carbamate (220 mg, 91%) as yellow oil. $^1$H NMR (400 MHz, DMSO-d$_6$) δ 10.02 (s, 1H), 8.59 (s, 1H), 7.92 (d, J=8.0 Hz, 1H), 7.45-7.20 (m, 6H), 5.13 (s, 2H), 4.99-4.93 (m, 1H), 4.65-4.34 (m, 2H), 0.86 (s, 9H), 0.07 (s, 3H), -0.005 (s, 3H) ppm. ESI-MS m/z calc. 404.1931, found 403.0 (M−1)$^−$; Retention time: 2.24 minutes.

Step 5:

A stirred solution of benzyl (6-(1-((tert-butyldimethylsilyl)oxy)-2-fluoroethyl)pyridin-3-yl)carbamate (2 g, 4.944 mmol) in MeOH (15 mL) degassed by bubbling argon through for 10 min. Pd/C (120 mg, 0.988 mmol) was added and the reaction mixture was stirred for 3 h under a hydrogen atmosphere. The reaction mixture was filtered through a pad of celite. The filtrate was concentrated in vacuo. Purification by flash chromatography (SiO$_2$, 10 to 30% ethyl acetate in hexanes) gave 6-(1-((tert-butyldimethylsilyl)oxy)-2-fluoroethyl)pyridin-3-amine (1.24 g, 92%) as a light yellow gum. $^1$H NMR (400 MHz, DMSO-d$_6$) δ 7.85 (s, 1H), 7.12 (d, J=8.3 Hz, 1H), 6.92 (d, J=8.1 Hz, 1H), 5.29 (s, 2H), 4.88-4.81 (m, 1H), 4.58-4.25 (m, 2H), 0.85 (s, 9H), 0.04 (s, 3H), -0.03 (s, 3H) ppm. ESI-MS m/z calc. 270.1564, found 271.1 (M+1)$^+$; Retention time: 1.58 minutes.

Intermediate M 6-(1-((tert-butyldimethylsilyl)oxy)-3-methoxypropyl)pyridin-3-amine

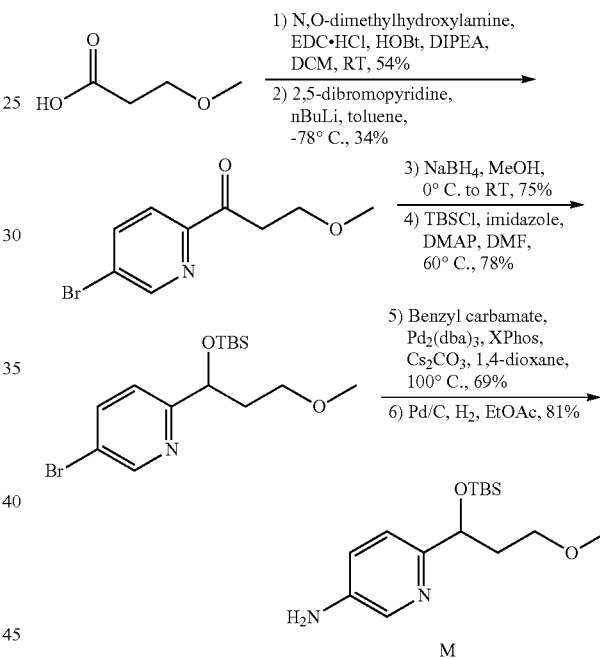

Step 1:

DIPEA (96.460 g, 130 mL, 746.35 mmol), EDC.HCl (85 g, 443.40 mmol), HOBt (50 g, 370.03 mmol) and N-methoxymethanamine hydrochloride (35 g, 358.81 mmol) were successively added to a stirred solution of 3-methoxypropanoic acid (30 g, 288.17 mmol) in DCM (800 mL). The reaction mixture was stirred at ambient temperature for 16 h. The reaction was quenched with water (500 mL) and extracted with DCM (2×500 mL). The combined organic extracts were washed with brine (300 mL), dried (Na$_2$SO$_4$) and concentrated in vacuo. Purification by flash chromatography (SiO$_2$, 10 to 40% ethyl acetate in hexanes) gave N,3-dimethoxy-N-methylpropanamide (23 g, 54%) as brown oil. $^1$H NMR (400 MHz, DMSO-d$_6$) δ 3.65 (s, 3H), 3.54 (t, J=12.7 Hz, 2H), 3.22 (s, 3H), 3.08 (s, 3H), 2.60 (t, J=12.4 Hz, 2H) ppm. ESI-MS m/z calc. 147.0895, found 148.1 (M+1)$^+$; Retention time: 1.53 minutes.

Step 2:

nBuLi (25 mL of 2 M, 50.000 mmol) was added to a stirred solution of 2,5-dibromopyridine (10 g, 42.213 mmol)

in toluene (300 mL) at −78° C. The reaction mixture was stirred for 45 min at −78° C. A solution of N,3-dimethoxy-N-methylpropanamide (7.5 g, 50.961 mmol) in toluene (100 mL) was added to the mixture and the stirring was continued for a further 30 min at −78° C. The reaction mixture was quenched with an aqueous saturated ammonium chloride (200 mL) solution. The aqueous phase was extracted with ethyl acetate (2×200 mL). The combined organic layers were washed with brine (200 mL), dried (Na$_2$SO$_4$), filtered and concentrated in vacuo. Purification by flash chromatography (SiO$_2$, 10 to 15% ethyl acetate in hexanes) gave 1-(5-bromopyridin-2-yl)-3-methoxypropan-1-one (3.5 g, 34%) as a yellow oil. $^1$H NMR (400 MHz, DMSO-d$_6$) δ 8.87 (s, 1H), 8.26 (dd, J=8.5, 1.8 Hz, 1H), 7.88 (d, J=8.3 Hz, 1H), 3.70 (t, J=6.2 Hz, 2H), 3.35 (t, J=6.2 Hz, 2H), 3.22 (s, 3H) ppm. ESI-MS m/z calc. 242.9895, found 244.0 (M+1)$^+$; Retention time: 3.42 minutes.

Step 3:

Sodium borohydride (1.6 g, 42.292 mmol) was added to a stirred solution of 1-(5-bromopyridin-2-yl)-3-methoxypropan-1-one (10 g, 43.467 mmol) in MeOH (100 mL) at 0° C. The reaction mixture was stirred at 0° C. for 30 min. The mixture was quenched by addition of water (30 mL). The mixture was concentrated in vacuo. The residue was diluted with water (100 mL) and extracted with ethyl acetate (2×200 mL). The combined organic layers were washed with brine (100 mL), dried (Na$_2$SO$_4$) and concentrated in vacuo to give 1-(5-bromopyridin-2-yl)-3-methoxypropan-1-ol (8 g, 75%) as a light yellow oil. $^1$H NMR (400 MHz, DMSO-d$_6$) δ 8.59 (d, J=1.9 Hz, 1H), 8.02 (dd, J=8.4, 2.2 Hz, 1H), 7.47 (d, J=8.4 Hz, 1H), 5.50 (d, J=5.2 Hz, 1H), 4.63 (quint, J=4.2 Hz, 1H), 3.52-3.46 (m, 1H), 3.41-3.32 (m, 1H), 3.21 (s, 3H), 2.02-1.94 (m, 1H), 1.78-1.70 (m, 1H) ppm. ESI-MS m/z calc. 245.0051, found 245.8 (M+1)$^+$; Retention time: 2.75 minutes.

Step 4:

Imidazole (8.299 g, 121.90 mmol) and DMAP (1.142 g, 9.346 mmol) were successively added to a stirred solution of 1-(5-bromopyridin-2-yl)-3-methoxypropan-1-ol (10 g, 40.634 mmol) in DMF (100 mL). TBSCl (9.187 g, 60.951 mmol) was added portionwise and the mixture was stirred at 60° C. for 3 h. The reaction mixture was quenched by addition of an aqueous ammonium chloride (500 mL) solution. The aqueous phase was extracted with ethyl acetate (200 mL). The organic layer was dried (MgSO$_4$), filtered and concentrated in vacuo. Purification by flash chromatography (SiO$_2$, 5 to 10% ethyl acetate in hexanes) gave 5-bromo-2-(1-((tert-butyldimethylsilyl)oxy)-3-methoxypropyl)pyridine (12 g, 78%) as a pale yellow oil. $^1$H NMR (400 MHz, Chloroform-d) δ 8.54 (d, J=1.7 Hz, 1H), 7.77 (dd, J=8.3, 2.0 Hz, 1H), 7.36 (d, J=8.3 Hz, 1H), 4.86-4.89 (m, 1H), 3.52-3.37 (m, 2H), 3.28 (s, 3H), 1.87-2.01 (m, 2H), 0.88 (s, 9H), 0.03 (s, 6H) ppm. ESI-MS m/z calc. 359.0916, found 362.2 (M+1)$^+$; Retention time: 2.83 minutes.

Step 5:

A 1,4-dioxane (100 mL) suspension of 5-bromo-2-(1-((tert-butyldimethylsilyl)oxy)-3-methoxypropyl)pyridine (10 g, 27.750 mmol), benzyl carbamate (6.3 g, 41.677 mmol) and cesium carbonate (18 g, 55.246 mmol) was degassed by bubbling nitrogen through for 30 min. Pd$_2$(dba)$_3$ (1.8 g, 1.966 mmol) and X-phos (1.9 g, 3.9856 mmol) were successively added under nitrogen at ambient temperature. The reaction mixture was heated to 100° C. in a preheated oil bath. The reaction mixture was stirred at 100° C. for 16 h. The reaction was filtered through a pad of celite. The filtrate was concentrated in vacuo. Purification by flash chromatography (SiO$_2$, 40 to 50% ethyl acetate in hexanes) gave benzyl (6-(1-((tert-butyldimethylsilyl)oxy)-3-methoxypropyl)pyridin-3-yl)carbamate (8.2 g, 69%) as a pale yellow oil. $^1$H NMR (400 MHz, DMSO-d$_6$) δ 9.96 (s, 1H), 8.56 (s, 1H), 7.90 (d, J=7.6 Hz, 1H), 7.43-7.31 (m, 6H), 5.17 (s, 2H), 4.81-4.78 (m, 1H), 3.47-3.41 (m, 1H), 3.31-3.27 (m, 1H), 3.20 (s, 3H), 1.90-1.88 (m, 1H), 1.80-1.75 (m, 1H), 0.85 (s, 9H), 0.01 (s, 3H), −0.16 (s, 3H) ppm. ESI-MS m/z calc. 430.2288, found 431.4 (M+1)$^+$; Retention time: 2.38 minutes.

Step 6:

A solution of benzyl (6-(1-((tert-butyldimethylsilyl)oxy)-3-methoxypropyl)pyridin-3-yl)carbamate (8 g, 18.578 mmol) in ethyl acetate (150 mL) was degassed by bubbling nitrogen through for 10 min. Pd/C (3 g, 10% w/w, 2.819 mmol) was added and the mixture was stirred for 18 h under an atmospheric pressure of hydrogen (balloon) at ambient temperature. The reaction mixture was filtered through a pad of celite, washing with more EtOAc. The filtrate was concentrated in vacuo. Purification by flash chromatography (SiO$_2$, 40 to 60% ethyl acetate in hexanes) gave 6-(1-((tert-butyldimethylsilyl)oxy)-3-methoxypropyl)pyridin-3-amine (4.5 g, 81%) as a pale yellow oil. $^1$H NMR (400 MHz, DMSO-d$_6$) δ: 7.80 (d, J=2.2 Hz, 1H), 7.04 (d, J=8.3 Hz, 1H), 6.90 (dd, J=2.5, 8.3 Hz, 1H), 5.16 (s, 2H), 4.68-4.65 (m, 1H), 3.43-3.37 (m, 1H), 3.32-3.24 (m, 1H), 3.19 (s, 3H), 1.83-1.73 (m, 2H), 0.83 (s, 9H), −0.01 (s, 3H), −0.18 (s, 3H) ppm. ESI-MS m/z calc. 296.192, found 297.2 (M+1)$^+$; Retention time: 2.16 minutes.

Intermediate N

3-Bromo-6-(difluoromethyl)-2-methoxypyridine

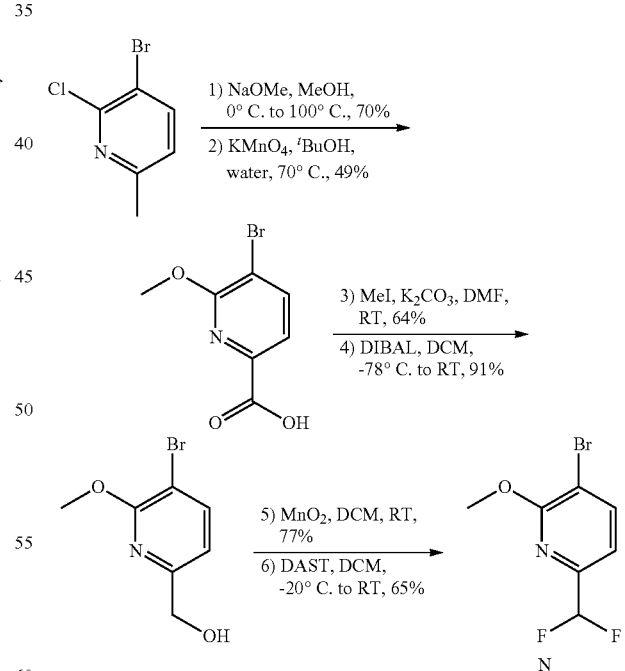

Step 1:

Sodium methoxide (20 mL of 25% w/v solution in MeOH, 92.552 mmol) was added at 0° C. to a stirred solution of 3-bromo-2-chloro-6-methylpyridine (8 g, 38.747 mmol) in MeOH (50 mL) in a sealed tube. The reaction mixture was heated at 100° C. for 16 h. The reaction mixture was concentrated in vacuo. The residue was diluted with water (100 mL) and extracted with EtOAc (3×100 mL). The combined organic layers were dried (Na$_2$SO$_4$), filtered and concentrated in vacuo to give 3-bromo-2-methoxy-6-methylpyridine (5.5 g, 70%) as a colourless oil. $^1$H NMR (400 MHz, DMSO-d$_6$) δ 7.82 (d, J=7.7 Hz, 1H), 6.76 (d, J=7.7 Hz, 1H), 3.88 (s, 3H), 2.35 (s, 3H) ppm. ESI-MS m/z calc. 200.9789, found 202.01 (M+1)$^+$; Retention time: 1.69 minutes.

Step 2:

KMnO$_4$ (13 g, 82.261 mmol) was added at ambient temperature to a stirred solution of 3-bromo-2-methoxy-6-methylpyridine (5.5 g, 27.221 mmol) in tert-butanol (150 mL) and water (300 mL). The reaction mixture was heated at 70° C. for 16 h. The reaction mixture was quenched by addition of a 1M aqueous solution of HCl (80 mL). The resulting mixture was stirred for 30 min, filtered and washed with EtOAc (2×100 mL). The mother liquors were extracted with EtOAc (2×50 mL). The combined organic layers were washed with a 0.5 N aqueous solution of NaOH (2×100 mL). The aqueous layer was collected, acidified by addition of a 12N aqueous solution of HCl and extracted with DCM (2×100 mL). The combined organic extracts were washed with brine, dried (Na$_2$SO$_4$), filtered and concentrated in vacuo to give 5-bromo-6-methoxypyridine-2-carboxylic acid (3.1 g, 49%) as white solid. H NMR (400 MHz, DMSO-d$_6$) δ 13.27 (br s, 1H), 8.19 (d, J=7.9 Hz, 1H), 7.57 (d, J=7.9 Hz, 1H), 3.98 (s, 3H) ppm. ESI-MS m/z calc. 230.9531, found 232.0 (M+1)$^+$; Retention time: 1.34 minutes.

Step 3:

Sodium carbonate (1.5 g, 14.153 mmol) was added to a stirred solution of 5-bromo-6-methoxypyridine-2-carboxylic acid (3 g, 12.929 mmol) in DMF (40 mL). Methyl iodide (3.8760 g, 1.7 mL, 27.308 mmol) was added and the mixture was stirred at ambient temperature for 16 h. The reaction mixture was quenched by addition of ice cold water (50 mL). The aqueous phase was extracted with ethyl acetate (3×50 mL). The combined organic layers were washed with water (2×100 mL), brine (50 mL), dried (Na$_2$SO$_4$), filtered and concentrated in vacuo to give methyl 5-bromo-6-methoxypyridine-2-carboxylate (2.02 g, 64%) as an off-white solid. $^1$H NMR (400 MHz, DMSO-d$_6$) δ 8.22 (d, J=7.8 Hz, 1H), 7.59 (d, J=7.8 Hz, 1H), 3.98 (s, 3H), 3.87 (s, 3H) ppm. ESI-MS m/z calc. 244.9688, found 246.1 (M+1)$^+$; Retention time: 3.21 minutes.

Step 4:

Diisobutylaluminum hydride (14 mL of 25% w/v solution in toluene, 24.610 mmol) was added at −78° C. to a stirred solution of methyl 5-bromo-6-methoxypyridine-2-carboxylate (2 g, 8.128 mmol) in DCM (80 mL). The reaction mixture was stirred at ambient temperature for 1 h. The reaction mixture was quenched by addition of a saturated aqueous solution of sodium tartrate (50 mL). The mixture was stirred for 30 min then extracted with DCM (3×100 mL). The combined organic layers were dried (Na$_2$SO$_4$), filtered and concentrated in vacuo to give (5-bromo-6-methoxy-2-pyridyl)methanol (1.62 g, 91%) as a white solid. $^1$H NMR (400 MHz, DMSO-d$_6$) δ 7.99 (d, J=7.8 Hz, 1H), 7.00 (d, J=7.6 Hz, 1H), 5.45 (t, J=11.8 Hz, 1H), 4.45 (d, J=5.9 Hz, 2H), 3.89 (s, 3H) ppm. ESI-MS m/z calc. 216.9738, found 218.0 (M+1)$^+$; Retention time: 2.93 minutes.

Step 5:

MnO$_2$ (8 g, 92.021 mmol) was added to a stirred solution of (5-bromo-6-methoxy-2-pyridyl)methanol (1.6 g, 7.3378 mmol) in DCM (80 mL). The reaction mixture was stirred at ambient temperature for 16 h. The reaction mixture was filtered and concentrated in vacuo to give 5-bromo-6-methoxypyridine-2-carbaldehyde (1.22 g, 77%) as off-white solid. $^1$H NMR (400 MHz, DMSO-d$_6$) δ 9.88 (s, 1H), 8.29 (d, J=7.7 Hz, 1H), 7.49 (d, J=7.7 Hz, 1H), 4.03 (s, 3H) ppm.

Step 6:

DAST (1.9740 g, 1.5 mL, 12.246 mmol) was slowly added at −20° C. to a stirred solution of 5-bromo-6-methoxypyridine-2-carbaldehyde (1.2 g, 5.5547 mmol) in DCM (30.000 mL). The reaction mixture was stirred at ambient temperature for 16 h. The reaction mixture was quenched by addition of ice-water. The pH of the solution was adjusted to 8-10 by addition of solid sodium hydrogen carbonate. The organic phase was collected, washed with water and brine, dried (Na$_2$SO$_4$), filtered and concentrated in vacuo. Purification by flash chromatography (SiO$_2$, 100% hexanes) gave 3-bromo-6-(difluoromethyl)-2-methoxypyridine (900 mg, 65%) as a pale yellow oil. $^1$H NMR (400 MHz, DMSO-d$_6$) δ 8.22 (d, J=7.8 Hz, 1H), 7.23 (d, J=7.7 Hz, 1H), 7.03-6.75 (m, 1H), 3.96 (s, 3H) ppm.

The following intermediate was prepared using the method described in Intermediate N step 6 except that 4-bromo-2-fluoro-3-methoxybenzaldehyde was used as the starting material:

| Compound Name | LC/MS | NMR (shifts in ppm) |
|---|---|---|
| 1-bromo-4-(difluoromethyl)-3-fluoro-2-methoxybenzene | ESI-MS m/z calc. 253.95541; Retention time: 0.92 minutes | $^1$H NMR (500 MHz, Chloroform-d) δ 7.35 (dd, J = 8.5, 1.8 Hz, 1H), 7.10 (ddt, J = 8.5, 6.5, 1.1 Hz, 1H), 6.77 (t, J = 54.8 Hz, 1H), 3.92 (d, J = 1.5 Hz, 3H) ppm. |

Intermediate O 1-(5-aminopyridin-2-yl)ethan-1-one

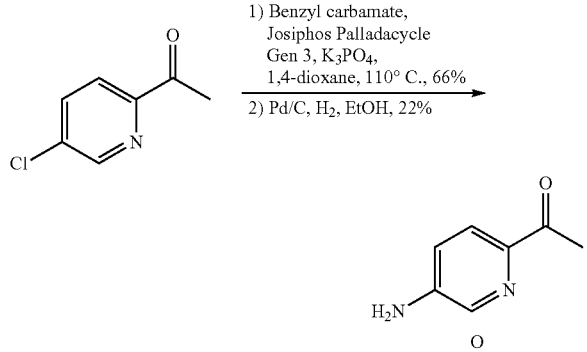

Step 1:

A 1,4-dioxane (4 mL) suspension of 1-(5-chloropyridin-2-yl)ethan-1-one (114 mg, 0.733 mmol), benzyl carbamate (170 mg, 1.125 mmol) and K$_3$PO$_4$ (310 mg, 1.460 mmol) was degassed and put under a nitrogen atmosphere. Josiphos Palladacycle Gen 3 (36 mg, 0.039 mmol) was added under nitrogen at ambient temperature. The suspension was degassed by bubbling nitrogen through and heated overnight at 110° C. The reaction mixture was cooled down to ambient temperature and partitioned between water and EtOAc. The aqueous layer was extracted further with EtOAc. The combined organic phases were dried (MgSO$_4$), filtered and concentrated in vacuo. Purification by flash chromatography (SiO$_2$, 0 to 100% EtOAc in heptane) gave benzyl (6-acetylpyridin-3-yl)carbamate (130 mg, 66%). $^1$H NMR (500 MHz, Chloroform-d) δ 8.55 (d, J=2.5 Hz, 1H), 8.11 (d, J=8.7 Hz, 1H), 8.04 (d, J=8.6 Hz, 1H), 7.46-7.31 (m, 5H), 6.98 (s, 1H), 5.24 (s, 2H), 2.68 (s, 3H) ppm. ESI-MS m/z calc. 270.10043, found 271.3 (M+1)$^+$; 269.3 (M−1)$^−$; Retention time: 0.75 minutes.

Step 2:

A solution of benzyl (6-acetylpyridin-3-yl)carbamate (1.37 g, 5.069 mmol) in EtOH (50 mL) was added under nitrogen to a flask containing Pd/C (190 mg of 10% w/w, 0.1785 mmol). The reaction mixture was degassed and stirred overnight under an atmospheric pressure of hydrogen. The reaction mixture was filtered through a pad of celite. The filtrate was concentrated in vacuo. Purification by flash chromatography (SiO$_2$, 0 to 100% of 3:1 ethyl acetate:EtOH containing 2% of NH$_4$OH in heptane) gave 1-(5-aminopyridin-2-yl)ethan-1-one (154 mg, 22%) as a light brown solid. $^1$H NMR (500 MHz, Chloroform-d) δ 8.06 (d, J=2.7 Hz, 1H), 7.91 (d, J=8.5 Hz, 1H), 6.98 (dd, J=8.5, 2.8 Hz, 1H), 2.64 (s, 3H) ppm; amine NH$_2$ not observed. ESI-MS m/z calc. 136.06366, found 137.1 (M+1)$^+$; Retention time: 0.31 minutes.

Intermediate P 2-(4-(benzyloxy)-3-fluoro-2-methoxyphenyl)acetic acid

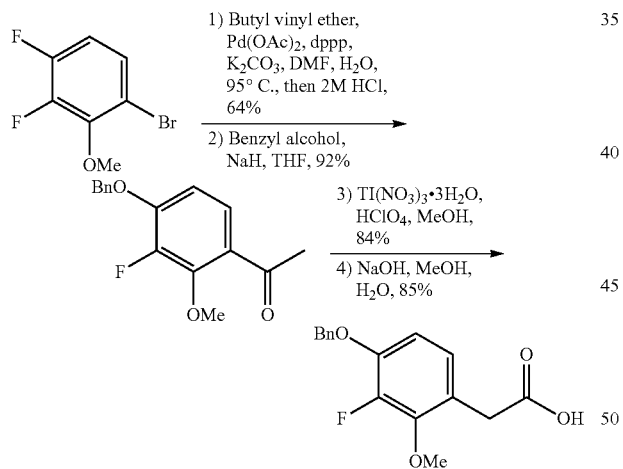

Step 1:

A mixture of 1-bromo-3,4-difluoro-2-methoxybenzene (5 g, 22.42 mmol), butyl vinyl ether (9 mL, 66.49 mmol), K$_2$CO$_3$ (3.7372 g, 27.04 mmol), dppp (612.81 mg, 1.486 mmol), and Pd(OAc)$_2$ (151.96 mg, 0.677 mmol) in DMF (50 mL) and H$_2$O (5 mL) was heated at 95° C. under a nitrogen atmosphere overnight. 2 M HCl (80 mL, 160.0 mmol) was added at ambient temperature and the mixture was stirred for 30 min. The mixture was extracted with EtOAc (2×20 mL). The combined organic extracts were washed with NaHCO$_3$ (10 mL of saturated aqueous solution), then brine, dried (MgSO$_4$), filtered and concentrated in vacuo. Purification by flash chromatography (120 g SiO$_2$, 0 to 5% EtOAc in hexanes) gave 1-(3,4-difluoro-2-methoxyphenyl)ethan-1-one (2.687 g, 64%) as a yellow oil. $^1$H NMR (400 MHz, Chloroform-d) δ 7.50 (ddd, J=9.0, 6.1, 2.3 Hz, 1H), 6.92 (td, J=9.0, 6.9 Hz, 1H), 4.08 (d, J=2.7 Hz, 3H), 2.60 (s, 3H) ppm. $^{19}$F NMR (376 MHz, Chloroform-d) δ −129.21 (d, J=19.0 Hz), −153.39 (d, J=19.0 Hz) ppm.

Step 2:

To a stirred suspension of sodium hydride (1.05 g, 60% w/w, 26.253 mmol) in DMF (40 mL) at room temperature was added a solution of benzyl alcohol (2.9 g, 26.818 mmol) in DMF (10 mL) and the mixture was stirred for 5 min. 1-(3,4-difluoro-2-methoxyphenyl)ethan-1-one (5 g, 26.859 mmol) was added and the reaction mixture was stirred at room temperature for 30 min. HCl (10 mL of 2 N aqueous solution) and brine (100 mL) were added and the mixture was extracted with EtOAc (100 mL then 50 mL). The combined organic extracts were washed with brine (2×20 mL), dried (Na$_2$SO$_4$), filtered and concentrated in vacuo. Purification by flash chromatography (SiO$_2$, 10 to 30% EtOAc in heptane) gave 1-(4-(benzyloxy)-3-fluoro-2-methoxyphenyl)ethan-1-one (5.03 g, 68%) as a yellow solid. $^1$H NMR (400 MHz, Chloroform-d) δ 7.51 (dd, J=8.9, 2.1 Hz, 1H), 7.44-7.34 (m, 5H), 6.76 (dd, J=8.9, 7.1 Hz, 1H), 5.17 (s, 2H), 4.03 (d, J=2.3 Hz, 3H), 2.58 (s, 3H) ppm. ESI-MS m/z calc. 274.1005, found 273.02 (M−1)$^−$; Retention time: 0.98 minutes.

Step 3:

A solution of 1-(4-(benzyloxy)-3-fluoro-2-methoxyphenyl)ethan-1-one (14.8 g, 53.958 mmol) in MeOH (50 mL) was added dropwise to a stirred solution of Tl(NO$_3$)$_3$·3H$_2$O (24 g, 54.0 mmol) and perchloric acid (50 mL of 60% w/v in water, 298.63 mmol) in MeOH (200 mL). The reaction mixture was stirred at room temperature for 4.5 h. The reaction mixture was filtered, washing through with MeOH (2×50 mL). The filtrate was poured into water (1 L) and extracted with dichloromethane (2×200 mL). The combined organic extracts were washed with water (100 mL) and brine (50 mL), dried (Na$_2$SO$_4$), filtered and concentrated in vacuo to give methyl 2-(4-benzyloxy-3-fluoro-2-methoxy-phenyl)acetate (15.25 g, 84%) as a yellow oil. $^1$H NMR (400 MHz, Chloroform-d) δ 7.44-7.32 (m, 5H), 6.84 (dd, J=8.7, 1.8 Hz, 1H), 6.67 (t, J=8.2 Hz, 1H), 5.11 (s, 2H), 3.93 (d, J=1.8 Hz, 3H), 3.69 (s, 3H), 3.58 (s, 2H) ppm. ESI-MS m/z calc. 304.1111, found 305.19 (M+1)$^+$; Retention time: 2.44 minutes.

Step 4:

Methyl 2-(4-benzyloxy-3-fluoro-2-methoxy-phenyl)acetate (15.2 g, 49.949 mmol) was added to a solution of sodium hydroxide (6 g, 150.01 mmol) in MeOH (30 mL) and water (10 mL). The solution was stood at room temperature for 14 h giving an orange solid. The crude product was diluted with 2 N sodium hydroxide solution (200 mL) and washed with dichloromethane (2×30 mL). The aqueous layer was acidified with 6 M hydrochloric acid (100 mL) and extracted with dichloromethane-isopropanol (9:1, 2×150 mL). The combined organic extracts were dried (Na$_2$SO4), filtered and concentrated in vacuo to give 2-(4-(benzyloxy)-3-fluoro-2-methoxyphenyl)acetic acid (13.15 g, 85%) as an orange solid. $^1$H NMR (400 MHz, Chloroform-d) δ 7.46-7.33 (m, 5H), 6.85 (dd, J=8.7, 1.8 Hz, 1H), 6.69 (t, J=8.0 Hz, 1H), 5.11 (s, 2H), 3.96 (d, J=2.3 Hz, 3H), 3.62 (s, 2H) ppm; OH acid not observed. ESI-MS m/z calc. 290.0954, found 289.0 (M−1)$^−$; Retention time: 2.19 minutes.

Intermediate O (R)-4,4,4-trifluoro-3-hydroxy-3-methylbutan-2-one

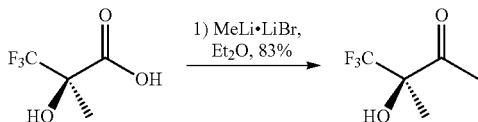

Step 1:

A jacketed glass reactor, dried and placed under nitrogen atmosphere, was charged with (R)-3,3,3-trifluoro-2-hydroxy-2-methylpropanoic acid (1.0 kg, 6.3261 mol) and diethyl ether (10 L). Methyllithium lithium bromide complex (3.4 L of 1.5 M in $Et_2O$, 5.1000 mol) was added slowly with evolution of gas and heat formation. The reactor was cooled to maintain a temperature of approximately 16° C. Then methyllithium with lithium bromide (6.1 L of 2.2 M in $Et_2O$, 13.420 mol) was added slowly. After addition of a total of 2 equivalents, the evolution of gas stopped and the rate of addition was decreased. The mixture was stirred overnight at ambient temperature. The reaction mixture was cooled to 0° C. and transferred to an extraction flask carrying a mixture of water (6 L), ice (2 L) and brine (2 L). The mixture was neutralized by the addition of citric acid (1.6 kg, 960.96 mL, 8.3280 mol) and was stirred for 30 min. The aqueous phase was separated and extracted with diethyl ether (2×2.5 L). The combined organic layers were concentrated in vacuo to approximately 2 L. The distillate was colored yellow and consisted of 0.8% w/w product. After further distillation only 25 g of product was recovered from the distillate. The distillation residue was further concentrated in a distillation setup with vigreux (30 cm height) at normal pressure. The distillation was continued at reduced pressure (770 mbar) and the pressure was gradually lowered (until 200 mbar) with the collection flask cooled in ice and a cold trap between pump and setup. Mixed fractions were collected until the distillation temperature reached 71° C. The major fraction (590 g) was then collected until the distillation temperature dropped below 70° C. The combined mixed fractions were poured in brine and extracted with diethyl ether (3×75 mL). The combined organic layers were dried ($Na_2SO4$), filtered and concentrated in a distillation setup at normal pressure. The product was distilled at reduced pressure (200 mbar) to give the product as a colourless oil (198 g). The collected mixed fractions were redistilled to afford more product (44.25 g). All portions of product were combined (857 g), dried by addition of potassium carbonate (52 g) and left standing for 6 h. The water level dropped below detectable level and the mixture was filtered over glass filter to give (R)-4,4,4-trifluoro-3-hydroxy-3-methylbutan-2-one (815 g, 83%) as a colourless oil (815 g). $^1$H NMR (300 MHz, Chloroform-d) δ 4.33 (s, 1H), 2.40 (d, J=1.1 Hz, 3H), 1.57 (d, J=1.1 Hz, 3H) ppm. $^{19}$F NMR (282 MHz, Chloroform-d) δ −77.96 ppm.

Example 13

E-VIPR Assay Detecting and Measuring $Na_V$ Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential*, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human $Na_V$ 1.8 with full channel activity were seeded into microtiter 384-well plates, pre-coated with matrigel, at a density of 25,000 cells per well. 2.5-5% KIR2.1 Bacmam virus was added to the final cell suspension before seeding into cell plates. HEK cells were grown in Dulbecco's Modified Eagle's Medium (DMEM) supplemented with 10% FBS (Fetal Bovine Serum, qualified; Sigma #F4135), 1% NEAA (Non-Essential Amino Acids, Gibco #11140), 1% HEPES (Gibco #15630), 1% Pen-Strep (Penicillin-Streptomycin; Gibco #15140) and 5 μg/ml Blasticidin (Gibco #R210-01). Cells were expanded in vented cap cell culture flasks, with 90-95% humidity and 5% $CO_2$.

Reagents and Stock Solutions:

100 mg/mL Pluronic F-127 (Sigma #P2443), in dry DMSO

Compound Plates: Corning 384-well Polypropylene Round Bottom #3656

Cell Plates: 384-well tissue culture treated plates (Greiner #781091-2B)

2.5-5% KIR 2.1 Bacmam virus (produced in-house), prepared as described in Section 3.3 of J. A. Fornwald et al., *Gene Expression in Mammalian Cells Using BacMam, a Modified Baculovirus System*, 1350 Methods in Molecular Biology 95-116 (2016), the entire contents of which are incorporated by reference. The concentration used can be dependent on viral titer of each batch.

5 mM $DiSBAC_6(3)$, a voltage sensitive oxonol acceptor (CAS number 169211-44-3; 5-[3-(1,3-dihexylhexahydro-4,6-dioxo-2-thioxo-5-pyrimidinyl)-2-propen-1-ylidene]-1,3-dihexyldihydro-2-thioxo-4,6(1H,5H)-pyrimidinedione), in dry DMSO. The preparation of $DiSBAC_6(3)$ is analogous to that of $DiSBAC_4(3)$ as described in *Voltage Sensing by Fluorescence Resonance Energy Transfer in Single Cells*, Gonzalez, J. E. and Tsien, R. Y. (1995) *Biophys. J.* 69, 1272-1280.

5 mM CC2-DMPE, a commercially available membrane-bound coumarin phospholipid FRET donor (ThermoFisher Scientific catalog number K1017, CAS number 393782-57-5; tetradecanoic acid, 1,1'-[(1R)-1-[8-(6-chloro-7-hydroxy-2-oxo-2H-1-benzopyran-3-yl)-3-hydroxy-3-oxido-8-oxo-2,4-dioxa-7-aza-3-phosphaoct-1-yl]-1,2-ethanediyl]ester) was prepared in dry DMSO. See also, *Improved indicators of cell membrane potential that use fluorescence resonance energy transfer*, Gonzalez, J. E. and Tsien, R. Y. (1997) *Chem. Biol.* 4, 269-277.

Voltage Assay Background Suppression Compound (VABSC-1) is prepared in $H_2O$ (89-363 mM, range used to maintain solubility)

Human Serum (HS, Millipore #S1P1-01KL, or Sigma SLBR5469V and SLBR5470V as a 50%/50% mixture, for 25% assay final concentration)

Bath 1 Buffer:

Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath 1 Buffer:

Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2× Concentration):

Bath 1 Buffer containing 0.5% β-cyclodextrin (made fresh prior to each use, Sigma #C4767), 8 µM CC2-DMPE and 2 µM DiSBAC$_6$(3). The solution was made by adding 10% Pluronic F127 stock equal to combined volumes of CC2-DMPE and DiSBAC$_6$(3). The order of preparation was first mix Pluronic and CC2-DMPE, then add DiSBAC$_6$(3), then while vortexing add Bath 1/β-Cyclodextrin.

Compound Loading Buffer (2× concentration): Na/TMA Cl Bath 1 Buffer containing HS (omitted in experiments run in the absence of human serum (HS))$_{50}$%, VABSC-1 1 mM, BSA 0.2 mg/ml (in Bath-1), KCl 9 mM, DMSO 0.625%.

Assay Protocol (7 Key Steps):

1) To reach the final concentration in each well, 375 nL of each compound was pre-spotted (in neat DMSO) into polypropylene compound plates at 240× desired final concentration from an intermediate stock concentration of 0.075 mM, in an 11 point dose response, 3-fold dilution, resulting in a top dose of 300 nM final concentration in the cell plate. Vehicle control (neat DMSO), and positive control (an established Na$_V$1.8 inhibitor, 25 µM final in assay in DMSO) were added manually to the outermost columns of each plate respectively. The compound plate was backfilled with 45 µL per well of Compound Loading Buffer resulting in a 240-fold dilution of compound following a 1:1 transfer of compound into the cell plate (see Step 6). Final DMSO concentration for all wells in the assay was 0.625% (0.75% DMSO was supplemented to the Compound Loading Buffer for a final DMSO concentration of 0.625%). This assay dilution protocol was adjusted to enable a higher dose range to be tested in the presence of HS or if the final assay volume was altered.

2) Hexyl Dye Solution was prepared.

3) Cell plates were prepared. On the day of the assay, the media was aspirated, and the cells were washed three times with 80 µL of Bath-1 buffer, maintaining 25 µL residual volume in each well.

4) 25 µL per well of Hexyl Dye Solution was dispensed into the cell plates. The cells were incubated for 20 minutes at room temperature or ambient conditions in darkness.

5) 45 µL per well of Compound Loading Buffer was dispensed into compound plates.

6) The cell plates were washed three times with 80 µL per well of Bath-1 Buffer, leaving 25 L of residual volume. Then 25 µL per well from compound plate was transferred to each cell plate. The mixture was incubated for 30 minutes at room temperature/ambient conditions.

7) The cell plate containing compound was read on E-VIPR using the current-controlled amplifier to deliver stimulation wave pulses using a symmetrical biphasic waveform. The user-programmed electrical stimulus protocols were 1.25-4 Amps and 4 millisecond pulse width (dependent on electrode composition) were delivered at 10 Hz for 10 seconds. A pre-stimulus recording was performed for each well for 0.5 seconds to obtain the un-stimulated intensities baseline. The stimulatory waveform was followed by 0.5 seconds of post-stimulation recording to examine the relaxation to the resting state. All E-VIPR responses were measured at 200 Hz acquisition rate.

Data Analysis:

Data were analyzed and reported as normalized ratios of emission intensities measured in the 460 nm and 580 nm channels. The response as a function of time was reported as the ratios obtained using the following formula:

$$R(t) = \frac{(intensity_{460\,nm})}{(intensity_{580\,nm})}$$

The data were further reduced (i.e. normalized) by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound (i.e. the maximum amplitude of the ratio response or number of action potential peaks, at the beginning of the pulse train in the presence of the test compound). Using this analysis protocol, dose response curves were plotted and IC$_{50}$ values were generated for various compounds of the present invention.

Compounds having a measured IC$_{50}$ value less than 0.01 µM in the E-VIPR assay described above include: 1, 2, 3, 4, 6, 7, 8, 11, 14, 15, 16, 37, 38, 40, 42, 47, 49, 51, 53, 54, 60, 70, 80, 82, 83, and 84.

Compounds having a measured IC$_{50}$ value less than 0.1 µM and greater than or equal to 0.01 µM in the E-VIPR assay described above include: 9, 10, 12, 17, 18, 19, 20, 21, 22, 35, 45, 56, 59, 66, 73, 85, 86, and 91.

Compounds having a measured IC$_{50}$ value less than 1 µM and greater than or equal to 0.1 µM in the E-VIPR assay described above include: 23, 24, 26, 29, 31, 33, 36, 55, 62, 71, 87, and 88.

Compounds having a measured IC$_{50}$ value greater than or equal to 1 µM in the E-VIPR assay described above include: 25, 27, 28, 30, 32, 34, 39, 41, 43, 44, 46, 48, 50, 52, 57, 58, 61, 63, 64, 65, 67, 68, 69, 72, 74, 75, 77, 78, 79, 81, 89, and 90.

An IC$_{50}$ value was not determined in the E-VIPR assay described above for Compounds 5, 13, and 76.

Many modifications and variations of the embodiments described herein may be made without departing from the scope, as is apparent to those skilled in the art. The specific embodiments described herein are offered by way of example only.

What is claimed is:

1. A compound of formula (I-A-1):

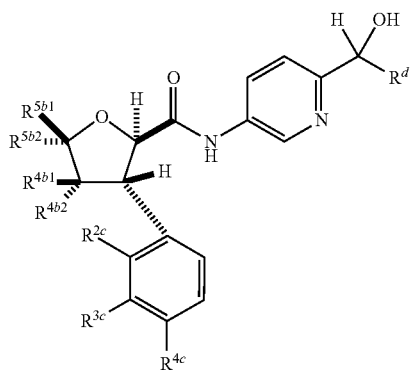

or a pharmaceutically acceptable salt thereof, wherein:

$R^d$ is $(CH_2)_m(CHR^e)_n(CH_2)_pH$;

m, n, and p are each independently 0 or 1;

$R^e$ is H, OH, halo, $C_1$-$C_6$ alkoxy, or $C_1$-$C_6$ haloalkoxy;

$R^{4b1}$ and $R^{4b2}$ are each independently H, $C_1$-$C_6$ alkyl, $C_3$-$C_6$ cycloalkyl, or $C_1$-$C_6$ haloalkyl;

$R^{5b1}$ and $R^{5b2}$ are each independently H, $C_1$-$C_6$ alkyl, $C_3$-$C_6$ cycloalkyl, or $C_1$-$C_6$ haloalkyl;

$R^{2c}$ is H, OH, halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, or -$L^1$-$L^2$-($C_3$-$C_6$ cycloalkyl), wherein said cycloalkyl is optionally substituted with 1-2 halo;

$L^1$ is a bond or O;

$L^2$ is a bond or $C_1$-$C_6$ alkylene;

$R^{3c}$ is H, halo, $C_1$-$C_6$ alkyl, or $C_1$-$C_6$ haloalkyl; or $R^{2c}$ and $R^{3c}$, together with the carbon atoms to which they are attached, form a ring of formula:

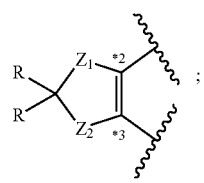

$Z_1$ and $Z_2$ are each independently O or $CH_2$;

each R is independently H or halo; and $R^{4c}$ is H, halo, $C_1$-$C_6$ alkyl, $C_1$-$C_6$ haloalkyl, $C_1$-$C_6$ alkoxy, or $C_1$-$C_6$ haloalkoxy.

2. The compound of claim 1, wherein the compound has formula (I-B-1):

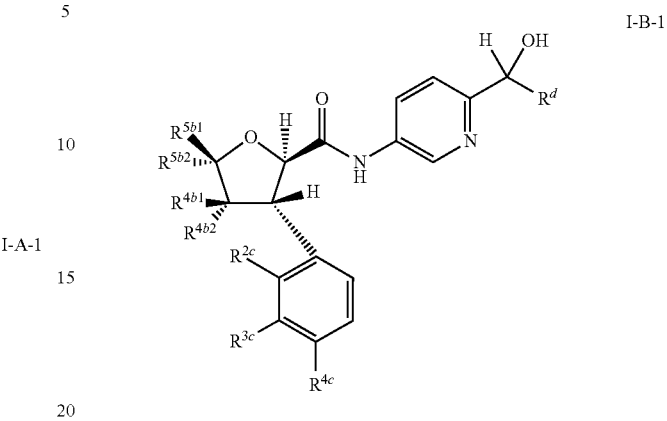

or a pharmaceutically acceptable salt thereof.

3. The compound of claim 1, or a pharmaceutically acceptable salt thereof, wherein $R^{4b1}$ is H or $C_1$-$C_6$ alkyl, optionally wherein $R^{4b1}$ is H or $CH_3$.

4. The compound of claim 1, or a pharmaceutically acceptable salt thereof, wherein $R^{4b2}$ is H or $C_1$-$C_6$ alkyl, optionally wherein $R^{4b2}$ is H or $CH_3$.

5. The compound of claim 1, or a pharmaceutically acceptable salt thereof, wherein $R^{5b1}$ is $C_1$-$C_6$ alkyl or $C_1$-$C_6$ haloalkyl, optionally wherein $R^{5b1}$ is $CH_3$ or $CF_3$.

6. The compound of claim 1, or a pharmaceutically acceptable salt thereof, wherein $R^{5b2}$ is $C_1$-$C_6$ alkyl or $C_1$-$C_6$ haloalkyl, optionally wherein $R^{5b2}$ is $CH_3$ or $CF_3$.

7. The compound of claim 1, or a pharmaceutically acceptable salt thereof, wherein $R^{2c}$ is OH, halo, $C_1$-$C_6$ alkyl, $C_1$-$C_6$ alkoxy, or $C_1$-$C_6$ haloalkoxy, optionally wherein $R^{2c}$ is OH, $C_1$, $CH_3$, $OCH_3$, $OCD_3$, $OCH_2CH_3$, $OCH(CH_3)_2$, $OCH_2CH_2F$, or $OCH_2CHF_2$.

8. The compound of claim 1, or a pharmaceutically acceptable salt thereof, wherein $R^{3c}$ is H, halo, $C_1$-$C_6$ alkyl, or $C_1$-$C_6$ haloalkyl, optionally wherein $R^{3c}$ is H, F, $CH_3$, $CHF_2$, or $CF_3$.

9. The compound of claim 1, or a pharmaceutically acceptable salt thereof, wherein $R^{4c}$ is H, halo, $C_1$-$C_6$ haloalkyl, $C_1$-$C_6$ alkoxy, or $C_1$-$C_6$ haloalkoxy, optionally wherein $R^{4c}$ is H, F, $CHF_2$, $OCH_2CH_3$, $OCHF_2$, $OCF_3$.

10. The compound of claim 1, or a pharmaceutically acceptable salt thereof, wherein $R^d$ is $(CH_2)_pH$, optionally wherein $R^d$ is H or $CH_3$.

11. The compound of claim 1, or a pharmaceutically acceptable salt thereof, wherein $R^d$ is $(CHR^e)_n(CH_2)_pH$, optionally wherein $R^d$ is $CH_2F$, $CH_2OH$, or $CH(OH)CH_3$.

12. The compound of claim 1, or a pharmaceutically acceptable salt thereof, wherein $R^d$ is $(CH_2)_m(CHR^e)_nH$, optionally wherein $R^d$ is $CH_2OCH_3$ or $CH_2CH_2OCH_3$.

13. The compound of claim 1, wherein the compound is selected from:

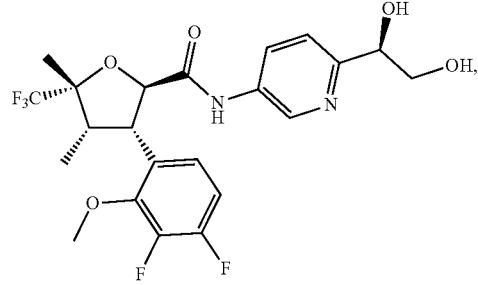

(2R,3S,4S,5R)-3-(3,4-difluoro-2-
methoxyphenyl)-N-(6-((R)-1,2-
dihydroxyethyl)pyridin-3-yl)-4,5-dimethyl-5-
(trifluoromethyl)tetrahydrofuran-2-carboxamide

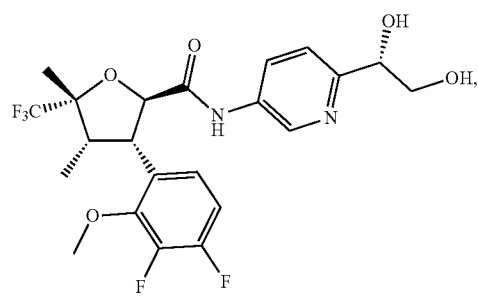

(2R,3S,4S,5R)-3-(3,4-difluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide

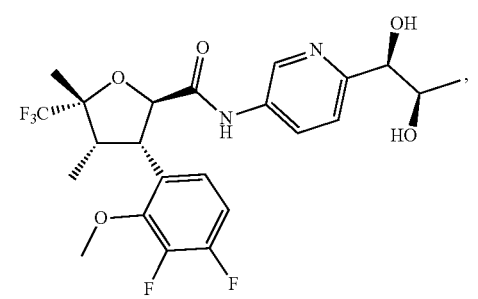

(2R,3S,4S,5R)-3-(3,4-difluoro-2-
methoxyphenyl)-N-(6-((1R,2R)-1,2-
dihydroxyethyl)pyridin-3-yl)-4,5-dimethyl-5-
(trifluoromethyl)tetrahydrofuran-2-carboxamide

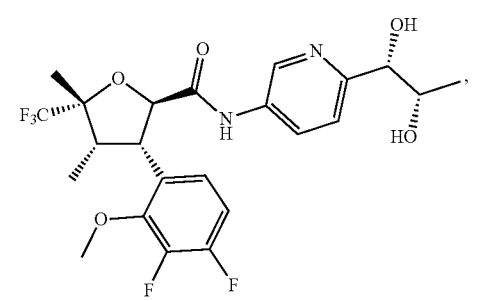

(2R,3S,4S,5R)-3-(3,4-difluoro-2-
methoxyphenyl)-N-(6-((1S,2S)-1,2-
dihydroxyethyl)pyridin-3-yl)-4,5-dimethyl-5-
(trifluoromethyl)tetrahydrofuran-2-carboxamide

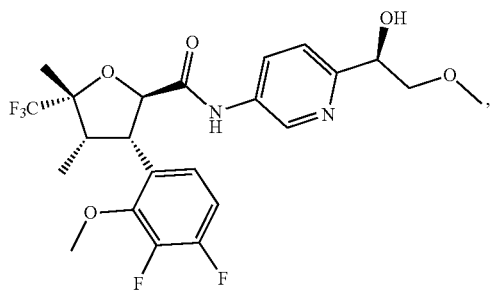

(2R,3S,4S,5R)-3-(3,4-difluoro-2-
methoxyphenyl)-N-(6-((R)-1-hydroxy-2-
methoxyethyl)pyridin-3-yl)-4,5-dimethyl-5-
(trifluoromethyl)tetrahydrofuran-2-carboxamide

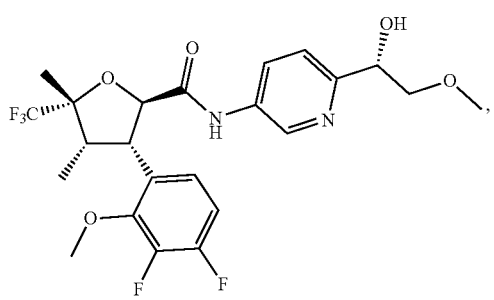

(2R,3S,4S,5R)-3-(3,4-difluoro-2-
methoxyphenyl)-N-(6-((S)-1-hydroxy-2-
methoxyethyl)pyridin-3-yl)-4,5-dimethyl-5-
(trifluoromethyl)tetrahydrofuran-2-carboxamide

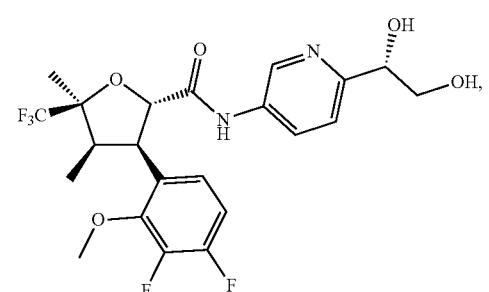

(2S,3R,4R,5S)-3-(3,4-difluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide

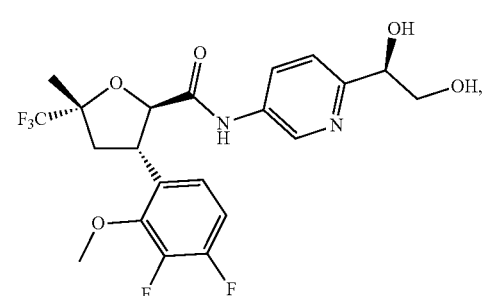

(2R,3S,5R)-3-(3,4-difluoro-2-methoxyphenyl)-
N-(6-((R)-1,2-dihydroxyethyl)pyridin-3-yl)-5-
methyl-5-(trifluoromethyl)tetrahydrofuran-2-
carboxamide

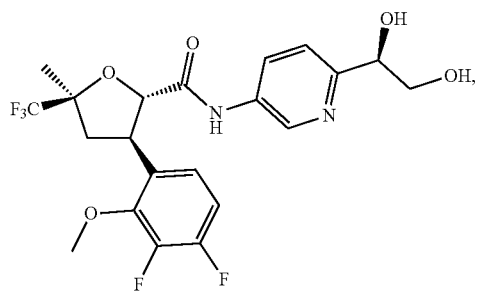

(2R,3R,5S)-3-(3,4-difluoro-2-methoxyphenyl)-
N-(6-((R)-1,2-dihydroxyethyl)pyridin-3-yl)-5-
methyl-5-(trifluoromethyl)tetrahydrofuran-2-
carboxamide

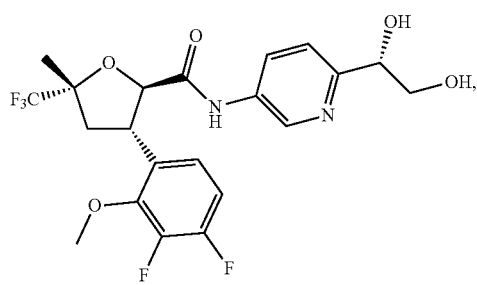

(2R,3S,5R)-3-(3,4-difluoro-2-methoxyphenyl)-N-(6-
((S)-1,2-dihydroxyethyl)pyridin-3-yl)-5-methyl-5-
(trifluoromethyl)tetrahydrofuran-2-carboxamide

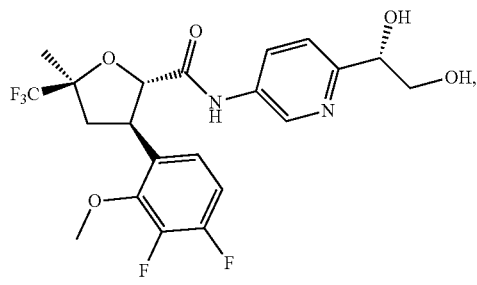

(2S,3R,5S)-3-(3,4-difluoro-2-methoxyphenyl)-N-
(6-((S)-1,2-dihydroxyethyl)pyridin-3-yl)-5-methyl-
5-(trifluoromethyl)tetrahydrofuran-2-carboxamide

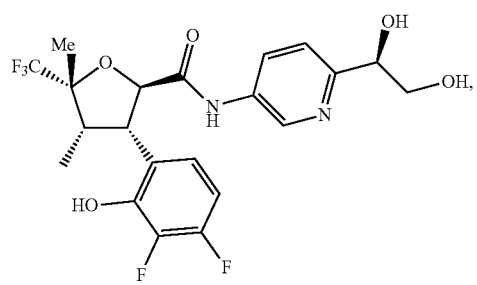

(2R,3S,4S,5R)-3-(3,4-difluoro-2-hydroxyphenyl)-
N-(6-((R)-1,2-dihydroxyethyl)pyridin-3-yl)-4,5-
dimethyl-5-(trifluoromethyl)tetrahydrofuran-2-
carboxamide

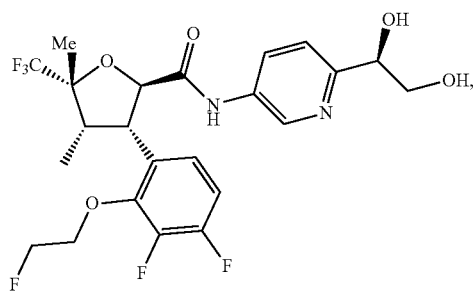

(2R,3S,4S,5R)-3-(3,4-difluoro-2-(2-
fluoroethoxy)phenyl)-N-(6-((R)-1,2-
dihydroxyethyl)pyridin-3-yl)-4,5-dimethyl-5-
(trifluoromethyl)tetrahydrofuran-2-carboxamide

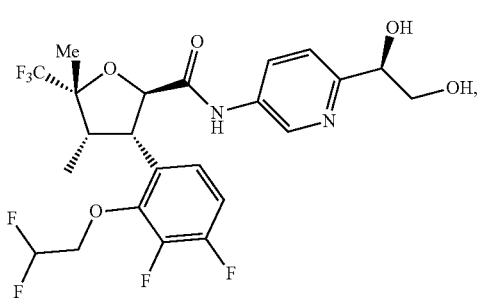

(2R,3S,4S,5R)-3-(2-(2,2-difluoroethoxy-3,4-
difluorophenyl)-N-(6-((R)-1,2-
dihydroxyethyl)pyridin-3-yl)-4,5-dimethyl-5-
(trifluoromethyl)tetrahydrofuran-2-carboxamide

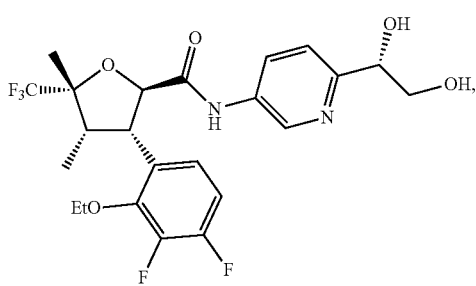

(2R,3S,4S,5R)-N-(6-((S)-1,2-
dihydroxyethyl)pyridin-3-yl)-3-(2-ethoxy-3,4-
difluorophenyl)-4,5-dimethyl-5-
(trifluoromethyl)tetrahydrofuran-2-carboxamide

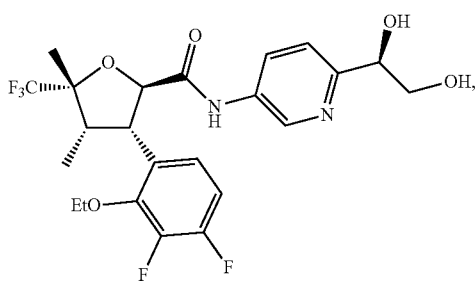

(2R,3S,4S,5R)-N-(6-((R)-1,2-
dihydroxyethyl)pyridin-3-yl)-3-(2-ethoxy-3,4-
difluorophenyl)-4,5-dimethyl-5-
(trifluoromethyl)tetrahydrofuran-2-carboxamide

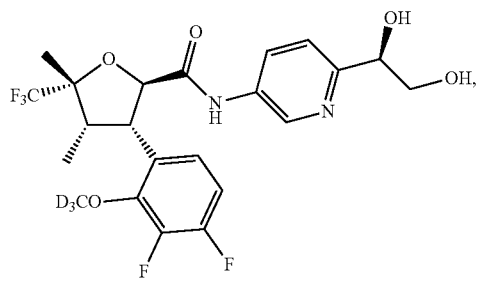

(2R,3S,4S,5R)-3-(3,4-difluoro-2-(methoxy-d₃)phenyl)-N-(6-((R)-1,2-dihydroxyethyl)pyridin-3-yl)-4,5-dimethyl-5-(trifluoromethyl)tetrahydrofuran-2-carboxamide

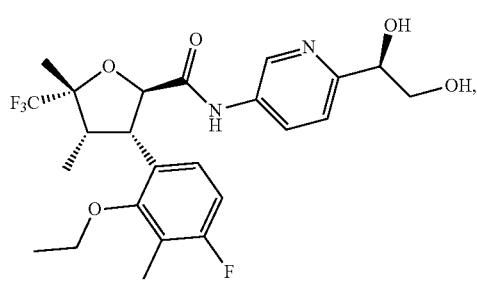

(2R,3S,4S,5R)-N-(6-((R)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide

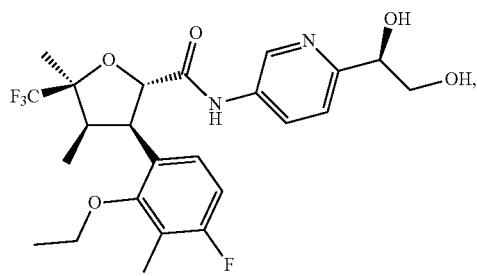

(2S,3R,4R,5S)-N-(6-((R)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide

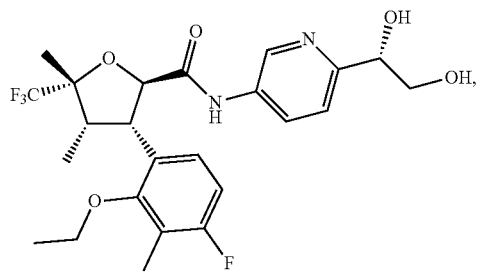

(2R,3S,4S,5R)-N-(6-((S)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide

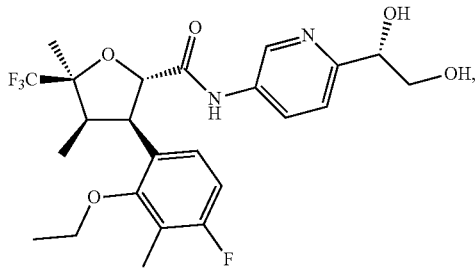

(2S,3R,4R,5S)-N-(6-((S)-1,2-dihydroxyethyl)pyridin-3-yl)-3-(2-ethoxy-4-fluoro-3-methylphenyl)-4,5-dimethyl-5-(trifluoromethyl)tetrahydrofuran-2-carboxamide

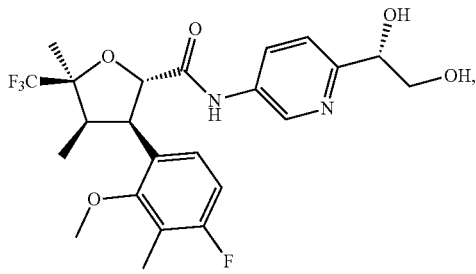

(2S,3R,4R,5S)-N-(6-((S)-1,2-dihydroxyethyl)pyridin-3-yl)-3-(4-fluoro-2-methoxy-3-methylphenyl)-4,5-dimethyl-5-(trifluoromethyl)tetrahydrofuran-2-carboxamide

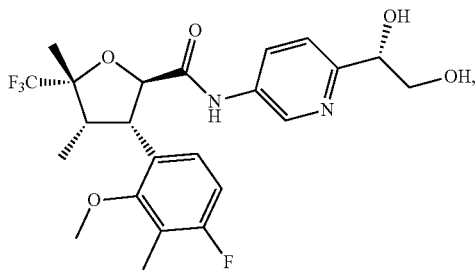

(2R,3S,4S,5R)-N-(6-((S)-1,2-dihydroxyethyl)pyridin-3-yl)-3-(4-fluoro-2-methoxy-3-methylphenyl)-4,5-dimethyl-5-(trifluoromethyl)tetrahydrofuran-2-carboxamide

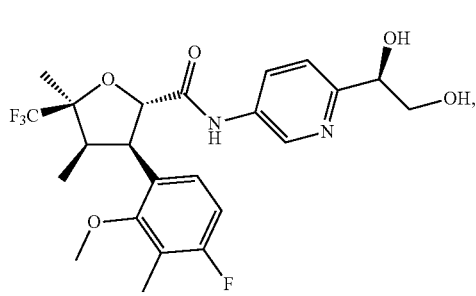

(2S,3R,4R,5S)-N-(6-((R)-1,2-dihydroxyethyl)pyridin-3-yl)-3-(4-fluoro-2-methoxy)-3-methylphenyl)-4,5-dimethyl-5-(trifluoromethyl)tetrahydrofuran-2-carboxamide

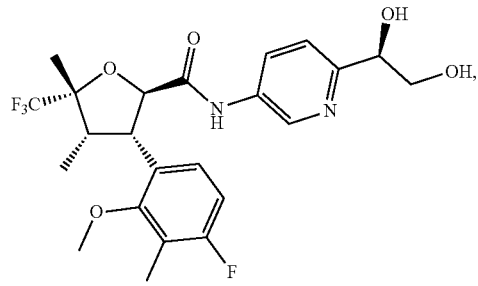 [SMILES: COc1c([C@H]2[C@H](C(=O)Nc3ccc([C@@H](O)CO)nc3)O[C@@](C)(C(F)(F)F)[C@H]2C)ccc(F)c1C]

(2R,3S,4S,5R)-N-(6-((R)-1,2-
dihydroxyethyl)pyridin-3-yl)-3-(4-fluoro-2-
methoxy-3-methylphenyl)-4,5-dimethyl-5-
(trifluoromethyl)tetrahydrofuran-2-carboxamide

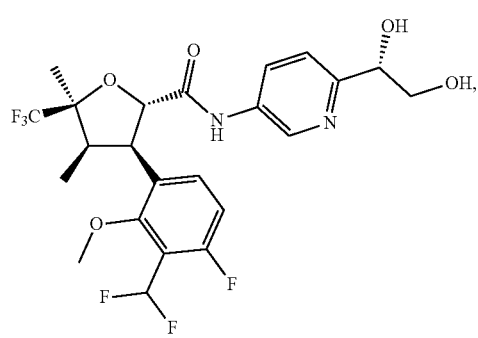 [SMILES: COc1c([C@@H]2[C@@H](C(=O)Nc3ccc([C@H](O)CO)nc3)O[C@](C)(C(F)(F)F)[C@@H]2C)ccc(F)c1C(F)F]

(2S,3R,4R,5S)-3-(3-(difluoromethyl)-4-fluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide

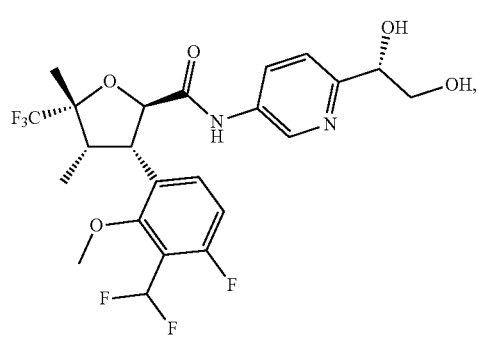 [SMILES: COc1c([C@H]2[C@H](C(=O)Nc3ccc([C@H](O)CO)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-((S)-1,2-
dihydroxyethyl)pyridin-3-yl)-4,5-dimethyl-5-
(trifluoromethyl)tetrahydrofuran-2-carboxamide

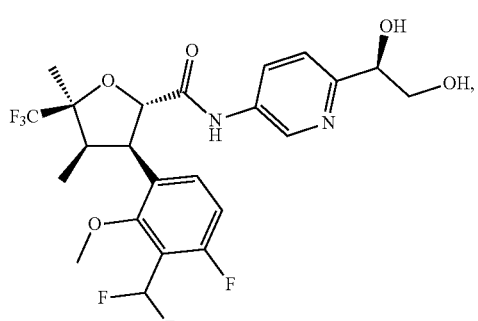

(2S,3R,4R,5S)-3-(3-(difluoromethyl)-4-fluoro-2-
methoxyphenyl)-N-(6-((R)-1,2-
dihydroxyethyl)pyridin-3-yl)-4,5-dimethyl-5-
(trifluoromethyl)tetrahydrofuran-2-carboxamide

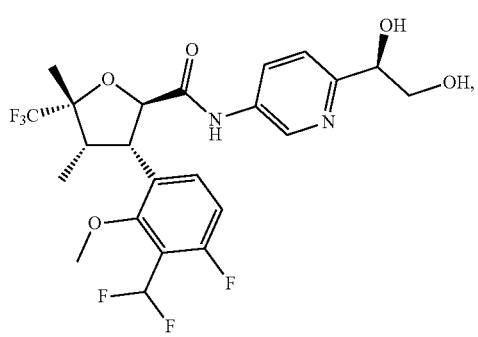 [SMILES: COc1c([C@H]2[C@H](C(=O)Nc3ccc([C@@H](O)CO)nc3)O[C@@](C)(C(F)(F)F)[C@H]2C)ccc(F)c1C(F)F]

(2R,3S,4S,5R)-3-(3-(difluoromethyl)-4-fluoro-2-
methoxyphenyl)-N-(6-((R)-1,2-
dihydroxyethyl)pyridin-3-yl)-4,5-dimethyl-5-
(trifluoromethyl)tetrahydrofuran-2-carboxamide

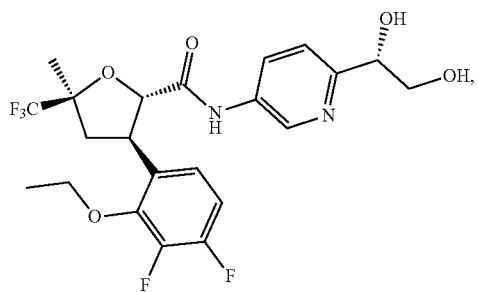 [SMILES: CCOc1c([C@H]2C[C@@](C)(C(F)(F)F)O[C@@H]2C(=O)Nc2ccc([C@H](O)CO)nc2)ccc(F)c1F]

(2S,3R,5S)-N-(6-((S)-1,2-dihydroxyethyl)pyridin-
3-yl)-3-(2-ethoxy-3,4-difluorophenyl)-5-methyl-5-
(trifluoromethyl)tetrahydrofuran-2-carboxamide

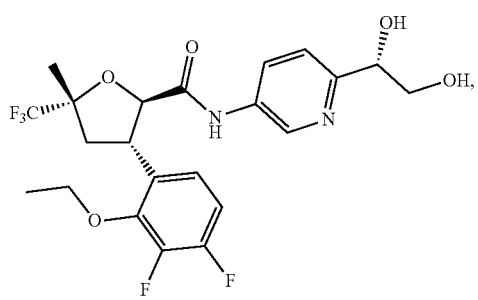 [SMILES: CCOc1c([C@@H]2C[C@](C)(C(F)(F)F)O[C@H]2C(=O)Nc2ccc([C@H](O)CO)nc2)ccc(F)c1F]

(2R,3S,5R)-N-(6-((S)-1,2-
dihydroxyethyl)pyridin-3-yl)-3-(2-ethoxy-3,4-
difluorophenyl)-5-methyl-5-
(trifluoromethyl)tetrahydrofuran-2-carboxamide

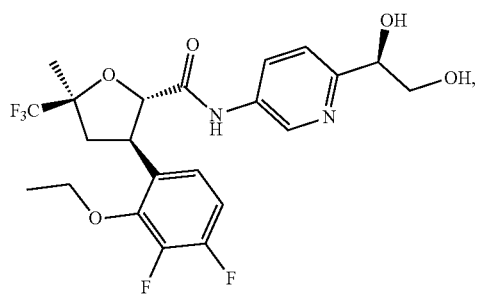 [SMILES: CCOc1c([C@H]2C[C@@](C)(C(F)(F)F)O[C@@H]2C(=O)Nc2ccc([C@@H](O)CO)nc2)ccc(F)c1F]

(2S,3R,5S)-N-(6-((R)-1,2-dihydroxyethyl)pyridin-3-yl)-3-(2-ethoxy-3,4-difluorophenyl)-5-methyl-5-(trifluoromethyl)tetrahydrofuran-2-carboxamide

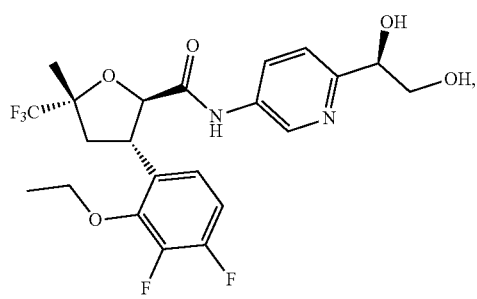 [SMILES: CCOc1c([C@@H]2C[C@](C)(C(F)(F)F)O[C@H]2C(=O)Nc2ccc([C@@H](O)CO)nc2)ccc(F)c1F]

(2R,3S,5R)-N-(6-((R)-1,2-dihydroxyethyl)pyridin-3-yl)-3-(2-ethoxy-3,4-difluorophenyl)-5-methyl-5-(trifluoromethyl)tetrahydrofuran-2-carboxamide

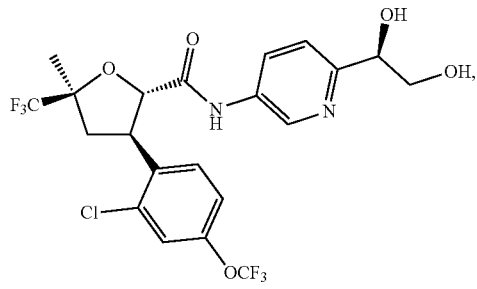 [SMILES: C[C@@]1(C(F)(F)F)C[C@H](c2ccc(OC(F)(F)F)cc2Cl)[C@@H](C(=O)Nc2ccc([C@@H](O)CO)nc2)O1]

(2S,3R,5S)-3-(2-chloro-4-(trifluoromethoxy)phenyl)-N-(6-((R)-1,2-dihydroxyethyl)pyridin-3-yl)-5-methyl-5-(trifluoromethyl)tetrahydrofuran-2-carboxamide

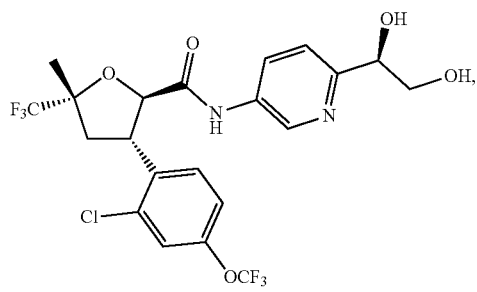

(2R,3S,5R)-3-(2-chloro-4-(trifluoromethoxy)phenyl)-N-(6-((R)-1,2-dihydroxyethyl)pyridin-3-yl)-5-methyl-5-(trifluoromethyl)tetrahydrofuran-2-carboxamide

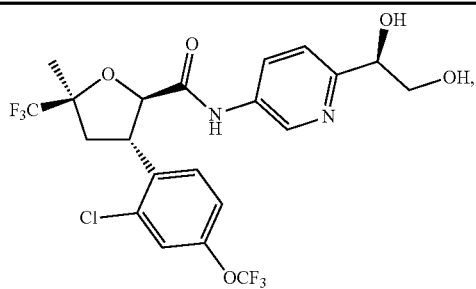

(2R,3S,5S)-3-(2-chloro-4-(trifluoromethoxy)phenyl)-N-(6-((R)-1,2-dihydroxyethyl)pyridin-3-yl)-5-methyl-5-(trifluoromethyl)tetrahydrofuran-2-carboxamide

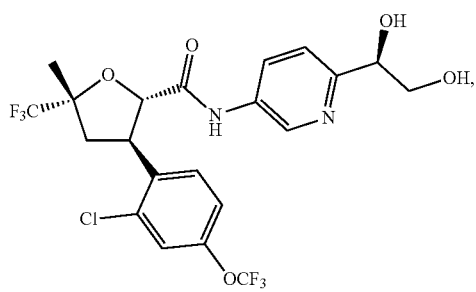 [SMILES: C[C@]1(C(F)(F)F)C[C@H](c2ccc(OC(F)(F)F)cc2Cl)[C@@H](C(=O)Nc2ccc([C@@H](O)CO)nc2)O1]

(2S,3R,5R)-3-(2-chloro-4-(trifluoromethoxy)phenyl)-N-(6-((R)-1,2-dihydroxyethyl)pyridin-3-yl)-5-methyl-5-(trifluoromethyl)tetrahydrofuran-2-carboxamide

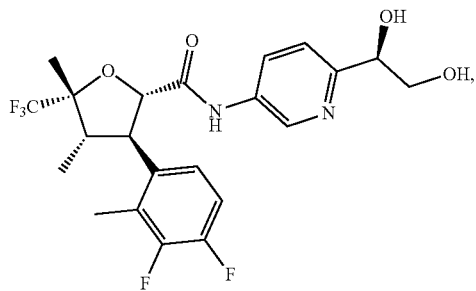 [SMILES: Cc1c([C@@H]2[C@@H](C(=O)Nc3ccc([C@@H](O)CO)nc3)O[C@@](C)(C(F)(F)F)[C@H]2C)ccc(F)c1F]

(2S,3R,4S,5R)-3-(3,4-difluoro-2-methylphenyl)-N-(6-((R)-1,2-dihydroxyethyl)pyridin-3-yl)-4,5-dimethyl-5-(trifluoromethyl)tetrahydrofuran-2-carboxamide

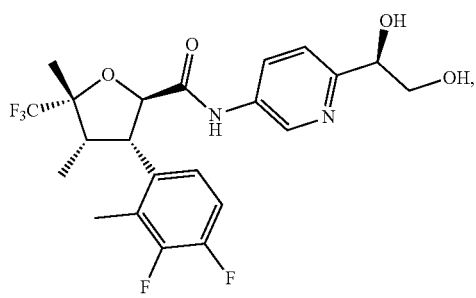 [SMILES: Cc1c([C@H]2[C@H](C(=O)Nc3ccc([C@@H](O)CO)nc3)O[C@@](C)(C(F)(F)F)[C@H]2C)ccc(F)c1F]

(2R,3S,4S,5R)-3-(3,4-difluoro-2-methylphenyl)-N-(6-((R)-1,2-dihydroxyethyl)pyridin-3-yl)-4,5-dimethyl-5-(trifluoromethyl)tetrahydrofuran-2-carboxamide

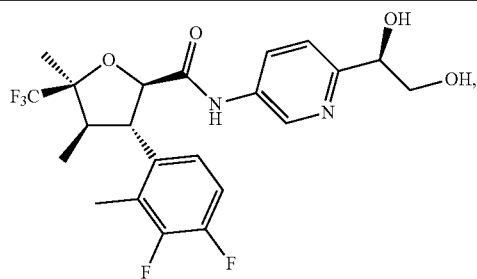

(2R,3S,4R,5S)-3-(3,4-difluoro-2-methylphenyl)-
N-(6-((R)-1,2-dihydroxyethyl)pyridin-3-yl)-4,5-
dimethyl-5-(trifluoromethyl)tetrahydrofuran-2-
carboxamide

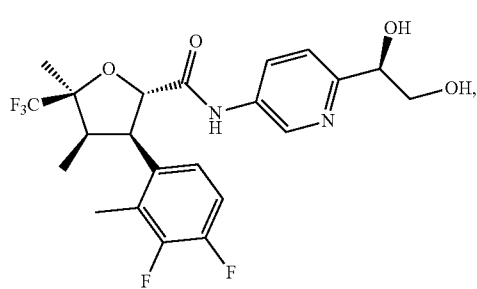 [SMILES: Cc1c([C@@H]2[C@@H](C(=O)Nc3ccc([C@@H](O)CO)nc3)O[C@](C)(C(F)(F)F)[C@@H]2C)ccc(F)c1F]

(2S,3R,4R,5S)-3-(3,4-difluoro-2-methylphenyl)-
N-(6-((R)-1,2-dihydroxyethyl)pyridin-3-yl)-4,5-
dimethyl-5-(trifluoromethyl)tetrahydrofuran-2-
carboxamide

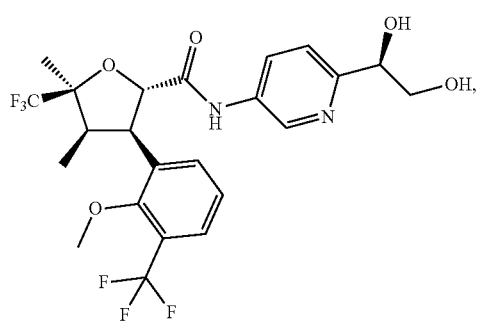 [SMILES: COc1c([C@@H]2[C@@H](C(=O)Nc3ccc([C@@H](O)CO)nc3)O[C@](C)(C(F)(F)F)[C@@H]2C)cccc1C(F)(F)F]

(2S,3R,4R,5S)-N-(6-((R)-1,2-
dihydroxyethyl)pyridin-3-yl)-3-(2-methoxy-3-
(trifluoromethyl)phenyl)-4,5-dimethyl-5-
(trifluoromethyl)tetrahydrofuran-2-carboxamide

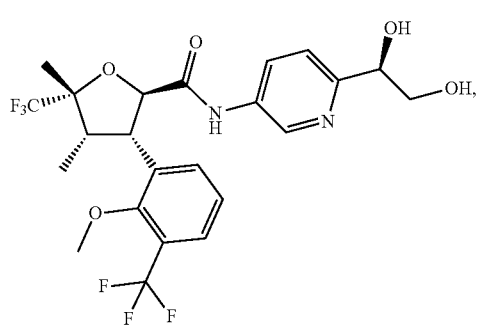 [SMILES: COc1c([C@H]2[C@H](C(=O)Nc3ccc([C@@H](O)CO)nc3)O[C@@](C)(C(F)(F)F)[C@H]2C)cccc1C(F)(F)F]

(2R,3S,4S,5R)-N-(6-((R)-1,2-
dihydroxyethyl)pyridin-3-yl)-3-(2-methoxy-3-
(trifluoromethyl)phenyl)-4,5-dimethyl-5-
(trifluoromethyl)tetrahydrofuran-2-carboxamide

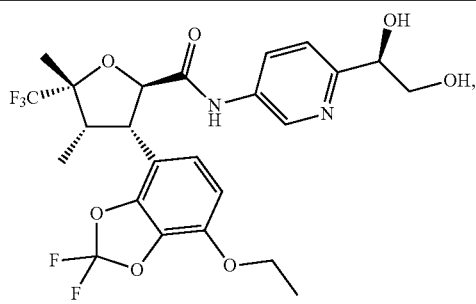

(2R,3S,4S,5R)-N-(6-((R)-1,2-
dihydroxyethyl)pyridin-3-yl)-3-(7-ethoxy-2,2-
difluorobenzo[d][1,3]dioxol-4-yl)-4,5-dimethyl-5-
(trifluoromethyl)tetrahydrofuran-2-carboxamide

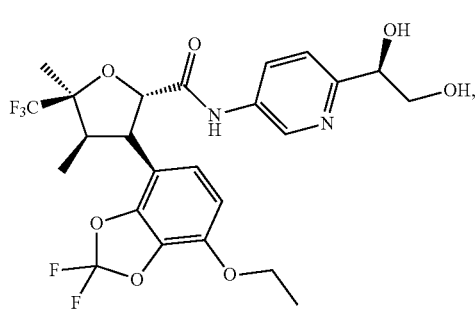

(2S,3R,4R,5S)-N-(6-((R)-1,2-dihydroxyethyl)pyridin-
3-yl)-3-(7-ethoxy-2,2-difluorobenzo[d][1,3]dioxol-4-
yl)-4,5-dimethyl-5-(trifluoromethyl)tetrahydrofuran-2-
carboxamide

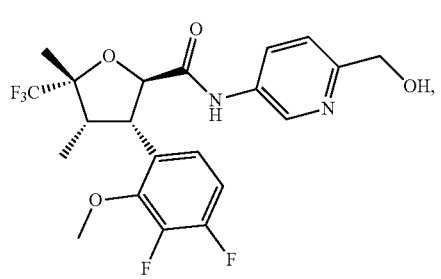 [SMILES: COc1c([C@H]2[C@H](C(=O)Nc3ccc(CO)nc3)O[C@@](C)(C(F)(F)F)[C@H]2C)ccc(F)c1F]

(2R,3S,4S,5R)-3-(3,4-difluoro-2-
methoxyphenyl)-N-(6-(hydroxymethyl)pyridin-
3-yl)-4,5-dimethyl-5-
(trifluoromethyl)tetrahydrofuran-2-carboxamide

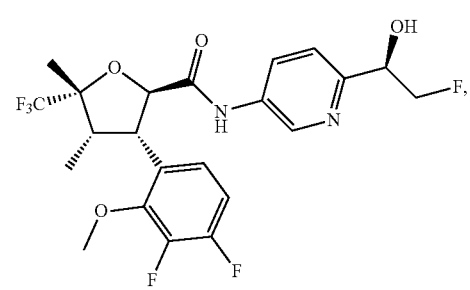 [SMILES: COc1c([C@H]2[C@H](C(=O)Nc3ccc([C@@H](O)CF)nc3)O[C@@](C)(C(F)(F)F)[C@H]2C)ccc(F)c1F]

(2R,3S,4S,5R)-3-(3,4-difluoro-2-
methoxyphenyl)-N-(6-((R)-2-fluoro-1-
hydroxyethyl)pyridin-3-yl)-4,5-dimethyl-5-
(trifluoromethyl)tetrahydrofuran-2-carboxamide -continued

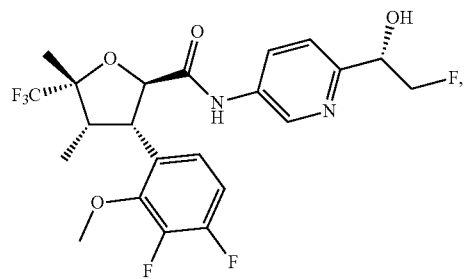 [SMILES: COc1c([C@H]2[C@H](C(=O)Nc3ccc([C@H](O)CF)nc3)O[C@@](C)(C(F)(F)F)[C@H]2C)ccc(F)c1F]

(2R,3S,4S,5R)-3-(3,4-difluoro-2-methoxyphenyl)-N-(6-((S)-2-fluoro-1-hydroxyethyl)pyridin-3-yl)-4,5-dimethyl-5-(trifluoromethyl)tetrahydrofuran-2-carboxamide

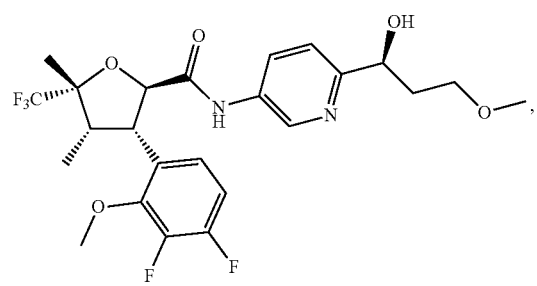 [SMILES: COCC[C@H](O)c1ccc(NC(=O)[C@@H]2O[C@@](C)(C(F)(F)F)[C@@H](C)[C@H]2c2ccc(F)c(F)c2OC)cn1]

(2R,3S,4S,5R)-3-(3,4-difluoro-2-methoxyphenyl)-N-(6-((S)-1-hydroxy-3-methoxypropyl)pyridin-3-yl)-4,5-dimethyl-5-(trifluoromethyl)tetrahydrofuran-2-carboxamide

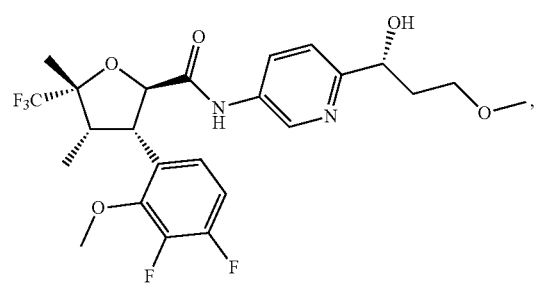 [SMILES: COCC[C@@H](O)c1ccc(NC(=O)[C@@H]2O[C@@](C)(C(F)(F)F)[C@@H](C)[C@H]2c2ccc(F)c(F)c2OC)cn1]

(2R,3S,4S,5R)-3-(3,4-difluoro-2-methoxyphenyl)-N-(6-((R)-1-hydroxy-3-methoxypropyl)pyridin-3-yl)-4,5-dimethyl-5-(trifluoromethyl)tetrahydrofuran-2-carboxamide

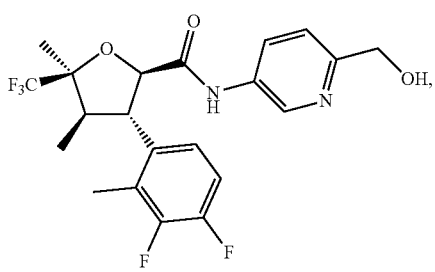 [SMILES: Cc1c([C@@H]2[C@@H](C)[C@@](C)(C(F)(F)F)O[C@H]2C(=O)Nc2ccc(CO)nc2)ccc(F)c1F]

(2R,3S,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide -continued

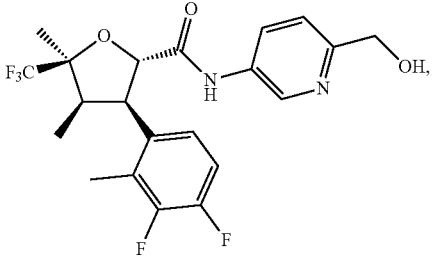 [SMILES: Cc1c([C@@H]2[C@@H](C(=O)Nc3ccc(CO)nc3)O[C@](C)(C(F)(F)F)[C@@H]2C)ccc(F)c1F]

(2S,3R,4R,5S)-3-(3,4-difluoro-2-methylphenyl)-N-(6-(hydroxymethyl)pyridin-3-yl)-4,5-dimethyl-5-(trifluoromethyl)tetrahydrofuran-2-carboxamide

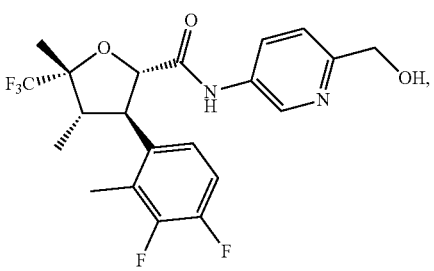 [SMILES: Cc1c([C@@H]2[C@@H](C(=O)Nc3ccc(CO)nc3)O[C@@](C)(C(F)(F)F)[C@H]2C)ccc(F)c1F]

(2S,3R,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide

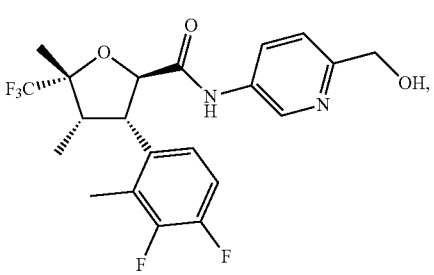 [SMILES: Cc1c([C@H]2[C@H](C(=O)Nc3ccc(CO)nc3)O[C@@](C)(C(F)(F)F)[C@H]2C)ccc(F)c1F]

(2R,3S,4S,5R)-3-(3,4-difluoro-2-methylphenyl)-N-(6-(hydroxymethyl)pyridin-3-yl)-4,5-dimethyl-5-(trifluoromethyl)tetrahydrofuran-2-carboxamide

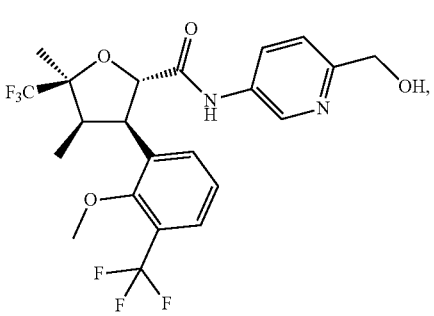 [SMILES: COc1c([C@@H]2[C@@H](C(=O)Nc3ccc(CO)nc3)O[C@](C)(C(F)(F)F)[C@@H]2C)cccc1C(F)(F)F]

(2S,3R,4R,5S)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide

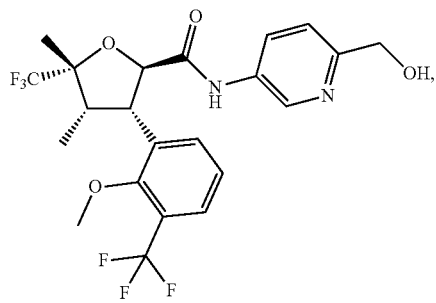 [SMILES: COc1c([C@H]2[C@H](C(=O)Nc3ccc(CO)nc3)O[C@@](C)(C(F)(F)F)[C@H]2C)cccc1C(F)(F)F]

(2R,3S,4S,5R)-N-(6-(hydroxymethyl)pyridin-3-yl)-3-(2-methoxy-3-(trifluoromethyl)phenyl)-4,5-dimethyl-5-(trifluoromethyl)tetrahydrofuran-2-carboxamide

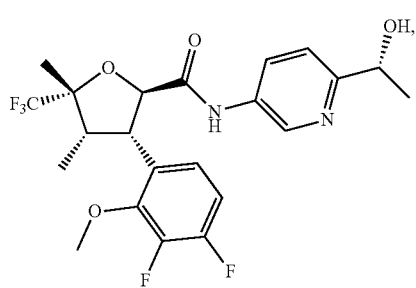 [SMILES: COc1c([C@H]2[C@H](C(=O)Nc3ccc([C@@H](C)O)nc3)O[C@@](C)(C(F)(F)F)[C@H]2C)ccc(F)c1F]

(2R,3S,4S,5R)-3-(3,4-difluoro-2-methoxyphenyl)-N-(6-((R)-1-hydroxyethyl)pyridin-3-yl)-4,5-dimethyl-5-(trifluoromethyl)tetrahydrofuran-2-carboxamide

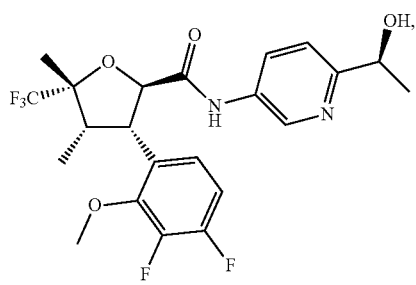 [SMILES: COc1c([C@H]2[C@H](C(=O)Nc3ccc([C@H](C)O)nc3)O[C@@](C)(C(F)(F)F)[C@H]2C)ccc(F)c1F]

(2R,3S,4S,5R)-3-(3,4-difluoro-2-methoxyphenyl)-N-(6-((S)-1-hydroxyethyl)pyridin-3-yl)-4,5-dimethyl-5-(trifluoromethyl)tetrahydrofuran-2-carboxamide

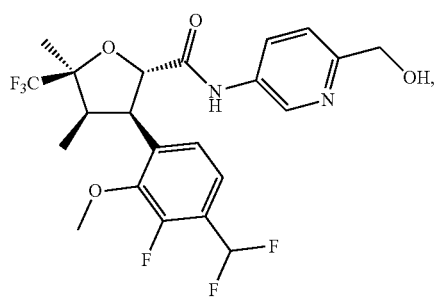 [SMILES: COc1c([C@@H]2[C@@H](C(=O)Nc3ccc(CO)nc3)O[C@](C)(C(F)(F)F)[C@@H]2C)ccc(C(F)F)c1F]

(2S,3R,4R,5S)-3-(4-(difluoromethyl)-3-fluoro-2-methoxyphenyl)-N-(6-(hydroxymethyl)pyridin-3-yl)-4,5-dimethyl-5-(trifluoromethyl)tetrahydrofuran-2-carboxamide

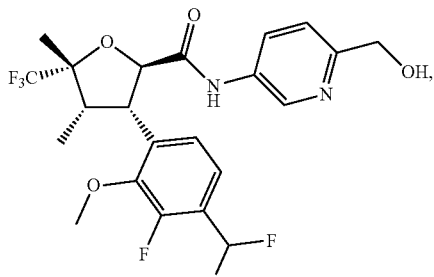

(2R,3S,4S,5R)-3-(4-(difluoromethyl)-3-fluoro-2-methoxyphenyl)-N-(6-(hydroxymethyl)pyridin-3-yl)-4,5-dimethyl-5-(trifluoromethyl)tetrahydrofuran-2-carboxamide

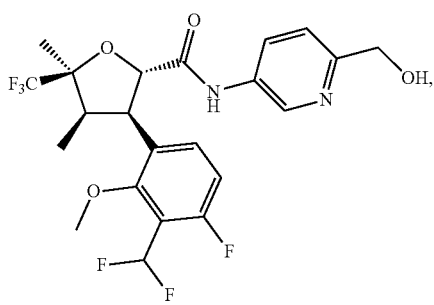 [SMILES: COc1c([C@@H]2[C@@H](C(=O)Nc3ccc(CO)nc3)O[C@](C)(C(F)(F)F)[C@@H]2C)ccc(F)c1C(F)F]

(2S,3R,4R,5S)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide

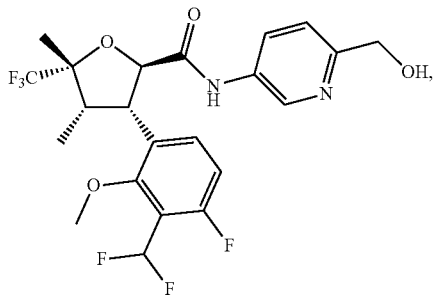 [SMILES: COc1c([C@H]2[C@H](C(=O)Nc3ccc(CO)nc3)O[C@@](C)(C(F)(F)F)[C@H]2C)ccc(F)c1C(F)F]

(2R,3S,4S,5R)-3-(3-(difluoromethyl)-4-fluoro-2-methoxyphenyl)-N-(6-(hydroxymethyl)pyridin-3-yl)-4,5-dimethyl-5-(trifluoromethyl)tetrahydrofuran-2-carboxamide

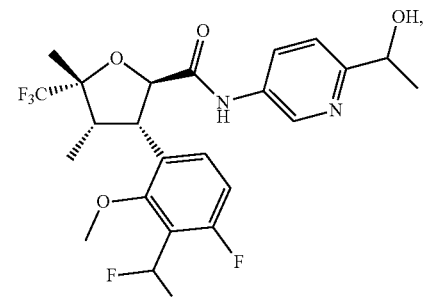

(2R,3S,4S,5R)-3-(3-(difluoromethyl)-4-fluoro-2-methoxyphenyl)-N-(6-(1-hydroxyethyl)pyridin-3-yl)-4,5-dimethyl-5-(trifluoromethyl)tetrahydrofuran-2-carboxamide 215
-continued

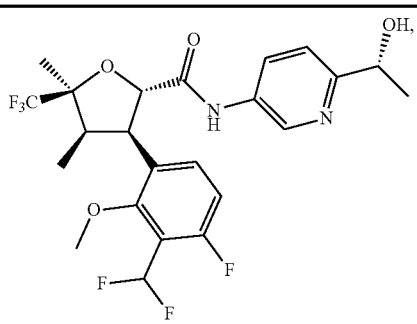

(2S,3R,4R,5S)-3-(3-(difluoromethyl)-4-fluoro-2-methoxyphenyl)-N-(6-((R)-1-hydroxyethyl)pyridin-3-yl)-4,5-dimethyl-5-(trifluoromethyl)tetrahydrofuran-2-carboxamide

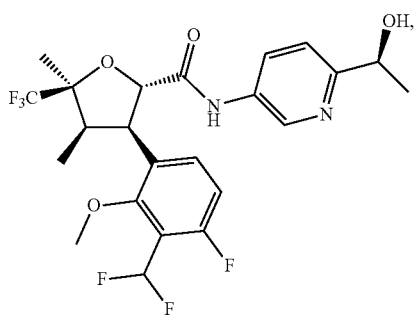 [SMILES: COc1c([C@@H]2[C@@H](C(=O)Nc3ccc([C@H](C)O)nc3)O[C@](C)(C(F)(F)F)[C@@H]2C)ccc(F)c1C(F)F]

(2S,3R,4R,5S)-3-(3-(difluoromethyl)-4-fluoro-2-methoxyphenyl)-N-(6-((S)-1-hydroxyethyl)pyridin-3-yl)-4,5-dimethyl-5-(trifluoromethyl)tetrahydrofuran-2-carboxamide

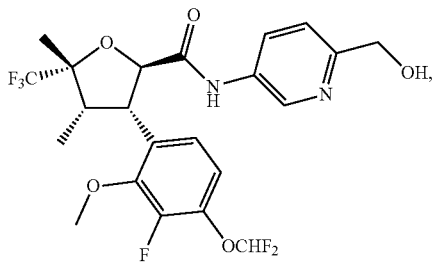 [SMILES: COc1c([C@H]2[C@H](C(=O)Nc3ccc(CO)nc3)O[C@@](C)(C(F)(F)F)[C@H]2C)ccc(OC(F)F)c1F]

(2R,3S,4S,5R)-3-(4-(difluoromethoxy)-3-fluoro-2-methoxyphenyl)-N-(6-(hydroxymethyl)pyridin-3-yl)-4,5-dimethyl-5-(trifluoromethyl)tetrahydrofuran-2-carboxamide

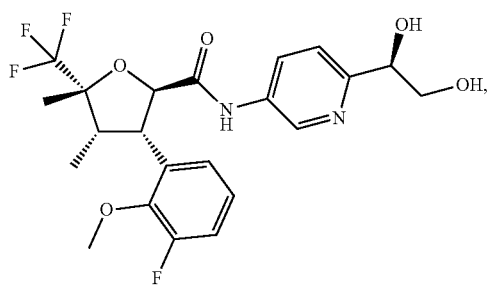 [SMILES: COc1c(F)cccc1[C@H]1[C@H](C(=O)Nc2ccc([C@@H](O)CO)nc2)O[C@@](C)(C(F)(F)F)[C@H]1C]

(2R,3S,4S,5R)-N-(6-((R)-1,2-dihydroxyethyl)pyridin-3-yl)-3-(3-fluoro-2-methoxyphenyl)-4,5-dimethyl-5-(trifluoromethyl)tetrahydrofuran-2-carboxamide 216
-continued

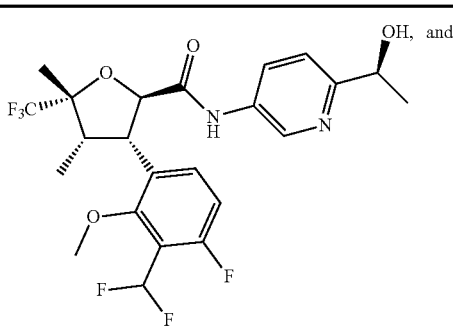

(2R,3S,4S,5R)-3-(3-(difluoromethyl)-4-fluoro-2-methoxyphenyl)-N-(6-((S)-1-hydroxyethyl)pyridin-3-yl)-4,5-dimethyl-5-(trifluoromethyl)tetrahydrofuran-2-carboxamide

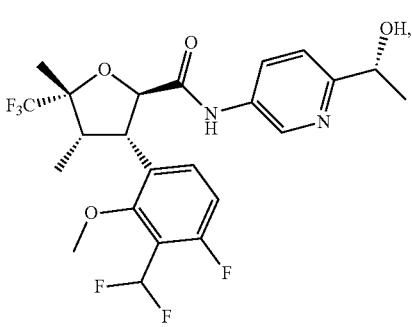

(2R,3S,4S,5R)-3-(3-(difluoromethyl)-4-fluoro-2-methoxyphenyl)-N-(6-((R)-1-hydroxyethyl)pyridin-3-yl)-4,5-dimethyl-5-(trifluoromethyl)tetrahydrofuran-2-carboxamide or a pharmaceutically acceptable salt thereof.

14. A pharmaceutical composition comprising the compound of claim 1, or a pharmaceutically acceptable salt thereof, and one or more pharmaceutically acceptable carriers or vehicles.

15. A method of inhibiting a voltage-gated sodium channel in a subject comprising administering to the subject the compound of claim 1, or a pharmaceutically acceptable salt thereof.

16. A method of treating or lessening the severity in a subject of pain comprising administering to the subject an effective amount of the compound of claim 1, or a pharmaceutically acceptable salt thereof.

17. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

18. The compound of claim 1, wherein the compound is selected from:

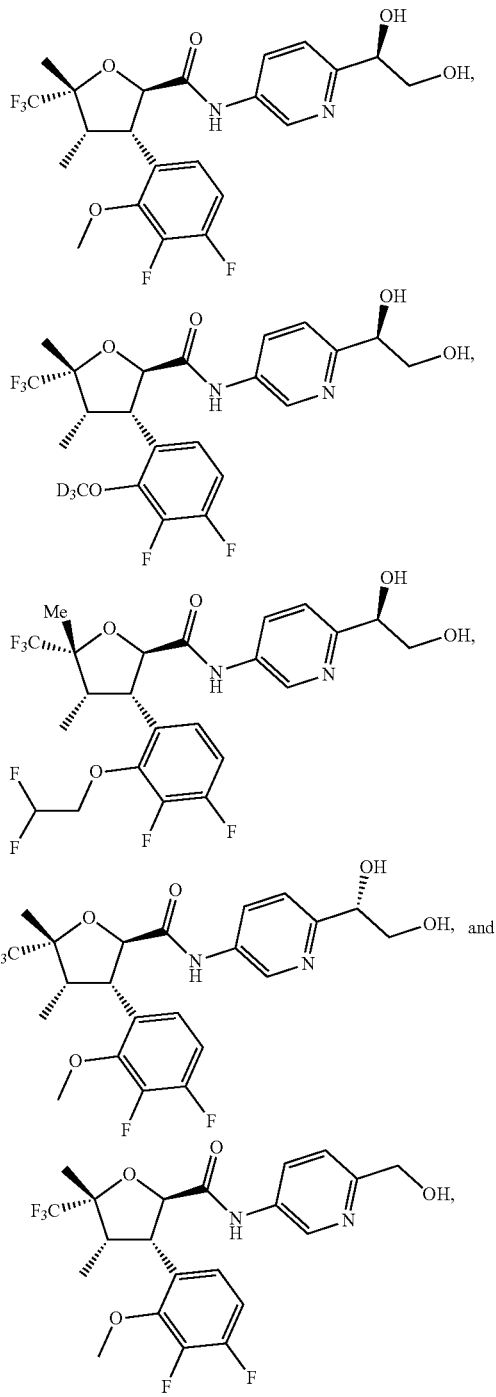

or a pharmaceutically acceptable salt thereof.

19. A pharmaceutical composition comprising the compound of claim 18, or a pharmaceutically acceptable salt thereof, and one or more pharmaceutically acceptable carriers or vehicles.

20. A method of inhibiting a voltage-gated sodium channel in a subject comprising administering to the subject the compound of claim 18, or a pharmaceutically acceptable salt thereof.

21. A method of treating or lessening the severity in a subject of pain comprising administering to the subject an effective amount of the compound of claim 18, or a pharmaceutically acceptable salt thereof.

22. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 18, or a pharmaceutically acceptable salt thereof.

23. The compound of claim 1, wherein the compound is:

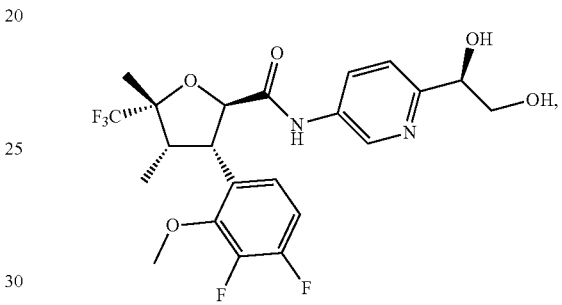

or a pharmaceutically acceptable salt thereof.

24. The compound of claim 1, wherein the compound is:

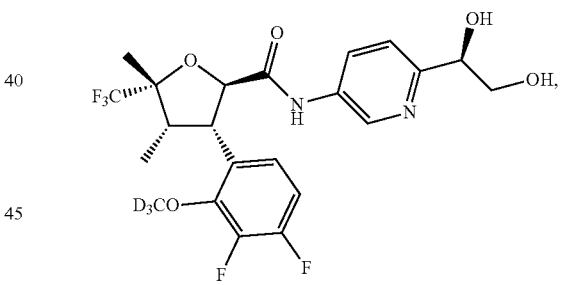

or a pharmaceutically acceptable salt thereof.

25. The compound of claim 1, wherein the compound is:

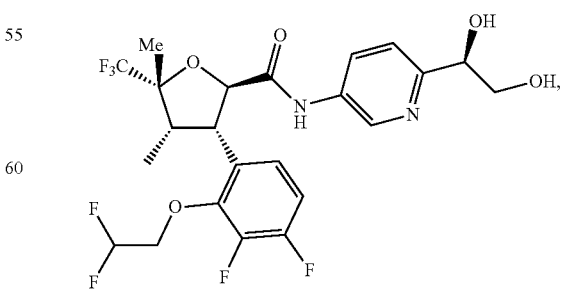

or a pharmaceutically acceptable salt thereof.

26. The compound of claim 1, wherein the compound is:

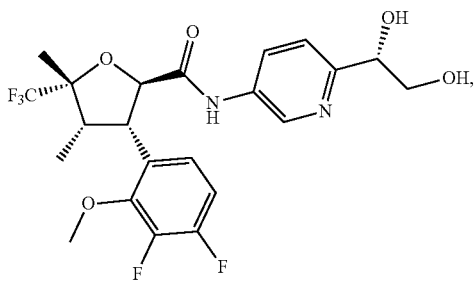 [SMILES: COc1c([C@H]2[C@H](C(=O)Nc3ccc([C@H](O)CO)nc3)O[C@@](C)(C(F)(F)F)[C@H]2C)ccc(F)c1F]

or a pharmaceutically acceptable salt thereof.

27. The compound of claim 1, wherein the compound is:

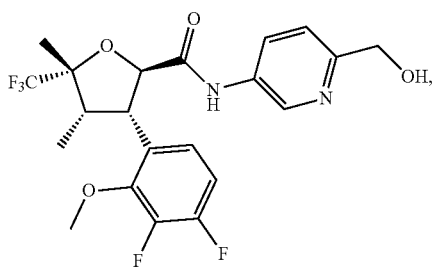 [SMILES: COc1c([C@H]2[C@H](C(=O)Nc3ccc(CO)nc3)O[C@@](C)(C(F)(F)F)[C@H]2C)ccc(F)c1F]

or a pharmaceutically acceptable salt thereof.

28. A pharmaceutical composition comprising the compound of claim 23, or a pharmaceutically acceptable salt thereof, and one or more pharmaceutically acceptable carriers or vehicles.

29. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 23, or a pharmaceutically acceptable salt thereof.

30. A pharmaceutical composition comprising the compound of claim 24, or a pharmaceutically acceptable salt thereof, and one or more pharmaceutically acceptable carriers or vehicles.

31. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 24, or a pharmaceutically acceptable salt thereof.

32. A pharmaceutical composition comprising the compound of claim 25, or a pharmaceutically acceptable salt thereof, and one or more pharmaceutically acceptable carriers or vehicles.

33. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 25, or a pharmaceutically acceptable salt thereof.

34. A pharmaceutical composition comprising the compound of claim 26, or a pharmaceutically acceptable salt thereof, and one or more pharmaceutically acceptable carriers or vehicles.

35. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 26, or a pharmaceutically acceptable salt thereof.

36. A pharmaceutical composition comprising the compound of claim 27, or a pharmaceutically acceptable salt thereof, and one or more pharmaceutically acceptable carriers or vehicles.

37. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 27, or a pharmaceutically acceptable salt thereof.

* * * * *